US012678430B2

(12) United States Patent
Lian et al.

(10) Patent No.: US 12,678,430 B2
(45) Date of Patent: Jul. 14, 2026

(54) COMPOSITIONS AND METHODS FOR THE TREATMENT OF LIVER DISORDERS

(71) Applicant: Viking Therapeutics, Inc., San Diego, CA (US)

(72) Inventors: Brian Lian, Rancho Santa Fe, CA (US); Geoffrey E. Barker, Carlsbad, CA (US); Kader Yagiz, San Diego, CA (US); Maureen Barnes, San Diego, CA (US); Erland Stevens, Davidson, CA (US)

(73) Assignee: Viking Therapeutics, Inc., San Diego, CA (US)

( * ) Notice: Subject to any disclaimer, the term of this patent is extended or adjusted under 35 U.S.C. 154(b) by 604 days.

(21) Appl. No.: 18/008,425

(22) PCT Filed: Jun. 7, 2021

(86) PCT No.: PCT/US2021/036249

§ 371 (c)(1),
(2) Date: Dec. 5, 2022

(87) PCT Pub. No.: WO2021/252392

PCT Pub. Date: Dec. 16, 2021

(65) Prior Publication Data

US 2023/0226038 A1 Jul. 20, 2023

Related U.S. Application Data

(60) Provisional application No. 63/036,922, filed on Jun. 9, 2020, provisional application No. 63/036,906, filed on Jun. 9, 2020.

(51) Int. Cl.

| | |
|---|---|
| ***A61K 31/46*** | (2006.01) |
| ***A61K 31/53*** | (2006.01) |
| ***A61K 31/675*** | (2006.01) |
| ***A61P 1/16*** | (2006.01) |
| ***C07D 451/06*** | (2006.01) |
| ***C07F 9/6561*** | (2006.01) |

(52) U.S. Cl.
CPC .............. *A61K 31/46* (2013.01); *A61K 31/53* (2013.01); *A61K 31/675* (2013.01); *A61P 1/16* (2018.01); *C07D 451/06* (2013.01); *C07F 9/6561* (2013.01)

(58) Field of Classification Search
CPC ...................................................... A61K 31/46
See application file for complete search history.

(56) References Cited

U.S. PATENT DOCUMENTS

| | | | |
|---|---|---|---|
| 3,120,551 | A | 2/1964 | Goldschmidt et al. |
| 3,357,887 | A | 12/1967 | Kagan et al. |
| 4,069,343 | A | 1/1978 | Sellstedt et al. |
| 4,069,347 | A | 1/1978 | McCarthy et al. |
| 4,423,227 | A | 12/1983 | Batz et al. |
| 4,426,453 | A | 1/1984 | Cree et al. |
| 4,554,290 | A | 11/1985 | Boger et al. |
| 4,673,691 | A | 6/1987 | Bachynsky |
| 4,766,121 | A | 8/1988 | Ellis et al. |
| 4,826,876 | A | 5/1989 | Ellis et al. |
| 4,910,305 | A | 3/1990 | Ellis et al. |
| 5,061,798 | A | 10/1991 | Emmett et al. |
| 5,116,828 | A | 5/1992 | Miura et al. |
| 5,158,978 | A | 10/1992 | Rubin |
| 5,232,946 | A | 8/1993 | Hurnaus et al. |
| 5,284,971 | A | 2/1994 | Walker et al. |
| 5,324,522 | A | 6/1994 | Krenning et al. |
| 5,401,772 | A | 3/1995 | Yokoyama et al. |
| 5,519,163 | A | 5/1996 | Gibbs et al. |
| 5,569,674 | A | 10/1996 | Yokoyama et al. |
| 5,571,840 | A | 11/1996 | Mayor et al. |
| 5,627,173 | A | 5/1997 | Graeve et al. |
| 5,654,468 | A | 8/1997 | Yokoyama et al. |
| 5,663,159 | A | 9/1997 | Starrett, Jr. et al. |
| 5,741,803 | A | 4/1998 | Pool et al. |
| 5,753,254 | A | 5/1998 | Khan et al. |
| 5,854,282 | A | 12/1998 | Mellin |
| 5,883,294 | A | 3/1999 | Scanlan et al. |
| 5,922,775 | A | 7/1999 | Kun et al. |
| 5,951,989 | A | 9/1999 | Heymann |
| 6,107,517 | A | 8/2000 | Scanlan et al. |
| 6,117,873 | A | 9/2000 | Acklin et al. |

(Continued)

FOREIGN PATENT DOCUMENTS

| | | |
|---|---|---|
| CN | 107469086 A | 12/2017 |
| CN | 110590898 | 12/2019 |

(Continued)

OTHER PUBLICATIONS

Alexander et al.,Drugs and Their Structural Motifs, Chapter 1, pp. 28-29, Metabolism, Pharmacokinetics and Toxicity of Functional Groups—Impact of Chemical Building Blocsk on ADMET, 2010.
Alonso-Merino, et al., "Thyroid hormones inhibit TGF-β signaling and attenuate fibrotic responses," PNAS, 2016, vol. 113(24), pp. E3451-E3460.
Amma, L.L., et al., "Distinct Tissue-Specific Roles for Thyroid Hormone Receptors p and al in Regulation of Type 1 Deiodinase Expression," Mot. Endocrinol. 15:467-475, The Endocrine Society (2001).
Anderson, S.N., et al., "Activation of Electrophilic Aromatic Substitution by the Substituent—CH2Co(dmgH)2py. Products of Reaction of Benzylcobaloximes with Halogens in Acetic Acid," J. Chem. Soc. Perkin Trans. II 311-318, Royal Society of Chemistry (1972).

(Continued)

*Primary Examiner* — Rei Tsang Shiao
(74) *Attorney, Agent, or Firm* — Knobbe, Martens, Olson & Bear, LLP

(57) ABSTRACT

The present disclosure is directed to FXR agonists, pharmaceutical compositions thereof, and methods of using the same for preventing, treating, or ameliorating fatty liver diseases such as steatosis, non-alcoholic fatty liver disease, and non-alcoholic steatohepatitis, either alone or in combination with thyroid receptor agonists.

20 Claims, 12 Drawing Sheets

(56) References Cited

U.S. PATENT DOCUMENTS

| | | | |
|---|---|---|---|
| 6,147,061 | A | 11/2000 | Reiter |
| 6,194,454 | B1 | 2/2001 | Dow |
| 6,221,911 | B1 | 4/2001 | Lavin et al. |
| 6,236,946 | B1 | 5/2001 | Scanlan et al. |
| 6,266,622 | B1 | 7/2001 | Scanlan et al. |
| 6,326,398 | B1 | 12/2001 | Chiang et al. |
| 6,344,481 | B1 | 2/2002 | Cornelius et al. |
| 6,361,992 | B1 | 3/2002 | Szkudlinski et al. |
| 6,380,255 | B1 | 4/2002 | Lavin et al. |
| 6,414,002 | B1 | 7/2002 | Cheng et al. |
| 6,414,026 | B1 | 7/2002 | Billingham |
| 6,441,015 | B2 | 8/2002 | Aspnes et al. |
| 6,465,687 | B1 | 10/2002 | Li et al. |
| 6,468,755 | B1 | 10/2002 | Shoelson |
| 6,492,424 | B1 | 12/2002 | Apelqvist et al. |
| 6,495,533 | B1 | 12/2002 | Matsui et al. |
| 6,534,676 | B2 | 3/2003 | Markin et al. |
| 6,545,015 | B2 | 4/2003 | Cheng et al. |
| 6,545,018 | B2 | 4/2003 | Chiang et al. |
| 6,555,582 | B1 | 4/2003 | Schwartz et al. |
| 6,566,372 | B1 | 5/2003 | Zhi et al. |
| 6,576,636 | B2 | 6/2003 | Webb et al. |
| 6,608,049 | B2 | 8/2003 | Waltering et al. |
| 6,620,830 | B2 | 9/2003 | Chiang |
| 6,625,201 | B1 | 9/2003 | Wang et al. |
| 6,664,291 | B2 | 12/2003 | Chiang et al. |
| 6,673,815 | B2 | 1/2004 | Devasthale et al. |
| 6,680,340 | B2 | 1/2004 | Cheng et al. |
| 6,689,896 | B2 | 2/2004 | Kukkola |
| 6,716,877 | B2 | 4/2004 | Markin |
| 6,723,744 | B2 | 4/2004 | Aspnes et al. |
| 6,727,271 | B2 | 4/2004 | Cheng et al. |
| 6,747,048 | B2 | 6/2004 | Zhang et al. |
| 6,763,607 | B2 | 7/2004 | Beyernck et al. |
| 6,787,652 | B1 | 9/2004 | Dow et al. |
| 6,794,406 | B2 | 9/2004 | Haning et al. |
| 6,806,381 | B2 | 10/2004 | Chidambaram et al. |
| 6,825,201 | B2 | 11/2004 | Wang et al. |
| 6,831,102 | B2 | 12/2004 | Rangeland |
| 6,852,706 | B1 | 2/2005 | Heber-Katz |
| 6,875,782 | B2 | 4/2005 | Cheng et al. |
| 6,982,348 | B2 | 1/2006 | Kori et al. |
| 7,015,246 | B2 | 3/2006 | Schmeck et al. |
| 7,402,602 | B2 | 7/2008 | Bigg et al. |
| 7,514,419 | B2 | 4/2009 | Erion et al. |
| 7,799,782 | B2 | 9/2010 | Munson et al. |
| 7,829,552 | B2 | 11/2010 | Erion et al. |
| 10,130,643 | B2 | 11/2018 | Cable et al. |
| 10,925,885 | B2 | 2/2021 | Cable et al. |
| 11,202,789 | B2 | 12/2021 | Lian |
| 11,351,183 | B2 | 6/2022 | Lian et al. |
| 11,707,472 | B2 | 7/2023 | Lian et al. |
| 11,707,475 | B2 | 7/2023 | Tunac |
| 11,787,828 | B2 | 10/2023 | Lian et al. |
| 12,102,646 | B2 * | 10/2024 | Lian ........................ A61P 29/00 |
| 12,227,533 | B2 | 2/2025 | Lian et al. |
| 2001/0051645 | A1 | 12/2001 | Chiang |
| 2001/0051657 | A1 | 12/2001 | Chiang et al. |
| 2002/0006946 | A1 | 1/2002 | Aspnes et al. |
| 2002/0045751 | A1 | 4/2002 | Kukkola |
| 2002/0049226 | A1 | 4/2002 | Chiang et al. |
| 2002/0107390 | A1 | 8/2002 | Kukkola |
| 2002/0123521 | A1 | 9/2002 | Lavin |
| 2003/0027862 | A1 | 2/2003 | Haning et al. |
| 2003/0040535 | A1 | 2/2003 | Aspnes et al. |
| 2003/0078288 | A1 | 4/2003 | Haning et al. |
| 2003/0078289 | A1 | 4/2003 | Aspnes et al. |
| 2003/0114521 | A1 | 6/2003 | Chiang et al. |
| 2003/0153513 | A1 | 8/2003 | Shiomi et al. |
| 2003/0166724 | A1 | 9/2003 | Rangeland |
| 2004/0029187 | A1 | 2/2004 | Palmer |
| 2004/0039028 | A1 | 2/2004 | Zhang et al. |
| 2004/0077694 | A1 | 4/2004 | Chiang et al. |
| 2004/0097589 | A1 | 5/2004 | Yi-Lin et al. |
| 2004/0110951 | A1 | 6/2004 | Chiang |
| 2004/0116387 | A1 | 6/2004 | Malm et al. |
| 2004/0116391 | A1 | 6/2004 | Piccariello et al. |
| 2004/0142868 | A1 | 7/2004 | Sleeman |
| 2004/0152783 | A1 | 8/2004 | Olon et al. |
| 2004/0157844 | A1 | 8/2004 | Dow et al. |
| 2004/0219218 | A1 | 11/2004 | Martino et al. |
| 2004/0220147 | A1 | 11/2004 | Malm et al. |
| 2005/0004184 | A1 | 1/2005 | Ryono et al. |
| 2005/0038122 | A1 | 2/2005 | Rangeland |
| 2005/0054727 | A1 | 3/2005 | Rangeland |
| 2005/0085541 | A1 | 4/2005 | Shiohara et al. |
| 2006/0046980 | A1 | 3/2006 | Erion et al. |
| 2008/0261913 | A1 | 10/2008 | Sommadossi et al. |
| 2009/0232879 | A1 | 9/2009 | Cable et al. |
| 2010/0081634 | A1 | 4/2010 | Erion et al. |
| 2013/0059781 | A1 | 3/2013 | Kofoed et al. |
| 2015/0045389 | A1 | 2/2015 | Madden et al. |
| 2016/0319548 | A1 | 11/2016 | Shevlin |
| 2017/0105956 | A1 | 4/2017 | Kaminski et al. |
| 2017/0112864 | A1 | 4/2017 | Cable et al. |
| 2017/0348293 | A1 | 12/2017 | Miao et al. |
| 2018/0243263 | A1 | 8/2018 | Jain et al. |
| 2018/0360846 | A1 | 12/2018 | Lefebvre |
| 2019/0255080 | A1 | 8/2019 | Lian et al. |
| 2020/0179412 | A1 | 6/2020 | Lian et al. |
| 2022/0016136 | A1 | 1/2022 | Lian et al. |
| 2024/0189332 | A1 | 6/2024 | Lian et al. |
| 2025/0034183 | A1 | 1/2025 | Barker et al. |
| 2025/0134913 | A1 | 5/2025 | Lian et al. |

FOREIGN PATENT DOCUMENTS

| | | |
|---|---|---|
| CN | 112812114 | 5/2021 |
| CN | 113024552 | 6/2021 |
| EP | 080550 | 1/1994 |
| EP | 1297833 | 4/2003 |
| EP | 1471049 | 10/2004 |
| EP | 1666035 | 6/2006 |
| EP | 1653928 | 3/2012 |
| JP | 7168660 B2 | 11/2022 |
| KR | 10-2006-0109926 | 10/2006 |
| KR | 10-2007-0029196 | 3/2007 |
| WO | WO 1989/08458 | 9/1989 |
| WO | WO 1990/08155 | 7/1990 |
| WO | WO 1990/10636 | 9/1990 |
| WO | WO 1991/06569 | 5/1991 |
| WO | WO 1991/11181 | 8/1991 |
| WO | WO 1995/00135 | 1/1995 |
| WO | WO 1995/24919 | 9/1995 |
| WO | WO 1996/05190 | 2/1996 |
| WO | WO 1996/40048 | 12/1996 |
| WO | WO 1997/21993 | 6/1997 |
| WO | WO 1998/07435 | 2/1998 |
| WO | WO 1998/41216 | 9/1998 |
| WO | WO 1998/57919 | 12/1998 |
| WO | WO 1999/00353 | 1/1999 |
| WO | WO 1999/26966 | 6/1999 |
| WO | WO 1999/29321 | 6/1999 |
| WO | WO 1999/38376 | 8/1999 |
| WO | WO 1999/45016 | 9/1999 |
| WO | WO 1999/62507 | 12/1999 |
| WO | WO 2000/00468 | 1/2000 |
| WO | WO 2000/07972 | 2/2000 |
| WO | WO 2000/39077 | 7/2000 |
| WO | WO 2000/51971 | 9/2000 |
| WO | WO 2000/52015 | 9/2000 |
| WO | WO 2000/58279 | 10/2000 |
| WO | WO 2001/13936 | 3/2001 |
| WO | WO 2001/18013 | 3/2001 |
| WO | WO 2001/36365 | 5/2001 |
| WO | WO 2001/60784 | 8/2001 |
| WO | WO 2001/72692 | 10/2001 |
| WO | WO 2001/79287 | 10/2001 |
| WO | WO 2001/94293 | 12/2001 |
| WO | WO 2001/98256 | 12/2001 |
| WO | WO 2002/03914 | 1/2002 |
| WO | WO 2002/04515 | 1/2002 |
| WO | WO 2002/05834 | 1/2002 |
| WO | WO 2002/11666 | 2/2002 |

(56) References Cited

FOREIGN PATENT DOCUMENTS

| | | |
|---|---|---|
| WO | WO 2002/26752 | 4/2002 |
| WO | WO 2002/32408 | 4/2002 |
| WO | WO 2002/060374 | 8/2002 |
| WO | WO 2002/062780 | 8/2002 |
| WO | WO 2002/066017 | 8/2002 |
| WO | WO 2002/072528 | 9/2002 |
| WO | WO 2002/079181 | 10/2002 |
| WO | WO 2002/092550 | 11/2002 |
| WO | WO 2003/003013 | 1/2003 |
| WO | WO 2003/015771 | 2/2003 |
| WO | WO 2003/018515 | 3/2003 |
| WO | WO 2003/039456 | 5/2003 |
| WO | WO 2003/061557 | 7/2003 |
| WO | WO 2003/061567 | 7/2003 |
| WO | WO 2003/070169 | 8/2003 |
| WO | WO 2003/075835 | 9/2003 |
| WO | WO 2003/084915 | 10/2003 |
| WO | WO 2003/094845 | 11/2003 |
| WO | WO 2003/099864 | 12/2003 |
| WO | WO 2003/105760 | 12/2003 |
| WO | WO 2004/005342 | 1/2004 |
| WO | WO 2004/007430 | 1/2004 |
| WO | WO 2004/014318 | 2/2004 |
| WO | WO 2004/018421 | 3/2004 |
| WO | WO 2004/026097 | 4/2004 |
| WO | WO 2004/041208 | 5/2004 |
| WO | WO 2004/065620 | 8/2004 |
| WO | WO 2004/066929 | 8/2004 |
| WO | WO 2004/067482 | 8/2004 |
| WO | WO 2004/078947 | 9/2004 |
| WO | WO 2004/091636 | 10/2004 |
| WO | WO 2004/093799 | 11/2004 |
| WO | WO 2004/103289 | 12/2004 |
| WO | WO 2005/009433 | 2/2005 |
| WO | WO 2005/016862 | 2/2005 |
| WO | WO 2005/021895 | 3/2005 |
| WO | WO 2005/028488 | 3/2005 |
| WO | WO 2005/042556 | 5/2005 |
| WO | WO 2005/123729 | 12/2005 |
| WO | WO 2006/128055 | 11/2006 |
| WO | WO 2006/128056 | 11/2006 |
| WO | WO 2006/128058 | 11/2006 |
| WO | WO 2007/009913 | 1/2007 |
| WO | WO 2007/109605 | 9/2007 |
| WO | WO 2009/089093 | 7/2009 |
| WO | WO 2010/074992 | 7/2010 |
| WO | WO 2010/125565 | 11/2010 |
| WO | WO 2011/038207 | 3/2011 |
| WO | WO 2012/087519 | 6/2012 |
| WO | WO 2013/163675 | 11/2013 |
| WO | WO 2015/134365 | 9/2015 |
| WO | WO 2016/097933 | 6/2016 |
| WO | WO 2016/111971 | 7/2016 |
| WO | WO 2016/123086 | 8/2016 |
| WO | WO 2017/148787 | 9/2017 |
| WO | WO 2017/184811 | 10/2017 |
| WO | WO 2017/210526 | 12/2017 |
| WO | WO 2018/053036 | 3/2018 |
| WO | WO 2018/094265 | 5/2018 |
| WO | WO 2018/193006 | 10/2018 |
| WO | WO 2018/226604 | 12/2018 |
| WO | WO 2019/005816 | 1/2019 |
| WO | WO 2020/023382 | 1/2020 |
| WO | WO 2020/033382 | 2/2020 |
| WO | WO 2020/117962 | 6/2020 |
| WO | WO 2020/117987 | 6/2020 |
| WO | WO 2021/190624 | 9/2021 |
| WO | WO 2021/252392 | 12/2021 |
| WO | WO 2022/159395 | 7/2022 |
| WO | WO 2023/158607 | 8/2023 |
| WO | WO 2023/158616 | 8/2023 |

OTHER PUBLICATIONS

Annett, R.G., et al., "Enzymatically catalysed decarboxylation of P-carboxyaspartic acid (Asa)," Can. J. Chem. 68:886-887, NRC Research Press (1990).

Antons, K.A., et al., "Clinical Perspectives of Starin-Induced Rhabdomyolysis," Am. J. Med. 119:400-409, Excerpta Medica (May 2006).

Apriletti, J.W., et al., "Molecular and Structural Biology of Thyroid Hormone Receptors," Clin. Exp. Pharmacol. Physiol. 25:S2-SI 1, Blackwell Science Asia (1998).

Archer, S.J., et al., "Hepatitis C Virus NS3 Protease Requires Its NS4A Cofactor Peptide for Optimal Binding of a Boronic Acid Inhibitor as Shown by NMR," Chem. Biol. 9:79-92, Elsevier Science Ltd (Jan. 2002).

Arnold, S., et al., "3,5-Diiodothyronine binds to subunit Va of cytochrome-c oxidase and abolishes the allosteric inhibition of respiration by ATP," Eur. J. Biochem. 252:325-330, Blackwell Science Ltd (1998).

Arnold, L.A., et al., "Discovery of Small Molecule Inhibitors of the Interaction of the Thyroid Hormone Receptor with Transciptional Coregulators," J. Biol. Chem. 280:43048-43055, American Society for Biochemistry and Molecular Biology (Dec. 2005).

Asahara, Solvent Handbook, with English translation, pp. 47-51 (1985).

Auerbach, B.J., et al., "Comparative Effects of HMG-CoA reductase inhibitors on apo B production in the casein-fed rabbit: Atorvastatin versus Lovastatin," Atherosclerosis 115:173-180, Elsevier Science Ltd (1995).

Auberson, Y.P., et al., "N-Phosphonoalkyl-5-Aminomethylquinoxaline-2,3- Diones: In Vivo Active AMPA and NMDA (Glycine) Antagonists," Bioorg. Med. Chem. Lett. 9:249-254, Elsevier Science Ltd (1999).

Austin, Glycogen Storage Disease, The Paitient-Parent Handbook. May 1, 2016.

Ayajiki, K., et al., "Endothelial and Neuronal Functions in Cerebral and Temporal Arteries from Monkeys Fed a High Cholesterol Diet," J. Cardiovascular Pharmacol. 40:456-466, Lippincott Williams & Wilkins (Sep. 2002).

Ayers, et al., "Thyroid hormone analogues: their role in treatment of hyperlipidemia," J. Endocrinol. Diabetes Obes 2(3): 1042. 2014.

Ayers, "Viking's VK2809: A question of safety, not efficacy", Seeking Alpha, Jan. 8, 2018, XP055945971, https://seekingalpha.com/article/4136028-vikings-vk2809-question-of-safety-not-efficacy.

Ball, S.G., et al., "3,5-Diiodo-L-thyronine (T2) has selective thyromimetic effects in vivo and in vitro," J. Mal. Endocrinol. 19:137-147, Society for Endocrinology (1997).

Baxter, J.D., et al., "Structure-Based Design and Synthesis of a Thyroid Homone Receptor (TR) Antagonist," Endocrinology 143:517-524, Endocrine Society (Feb. 2002).

Baxter, J.D., et al., "Selective activation of thyroid hormone signaling pathways by GC-1: a new approach to controlling cholesterol and body weight," Trends Endocrinol. Metab. 15:154-157, Elsevier Science Ltd (May/Jun. 2004).

Beg, M.A.A. and Clark, H.C., "Chemistry of the Trifluoromethyl Group, Part III. Phenyltrifluoromethylphospine and Related Compounds," Can. J. Chem. 39:564-570, NRC Research Press (1962).

Beg, M.A.A. and Clark, H.C., "Chemistry of the Trifluoromethyl Group, Part IV. Diphenyltrifluoromethylphophine and Complex Formation by Phenyltrifluoromethylphospines," Can. J. Chem. 40:283-288, NRC Research Press (1962).

Benayoud, F. and Hammond, G.B., "An expedient synthesis of (a,a-difluoroprop-2-ynyl) phosphonate esters," Chem. Commun. 1447-1448, Royal Society of Chemistry (1996).

Bhattacharya, "Investigation and management of the hepatic glycogen storage diseases," Transl Pediatrics, vol. 4, No. 3, Jan. 1, 2015.

Bianco, AC., et al., "Biochemistry, Cellular and Molecular Biology, and Physiolgical Roles of the Iodothyronine Selenodeiodinases," Endocrine Rev. 23:38-89, The Endocrine Society (Feb. 2002).

(56) References Cited

OTHER PUBLICATIONS

Bilger, C., et al., "A Convenient One-Pot Synthesis of Aralkyl Bromides and Iodides by Reductive Halogenation of Aromatic Carbonyl Compounds," Synthesis 902-904, Georg Thieme Verlag (1988).
Blennemann, B., et al., "Tissue-Specific Regulation of Fatty Acid Synthesis by Thyroid Hormone," Endocrinology 130:637-643, The Endocrine Society (1992).
Bobyleva, V., et al., "Decrease in mitochondrial energy coupling by thyroid hormones: a physiological effect rather than a pathological hyperthyroidism consequence," FEBS Lett. 430:409-413, Elsevier Science Ltd (1998).
Bocan, T.M.A., et al., "HMG-CoA reductase and ACAT inhibitors act synergistically to lower plasma cholesterol and limit atherosclerotic lesion development in the cholesterol-fed rabbit," Atherosclerosis 139:21-30, Elsevier Science Ltd. (1998).
Bogardus, J.B. and Higuchi, T., "Kinetics and Mechanism of Hydrolysis of Labile Quaternary Ammonium Derivatives of Tertiary Amines," J. Pharm. Sci. 71:729-735, Wiley (1982).
Bohmer, V. and Vogt, W., "7.(o-Hydroxyphenyl)methylphosphonic acids: Synthesis and Potentiometric Determination of their pKa Values," Helvetica Chimica Acta 76:139-149, Verlag Helvetica Chimica Acta (1993).
Boyd, E.A., et al., "Facile Synthesis of Functionalised Phenylphosphinic Acid Derivatives," Tetrahedron Lett. 37:1651-1654, Elsevier Science Ltd (1996).
Boyd, E.A. and Regan, AC., "Synthesis of y-Keto-substituted Phosphinic Acids from Bis(trimethylsilyl)phosponite and a,P-Unsaturated Ketones," Tetrahedron Lett. 332:813-816, Elsevier Science Ltd (1992).
Boyer et al., "Synthesis and Biological Evaluation of a Series of Liver-Selective Phosphonic Acid Thyroid Hormone Receptor Agonists and Their Prodrugs", J. Med. Chem., 51:7075-7093 (2008).
Briel, D., et al., "3-Amino-5-phenoxythiophenes: Syntheses and Structure-Function Studies of a Novel Class of Inhibitors of Cellular L-Triiodothyronine Uptake," J. Med. Chem. 42:1849-1854, American Chemical Society (1999).
Brooks, et al., "Large Animal Models and New Therapies for Glycogen Storage Disease," J Inherit Metab Dis. May 2015; 38(3): 505-509.
Brown, K., et al., "Accelerator Mass Spectrometry for Biomedical Research," Meth. Enzymol. 402:423-443, Academic Press (Nov. 2005).
Byrn et al., "Pharmaceutical solids: A strategic approach to regulatory considerations", Pharmaceutical Research, vol. 12(7):945-954, (1995).
Cabalska, et al., "Treatment with D-thyroxine of patients with glycogen storage diseases type VI and Via," Materia Medica Polona, Wydawnietwa Handlu Zagranicznego, Warsaw, PL, vol. 19, No. 4, Sep. 30, 1987.
Cable, et al., "Reduction of Hepatic Steatosis in Rats and Mice After Treatment with a Liver-Targeted Thyroid Hormone Receptor Agonist," Hepatology, 2009, vol. 49, pp. 407-417.
Caira, "Crystalline polymorphism or organic compounds", Topics in Current Chemistry, vol. 198:163-208 (1998).
Carvalho, et al., "Glycogen Storage Disease type 1a—a secondary cause for hyperlipidemia: report of five cases," Journal of Diabetes & Metabolic Disorders 2013, 12:25.
Christian, M.S. and Trenton, N.A., "Evaluation of thyroid function in neonatal and adult rats: The neglected endocrine mode of action," Pure Appl. Chem. 75:2055-2068, International Union of Pure and Applied Chemistry (Nov. 2003).
Chou, et al., "Glycogen storage disease type 1 and G6Pase-β deficiency: etiology and therapy," Nat Rev Endocrinol. Dec. 2010; 6(12): 676-688.
Cimmino, M., et al., "Demonstration of in vivo metabolic effects of 3,5-di-iodothyronine," J. Endocrinol. 149:319-325, Society for Endocrinology (1996).
Clutterbuck, P.W. and Cohen, J.B., "The Aryl and Alkyl Sulphonamides," J. Chem. Soc. 123:2507-2515, Royal Society of Chemistry (1923).
Collazo, A-M.G., et al., "Thyroid receptor ligands. Part 5: Novel bicyclic agonist ligands selective for the thyroid hormone recepter B," Bioorg. Med. Chem. Lett. 16:1240-1244, Elsevier Science Ltd. (Mar. 2006).
Columbano, A., et al., "The Thyroid Hormone Receptor—Agonist GC-1 Induces Cell Proliferation in Rat Liver and Pancreas," Endocrinology 147:3211-3218, Endocrine Society (Mar. 2006).
Connolly, et al., "Future Pharmacotherapy for Non-alcoholic Steatohepatitis (NASH): Review of Phase 2 and 3 Trials," Journal of Clinical and Translational Hepatology (2018) vol. 6, pp. 264-275. Epub Jun. 28, 2018.
Corrie, J.E.T. and Trentham, D.R., "Synthetic, Mechanistic and Photochemical Studies of Phosphate Esters of Substituted Benzoins," J. Chem. Soc. Perkin Trans. 1: 2409-2417, Chemical Society (1992).
Crimmins, M.T., et al., "Asymmetric Aldol Additions: Use of Titanium Tetrachloride and (−)-Sparteine for the Soft Enolization of N-Acyl Oxazolidinones, Oxazolidinethiones, and Thiazolidinethiones," J. Org. Chem. 66:894-902, American Chemical Society (2001).
Croxall, W.J., et al., "Organic Reactions with Boron Fluoride. XI. The Condensation of Propylene with m-andp-Hydroxybenzoic acids," J. Am. Chem. Soc. 57:1549-1551, American Chemical Society (1935).
Danzi, S., et al., "Triiodothyronine-mediated myosin heavy chain gene transcription in the heart," Am. J. Physiol. Heart Circ. Physiol. 284:H2255-H2262, The American Physiological Society (2003).
Database Beilstein, (Online), Beilstein Registry No. 7222862, 6 pages, Beilstein Institute for Organic Chemistry, Frankfurt-Main, DE.
Database Beilstein, (Online), Beilstein Registry No. 7505261, 2 pages, Beilstein Institute for Organic Chemistry, Frankfurt-Main, DE.
Database Beilstein, (Online), Beilstein Registry No. 6636402, 4 pages, Beilstein Institute for Organic Chemistry, Frankfurt-Main, DE.
Database CAplus, Chemical Abstract Service, Columbus Ohio, Enrion, M.D., et al., "Preparation of phosphonic acid-containing liver-selective thyromimetics effective against metabolic diseases," WO 2005-0512986, 16 pages (created Jun. 2005).
Davis, R. and Untch, K.G., "Direct one-step Conversion of Alcohols into Nitriles," J. Org. Chem. 46:2985-2987, American Chemical Society (1981).
Davis, P.J., et al., "Comparison of the mechanisms of nongenomic actions of thyroid hormone and steroid hormones," J. Endocrinol. Invest. 25: 377-388, Italian Society of Endocrinology (Apr. 2002).
De Brabandere, V.I., et al., "Isotope Dilution-Liquid Chromatography/Electrospray Ionization-Tandem Mass Spectrometry for the Determination of Serum Thyroxine as a Potential Reference Method," Rapid Commun. Mass Spectrometry 12:1099-1103, Wiley (1998).
De Sandro, V., et al., "Comparison of the Effects of Propylthiouracil, Amiodarone, Diphenylhydantoin, Phenobarbital, and 3-Methylcholanthrene on Hepatic and Renal T4 Metabolisn and Thyroid Gland Function in Rats," Toxicol. Appl. Pharmacol. 111:263-278, Academic Press (1991).
Demori, I., et al., "3,-5-diiodothyronine Mimics the Effect of Triiodothyronine on Insulin-like growth Factor Binding Protein-4 Expression in Cultured Rat Hepatocytes," Harm. Metab. Res. 36:679-685, Georg Thieme Verlag (Oct. 2004).
Deprele, S. and Montchamp, J.-L., "A novel and convenient preparation of hypophosphite esters," J. Organometallic Chem. 643-644:154-163, Elsevier Science Ltd (Aug. 2002).
Detoisien et al., "A rapid method for screening crystallization conditions and phases of an active pharmaceutical ingredient", Organic Process Research & Development, vol. 13:1338-1342 (2009).
Dhawan, B. and Redmore, D., "1,2-Alkanediol Bis(Dihydrogen Phosphates)," Synth. Commun. 18:327-331, Georg Thieme Verlag (1988).
Dingwall, J.G., et al., "Diethoxymethylphosphonites and Phospinates. Intermediates for the Synthesis of a,P-and y-Aminoalkylphosphonous Acids," Tetrahedron 45:3787-3808, Pergamon Press (1989).

(56) References Cited

OTHER PUBLICATIONS

DiStefano III, J.J. and Feng, D., "Comparative Aspects of the Distrubution, Metabolism, and Excretion of Six Iodothyronines in the Rat," Endocrinology 123:2514-2525, Endocrine Society (1988).
Docter, R., et al., "Inhibition of Uptake of Thyroid Hormone into Rat Hepatocytes by Preincubation with N-Bromoacety 1-3,3 ',5-Triiodothyronine," Endocrinology 123:1520-1525, The Endocrine Society (1988).
Dow, R.L., et al., "Discovery of a Novel Series of 6-Azauracil-Based Thyroid Hormone Receptor Ligands: Potent, TRP Subtype-Selective Thyromimetics," Bioorg. Med. Chem. Lett. 13:379-382, Elsevier Science Ltd (Nov. 2003).
Duntas, "Thyroid Disease and Lipids," Thyroid, vol. 12, No. 4, 2002.
Drechsler, U. and Hanack, M., "An Easy Route from Catechols to Phthalonitriles," Synlett 1207-1208, Georg Thieme Verlag (1998).
Earle, M.J., et al., "The first high yield green route to a pharmaceutical in a room temperature ionic liquid," Green Chem. 2:261-262, Royal Society of Chemistry (2000).
Ebdrup, S., et al., "Structure-activity relationship for aryl and heteroarly boronic acid inhibitors of homone-sensitive lipase," Bioorg. Med. Chem. 13:2305-2312, Elsevier Science Ltd (Jan. 2005).
Edmundson, R.S., et al., "Cyclic Organophosphorus Compounds. Part 23. Configurational Assignments in the 4-Phenyl-l , 3,2A.5-dioxaphosphorinane Series. X-Ray Molecular Structure of cis-2-Benzylamino-4-phenyl-1,3,2-dioxaphosphorinane 2-Oxide," J. Chem. Res. Synop. 5:122-123, Science Reviews, Ltd. (1989).
Edwards, M.L., et al., "Difluoromethyldiphenylphosphine oxide. A new reagent for conversion of carbonyl compounds to 1,1-difluoroolefins," Tetrahedron Lett. 31:5571-5574, Elsevier Science Ltd (1990).
Eisch, J.J., et al., "Rearrangement and Cleavage of [(Aryloxy)methyl]silanes by Organolithium Reagents: Conversion of Phenols into Benzylic alcohols," J. Org. Chem. 47:5051-5056, American Chemical Society (1982).
Ekins, R., "Validity of Analog Free Thyroxin Immunoassays" Clin. Chem. 33:2137-2152, American Association For Clinical Chemistry (1987).
Endres, et al., "D-Thyroxine Treatment in Glycogen Storage Disease Type Via," Pediatric Research, vol. 18, No. 8, Aug. 1, 1984.
Erion, M.D., et al., "Design, Synthesis, and Characterization of a Series of Cytochrome P450 3A-Activated Prodrugs (HepDirect Prodrugs) Useful for Targeting Phosph(on)ate-Based Drugs to the Liver," J. Am. Chem. Soc. 126:5154-5163, American Chemical Society (Apr. 2004).
Erion, M.D., et al., "Liver-Targeted Drug Delivery Using HepDirect Prodrugs," J. Pharmacol. Exper. Ther. 312:554-560, American Society for Pharmacology and Experimental Therapeutics (Feb. 2005).
Erion, et al., "Targeting thyroid hormone receptor-β agonists to the liver reduces cholesterol and triglycerides and improves the therapeutic index," PNAS, Sep. 25, 2007, vol. 104, No. 39.
Fabiano, E., et al., "A Simple Conversion of Alcohols into Amines," Synthesis 190-192, Georg Thieme Verlag (1987).
Faergemann, J., et al., "Dose-Response Effects of Tri-iodothyroacetic Acid (Triac) and other Thyroid Hormone Analogues on Glucocorticoid-Induced Skin Atrophy in the Haired Mouse," Acta Derm. Venereal. 82:179-183, Society for the Publication of Acta Dermato-Venereologica (Mar. 2002).
Farquhar, D., et al., "Biologically-Cleavable Phosphate Protective Groups: 4-Acyloxy-1,3,2-Dioxaphosphorinanes as Neutral Latent Precursors of Dianionic Phosphates," Tetrahedron Lett. 36:655-658, Elsevier Science Ltd. (1995).
Feinstein, S., et al., "Submitral Atheromatous Lesions in Monkey and Man", Clin. Cardiol. 6:109-115, John Wiley & Sons, Inc. (1983).
Feng, W., et al., "Hormone-Dependent Coactivator Binding to a Hydrophobic Cleft on Nuclear Receptors," Science 280:1747-1749, American Association for the Advancement of Science (1998).
Field, L.D. and Wilkinson, M.P., "A new Synthesis of 1,2-Bis(Bis(Trifluoromethyl)Phosphino)ethane," Tetrahedron Lett. 33:7601-7604, Elsevier Science Ltd (1992).
Fieser, L.F. andArdao, M.I., "Investigation of the Chemical Nature of Gonyleptidine," J. Am. Chem. Soc. 78:774-781, American Chemical Society (1956).
Fiorucci et al., "Future trends in the treament of non-alcoholic steatohepatitis", Pharmacological Research, vol. 134(17):289-298 (2018).
Fleischmann, K., et al., "Synthesis of HR 916 B: The First Technically Feasible Route to the 1-(Pivaloyloxy)ethyl Esters of Cephalosporins," Liebigs Ann. 1735-1741, Verlag Chemie (1996).
Fong, T.-L., et al., "Hyperthyroidism and Hepatic Dysfunction," J. Clin. Gastroenterol. 14:240-244, Raven Press (1992).
Freitas, F.R.S., et al., "Spared bone mass in rats treated with thyroid hormone receptor TRf3-selective compound GC-1," Am. J. Physiol. Endocrinol. Metab. 285:EI 135-EI 141, American Physiological Society (Sep. 2003).
Freitas, F.R.S., et al.,"The Thyroid Hormone Receptor f3-Specific Agonist GC-1 Selectivity Affects the Bone Development of Hypothyroid Rats," J. Bone Mineral Res. 20:294-304, American Society for Bone and Mineral Research (Nov. 2004).
Froestl, W., et al., "Phosphinic Acid Analogues of GABA. I. New Potent and Selective GABAB Agonists," J. Med. Chem. 38:3297-3312, American Chemical Society (1995).
Froestl, W., et al., "Phosphinic Acid Analogues of GABA. 2. Selective, Orally Active GABAB Antagonists," J. Med. Chem. 38:3313-3331, American Chemical Society (1995).
Fujitaki, et al., "Preclinical Pharmacokinetics of a HepDirect Prodrug of a Novel Phosphonate-Containing Thyroid Hormone Receptor Agonist," The American Society for Pharmacology and Experimental Therapeutics, vol. 36, No. 11, 2008.
Gallagher, M. J. and Honegger, H., "Organophosphorus Intermediates. VI. The Acid-Catalysed Reaction of Trialkyl Orthoformates with Phosphinic Acid," Aust. J. Chem. 33:287-294, Commonwealth Scientific And Industrial Research Organization (1980).
Garibaldi, et al. "Destrothyroxine treatment of phosphorylase-kinase deficiency glycogenosis in four boys," Helvetica Paediatrica Acta, Schwabe, Basel, CH, vol. 33, No. 4-5, Oct. 31, 1978.
Gilman, H. and Calloway, N_O_, "Super-Aromatic Properties ofFuran. II. The Friedel-Crafts Reaction," J. Am. Chem. Soc. 55:4197-4205, American Chemical Society (1933).
Goglia, F., et al., "In Vitro binding of 3,5-di-iodo-L-thyronine to rat liver mitochondria," J. Mo !. Endocrinol. 13: 275-282, Society for Endocrinology (1994).
Goglia, F., "Biological Effects of 3,5-Diiodothyronine (T2) ," Biochemistry (Moscow) 70:164-172, Pleiades Publishing, Inc. (Feb. 2005).
Goglia, F., et al., "Interaction of diiodothyronines with isolated cytochrome c oxidase," FEBS Lett. 346:295-298, Elsevier Science Ltd. (1994).
Goodrich, P., et al., "Kinetic Study of the Metal Triflate Catalyzed Benzoylation of Anisole in an Ionic Liquid," Ind. Eng. Chem. Res. 45:6640-6647, American Chemical Society (Sep. 2006).
Goswami, A., et al., "Inhibition by coumadin anticoagulants of enzymatic outer ring monodeiodination of iodothyronines," Biochem. Biophys. Res. Commun. 104:1231-1238, Academic Press (1982).
Goya, R.G., et al., "Effects of Growth Hormone and Thyroxine on Thymulin Secretion in Aging Rats," Neuroendocrinology 58:338-343, S. Karger AG, Basel (1993).
Greco, M.N., et al., "Discovery of Potent, Selective, Orally Active, Nonpeptide Inhibitors of Human Mast Cell Chymase," J. Med. Chem. 50:1727-1730, American Chemical Society (Mar. 2007).
Gregory, R.B. and Berry, M.N., "On the thyroid hormone-induced increase in respiratory capacity of isolated rat hepatocytes," Biochim. Biophys. Acta I 098:6 I- 67, Elsevier Science Ltd. (1991).
Gronemeyer, H., et al., "Principles for Modulation of the Nuclear Receptor Superfamily" Nature Reviews, Drug Discovery 3:950-964, Nature Publishing Group (Nov. 2004).
Grover, G.J., et al., "Development of the Thyroid Homone Receptor P-Subtype Agonist KB-141: A Strategy for Body Weight Reduction and Lipid Lowering with Minimal Cardiac Side Effects," Cardiovascular Drug Rev. 23:133-148, Blackwell Publishing (Nov. 2005).

(56) References Cited

OTHER PUBLICATIONS

Grover, G.J., et al., "Selective thyroid hormone receptor-P activation: A strategy for reduction of weight, cholesterol, and lipoprotein (a) with reduced cardiovascular liability," PNAS J00:I0067-I0072, National Academy of Sciences (Aug. 2003).
Grundy, et al., "Implications of Recent Clinical Trials for the National cholesterol Education Program Adult Treatment Panel III Guidelines," Circulation. 2004;110:227-239; downloaded from http://circ.ahajournals.org/.
Guernik, S., et al., "A novel system consisting of Rh-DuPHOS and ionic liquid for asymmetric hydrogenations," Chem. Commun. 2314-2315, Royal Society of Chemistry (2001).
Hadvary, P. and Weller, T., "202. Conformationally Restricted Analogs of Platelet-Activating Factor (PAP)," Helvetica ChimicaActa 69:1862-1871, Verlag Helvetica Chimica Acta (1986).
Hansen, et al., "Mouse models of nonalcoholic steaohepatitis in preclinical drug development," Drug Discovery Today, vol. 22, No. 11, Nov. 2017.
Hashimoto, A., et al., "Design and synthesis of complementing ligands for mutant thyroid hormone receptor TRP(R320H): a tailor-made approach toward the treatment of resistance to thyroid hormone," Bioorg. Med. Chem. 13:3627-3639, Elsevier Science Ltd (Jun. 2005).
Haugen, et al., "Drugs That Suppress TSH or Cause Central Hypothyroidism," Best Pract Res Clin endocrinol. Metab. Dec. 2009; 23(6): 793-800.
Hayakawa, Y., et al., "A General Approach to Nucleoside 3'- and 5'-Monophosphates," Tetrahedron Lett. 28:2259-2262, Elsevier Science Ltd. (1987).
Hedfors, A., et al., "Thyroid Receptor Ligands. 3. Design and Synthesis of 3,5-Dihalo-4-alkoxyphenylalkanoic Acids as Indirect Antagonistis of the Thyroid Hormone Receptor," J. Med. Chem. 48:3114-3117, American Chemical Society (May 2005).
Heimberg, M., et al., "Plasma Lipoproteins and Regulation of Heptic Metabolism of Fatty Acids in Altered Thyroid States," Endocrine Rev. 6:590-607, Endocrine Society (1985).
Hennemann, G., et al., "Carrier-Mediated Transport of Thyroid Hormone into Rat Hepatocytes is Rate-Limiting in Total Cellular Uptake and Metabolism," Endocrinology 119:1870-1872, Endocrine Society (1986).
Hennemann, G., "Notes on the History of Cellular Uptake and Deiodination of Thyroid Hormone," Thyroid 15:753-756, Mary Ann Liebert Publishers (Aug. 2005).
Hilfiker et al., "Polymorphism in the pharmaceutical industry", XP002528052:1-19 (2006).
Hirayama, Organic Compound Crystal Preparation Handbook—Principles and Know-How, Maruzen Co., Ltd. Jul. 25, 2008, pp. 57-84, with English translation.
Holt, "Thyroxine Therapy in Glycogen-Storage Disease," Nutrition Reviews, vol. 14, No. 7, Jul. 27, 1956.
Holy, A, "Phosphonomethoxyalkyl Analogs of Nucleotides," Curr. Pharm. Des. 9:2567-2592, Bentham Science Publishers (Dec. 2003).
Hopper et al., 1999, CAS: 130:332269.
Horst, C., et al., "3,5-Di-iodo-L-thyronine suppresses TSH in rats in vivo and in rat pituitary fragments in vitro," J. Endocrinol. 145:291-297, Society for Endocrinology (1995).
Horst, C., et al., "Rapid Stimulation of hepatic oxygen consumption by 3,5-di-iodo-L-thyronine," Biochem. J. 261:945-950, Portland Press (1989).
Howarth, J., et al., "Sodium Borohydride Reduction of Aldehydes and Ketones in the Recyclable Ionic Liquid [BMIM]PF 6," Synth. Commun. 31:2935-2938, Taylor & Francis (2001).
Huddleston, J.G., et al., "Characterization and comparison of hydrophilic and hydrophobic room temperature ionic liquids incorporating the imidazolium cation," Green Chem. 3:156-164, Royal Society of Chemistry (2001).
Hum, G., et al., "Synthesis of [Difluoro-(3-alkenylphenyl)-methyl]-phosphonic Acids on Non-crosslinked Polystyrene and Their Evaluation as Inhibitors of PTPIB," Bioorg. Med. Chem. Lett. 12:3471-3474, Elsevier Science Ltd (Aug. 2002).
Hume, J.R., et al., "Anion Transport in Heart," Physiol. Rev. 80:31-81, The American Physiological Society (2000).
Hunter, D.H., et al., "Crown ether catalysis of decarboxylation and decarbalkoxylation of j3-keto acids and malonates: a synthetic application," Can. J. Chem. 58:2271-2277, NRC Research Press (1980).
Ibrahini et al., 2000, CAS: 133:14000.
Ichikawa, K., et al., "Mechanism ofliver-selective thyromimetic activity of Sk&F L-94901: evidence for the presence of a cell-type-specific nuclear iodothyronine transport process," J Endocrinol. 165:391-397, Society for Endocrinology (2000).
Ing, H.R., "The Pharmacology of Homologous Series," Fortschritte der Arzneimittelforschung. Progress in drug research. Progres des recherches pharmaceutiques 20:306-309, Birkhauser Verlag (1964).
Iyer, S. and Liebeskind, L.S., "Regiospecific Synthesis of 2-Methoxy-3-methyl-1,4-benzoquinones fromMaleoylcobalt Complexes andAlkynes via Lewis Acid Catalysis. A Highly Convergent Route to Isoquinoline Quinones," J Am. Chem. Soc. 109:2759-2770, American Chemical Society (1987).
Jain, M.R., et al., "Dual PPARα/γ agonist saroglitazar improves liver histopathology and biochemistry in experimental NASH models", Liver International, (2018) vol. 38, pp. 1084-1094. Epub Dec. 14, 2017.
Jakobsson, T., et al., " Potential Role of Thyroid Receptor β Agonists in the Treatment of Hyperlipidemia", Drugs (2017) vol. 77, pp. 1613-1621.
Jiang et al., "Structural basis of tropifexor as a potent and selective agonist of farnesoid X receptor", Biochemical Biophysical Research Communications, vol. 534:1047-1052 (2021).
Jepson, E.M., "Thyroxine analogues as hypocholesterolemic agents," Am. Heart J 67:422-424, Mosby (1964).
Johnson, E.O., et al., "Experimentally-induced hyperthyroidism is associated with activation of the rat hypothalamic-pituitay-adrenal axis," Eur. J Endocrinol. 153:177-185, BioScientifica Ltd (Jul. 2005).
Jones, P.B. and Porter, N.A., "2-Aroylbenzoyl Serine Proteases: Photoreversible Inhibtion or Photoaffinity Labeling?," J Am. Chem. Soc. 121:2753-2761, American Chemical Society (1999).
Jorgensen, E.C., "Thyroid Hormones and Analogs. II. Structure-Activity Relationships," in: Hormonal Proteins and Peptides, Li, C.H., eds., Academic Press, New York, NY, pp. 107-204 (1978).
Jorgensen, E.C., "Thyroid Hormones and Analogs. I. Synthesis, Physical Properties and Theoretical Calculations," in: Hormonal Proteins and Peptides, Li, C.H., eds., Academic Press, New York, NY, pp. 56-105 (1978).
Jorgensen, E.C. and Murray, W.J., "Thyroxine Analogs. 22. Thyromimetic Activity of Halogen-Free Derivatives of 3,5-Dimethyl-L-Thyronine, "J Med. Chem. 17:434-439 (1974).
Kadenbach, B., et al., "Mitochondrial Energy Metabolsim is Regulated via Nuclear-Coded Subunits of Cytochrome C Oxidase," Free Radical Biol. Med. 29:211-221, Elsevier Science Ltd (2000).
Kazemifard, A.G., et al., "Identification and quantitation of sodium-thyroxine and its degradation products by LC using electrochemical and MS detection," J Pharm. Biomed. Anal. 25:697-71 I, Elsevier Science Ltd. (2001).
Kennedy, J.A., et al., "Influence oflmiprarnine on the Hypothalamic/Pituitary/Thyroid Axis of the Rat," Metabolism 46:1429-1434, W.B. Saunders (1997).
Kennedy, J.F, et al., "Isolation of thyroxine-binding globulin (TBG) by immunoadsorption chromatography: some physical and immunochemical characteristics of TBG," Clinica Chimica Acta 129:251-261, Elsevier Science Ltd (1983).
Kido et al., "Current status of hepatic glycogen storage disease in Japan: clinical manifestations, treatments and long-term outcomes," Joural of Human Genetics (2013) 58, 285-292.
Kishnani, et al., "Diagnosis and management of glycogen storage disease type I: a practice guideline of the American College of Medical Genetics and Genomics," Genetics in Medicine, submitted Aug. 12, 2014.
Knolker, H-J. and Filali, S., "Transition Metal Complexes in Organic Synthesis, Part 69. Total Synthesis of theAmaryllidaceae Alkaloids

(56) References Cited

OTHER PUBLICATIONS

Anhydrolycorinone and Hippadine Using Iron-and Palladium-Mediated Coupling Reactions," Synlett 1752-1754, Georg Thieme Verlag (Jun. 2003).
Kobayashi, H., et al., "Organization ofNucleosides Supported by Boronic-Acid-Appended Poly(L-lysine): Creation of a Novel RNA Mimic," Bull. Chem. Soc. Jpn. 74:1311-1317, The Chemical Society of Japan (2001).
Koehler, K., et al., "Thyroid Receptor Ligands. 6. A High Affinity "Direct Antagonist" Selective for the Thyroid Hormone Receptor," J. Med. Chem. 49:6635-6637, American Chemical Society (Oct. 2006).
Koerner, D., et al., "Binding of Selected Iodothyronine Analogues to Receptor Sites of Isolated Rat Hepatic Nuclei," J. Biol. Chem. 250:6417-6423, American Society for Biochemistry and Molecular Biology (1975).
Koulischer, "Glycogen-Storage Disease : A Study on the Effect of Sodium/-Thyroxine and Glucagon," AMA Journal of Diseases of Children, vol. 91, No. 2, Feb. 1, 1956.
Kowalik et al., "Thyroid hormones, thyromimetics and their metabolites in the treatment of liver disease", Frontiers in Endocrinology, vol. 9:1-11, (Jul. 10, 2018).
Krause, B.R., et al., "Opposite effects of beza:fibrate and gemfibrozil in both normal and hypertriglyceridemic rats," Atherosclerosis 127:91-101, Elsevier Science Ltd (1996).
Kvetny, J., "3,5-T2 Stimulates Oxygen Consumption, But Not Glucose Uptake in Human Mononuclear Blood Cells," Horm. Metab. Res. 24:322-325, Georg Thieme Verlag (1992).
Lacoste, AM., et al., "Research Regarding Aminoalkylphosphonic Acids. II.—Iodine Derivatives of the Phosphonic Analog of Tyrosine," Bull. Soc. Chim. Biol. 49:1827-1835, Masson Et Cie (1967).
Lacoste, A.-M., et al., "Biochemistry—Synthesis and biological properties of the phosphonic analog of thyroxine," C.R. Acad. Sci. Paris 267:1890-1892, Gauthier Villars Editeur (1968).
Lacoste, A.-M., et al., "Endrocrinology. Action of the phosphonic analog of thyroxine on post-embryonic development of the tadpole of Rana dalmatina Bon," Biol. Soc. Bordeaux 1684-1689 (1967).
Lanni, A., et al., "Specific Binding sites for 3,3'-diiodo-L-thyronine (3,3'-T2) in rat liver mitochondria," FEES Lett. 351:237-240, Elsevier Science Ltd (1994).
Lanni, A., et al., "Effect of 3,3'-di-iodothyronine and 3,5-di-iodothyronine on rat liver mitochondria," J. Endocrinol. 136:59-64, Society for Endocrinology (1993).
Lanni, A., et al., "Effect of 3,3'-diiodothyronine and 3,5-diiodothyronine on rat liver oxidative capacity," Mol. Cell. Endocrinol. 86:143-148, Elsevier Scientific Publishers Ireland (1992).
Lanni, A., et al., "Rapid stimulation in vitro ofrat liver cytochrome oxidase activity by 3,5-diiodo-I-thyronine and by 3,3'-diiodo-L-thyronine," Mol. Cell. Endocrinol. 99:89-94, Elsevier Science Ltd (1994).
Lanni, A., et al., "Expression of uncoupling protein-3 and mitochondrial activity in the transition from hypothyroid to hyperthyroid state in rat skeletal muscle," FEBS Lett. 444:250-254, Elsevier Science Ltd. (1999).
Lanni, A., et al., "Calorigenic effect of diiodothyronines in the rat," J. Physiol. 494:831-837, Blackwell Publishing (1996).
Laskorin, B.N., et al., "Preparation and Investigation of the Steric Structure of Sterically Hindered a-oxo Phosphoryl Compounds," Zhurnal Obshchei Khimii 44:1716-1720, RossiiskayaAkademiya Nauk (1974).
Lee, S.-G., et al., "Microwave-assisted Kabachnik-Fields Reaction in Ionic Liquid," Bull. Korean Chem. Soc. 23:667-668, The Korean Chemical Society (Mar. 2002).
Lee, Y.-P., et al., "Effects of Thyroid Hormones on the Guinea Pig," Endocrinology 86:241-250, The Endocrine Society (1970).
Leonard, J.L. and Rosenberg, I.N., "Iodothyronine 5'-Deiodinase from Rat Kidney: Substrate Specificity and the 5'-Deiodination of Reverse Triiodothrvonine," Endocrinolof!V 107:1376-1383, The Endocrine Society (1980).
Leonard, J.L. and Rosenberg, I.N., "Thyroxine 5'-Deiodinase Activity of Rat Kidney: Observations on Activation by Thiols and Inhibition by Propylthiouracil," Endocrinology 103:2137-2144, The Endocrine Society (1978).
Lewis, D.S., "Effects of dietary cholestrol on adipose tissue lipoprotein lipase in the baboon," Biochim. Biophys. Acta 879:44-50, Elsevier Science Ltd (1986).
Li, Y.-L., et al., "Thyroid receptor ligands. Part 4: 4'-amido bioisosteric ligands selective for the thyroid hormone receptor beta," Bioorg. Med. Chem. Lett. 16:884-886, Elsevier Science Ltd (Feb. 2006).
Lian, B., "Evaluation of the Thyroid Receptor Agonist VK2809 on Liver Disease in DIO-NASH Mice,", Hepatology, Oct. 2017, vol. 66, No. Suppl. 1, Sp. Iss. SI, p. 1038A.
Liddle, C., et al., "Separate and Interactive Regulation of Cytochrome P450 3A4 by Triiodothyronine, Dexamethasone, and Growth Hormone in Cultured Hepatocytes," J. Clin. Endocrinol. Metab. 83:2411-2416, The Endocrine Society (1998).
Lin, C.-C., et al., Pharmacokinetics of Pradefovir and PMEA in Healthy Volunteers After Oral Dosing of Pradefovir,11 J Clin. Pharmacol. 45:1250-1258, Sage Science Press (Nov. 2005).
Linsel-Nitschke, P. and Tall, AR., "HDL as a Target in the Treatment of Atherosclerotic Cardiovascular Disease," Nature Reviews, Drug Discovery 4:193-205, Nature Publishing Group (Mar. 2005).
Liotta, D., et al., "A Simple, Inexpensive Procedure for the Large-Scale Production of Alkyl Quinones," J Org. Chem. 48:2932-2933, American Chemical Society (1983).
Lombardi, A., et al., "Characterization of the binding of 3, 3'-di-iodo-L-thyronine to rate liver mitochondria," J Endocrinol. 154:119-124, Society for Endocrinology (1997).
Lombardi, A., et al., "Effect of 3,5-di-iodo-L-thyronine on the mitochondrial energy-transduction apparatus," Biochem. J 330:521-526, Portland Press (1998).
Lonsdale, et al., "Normalization of Hepatic Phosphorylase Kinase Activity and Glycogen Concentration in Glycogen Storage Diseas Type IX During Treatment with Sodium D Thyroxine," American Journal of Human Genetics; Annual Meeting of the American Society of Human Genetics, vol. 29, No. 6, Nov. 1, 1977.
Lukashev, N.V., et al., "Palladium-Catalyzed Cross-Coupling Reactions of Organocopper Derivatives of Methylphosphonic Esters and Amides with Aryl and Hetaryl Iodides," Russian J. Gen. Chem. 71:172-178, Kluwer Academic Publishers (2001).
Mackenzie, P.I., et al., "Regulation of UDP Glucuronosyltransferase Genes," Curr. Drug Metab. 4:249-257, Bentham Science Publishers (Jun. 2003).
Madrigal-Matute, et al., "Regulation of Liver Metabolism by Autophagy," Reviews in Basic and Clinical Gastroenterology and Hepatology, Gastroenterology 2016 150:328-339.
Mains, R.E. and Eipper, B.A., "Tissue Culture of Primary Rat Anterior Pituitary Cells" in Regulatory Peptides: From Molecular Biology to Function, Costa, E., Trabucchi, M., eds., Raven Press, New York City, NY, pp. 1-8 (1982).
Makinen, M.W. and Lee, C.-P., "Biochemical Studies of Skeletal Muscle Mitochondria: I. Microanalysis of Cytochrome Content, Oxidative and Phosphorylative Activities of Mammalian Skeletal Muscle Mitochondria," Arch. Biochem. Biophys. 126:75-82, Academic Press (1968).
Malevannaya, R.A., et al., "(Dialkoxyphosphinyl) Acetic Acids and Some of Their Analogs," Zhurnal Obshchei Khimii 41:1426-1434, Rossiiskaya Akademiya Nauk (1971).
Marcus et al., "Alternate-day dosing with statins", The American Journal of Medicine, vol. 126:99-104 (2013).
Marcune, B.F., et al., "Selective displacement of aryl fluorides with hydroquinone: synthesis of 4-phenoxyphenols" Tetrahedron Lett. 46:7823-7826, Elsevier Science Ltd (Nov. 2005).
Marimuthu, A., et al., "TR Surfaces and Conformations Required to Bind Nuclear Receptor Corepressor" Mal. Endocrinol. 16:271-286, The Endocrine Society (Feb. 2002).
Matsui, T., et al., "Discovery of Novel Phosphonic Acid Derivatives as New Chemical Leads for Inhibitors ofTNF-a Production," Bioorg. Med. Chem. 10:3807-3815, Elsevier Science Ltd (Aug. 2002).
McClain, R.M., "Mechanistic considerations for the relevance of animal data on thyroid neoplasia to human risk assessment," Mutation Res. 333:131-142, Elsevier Science Ltd. (1995).

(56) References Cited

OTHER PUBLICATIONS

Mertins, K., et al., "Transition-Metal-Catalyzed Benzylation of Arenes and Heteroarenes," Angew. Chem. Int. Ed. 44:238-242, Wiley-VCR Verlag GmbH & Co. (Dec. 2004).
Middleton, W.J., "New Fluorinating Reagents. Dialkylaminosulfur Fluorides," J. Org. Chem. 40:574-578, American Chemical Society (1975).
Miyahara, E.H., et al., "Thyroid hormone receptor-P-selective agonist GC-24 spares skeletal muscle type I to II fiber shift," Cell Tissue Res. 321:233-241, Springer-Verlag (Aug. 2005).
Mocchegiani, E., et al., "Neuroendocrine-thymus interactions. I. In vitro modulation of thymic factor secretion by thyroid hormones," J. Endocrinol. Invest. 13:139-147, Italian Society of Endocrinology (1990).
Moreno, M., et al., "How the thyroid controls metabolism in the rat: different roles for triiodothyronine and diiodothyronines," J. Physiol. 505:529-538, Cambridge Univ. Press (1997).
Morkin, E., et al., "Pilot Studies on the Use of 3, 5-Diiodothyropropionic Acid, a Thyroid Hormone Analog, in the Treatment of Congestive Heart Failure," Cardiology 97:218-225, S. Karger AG, Basel (Jul. 2002).
Moscioni, AD. and Gartner, L.M., "Thyroid Hormone and Hepatic UDP-Glucuronosyl Transferase Activity: Contrary Effects in Rat and Mouse," Res. Commun. Chem. Pathol. Pharmacol. 39:445-462, Pjd Publications Ltd (1983).
Murphy-Jolly, M.B., et al., "The synthesis of tris(perfluoroalkyl)phosphines," Chem. Commun. 4479-4480, Royal Society of Chemistry (Aug. 2005).
Nabeshima, T., et al., "Rate-accelerating Metal Ion Effects on Decarboxylation of a-Keto Acids by a Thiazolium Ion bearing a Metal Binding Site," J. Chem. Soc. Chem. Commun. 373-374, Royal Society of Chemistry (1991).
Ness, G.C., et al., "Effects of L-Triiodothyronine and the Thyromimetic L-94901 on Serum Lipoprotein Levels and Hepatic Low-Density Lipoprotein Receptor, 3-Hydroxy-3-methylglutaryl Coenzyme A Reductase, and Apo A-I Gene Expression," Biochem. Pharmacol. 56:121-129, Elsevier Science Ltd (1998).
Nguyen, N.-H., et al., "Hammett Analysis of Selective Thyroid Hormone Receptor Modulators Reveals Structural and Electronic Requirements for Homone Antagonists," J. Am. Chem. Soc. 127:4599-4608, American Chemical Society (Mar. 2005).
Nishinaga, et al., "Model Reactions for the Biosynthesis of Thyroxine. XII. The Nature of a Thyroxine Precursor Formed in the Synthesis of Thyroxine from Diiodotyrosine and Its Keto Acid Analog," Biochemistry 7:388-397, American Chemical Society (1968).
Nurtdinov, S.Kh., et al., "Reactions of Alkylphosphonous Dichlorides with Carboxylic Acid Chlorides," Zhurnal Obshchei Khimii 41:2486-2490, Rossiiskaya Akademiya Nauk (1971).
Ocasio, Cory A, and Scanlan, T.S., "Clinical prospects for new thyroid hormone analogues" Curr. Opin. Endocrinol. Diabetes 12:363-370, Lippincott Williams & Wilkins (Oct. 2005).
Ocasio, Cory A, and Scanlan, T.S., "Design and characterization of a thyroid hermone receptor a (TRa)-Specific Agonist," ACS Chem. Biol. 1:585-593, American Chemical Society (Oct. 2006).
O'Reilly, Ian, and Murphy, M.P., "Studies on the rapid stimulation of mitochondrial respiration by thyroid hormones." Acta Endocrinol. 127:542-546, Romanian Society for Endocrinology (1992).
O'Reilly, Ian, and Murphy, M.P., "Treatment of hypothyroid rats with T2 (3,5-di-iodo-L-thyronine) rapidly stimulates respiration in subsequently isolated mitochondria," Biochem. Soc. Trans. 20:59S, Portland Press (1991).
Osuka, A, et al., "Synthesis of Arenephosphonates by Copper(!) Iodide—Promoted Arylation of Phosphite Anions," Synthesis 69-71, George Thieme Verlag-Stuttart (1983).
Pan, S.-Y., et al., "Bifendate treatment attenuates hepatic steatosis in cholesterol/bile salt- and high-fat diet-induced hypercholesterolemia in mice," Eur. J. Pharmacol. 552:170-175 Elsevier Science Ltd (Dec. 2006).
Panne, P., et al., "Cyanide initiated perfluoroorganylations with perfluoroorgano silicon comoounds" J. Fluorine Chem. 112:283-286 Elsevier Science Ltd (2001).
Petervari, E., et al., "Hyperphagia of hyperthyroidism: Is neuropeptide Y involved?" Regulatory Peptides 131:103-110, Elsevier Science Ltd (Nov. 2005).
Prashad, M., "Phosphonate vs. Phosphinate Elimination during Olefination of Aldehydes," Tetrahedron Lett. 34:1585-1588, Elsevier Science Ltd (1993).
Psarra, A.-M.G., et al., "The mitochondrion as a primary site of action of steroid and thyroid hormones: Presence and action of steroid and thyroid hormone receptors in mitochondria of animal cells." Mo !. Cell. Endocrinol. 246:21-33, Elsevier Science Ltd (Feb. 2006).
PubChem CID 15942005, National Center for Biotechnology Information, PubChem Compound Summary for CID 15942005, Unii3Z11398fnq, https://pubchem.ncbi.nlm.nih.gov/compound/15942005, accessed Aug. 18, 2022, create date Feb. 21, 2007.
Pue, M.A., et al., "The disposition of SK&F L-94901, a selective thyromimetic in rat, dog and cynomolgus monkey," Eur. J. Drug Metab. Pharmacokinetics 14:209-219, Edition Medecine Et Hygiene (1989).
Radominska-Pandya, A., et al., "A Historical Overview of the Heterologous Expression of Mammalian UDP-Glucuronosyltransferase Isoforms Over the Past Twenty Years," Curr. Drug Metab. 6:141-160, Bentham Science Publishers Ltd. (Apr. 2005).
Rai, R., and Katzenellenbogen, J.A., "Effect of Conformational Mobility and Hydrogen-Bonding Interactions on the Selectivity of Some Guanidinoaryl-Substituted Mechanism-Based Inhibitors of Trypsin-like Serine Proteases," J. Med. Chem. 35:4297-4305, American Chemical Society (1992).
Raparti et al., "Selective thyroid hormone receptor modulators," Indian J. Endocrinol. Metab. Mar.-Apr. 2013; 17(2): 211-218.
Rashid, S., et al., "Effect of Atorvastatin on High-Density Lipoprotein Apolipoprotein A-I Production and Clearance in the New Zealand White Rabbit," Circulation 106:2955-2960, Lippincott Williams & Wilkins (Dec. 2002.
Razumov, A.I. and Gazizov, M.B., "Reactivity of Organophosphorus Carbonyl—Containing Compounds IV. Synthesis, Properties, and Structure of Acylphosphinic Esters," Zhurnal Obshchei Khimii 37:2738-2742, Rossiiskaya Akademiya Nauk (1967).
Reiter et al. {Phosphinic acid-based MMP-13 inhibitors that spare MMP-1 and MMP-3, Bioorganic & Medicinal Chemistry Letters (2003), 13(14), 2331-2336.
Ren, S.G., et al., "Dose-Response Relationship Between Thyroid Hormone and Growth Velocity in Cynomolgus Monkeys," J. Clin. Endocrinol. Metab. 66:1010-1013, The Endocrine Society (1988).
REUTERS Market News, "BRIEF-Viking Therapeutics says statistically significant reductions in fibrosis, liver collage, after 8 weeks of VK2809 treatment," [retrieved from Internet on Jul. 28, 2018] <URL: https://www.reuters.com/article/brief-viking-therapeutics-says-statistic/brief-viking-therapeutics-says-statistically-significant-reductions-in-fibrosis-liver-collagen-after-8-weeks-of-vk2809-treatment-idUSFWN1J308Y> Published online Jun. 6, 2017.
Ribeiro, R.C.J., et al., "X-ray Crystallographic and Functional Studies of Thyroid Hormone Receptor," J. Steroid Biochem. Molec. Biol. 65:133-141, Pergamon Press (1998).
Rooda, S.J.E., et al., "Metabolism of Triiodothyronine in Rat Hepatocytes," Endocrinology 125:2187-2197, The Endocrine Society (1989).
Ross, J. and Xiao, J., "Friedel-Crafts acylation reactions using metal triflates in ionic liquid," Green Chem. 4:129-133, Royal Society of Chemistry (Feb. 2002).
Ruhlandt-Senge, K. and Englich, U., "Synthesis and characterization of the first discrete potassium thiolates displaying three different coordination spheres at potassium in one molecule," Chem. Commun. 147-148, Royal Society of Chemistry (1996).
Ryono et al. CAS: 141:395288.
Ryono et al., 2004, CAS: 927006.
Saitoh, H. and Aungst, B.J., "Improvement of the Intestinal Absorption of a Peptidomimetic, Boronic Acid Thrombin Inhibitor Possibly Utilizing the Oligopeptide Transporter," Pharm. Res. 16:1786-1789, Plenum Publishing Corporation (1999).

(56) References Cited

OTHER PUBLICATIONS

Sakamoto, T., et al., "Cross-Coupling of N-Heteroaryl Halides with Active Methylene Compounds in the Presence of Tetrakis(triphenylphosphine)palladium," Chem. Pharm. Bull. 36:1664-1668, Pharmaceutical Society of Japan (1988).
Sakamoto, T., et al., "Palladium-Catalyzed Condensation of Aryl Halides with Phenylsulfonylacetonitrile and Diethyl Cyanomethylphosphonate," Chem. Pharm. Bull. 38:1513-1517, Pharmaceutical Society of Japan (1990).
Samuels, H.H., et al., "Depletion ofL-3,5,3'-Triiodothyronine and L-Thyroxine in Euthyroid Calf Serum for Use in Cell Culture Studies of the Action of Thyroid Hormone," Endocrinolof!V 105:80-85, The Endocrine Society (1979).
Sano, M. and Yamatera, H., "Potential Energy Surface of [Cu(H2o)6]2+ and [Zn(H20)6] 2+ Derived From Ab Initio MO Calculations," Chem. Lett. 1495-1496, The Chemical Society of Japan (1980).
Sass, D.A., et al., "Nonalcoholic Fatty Liver Disease: A Clinical Review," Dig. Dis. Sci. 50:171-180, Springer Science Business Media, Inc. (Jan. 2005).
Saulnier, M.G., et al., "Microwave-assisted synthesis of primary amine HX salts from halides and 7M ammonia in methanol," Tetrahedron Lett. 45:397-399, Elsevier Science Ltd. (Jan. 2004).
Schlosser, M. and Geneste, H., "The Organometallic Route to Benzylamine Type Monoamine Oxidase Inhibitors," Tetrahedron 54:10119-10124, Pergamon Press (1998).
Schmitt, L., et al., "Synthesis of Arylalkylmonofluorophosphonates as Myo-Inositol monophosphatase Ligands," Tetrahedron Lett. 39:4009-4012, Elsevier Science Ltd. (1998).
Schroder-van der Elst, J.P., et al., "Effects of 5,5'-diphenylhydantoin on the thyroid status in rats," Eur. J. Endocrinol. 134:221-224, BioScientifica Ltd (1996).
Selenkow, H.A. and Asper, Jr., S.P., "Biological Activity of Compounds Structurally Related to Thyroxine," Physiol. Rev. 35:426-474, American Physiological Society (1955).
Shi, Y., et al., "Mutant-Selective Thyromimetics for the Chemical Rescue of Thyroid Hormone Receptor Mutants Associated with Resistance to Thyroid Hormone," Biochemistry 44:4612-4626, American Chemical Society (Mar. 2005).
Smith, C.L. and O'Malley, B.W., "Coregulator Function: A Key to Understanding Tissue Specificity of Selective Receptor Modulators," Endocrine Rev. 25:45-71, The Endocrine Society (Feb. 2004).
Soldin, SJ., et al., "The measurement of free thyroxine by isotope dilution tandem mass spectrometry," Clinica Chimica Acta 358:113-118, Elsevier Science Ltd (Aug. 2005).
Song, K., et al., "Induction of angiotensin converting enzyme and angiotensin II receptors in the atherosclerotic aorta of high-cholesterol fed Cynomolgus monkeys," Atherosclerosis 138:171-182, Elsevier Science Ltd (1998).
Stanton, J.L., et al., "Synthesis and Biological Activity of Phenoxyphenyl Oxamic Acid Derivatives Related to L-Thyronine," Bioorg. Med. Chem. Lett. 10:1661-1663, Elsevier Science Ltd (2000).
Sterling, K. and Brenner, M.A., "Thyroid Hormone Action: Effect of Triiodothyronine on Mitochondrial Adenine Nucleotide Translocase In Vivo and In Vitro," Metabolism 44:193-199, W.B. Saunders (1995).
Tacke, et al., "An update on the recent advances in antifibrotic therapy," Expert Review of Gastroenterology & Hepatology (2018) vol. 12(11), pp. 1143-1152. Epub Oct. 3, 2018.
Tai, S.S.-C., et al., "Candidate Reference Method for Total Thyroxine in Human Serum: Use of Isotope-Dilution Liquid Chromatography-Mass Spectrometry with Electrospray Ionizaton," Clin. Chem. 48:637-642, American Association For Clinical Chemistry (Jan. 2002).
Takayama, S., et al., "Antithyroid Effects of Propylthiouracil and Sulfamonomethoxine in Rats and Monkeys," Toxicol. Applied Pharmacol. 82:191-199, Academic Press (1986).
Tal, D.M. and Karlish, S.J.D., "Synthesis of a Novel Series of ArylmethylisothiouroniumDerivatives," Tetrahedron 51:3823-3830, Pergamon Press (1995).
Taylor, A.H., et al., "Beneficial Effects of a Novel Thyromimetic on Lipoprotein Metabolism," Mo !. Pharmacol. 52:542-547, American Society for Pharmacology and Experimental Therapeutics (1997).
Taylor, S.D., et al., "Synthesis of Aryl(DifluoromethylenePhosphonates) via Electrophilic Fluorination of a-Carbanions ofBenzylic Phosphonates with N-Fluorobenzenesulfonimide," Tetrahedron 54:1691-1714, Pergamon Press (1998).
Thienpont, L.M., et al., "Isotope Dilution-Gas Chromatography/ Mass Spectrometry and Liquid Chromatography/Electrospray Ionization-Tandem Mass Spectrometry for the Determination of Triiodo-L-Thyronine in Serum," Rapid Commun. Mass Spectrometry 13:1924-1931, John Wiley & Sons, Ltd (1999).
Thornber, C.W., "Isosterismand Molecular Modification in Drug Design," Chem. Soc. Rev. 8:563-580, Chemical Society (1979).
Togashi, M., et al., "Conformational adaptation of nuclear receptor ligand binding domains to agonists: Potential for novel approaches to ligand design," J. Steroid Biochem. Mo !. Biol. 93:127-137, Elsevier Science Ltd (Feb. 2005).
Tomilov, AP., et al., "Electrochemical synthesis of diethyl fluoromethanephosphonate," J. Fluorine Chem. 82:39-41, Elsevier Science Ltd. (1997).
Toussaint, 0., et al., "The Copper(I)-Catalyzed Decarboxylation of Malonic Acids: AN ew Mild and Quantitative Method," Synthesis 1029-1031, Georg Thieme Verlag (1986).
Trost, S.U., et al., "The Thyroid Hormone Receptor-13-Selective Agonist GC-1 Differentially Afftects Plasma Lipids and Cardiac Activity," Endocrinology 141:3057-3064, The Endocrine Society (2000).
Tsuchimoto, T., et al., "Scandium(III) Triflate Catalyzed Friedel-Crafts Alkylation Reactions," J. Org. Chem. 62:6997-7005, American Chemical Society (1997).
Tully et al., "Discovery of Tropifexor (LJN452), a highly potent non-bile acid FXR agonist for the treatment of cholestatic liver deseases and nonalcoholic steatohepatitis (NASH)", J. Med. Chem. vol. 60:9960-9973 (2017).
Tyree, E.B., et al., "Effect of L-Triiodothyronine on Radiation-Induced Pulmonary Fibrosis in Dogs", Radiation Research (1966) vol. 28, pp. 30-36.
Underwood, A.H., et al., "A thyromimetic that decreases plasma cholesterol levels without increasing cardiac activity," Nature 324:425-429, Nature Publishing Group (1986).
Van Rompaey, K., et al., "A versatile synthesis of 2-substituted 4-amino-1,2,4,5-tetrahydro-2-benzazepine-3-ones," Tetrahedron 59:4421-4432, Pergamon Press (Apr. 2003).
Vaughan, M.K., et al., "Chronic Exposure to Short Photoperiod Inhibits Free Thyroxine Index and Plasma Levels of TSH, T4, Triiodothyronine (T3) and Cholesterol in Female Syrian Hamsters," Comp. Biochem. Physiol. 7JA:615-618, Pergamon Press Ltd (1982).
Veer, G.V.D.S., et al., "Temperature Effects on Free-Thyroxine Measurements: Analytical and Clinical Consequences," Clin. Chem. 38:1327-1331, American Association For Clinical Chemistry (1992).
Verd, J.C., et al., "Different effect of simvastatin and atorvastatin on key enzymes :involved in VLDL synthesis and catabolismin high fat/cholestrol fed rabbits," Br. J. Pharmacol. 127:1479-1485, Nature Publishing Group (1999).
Villicev, C.M., et al., "Thyroid hormone receptor -specific agonist GC-1 increases energy expenditure and prevents fat-mass accumulation in rats," J. Endocrinol. 193:21-29, Society for Endocrinology (Jan. 2007).
Visser, T.J., et al., "Deiodination of Thyroid Hormone by Human Liver," J. Clin. Endocrinol. Metab. 67:17-24, The Endocrine Society (1988).
Walker, D.M., et al., "Design and Synthesis of y-Oxygenated Phosphinothricins as Inhibitors of Gluamine Synthetase," J. Chem. Soc. Perkin Trans. 1 659-666, Royal Society of Chemistry (1990).
Wang, B., et al., "Effects of triiodo-thyronine on angiotensin-induced cardiomyocyte hypertrophy: reversal of increased-myosin heavy chain gene expression," Can. J. Physiol. Pharmacol. 84:935-941, NRC Research Press (Aug. 2006).
Wang, R., et al., "Salsalate Administration—A Potential Pharmacological Model of the Sick Euthyroid Syndrome," J. Clin. Endocrinol. Metab. 83:3095-3099, Endocrine Society (1998).

(56) References Cited

OTHER PUBLICATIONS

Waschbiisch, R., et al., "A high yield:ing synthesis of diethyl-I-fluoromethylphosphonate in pure form," C. R Acad. Sci. Paris, t. I, Serie II c 1:49-52, Elsevier Science Ltd (1998).
Wasserscheid, P. and Keim, W., "Ionic Liquids-New "Solutions" for Transition Metal Catalysis," Angew Chem. Int. Ed. 39:3772-3789, Wiley-VCR Verlag GmbH (2000).
Webb, P., et al., "Design of thyroid hormone receptor antagonists from first principles," J. Steroid Biochem. Mo !. Biol. 83:59-73, Elsevier Science Ltd (Dec. 2002).
Wechter, W.J., et al., "Hypocholesterolemic Agents. Thyroalkanols," J. Med. Chem. 8:474-478, American Chemical Society (1965).
Weiskirchen, "Hepatoprotective and anti-fibrotic agents: It's time to take the next step", Frountiers in Pharmacology, vol. 6(7):1-40 (2016).
Wells, P.G., et al., "Effect ofthyrotoxicosis on liver blood flow andpropranolol disposition after long-term dosing," Clin. Pharmacol. Ther. 33:603-608, Nature Publishing Group (1983).
Welton, T., "Room-Temperature Ionic Liquids. Solvents for Synthesis and Catalysis," Chem. Rev. 99:2071-2083, American Chemical Society (1999).
Wibom, R., et al., "A sensitive method for measuring ATP-formation in rat muscle mitochondria," Scand. J Clin. Lab. Invest. 50:143-152, Taylor & Francis Health Sciences (1990).
Wienand, A, et al., "Design, Synthesis and Biological Evaluation of Selective Boron-containing Thrombin Inhibitors," Bioorg. Med. Chem. 7:1295-1307, Elsevier Science Ltd. (1999).
Willnow, T.E. and Herz, J., "Animal models for disorders of hepatic lipoprotein metabolism," J Mal. Med. 73:213-220, Springer-Verlag (1995).
Winder, W.W., et al., "Effects of thyroid hormone administration on skeletal muscle mitochondria," Am. J Physiol. 228:1341-1345, American Physiological Society (1975).
Wondisford, F.E., "Unlikely partners in weight loss?," Cell Metab. 3:81-82, Cell Press (Feb. 2006).
Wu, K.-M. and Farrelly, J.G., "Preclinical Development of New Drugs that Enhance Thyroid Hormone Metabolism and Clearance: Inadequacy of Using Rats as an Animal Model for Predicting Human Risks in an IND and NDA," Am. J Therap. 13:141-144, Lippincott Williams & Wilkins (Mar./Apr. 2006).
Wu, Y., et al., "Removal of Thiazolidinethione Auxiliaries with Benzyl Alcohol Mediated by DMAP," J Org. Chem. 69:6141-6144, American Chemical Society (May 2004).
Xu, L., et al., "Heck Reaction in Ionic Liquids and the in Situ Identification of N-Heterocyclic Carbene Complexes of Palladium," Organometallics 19:1123-1127, American Chemical Society (2000).
Yang, W., et al., "Boronic Acid Compounds as Potential Pharmaceutical Agents," Med. Res. Rev. 23:346-368, Wiley Periodicals, Inc. (May 2003).
Yang, C. and Pittman, Jr., C.U., "Reductions of Organic Functional Groups Using NaBHi or NaBH,JLiCl in Diglyme at 125 to 162° C.," Synth. Commun. 28:2027-2041, Georg Thieme Verlag (1998).
Yao, et al., "Regulation of fatty acid composition and lipid storage by thyroid hormone in mouse liver," Cell & Bioscience, Biomed Central Ltd. Vo. 4, No. 1 Jul. 30, 2014.
Ye, L., et al., "Thyroid Receptor Ligands. I. Agonist Ligands Selective for the Thyroid Receptor pl," J Med. Chem. 46:1580-1588, American Chemical Society (Mar. 2003).
Yen, P.M., "Physiological and Molecular Basis of Thyroid Hormone Action," Physiol. Rev. 81:1097-1142, American Physiological Society (2001).
Yoshihara, H.A.1., et al., "Structural Determinants of Selective Thyromimetics" J. Med. Chem. 46:3152-3161, American Chemical Society (Jul. 2003).
Yoshioka, R., et al., "The Optical Resolution and Asymmetric Transformation of DL-p-Hydroxypheny!glycine with (+)-1-Phenylethanesulfonic Acid," Bull. Chem. Soc. Jpn. 60:649-652, The Chemical Society of Japan (1987).
Yu, K.-L., et al., "Concerning the Phosphorylation of Vicinal Dials," Synth. Commun. 18:465-468, Taylor & Francis, Inc. (1988).
Yu et al., "Thyroid hormone inhibits lung fibrosis in mice by improving epithelial mitochondrial function", Nature Medicine (2018) vol. 24(1), pp. 39-49. Epub Dec. 4, 2017.
Viking Therapeutics, Press releases, "Viking Therapeutics Announces Presentation of Data from In Vivo Proof-of-Concept Study of VK2809 in Glycogen Storage Disease la (GSD la) at the 13th International Congress of Inborn Errors of Metabolism (ICIEM)", [retrieved from internet on Jun. 8, 2018] <URL: http://ir.vikingtherapeutics.com/2017-09-07-Viking-Therapeutics-Announces-Presentation-of-Data-from-In-Vivo-Proof-of-Concept-Study-of-VK2809-in-Glycogen-Storage-Disease-la-GSD-la-at-the-13th-International-Congress-of-Inborn-Errors-of-Metabolism-ICIEM> published on Sep. 7, 2017.
Viking Therapeutics—News & Events, "Viking Therapeutics Presents Results from In Vivo Study of VK2809 in Biopsy—Confirmed Non-Alcoholic Steatohepatitis (NASH) at the Annual Meeting of the American Association for the Study of Liver Diseases (AASLD)", Oct. 24, 2017, San Diego <URL: http://ir.vikingtherapeutics.com/2017-10-24-Viking-Therapeutics-Presents-Results-from-In-Vivo-Study-of-VK2809-in-Biopsy-Confirmed-Non-Alcoholic-Steatohepatitis-NASH-at-the-Annual-Meeting-of-the-American-Association-for-the-Study-of-Liver-Diseases-AASLD> [retrieved from Internet on Feb. 9, 2020].
Viking Therapeutics—News & Events, "Viking Therapeutics Announces Results of Gene Expression Analysis from In Vivo Study of VK2809 in Non-Alcoholic Steatohepatitis (NASH)", Sep. 11, 2017, San Diego <URL: http://ir.vikingtherapeutics.com/2017-09-11-Viking-Therapeutics-Announces-Results-of-Gene-Expression-Analysis-from-In-Vivo-Study-of-VK2809-in-Non-Alcoholic-Steatohepatitis-NASH> [retrieved from Internet on Feb. 9, 2020].
Zalkow, L.H., et al., "Studies in the Synthesis of Camptothecin. An Efficient Synthesis of2,3-Dihydro-1H-pyrrolo[3,4-b]quinoline," J. Chem. Soc. 3551-3554, Royal Society of Chemistry (1971).
Zenker, N. and Jorgensen, E.C., "Thyroxine Analogs. I. Synthesis of 3,5-Diiodo-4-(2'-alkylphenoxy)-DL-phenylalanines," J. Am. Chem. Soc. 81:4643-4647, American Chemical Society (1959).
Zhang, N. and Casida, J.E., "Novel Irreversible Butyrylcholinesterase Inhibitors: 2-Chloro-1-(substituted-phenyl)ethylphosphonic Acids," Bioorg. Med. Chem. 10:1281-1290, Elsevier Science Ltd (Nov. 2002).
Zhang, J. and Lazar, M.A., "The Mechanism of Action of Thyroid Hormones," Annu. Rev. Physiol. 62:439-466, Annual Reviews (2000).
Zhou et al., "A liver-specific thyromimetic, VK2809, Decreases Hepatosteatosis in Glycogen Storage Disease Type 1a", Thyroid, vol. 29(8):1158-1167 (2019).
International Search Report and Written Opinion for Application No. PCT/US2021/036249, mailed on Sep. 17, 2021, in 16 pages.
International Preliminary Report on Patentability and Written Opinion for Application No. PCT/US2021/036249, dated Dec. 13, 2022, in 10 pages.
Partial Supplemental European Seach Report in European Application No. 21822855, dated Apr. 17, 2024, in 14 pages.
Hepatology, Oct. 2018, vol. 68(1) Supp. 1, p. 1448A, Abstract No. LB-4, EMBASE (online), dated searched Oct. 24, 2023, retrieved from STN, Accession No. 0053280282.
Rojkind et al., "Collagen types in normal and cirrhotic liver", vol. 76(4):710-719 (1979).
Ofosu et al., "Non-alcoholic fatty liver disease: controlling an emerging epidemic, challenges, and future directions", Annals of Gastroenterology, vol. 31:288-295 (2018).

* cited by examiner

***: p < 0.001 compared to vehicle + vehicle

***: p < 0.001 compared to vehicle + vehicle

*: $p < 0.05$ compared to vehicle + vehicle
***: $p < 0.001$ compared to vehicle + vehicle

*: $p < 0.05$ compared to vehicle + vehicle
*: $p < 0.001$ compared to vehicle + vehicle Values expressed as a mean of n = 6-10 + SEM. Dunnett's test one-factor linear model. : P < 0.01, ***: P < 0.001 compared to Vehicle + Vehicle.

Values expressed as a mean of n = 6-10 + SEM. Dunnett's test one-factor linear model. *: $P < 0.05$, ***: $P < 0.001$ compared to Vehicle + Vehicle.

Values expressed as a mean of n = 6-10 + SEM. Dunnett's test one-factor linear model. ***: P < 0.001 compared to Vehicle + Vehicle.

Values expressed as a mean of n = 6-10 + SEM. Dunnett's test one-factor linear model. ***: P < 0.001 compared to Vehicle + Vehicle.

COMPOSITIONS AND METHODS FOR THE TREATMENT OF LIVER DISORDERS

BACKGROUND

Field

The present disclosure relates generally to the field of treatments for fatty liver diseases and more specifically to the field of small molecule drugs for the treatment of non-alcoholic steatohepatitis (NASH), non-alcoholic fatty liver disease (NAFLD).

Description of the Related Art

Thyroid hormones (TH) are synthesized in the thyroid in response to thyroid stimulating hormone (TSH), which is secreted by the pituitary gland in response to various stimulants (e.g., thyrotropin-releasing hormone (TRH) from the hypothalamus). Thyroid hormones are iodinated O-aryl tyrosine analogues excreted into the circulation primarily as 3,3',5,5'-tetraiodothyronine (T4). T4 is rapidly deiodinated in local tissues by thyroxine 5'-deiodinase to 3,3',5'-triiodothyronine (T3), which is the most potent TH. T3 is metabolized to inactive metabolites via a variety of pathways, including pathways involving deiodination, glucuronidation, sulfation, deamination, and decarboxylation. Most of the circulating T4 and T3 is eliminated through the liver.

The biological activity of THs is mediated largely through thyroid hormone receptors (TRs). TRs belong to the nuclear receptor superfamily, which, along with its common partner, the retinoid X receptor, form heterodimers that act as ligand-inducible transcription factors. Like other nuclear receptors, TRs have a ligand binding domain and a DNA binding domain and regulate gene expression through ligand-dependent interactions with DNA response elements (thyroid response elements, TREs). Currently, the literature shows that TRs are encoded by two distinct genes (TRα and TRβ), which produce several isoforms through alternative splicing (Williams, *Mol. Cell. Biol.* 20(22):8329-42 (2000); Nagaya et al., *Biochem. Biophys. Res. Commun.* 226(2):426-30 (1996)). The major isoforms that have so far been identified are TRα-1, TRα-2, TRβ-1 and TRβ-2. TRα-1 is ubiquitously expressed in the rat with highest expression in skeletal muscle and brown fat. TRβ-1 is also ubiquitously expressed with highest expression in the liver, brain and kidney. TRβ-2 is expressed in the anterior pituitary gland and specific regions of the hypothalamus as well as the developing brain and inner ear. In the rat and mouse liver, TRβ-1 is the predominant isoform (80%). The TR isoforms found in human and rat are highly homologous with respect to their amino acid sequences which suggest that each serves a specialized function.

Farnesoid X receptor (FXR), also known as bile acid receptor (BAR) or NR1H4, is a transcription factor belonging to the nuclear receptor family. FXR is expressed in the liver, kidney, intestine, and adrenal cortex, as well as in heart, lung, and adipose tissue. FXR plays an important role in lipid, cholesterol, bile acid, and glucose metabolism, as well as in fibrosis and inflammation. In particular, FXR has been found to be important in regulating hepatic triglyceride levels by suppressing lipogenesis and promoting fatty acid oxidation.

Non-alcoholic fatty liver disease (NAFLD) is the hepatic manifestation of metabolic syndrome and is the most common cause of chronic liver disease. NAFLD may progress to liver inflammation, fibrosis, cirrhosis and even hepatocellular carcinoma. Hepatic expression of FXR is decreased in subjects with NAFLD. Decreased FXR expression is associated with triglyceride accumulation in the liver. Indeed, FXR deficiency animal models display hepatic steatosis, hyperlipidaemia, hyperglycemia, inflammation, and fibrosis. However, FXR activation may be able to reverse such conditions. Due to its role in metabolic processes, FXR is a potential therapeutic target for a variety of diseases and disorders, particularly those associated with the liver. Currently, FXR is used as a target for drug therapies for obesity, type II diabetes, NALFD, and even atherosclerosis. FXR agonist compounds include obeticholic acid, tropifexor, nidufexor, and fexeramine, many of which are currently being investigated for their disease-altering potential.

Therefore, a need exists for novel FXR agonists compounds that can be used to treat liver diseases and other diseases and disorders.

SUMMARY

In some embodiments, provided herein is a compound of Formula (II):

(II)

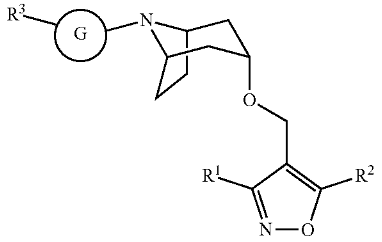

or a pharmaceutically acceptable salt thereof; wherein $R^1$ may be selected from the group consisting of: $C_{6-10}$ aryl, 5-10 membered heteroaryl, $C_{3-10}$ cycloalkyl, or 5-10 membered heterocyclyl, each of which is optionally substituted with 1-3 $R^{1A}$;

$R^2$ may be halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, or 5-10 membered heterocyclyl each of which is optionally substituted with 1-3 $R^{2A}$;

G may be selected from the group consisting of: $C_{6-10}$ aryl, 5-10 membered heteroaryl, $C_{3-10}$ cycloalkyl, or 5-10 membered heterocyclyl, each of which is optionally substituted with 1-3 $R^G$;

$R^3$ may be —P(=O)(X)(Y) or 5-10 membered heteroaryl containing 1-2 heteroatoms selected from N, O and S optionally substituted with 1-2 $R^A$ independently selected from halogen, —$OR^5$, $C_{1-6}$ alkyl, halo$C_{1-6}$ alkyl, halo$C_{1-6}$ alkoxy, or $C_{3-10}$ cycloalkyl;

each $R^{1A}$ may be independently selected from the group consisting of halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, and 5-10 membered heterocyclyl;

each $R^{2A}$ may be independently selected from the group consisting of halogen. $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, and 5-10 membered heterocyclyl;

each $R^G$ may be independently selected from the group consisting of halogen, $C_{1-6}$ alkyl, halo$C_{1-6}$ alkyl, $C_{1-6}$ alkoxy, and halo$C_{1-6}$ alkoxy;

X and Y may each be independently —$OR^4$, $NR^5R^6$, $C_{1-6}$ alkyl, or halo$C_{1-6}$ alkyl;

each $R^4$ may be independently hydrogen, $C_{1-6}$ alkyl, or halo$C_{1-6}$ alkyl;

each $R^5$ may be independently hydrogen or $C_{1-6}$ alkyl; and each $R^6$ may be independently hydrogen or $C_{1-6}$ alkyl.

In some embodiments, $R^1$ may be phenyl optionally substituted with 1-3 $R^{1A}$. In some specific embodiments, $R^1$ may be (trifluoromethoxy)phenyl. In some embodiments, $R^1$ may be pyridyl, optionally substituted with 1-3 $R^{1A}$.

In some embodiments, $R^2$ may be phenyl optionally substituted with 1-3 $R^{2A}$. In other embodiments, $R^2$ may be pyridyl optionally substituted with 1-3 $R^{2A}$. In yet other embodiments, $R^2$ may $C_{3-6}$ cycloalkyl optionally substituted with 1-2 $R^{2A}$. In some specific embodiments, $R^2$ may be cyclopropyl.

In some embodiments, G may be selected from the group consisting of: phenyl, pyridine, imidazole, pyrrole, triazole, thiazole, furanyl, pyrazine, pyrimidine, indole, quinoline, isoquinoline, benzothiazole, benzimidazole, benzoxazole, and naphthyl, each of which is optionally substituted with 1-3 $R^G$. In some embodiments, G may be benzothiazole substituted 1-3 $R^G$.

In some embodiments provided herein, the compound may be a compound having the Formula (IIa):

(IIa)

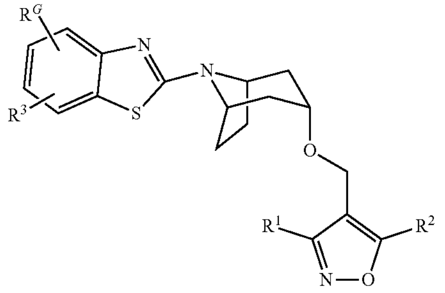

or a pharmaceutically acceptable salt thereof.

In some embodiments provided herein, the compound may be a compound having the Formula (IIaa):

(IIaa)

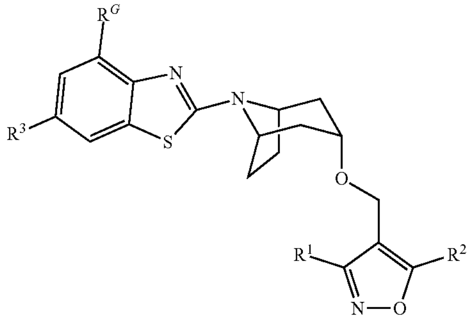

or a pharmaceutically acceptable salt thereof.

In some embodiments, $R^G$ may be halogen. In some specific embodiments, $R^G$ may be —F.

In some embodiments, $R^3$ may be —P(=O)(X)(Y). In some embodiments, X may be —$OR^4$ and $R^4$ may be hydrogen or $C_{1-6}$ alkyl. In some specific embodiments, $R^4$ may be —$CH_3$. In some embodiments, Y may be —$OR^4$ and $R^4$ may be hydrogen or $C_{1-6}$ alkyl. In some specific embodiments, $R^4$ may be —$CH_3$. In some embodiments, Y may be $C_{1-6}$ alkyl. In some embodiments, $R^3$ may be —P(=O)(X)(Y), wherein X may be $OR^4$ and Y may be $OR^4$. In some embodiments, $R^3$ may be —P(=O)(X)(Y), wherein X may be $OR^4$ and Y may be $C_{1-6}$ alkyl.

In some embodiments, $R^3$ may be -5-10 membered heteroaryl containing 1-2 heteroatoms selected from N, O and S optionally substituted with 1-2 $R^{3A}$ independently selected from halogen, —OR, $C_{1-6}$ alkyl, halo$C_{1-6}$ alkyl, $C_{1-6}$ alkoxy, halo$C_{1-6}$ alkoxy, or cyclopropyl. In some specific embodiments, $R^3$ is oxazolyl, optionally substituted with 1-2 $R^{3A}$ independently selected from the group consisting of halogen, —OR, $C_{1-6}$ alkyl, halo$C_{1-6}$ alkyl, $C_{1-6}$ alkoxy, halo$C_{1-6}$ alkoxy, or cyclopropyl.

In some embodiments, $R^3$ may be

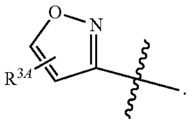

In other embodiments, $R^3$ may be

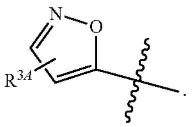

In some embodiments, $R^3$ may be

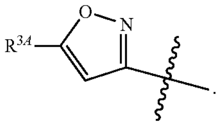

In other embodiments, $R^3$ may be

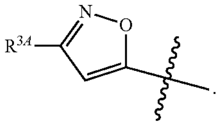

In some embodiments, $R^{3A}$ may be $C_{1-6}$ alkoxy. In other embodiments, $R^{3A}$ is hydroxy.

In some embodiments provided herein, the compound may be a compound selected from the group consisting of:

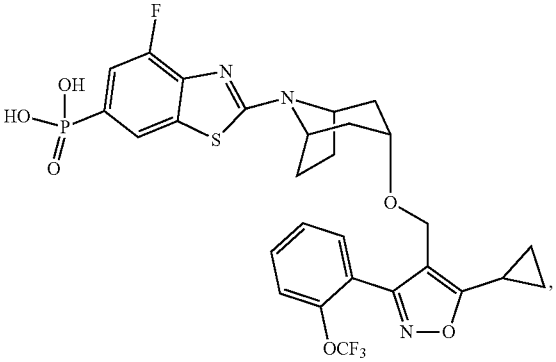
,

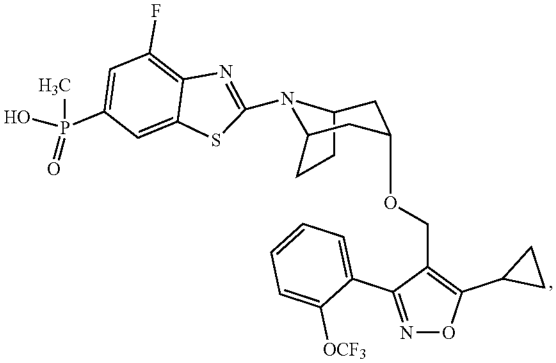
,

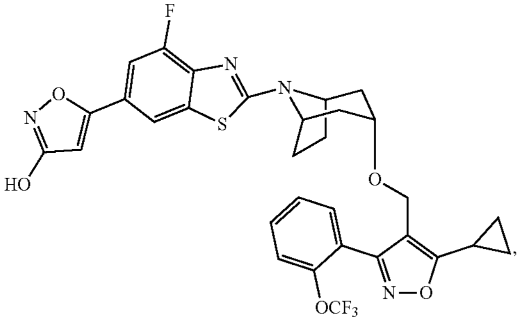
,

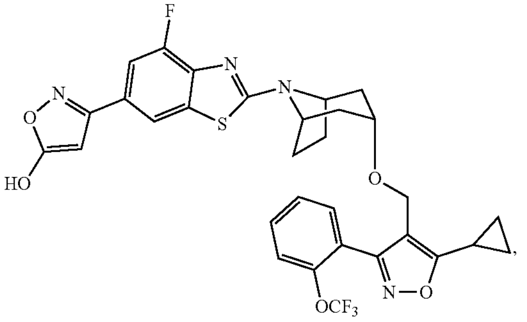
, and pharmaceutically acceptable salts thereof.

In some embodiments, provided herein are pharmaceutical compositions comprising a therapeutically effective amount of a compound of Formula (II), or a pharmaceutically acceptable salt thereof; and a pharmaceutically acceptable excipient.

In some embodiments, provided herein is a method of preventing, treating, or ameliorating one or more fatty liver diseases in a subject, comprising administering a compound of Formula (II), or a pharmaceutically acceptable salt thereof, to a subject in need thereof.

In some embodiments, the fatty liver disease may be selected from the group consisting of steatosis, non-alcoholic fatty liver disease, and non-alcoholic steatohepatitis.

In some embodiments, the administration of compounds of Formula (II) to a subject in need thereof may result in the prevention, treatment, or amelioration, of a fibrosis, fibrotic condition, or fibrotic symptoms.

In some embodiments, the administration of compounds of Formula (II) to a subject in need thereof may result in the reduction in the amount of extracellular matrix proteins present in one or more tissues of said subject.

In some embodiments, the administration of compounds of Formula (II) to a subject in need thereof may result in the reduction in the amount of collagen present in one or more tissues of said subject.

In some embodiments, the administration of compounds of Formula (II) to a subject in need thereof may result in the reduction in the amount of Type I, Type Ia, or Type III collagen present in one or more tissues of said subject.

In some embodiments, provided herein is a method of preventing, treating, or ameliorating one or more diseases or disorders in a subject, comprising administering a compound disclosed herein, or a pharmaceutically acceptable salt thereof, to a subject in need thereof. In some embodiments, the disease or disorder may be liver fibrosis, renal fibrosis, biliary fibrosis, pancreatic fibrosis, nonalcoholic steatohepatitis, non-alcoholic fatty liver disease, chronic kidney disease, diabetic kidney disease, primary sclerosing cholangitis, primary biliary cirrhosis, or idiopathic fibrosis. In some embodiments, the disease or disorder may nonalcoholic steatohepatitis, non-alcoholic fatty liver disease, chronic kidney disease, diabetic kidney disease, primary sclerosing cholangitis, or primary biliary cirrhosis.

Some embodiments disclosed herein relate to a method of preventing, treating, or ameliorating one or more diseases or disorders in a subject in need thereof comprising administering to said subject in need thereof at least one TR-β agonist compound in combination with a second pharmaceutical agent, wherein the second pharmaceutical agent is a FXR agonist. In some embodiments, the FXR agonist is a compound according to Formula (II):

(II)

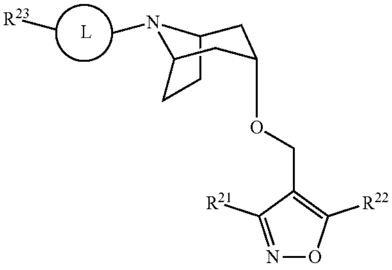

or pharmaceutically acceptable salts thereof, wherein $R^{21}$ may be selected from the group consisting of: $C_{6-10}$ aryl, 5-10 membered heteroaryl, $C_{3-10}$ cycloalkyl, or 5-10 membered heterocyclyl, each of which is optionally substituted with 1-3 $R^{21A}$;

$R^{22}$ may be halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, or 5-10 membered heterocyclyl each of which is optionally substituted with 1-3 $R^{22A}$;

L may be selected from the group consisting of: $C_{6-10}$ aryl, 5-10 membered heteroaryl, $C_{3-10}$ cycloalkyl, or 5-10 membered heterocyclyl, each of which is optionally substituted with 1-3 $R^L$;

$R^{23}$ may be —P(═O)(J)(K) or 5-10 membered heteroaryl containing 1-2 heteroatoms selected from N, O and S optionally substituted with 1-2 $R^{23A}$ independently selected from halogen, —$OR^{25}$, $C_{1-6}$ alkyl, halo$C_{1-6}$ alkyl, halo$C_{1-6}$ alkoxy, or $C_{3-10}$ cycloalkyl;

each $R^{21A}$ may be independently selected from the group consisting of halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, and 5-10 membered heterocyclyl;

each $R^{22A}$ may be independently selected from the group consisting of halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{1-6}$ cycloalkyl, and 5-10 membered heterocyclyl;

each $R^L$ may be independently selected from the group consisting of halogen, $C_{1-6}$ alkyl, halo$C_{1-6}$ alkyl, $C_{1-6}$ alkoxy, and halo$C_{1-6}$ alkoxy;

J and K may each be independently —$OR^{24}$, $NR^{25}R^{26}$, $C_{1-6}$ alkyl, or halo$C_{1-6}$ alkyl;

each $R^{24}$ may be independently hydrogen, $C_{1-6}$ alkyl, or halo$C_{1-6}$ alkyl;

each $R^{25}$ may be independently hydrogen or $C_{1-6}$ alkyl; and each $R^{26}$ may be independently hydrogen or $C_{1-6}$ alkyl.

In some embodiments, the TR-β agonist is a compound of Formula I:

(I)

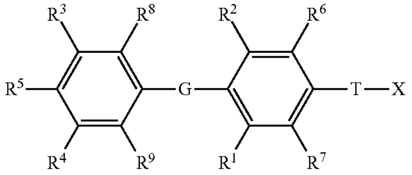

or a pharmaceutically acceptable salt thereof, wherein:

G is selected from the group consisting of —O—, —S—, —S(═O)—, —S(═O)$_2$—, —Se—, —$CH_2$—, —$CF_2$—, —CHF—, —C(O)—, —CH(OH)—, —CH($C_1$-$C_4$ alkyl)-, —CH($C_1$-$C_4$ alkoxy)-, —C(═$CH_2$)—, —NH—, and —N($C_1$-$C_4$ alkyl)-;

T is selected from the group consisting of —$(CR^a_2)_k$—, —$CR^b$═$CR^b$—$(CR^a_2)_n$—, —$(CR^a_2)_n$—$CR^b$═$CR^b$—, —$(CR^a_2)$—$CR^b$═$CR^b$—$(CR^a_2)$—, —O$(CR^b_2)(CR^a_2)_n$—, —S$(CR^b_2)(CR^a_2)_n$—, N$(R^c)(CR^b_2)(CR^a_2)_n$—, N$(R^b)$C(O)$(CR^a_2)_n$, —C(O)$(CR^a_2)_m$—, —$(CR^a_2)_m$C(O)—, —$(CR^a_2)$C(O)$(CR^a_2)_n$, —$(CR^a_2)_n$C(O)$(CR^a_2)$—, and —C(O)NH$(CR^b_2)(CR^a_2)_p$—;

k is an integer from 1-4;

m is an integer from 0-3;

n is an integer from 0-2;

p is an integer from 0-1;

each $R^a$ is independently selected from the group consisting of hydrogen, optionally substituted —$C_1$-$C_4$ alkyl, halogen, —OH, optionally substituted —O—$C_1$-$C_4$ alkyl, —$OCF_3$, optionally substituted —S—$C_1$-$C_4$ alkyl, —$NR^bR^c$, optionally substituted —$C_2$-$C_4$ alkenyl, and optionally substituted —$C_2$-$C_4$ alkynyl; with the proviso that when one $R^a$ is attached to C through an O, S, or N atom, then the other $R^a$ attached to the same C is a hydrogen, or attached via a carbon atom;

each $R^b$ is independently selected from the group consisting of hydrogen and optionally substituted —$C_1$-$C_4$ alkyl;

each $R^c$ is independently selected from the group consisting of hydrogen and optionally substituted —$C_1$-$C_4$ alkyl, optionally substituted —C(O)—$C_1$-$C_4$ alkyl, and —C(O)H;

$R^1$, and $R^2$ are each independently selected from the group consisting of halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano;

$R^6$, $R^7$, $R^8$, and $R^9$ are each independently selected from the group consisting of are each independently selected from the group consisting of hydrogen, halogen, optionally substituted —C $C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano; or $R^6$ and T are taken together along with the carbons they are attached to form a ring of 5 to 6 atoms including 0 to 2 heteroatoms independently selected from —$NR^i$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —$(CR^a_2)_2$— or —C(O)— bonded to a ring carbon or a ring nitrogen;

$R^i$ is selected from the group consisting of hydrogen, —C(O)$C_1$-$C_4$ alkyl, —$C_1$-$C_4$ alkyl, and —$C_1$-$C_4$-aryl;

$R^3$ and $R^4$ are independently selected from the group consisting of hydrogen, halogen, —$CF_3$, —$OCF_3$, cyano, optionally substituted —$C_1$-$C_{12}$ alkyl, optionally substituted —$C_2$-$C_{12}$ alkenyl, optionally substituted —$C_2$-$C_{12}$ alkynyl, —$SR^d$, —S(═O)$R^e$, —S(═O)$_2R^e$, —S(═O)$_2NR^fR^g$, —C(O)$OR^h$, —C(O)$R^e$, —N$(R^b)$C(O)$NR^fR^g$, —N$(R^b)$S(═O)$_2R^e$, —N$(R^b)$S(═O)$_2NR^fR^g$, and —$NR^fR^g$;

each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$ aryl, optionally substituted —$(CR^b_2)_n$ cycloalkyl, optionally substituted —$(CR^b_2)_n$ heterocycloalkyl, and —C(O)$NR^fR^g$;

each $R^e$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a_2)_n$ aryl, optionally substituted —$(CR^a_2)_n$ cycloalkyl, and optionally substituted —$(CR^a_2)_n$ heterocycloalkyl;

$R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$ aryl, optionally substituted —$(CR^b_2)_n$ cycloalkyl, and optionally substituted —$(CR^b_2)_n$ heterocycloalkyl, or $R^f$ and $R^g$ may together form an optionally substituted heterocyclic ring, which may contain a second heterogroup selected from the group consisting of O, $NR^C$, and S, wherein said optionally substituted heterocyclic ring may be substituted with 0-4 substituents selected from the group consisting of optionally substituted —$C_1$-$C_4$ alkyl, —$OR^b$, oxo, cyano, —$CF_3$, optionally substituted phenyl, and —C(O)$OR^h$;

each $R^h$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$ aryl, optionally substituted —$(CR^b{}_2)_n$ cycloalkyl, and optionally substituted —$(CR^b{}_2)_n$ heterocycloalkyl;

$R^5$ is selected from the group consisting of —OH, optionally substituted —$OC_1$-$C_6$ alkyl, $OC(O)R^e$, —OC(O)$OR^h$, —F, —NHC(O)$R^e$, —NHS(═O)$R^e$, —NHS(═O)$_2R^e$, —NHC(═S)NH($R^h$), and —NHC(O)NH($R^h$);

X is P(O)$YR^{11}Y'R^{11}$;

Y and Y' are each independently selected from the group consisting of —O—, and —$NR^v$—; when Y and Y' are —O—, $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^z)_2OC(O)NR^z{}_2$, —$NR^z$—C(O)—$R^y$, —$C(R^z)_2$—OC(O)$R^y$, —$C(R^z)_2$—O—C(O)$OR^y$, —$C(R^z)_2OC(O)SR^y$, -alkyl-S—C(O)$R^y$, -alkyl-S—S-alkylhydroxy, and -alkyl-S—S—S-alkylhydroxy;

when Y and Y' are —$NR^v$—, then $R^{11}$ attached to —$NR^v$— is independently selected from the group consisting of —H, —$[C(R^z)_2]_q$—$COOR^y$, —$C(R^x)_2COOR^y$, —$[C(R^z)_2]_q$—C(O)$SR^y$, and -cycloalkylene-$COOR^y$;

when Y is —O— and Y' is $NR^v$, then $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^z)_2OC(O)NR^z{}_2$, —$NR^z$—C(O)—$R^y$, —$C(R^z)_2$—OC(O)$R^y$, —$C(R^z)_2$—O—C(O)$OR^y$, —$C(R^z)_2OC(O)SR^y$, -alkyl-S—C(O)$R^y$, -alkyl-S—S-alkylhydroxy, and -alkyl-S—S—S-alkylhydroxy; and $R^{11}$ attached to —$NR^v$— is independently selected from the group consisting of H, —$[C(R^z)_2]_q$—$COOR^y$, —$C(R^x)_2COOR^y$, —$[C(R^z)_2]_q$—C(O)$SR^y$, and -cycloalkylene-$COOR^y$;

or when Y and Y' are independently selected from —O— and $NR^v$, then together $R^{11}$ and $R^{11}$ are -alkyl-S—S-alkyl- to form a cyclic group, or together $R^{11}$ and $R^{11}$ are the group:

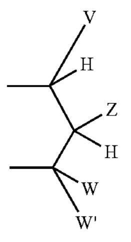

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus;

or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —$CHR_2OH$, —$CHR^zOC(O)R^y$, —$CHR^zOC(S)R^y$, —$CHR^2OC(S)OR^y$, —$CHR^zOC(O)SR^y$, —$CHR^zOCO_2R^y$, —$OR^z$, —$SR^z$, —$CHR^zN_3$, —$CH_2$-aryl, —CH(aryl)OH, —CH(CH═$CR^z{}_2$)OH, —CH(C≡$CR^z$)OH, —$R^z$, —$NR^z{}_2$—, —$OCOR^y$, —$OCO_2R^y$, —$SCOR^y$, —$SCO_2R^y$, —$NHCOR^z$, —$NHCO_2R^y$, —$CH_2$NH-aryl, —$(CH_2)_q$—$OR^z$, and —$(CH_2)_q$—$SR^z$;

q is an integer 2 or 3;

each $R^z$ is selected from the group consisting of $R^y$ and —H;

each $R^y$ is selected from the group consisting of alkyl, aryl, heterocycloalkyl, and aralkyl;

each $R^x$ is independently selected from the group consisting of —H, and alkyl, or together $R^x$ and $R^x$ form a cyclic alkyl group; and each $R^v$ is selected from the group consisting of —H, lower alkyl, acyloxyalkyl, alkoxycarbonyloxyalkyl, and lower acyl.

In some embodiments, the TR-β agonist is a compound having the structure of Formula (A)

(A)

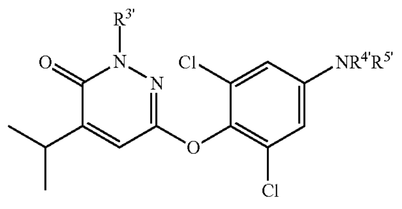

wherein $R^3$ is H or $CH_2R^{a'}$, in which $R^{a'}$ is hydroxyl, O-linked amino acid, —$OP(O)(OH)_2$ or $OC(O)R^{b'}$, $R^{b'}$ being lower alkyl, alkoxy, alkyl acid, cycloalkyl, aryl, heteroaryl, or —$(CH_2)_{n'}$-heteroaryl and n' being 0 or 1;

$R^{4'}$ is H, and $R^{5'}$ is $CH_2COOH$, $C(O)CO_2H$, or an ester or amide thereof, or $R^{4'}$ and $R^{5'}$ together are —N═C($R^{c'}$)—C—(O)—NH—C(O)—; in which $R^{c'}$ is H or cyano;

or pharmaceutically acceptable salts thereof.

In some embodiments, the TR-β agonist is

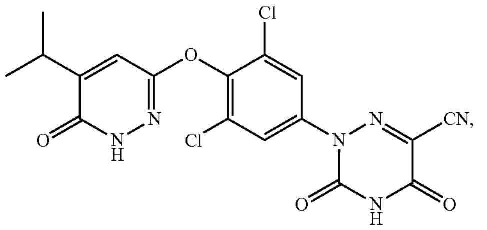 [SMILES: CC(C)c1cc(Oc2c(Cl)cc(-n3nc(C#N)c(=O)[nH]c3=O)cc2Cl)n[nH]c1=O]

or a pharmaceutically acceptable salt thereof.

In some embodiments, the FXR agonist may be a compound of Formula (II), wherein $R^{21}$ may be phenyl optionally substituted with 1-3 $R^{21A}$. In some specific embodiments, $R^{21}$ may be (trifluoromethoxy)phenyl. In some embodiments, $R^{21}$ may be pyridyl, optionally substituted with 1-3 $R^{21A}$.

In some embodiments, the FXR agonist may be a compound of Formula (II), wherein $R^{22}$ may be phenyl optionally substituted with 1-3 $R^{22A}$. In other embodiments, may be a compound of Formula (II), wherein $R^{22}$ may be pyridyl optionally substituted with 1-3 $R^{22A}$. In yet other embodiments, may be a compound of Formula (II), wherein $R^{22}$ may $C_{3-6}$ cycloalkyl optionally substituted with 1-2 $R^{22A}$. In some specific embodiments, $R^{22}$ may be cyclopropyl.

In some embodiments, the FXR agonist may be a compound of Formula (II), wherein L may be selected from the group consisting of phenyl, pyridine, imidazole, pyrrole, triazole, thiazole, furanyl, pyrazine, pyrimidine, indole, quinoline, isoquinoline, benzothiazole, benzimidazole, benzoxazole, and naphthyl, each of which is optionally substituted with 1-3 $R^L$. In some embodiments, may be benzothiazole substituted 1-3 $R^L$.

In some embodiments provided herein, the FXR agonist may be a compound having the Formula (IIa):

(IIa)

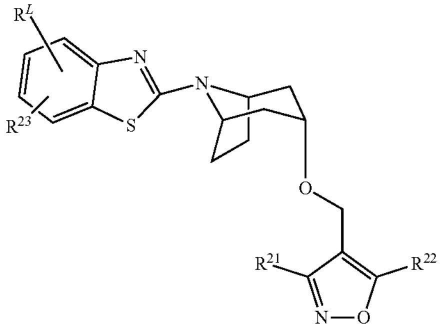

or a pharmaceutically acceptable salt thereof.

In some embodiments provided herein, the FXR agonist may be a compound having the Formula (IIaa):

(IIaa)

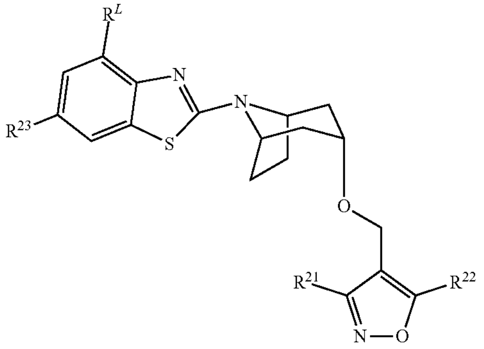

or a pharmaceutically acceptable salt thereof.

In some embodiments, the FXR agonist may be a compound of Formula (II), wherein $R^L$ may be halogen. In some specific embodiments, $R^L$ may be —F.

In some embodiments, the FXR agonist may be a compound of Formula (II), wherein $R^{23}$ may be —P(═O)(J)(K). In some embodiments, J may be —$OR^{24}$ and $R^{24}$ may be hydrogen or $C_{1-6}$ alkyl. In some specific embodiments, $R^{24}$ may be —$CH_3$. In some embodiments, K may be —$OR^{24}$ and $R^{24}$ may be hydrogen or $C_{1-6}$ alkyl. In some specific embodiments, $R^{24}$ may be $CH_3$. In some embodiments, K may be $C_{1-6}$ alkyl. In some embodiments, $R^{23}$ may be —P(═O)(J)(K), wherein J may be $OR^{24}$ and K may be $OR^{24}$. In some embodiments, $R^{23}$ may be —P(═O)(J)(K), wherein J may be $OR^{24}$ and K may be $C_{1-6}$ alkyl.

In some embodiments, the FXR agonist may be a compound of Formula (II), wherein $R^{23}$ may be -5-10 membered heteroaryl containing 1-2 heteroatoms selected from N, O and S optionally substituted with 1-2 $R^{23A}$ independently selected from halogen, —$OR^{25}$, $C_{1-6}$ alkyl, halo$C_{1-6}$ alkyl, $C_{1-6}$ alkoxy, halo$C_{1-6}$ alkoxy, or cyclopropyl. In some specific embodiments, $R^{23}$ is oxazolyl, optionally substituted with 1-2 $R^{23A}$ independently selected from the group consisting of halogen, —$OR^{23}$, $C_{1-6}$ alkyl, halo$C_{1-6}$ alkyl, $C_{1-6}$ alkoxy, halo$C_{1-6}$ alkoxy, or cyclopropyl.

In some embodiments, the FXR agonist may be a compound of Formula (II), wherein $R^{23}$ may be

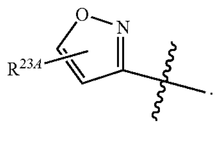

In other embodiments, $R^{23}$ may be

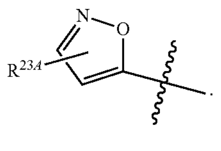

In some embodiments, the FXR agonist may be a compound of Formula (II), wherein $R^{23}$ may be

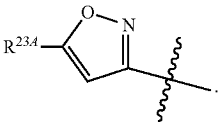

In other embodiments, $R^{23}$ may be

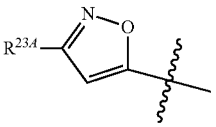

In some embodiments, $R^{23A}$ may be $C_{1-6}$ alkoxy. In other embodiments, $R^{23A}$ is hydroxy.

In some embodiments provided herein, the FXR agonist may be a compound selected from the group consisting of:

(II-1)

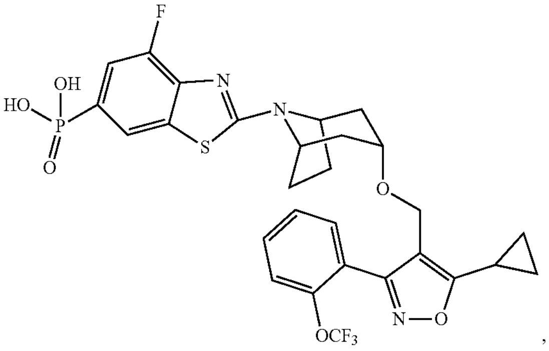

, (II-2)

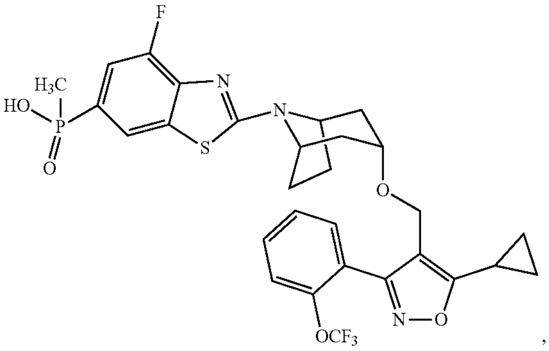

, (II-3)

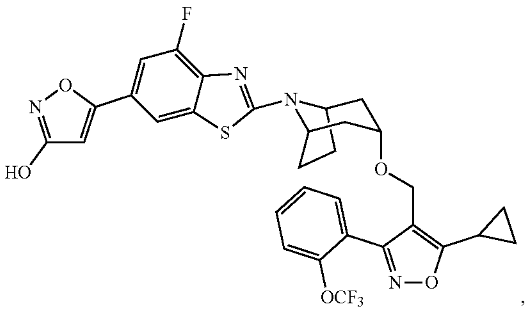

,

-continued (II-4)

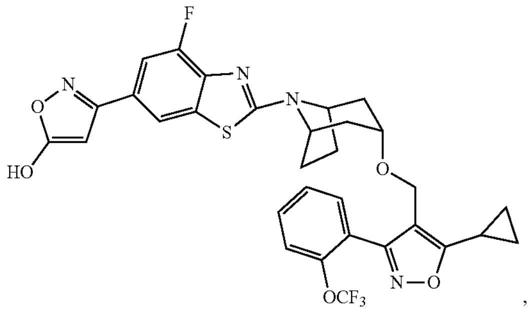

, and pharmaceutically acceptable salts thereof.

Some embodiments disclosed herein relate to a method of preventing, treating, or ameliorating one or more diseases or disorders in a subject in need thereof comprising administering to said subject in need thereof at least one compound selected from the group consisting of:

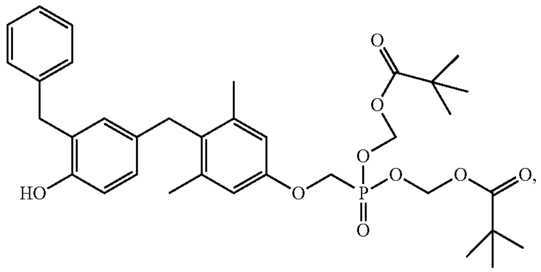

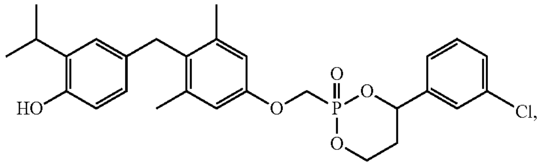

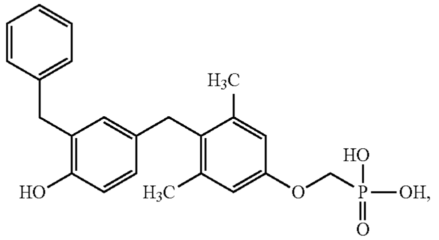

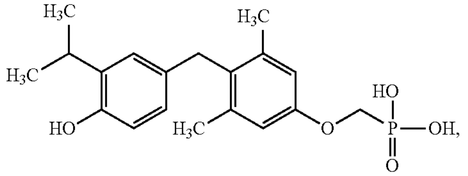

or pharmaceutically acceptable salts thereof to a subject in need thereof, in combination with a second pharmaceutical agent provided herein. In some embodiments, the second pharmaceutical agent is a compound of Formula (II), or a pharmaceutically acceptable salt thereof.

In some embodiments, the compounds and combinations provided herein may be used in a method of preventing, treating, or ameliorating one or more diseases or disorders in a subject in need thereof. In some embodiments, the disease or disorder may be a fatty liver disease. In some embodiments, the fatty liver disease can be of steatosis, non-alcoholic fatty liver disease (NAFLD), non-alcoholic steatohepatitis (NASH) and any combination of the foregoing.

In some embodiments, the compounds and combinations provided herein may be used in a method of preventing, treating, or ameliorating one or more diseases or disorders in a subject, comprising administering a compound disclosed herein, or a pharmaceutically acceptable salt thereof, to a subject in need thereof. In some embodiments, the disease or disorder may be liver fibrosis, renal fibrosis, biliary fibrosis, pancreatic fibrosis, nonalcoholic steatohepatitis, non-alcoholic fatty liver disease, chronic kidney disease, diabetic kidney disease, primary sclerosing cholangitis, primary biliary cirrhosis, or idiopathic fibrosis. In some embodiments, the disease or disorder may nonalcoholic steatohepatitis, non-alcoholic fatty liver disease, chronic kidney disease, diabetic kidney disease, primary sclerosing cholangitis, or primary biliary cirrhosis.

Some embodiments provided herein the compounds and combinations provided herein may be formulated into pharmaceutical compositions. In some embodiments, the compositions may formulated for oral, intravenous, intraarterial, intestinal, rectal, vaginal, nasal, pulmonary, topical, intradermal, transdermal, transbuccal, translingual, sublingual, or ophthalmic administration, or any combination thereof.

In some embodiments, the compounds and combinations provided herein may be administered sequentially. In some embodiments, the compounds and second pharmaceutical agents provided herein simultaneously. In some embodiments, the administration of the compounds and second pharmaceutical agents provided herein may result in the prevention, treatment, or amelioration, of a fibrosis, fibrotic condition, or fibrotic symptom in a subject. In some embodiments, the administration of the compounds and second pharmaceutical agents provided herein may result in the reduction in the amount of extracellular matrix proteins present in one or more tissues of a subject. In some embodiments, the administration of the compounds and second pharmaceutical agents provided herein may result in the reduction in the amount of collagen present in one or more tissues of a subject. In some embodiments, the administration of the compounds and second pharmaceutical agents provided herein may result in the reduction in the amount of Type I, Type Ia, or Type III collagen present in one or more tissues of the subject.

DETAILED DESCRIPTION

Figure 1:
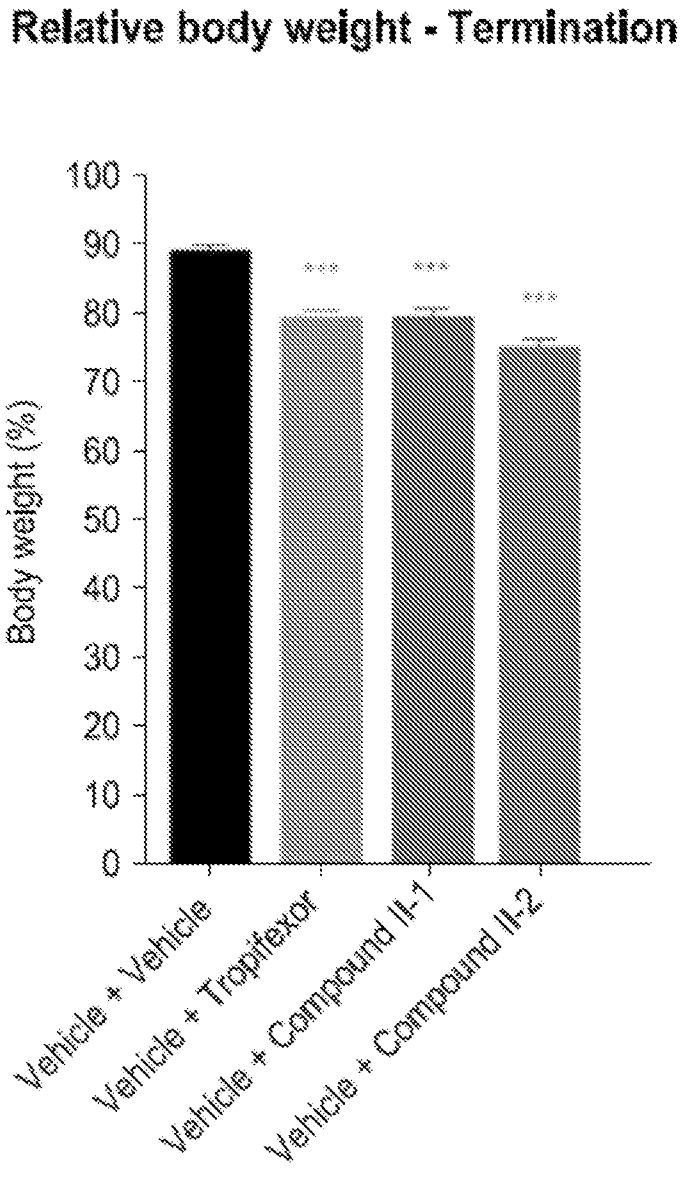
FIG. 1 shows the relative body weight of diet-induced NASH mice upon administration of vehicle, tropifexor, Compound II-1, or Compound II-2 for the duration of the 21-day study.

Fatty acids consist of an alkyl chain with a terminal carboxyl group. Unsaturated fatty acids occur commonly in humans and contain up to six double bonds per chain. Most fatty acids in humans have a length of C16, C18 or C20. Fatty acids are stored primarily as esters of glycerol. Triglycerides (TGs) are triacylglycerols, i.e., where all three hydroxyls are esterified with a fatty acid, hi addition to TGs, glycerol esterified with only one fatty acid (monoacylglycerol) or two fatty acids (diacylgycerols, DAGs) are found. The distribution of esterification sites on glycerol is influenced by many factors and may have important biological function. Fatty acids are also used in the synthesis of other molecules, e.g., esters of cholesterol which can be degraded back to the parent molecule by esterases, and various phospholipids, including lysophosphatidic acid and phosphatide acid, which consist of phosphorylated acylated glycerols. Many of these products have biological activity suggesting that modulation of their levels may result in beneficial or detrimental effects.

Fatty acids are taken up by the liver from the circulation. Fatty acids derived from the diet enter the circulation after ingestion and passage through the lymphatic system. Once in the circulation the fatty acids are taken up by tissues and used as a source of energy either immediately or in the future. If not used immediately, the fatty acids are usually converted to TGs. Subsequently, TGs are hydrolyzed to generate the free fatty acids and glycerol. Both are often transported from cells such as adipocytes, which store large quantities of TGs, to the liver. Lipolysis of TGs occurs through the action of lipases. For example, lipoprotein lipase hydrolyzes triacylglycerols in plasma lipoproteins. Another example is hormone sensitive lipase (HSL), which hydrolyzes TGs stored in the adipocyte. HSL is very sensitive to certain hormones, such as insulin which inactivates the enzyme, glucagon, epinephrine, and ACTH.

Fatty acids in the liver are also supplied by de novo synthesis from small molecule intermediates derived from metabolic breakdown of sugars, amino acids and other fatty acids. Accordingly, excess dietary protein and carbohydrate are readily converted to fatty acids and stored as TGs. A key enzyme in fatty acid synthesis is acetyl-CoA carboxylase, which controls the overall synthesis of fatty acid by controlling the synthesis of malonyl CoA from acetyl CoA. Fatty acid synthase then catalyzes the addition of two carbon units to the activated carboxyl end of a growing chain. The result is the fatty acid palmitate. Palmitate is the precursor fatty acid for nearly all other fatty acids. Enzymes are available that lead to unsaturated fatty acids or elongated fatty acids.

Fatty acids are used for energy production primarily through oxidation in mitochondria. The first step entails conversion of the fatty acid to a fatty acyl CoA by acyl-CoA synthetase. Since the oxidizing enzymes are located inside the inner mitochondrial membrane and the membrane is impermeable to CoA and its derivatives, carnitine is used along with carnitine palmitoyltransferase (CPT) to transfer acyl-CoAs into the mitochondria. This step is rate-limiting in fatty acid oxidation. Two carbon units are removed from the carboxy terminus using four enzyme-catalyzed reactions. The product is acyl-CoA which can then be used in the synthesis of fatty acids (futile cycling), ketone bodies, or enters the TCA cycle where it is converted to $CO_2$ and ATP. Some of the energy generated by fatty acid oxidation is stored as ATP, some used in the biosynthesis of other molecules, while some is lost in the form of heat. Agents that increase heat production can enable net energy expenditure.

Fat accumulation occurs when there is net energy intake relative to energy expenditure. Energy is often stored as fat, more specifically TGs. Ideally, fat is stored in the adipocyte which is its natural storage site. When in excess, however, fat is stored in other tissues, some of which can be negatively affected. Fat accumulation in the liver will depend on a multitude of factors, including fatty acid delivery from the circulation, lipogenesis (i.e., de novo lipid synthesis) in the liver, and free fatty acid oxidation.

Nonalcoholic fatty liver disease (NAFLD) is a clinicopathological term that encompasses a disease spectrum ranging from simple TG accumulation in hepatocytes to hepatic steatosis with inflammation (nonalcoholic steatohepatitis, NASH) to fibrosis and cirrhosis. NAFLD is the most frequent cause of liver enzyme elevations. The prevalence of NAFLD in the population is estimated to be 14-28%. Hepatic insulin resistance is associated with hepatic steatosis.

Products from TG metabolism, e.g., DAGs and long chain AcylCoAs (LCACoA) are thought to negatively effect insulin response through effects on the insulin receptor phosphorylation. Long chain CoAs and DAG increase Ser/Thr phosphorylation of insulin receptor substrates (IRS 1-3) and thereby disrupt Tyr phosphorylation of these substrates by the insulin receptor. The resulting hepatic insulin resistance contributes to the development of compensatory hyperinsulinemia which further drives fat accumulation via SREBPl. Reduction in TGs may reduce the levels of DAGs and LCACoAs and therefore improve the response to insulin. Improved response to insulin may also diminish further fat accumulation.

Oxidative stress results from an imbalance between prooxidant and antioxidant chemical species that leads to oxidative damage. Oxidation of fatty acids is an important source of reactive oxygen species (ROS). Some of the consequences of increased ROS is depleted ATP, destruction of membranes via lipid peroxidation, and release of proinflammatory cytokines. An increase in liver triglycerides may lead to increased oxidative stress in the hepatocytes, and the progression of hepatic steatosis to NASH. Human livers with NASH have increased lipid peroxidation and impaired mitochondrial function. This can result in cell death, hepatic stellate cell activation and fibrosis and inflammation. All of these activities may cause patients with NAFLD to be at risk for NASH, a more serious disease with higher risk of liver cirrhosis and hepatocellular carcinoma.

The present disclosure relates to compounds of Formula (II), and the use of compounds of Formula (II), in methods of decreasing fat content in the liver of an animal comprising administering to said animal a therapeutically effective amount of a compound of Formula (II), or a pharmaceutically acceptable salt thereof. The disclosure further relates to methods of preventing, treating, or ameliorating fatty liver disease in an animal comprising administering to said animal a therapeutically effective amount of a compound of Formula (II), a pharmaceutically acceptable salt thereof. The compounds of Formula (II) may be an active form or a prodrug of an active metabolite. Further included in the present disclosure is the use of pharmaceutically acceptable salts, including but not limited to acid addition salts and physiological salts, and co-crystals of said compounds of Formula (II).

The present disclosure also relates to the use of TR-β agonists in combination with one or more second pharmaceutical agents (e.g., an FXR agonist), in methods of decreasing fat content in the liver of an animal comprising administering to said animal a therapeutically effective amount of a TR-β agonist compound, a pharmaceutically acceptable salt thereof, or prodrugs thereof or pharmaceutically acceptable salts of said prodrugs, and one or more second pharmaceutical agents. The disclosure further relates to methods of preventing, treating, or ameliorating fatty liver disease in an animal comprising administering to said animal a therapeutically effective amount of a TR-β agonist compound, a pharmaceutically acceptable salt thereof, or prodrugs thereof or pharmaceutically acceptable salts of said prodrugs, and one or more second pharmaceutical agents (e.g., an FXR agonist). In some embodiments, the TR-β agonist compound is a compound of Formula I. The compounds of Formula I and/or the second pharmaceutical agent (e.g., an FXR agonist) may be an active form or a prodrug thereof. Further included in the present disclosure is the use of pharmaceutically acceptable salts, including but not limited to acid addition salts and physiological salts, and co-crystals of said compounds of Formula I and/or the second pharmaceutical agents. Further included in the present disclosure is the use of prodrugs of compounds of Formula I and/or the second pharmaceutical agents that are active forms, and pharmaceutically acceptable salts, including but not limited to acid addition salts and physiological salts, and co-crystals thereof. In some embodiments, the second pharmaceutical agent may be a compound of Formula (II).

Definitions

The term "mammal" is used in its usual biological sense. Thus, it specifically includes humans and non-human mammals such as dogs, cats, horses, donkeys, mules, cows, domestic buffaloes, camels, llamas, alpacas, bison, yaks, goats, sheep, pigs, elk, deer, domestic antelopes, and non-human primates as well as many other species.

"Subject" as used herein, means a human or a non-human mammal including but not limited to a dog, cat, horse, donkey, mule, cow, domestic buffalo, camel, llama, alpaca, bison, yak, goat, sheep, pig, elk, deer, domestic antelope, or a non-human primate selected for treatment or therapy.

"Subject in need thereof" means a subject identified as in need of a therapy or treatment.

A therapeutic effect relieves, to some extent, one or more of the symptoms of a disease or disorder, and includes curing the disease or disorder. "Curing" means that the symptoms of active disease are eliminated. However, certain long-term or permanent effects of the disease may exist even after a cure is obtained (such as extensive tissue damage).

The phrase "therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

"Treat," "treatment," or "treating," as used herein refers to administering a pharmaceutical composition for prophylactic and/or therapeutic purposes. The term "prophylactic treatment" refers to treating a patient who does not yet have the relevant disease or disorder, but who is susceptible to, or otherwise at risk of, a particular disease or disorder, whereby the treatment reduces the likelihood that the patient will develop the disease or disorder. The term "therapeutic treatment" refers to administering treatment to a patient already having a disease or disorder.

"Preventing" or "prevention" refers to delaying or forestalling the onset, development or progression of a condition or disease for a period of time, including weeks, months, or years.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Modulation" means a perturbation of function or activity. In certain embodiments, modulation means an increase in gene expression. In certain embodiments, modulation means a decrease in gene expression. In certain embodiments, modulation means an increase or decrease in total serum levels of a specific protein. In certain embodiments, modulation means an increase or decrease in free serum levels of a specific protein. In certain embodiments, modulation means an increase or decrease in total serum levels of a specific non-protein factor. In certain embodiments, modulation means an increase or decrease in free serum levels of a specific non-protein factor. In certain embodiments, modulation means an increase or decrease in total bioavailability of a specific protein. In certain embodiments, modulation means an increase or decrease in total bioavailability of a specific non-protein factor.

"Administering" means providing a pharmaceutical agent or composition to a subject, and includes, but is not limited to, administering by a medical professional and self-administering.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly. Oral and parenteral administrations are customary in treating the indications that are the subject of the preferred embodiments.

"Parenteral administration," means administration through injection or infusion. Parenteral administration includes, but is not limited to, subcutaneous administration, intravenous administration, intramuscular administration, intraarterial administration, and intracranial administration.

"Subcutaneous administration" means administration just below the skin.

"Intravenous administration" means administration into a vein.

"Intraarterial administration" means administration into an artery.

The term "agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances.

"Pharmaceutical agent" means a substance that provides a therapeutic effect when administered to a subject.

"Pharmaceutical composition" means a mixture of substances suitable for administering to an individual that includes a pharmaceutical agent. For example, a pharmaceutical composition may comprise a modified oligonucleotide and a sterile aqueous solution.

"Active pharmaceutical ingredient" means the substance in a pharmaceutical composition that provides a desired effect.

The term "pharmaceutically acceptable salt" refers to salts that retain the biological effectiveness and properties of the compounds with which they are associated and, which are not biologically or otherwise undesirable. In many cases, the compounds herein are capable of forming acid and/or base salts by virtue of the presence of phenol and/or phosphonate groups or groups similar thereto. One of ordinary skill in the art will be aware that the protonation state of any or all of these compounds may vary with pH and ionic character of the surrounding solution, and thus the present disclosure contemplates multiple charge states of each compound. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

"Solvate" refers to the compound formed by the interaction of a solvent and an EPI, a metabolite, or salt thereof. Suitable solvates are pharmaceutically acceptable solvates including hydrates.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, $R_2N$—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of the present disclosure fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, and/or pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

T groups that have more than one atom are read from left to right wherein the left atom of the T group is connected to the phenyl group bearing the $R^1$ and $R^2$ groups, and the right atom of the T group is linked to the carbon, phosphorus, or other atom in X or E. For example, when T is —O—$CH_2$— or —N(H)C(O)— it means -phenyl-O—$CH_2$—X and -phenyl-N(H)C(O)—X.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "haloalkyl" refers to a straight- or branched-chain alkyl group having from 1 to 12 carbon atoms in the chain, substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, —$CH_2CF_2CF_3$ and other groups that in light of the ordinary skill in the art and the teachings provided herein, would be considered equivalent to any one of the foregoing examples.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "polyethylene glycol" refers to the formula

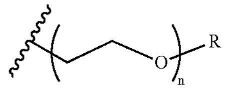

wherein n is an integer greater than one and R is a hydrogen or alkyl. The number of repeat units "n" may be indicated by referring to a number of members. Thus, for example, "2- to 5-membered polyethylene glycol" refers to n being an integer selected from two to five. In some embodiments, R is selected from methoxy, ethoxy, n-propoxy, 1-methylethoxy (isopropoxy), n-butoxy, iso-butoxy, sec-butoxy, and tert-butoxy.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. In various embodiments, the heteroalkyl may have from 1 to 4 heteroatoms, from 1 to 3 heteroatoms, 1 or 2 heteroatoms, or 1 heteroatom. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. In various embodiments, a heteroaryl contains from 1 to 4 heteroatoms, from 1 to 3 heteroatoms, from 1 to 2 heteroatoms, or 1 heteroatom. For example, in various embodiments, a heteroaryl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations.

In various embodiments, a heterocyclyl contains from 1 to 4 heteroatoms, from 1 to 3 heteroatoms, from 1 to 2 heteroatoms, or 1 heteroatom. For example, in various embodiments, a heterocyclyl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—$N(R_A)SO_2R_B$" group in which $R_A$ and $R^b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—$N(R_A)$OC(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—$N(R_A)$OC(=S)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—$N(R_A)$C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a "natural amino acid side chain" refers to the side-chain substituent of a naturally occurring amino acid. Naturally occurring amino acids have a substituent attached to the α-carbon. Naturally occurring amino acids include Arginine, Lysine, Aspartic acid, Glutamic acid, Glutamine, Asparagine, Histidine, Serine, Threonine, Tyrosine, Cysteine, Methionine, Tryptophan, Alanine, Isoleucine, Leucine, Phenylalanine, Valine, Proline, and Glycine.

As used herein, a "non-natural amino acid side chain" refers to the side-chain substituent of a non-naturally occurring amino acid. Non-natural amino acids include β-amino acids ($β^3$ and $β^2$), Homo-amino acids, Proline and Pyruvic acid derivatives, 3-substituted Alanine derivatives, Glycine derivatives, Ring-substituted Phenylalanine and Tyrosine Derivatives, Linear core amino acids and N-methyl amino acids. Exemplary non-natural amino acids are available from Sigma-Aldridge, listed under "unnatural amino acids & derivatives." See also, Travis S. Young and Peter G. Schultz, "Beyond the Canonical 20 Amino Acids: Expanding the Genetic Lexicon," J. Biol. Chem. 2010 285: 11039-11044, which is incorporated by reference in its entirety.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., $—CF_3$), halo($C_1$-$C_6$)alkoxy (e.g., $—OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (═O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $—CH_2—$, $—CH_2CH_2—$, $—CH_2CH(CH_3)CH_2—$, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

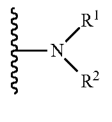

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

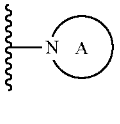

where ring A is a heterocyclyl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

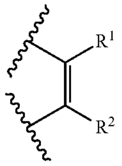

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

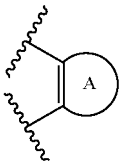

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

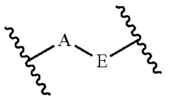

includes the substituent being oriented such that the A is attached at the leftmost attachment point of the molecule as well as the case in which A is attached at the rightmost attachment point of the molecule.

Compounds

In some embodiments, the compounds as described herein include a compound according to Formula (II):

(II)

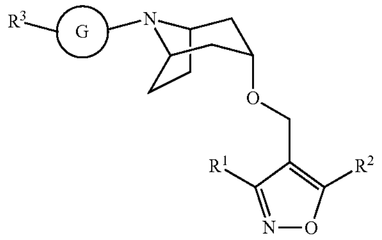

or pharmaceutically acceptable salts thereof, wherein $R^1$ may be selected from the group consisting of $C_{6-10}$ aryl, 5-10 membered heteroaryl, $C_{3-10}$ cycloalkyl, or 5-10 membered heterocyclyl, each of which is optionally substituted with 1-3 $R^{1A}$;

$R^2$ may be halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, or 5-10 membered heterocyclyl each of which is optionally substituted with 1-3 $R^{2A}$;

G may be selected from the group consisting of: $C_{6-10}$ aryl, 5-10 membered heteroaryl, $C_{3-10}$ cycloalkyl, or 5-10 membered heterocyclyl, each of which is optionally substituted with 1-3 $R^G$;

$R^3$ may be —P(═O)(X)(Y) or 5-10 membered heteroaryl containing 1-2 heteroatoms selected from N, O and S optionally substituted with 1-2 $R^A$ independently selected from halogen, —$OR^5$, $C_{1-6}$ alkyl, halo$C_{1-6}$ alkyl, halo$C_{1-6}$ alkoxy, or $C_{3-10}$ cycloalkyl;

each $R^{1A}$ may be independently selected from the group consisting of halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, and 5-10 membered heterocyclyl;

each $R^{2A}$ may be independently selected from the group consisting of halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, and 5-10 membered heterocyclyl;

each $R^G$ may be independently selected from the group consisting of halogen, $C_{1-6}$ alkyl, halo$C_{1-6}$ alkyl, $C_{1-6}$ alkoxy, and halo$C_{1-6}$ alkoxy;

X and Y may each be independently —$OR^4$, $NR^5R^6$, $C_{1-6}$ alkyl, or halo$C_{1-6}$ alkyl;

each $R^4$ may be independently hydrogen, $C_{1-6}$ alkyl, or halo$C_{1-6}$ alkyl;

each $R^5$ may be independently hydrogen or $C_{1-6}$ alkyl; and each $R^6$ may be independently hydrogen or $C_{1-6}$ alkyl.

In some embodiments, $R^1$ may be phenyl optionally substituted with 1-3 $R^{1A}$. In some specific embodiments, $R^1$ may be (trifluoromethoxy)phenyl. In some embodiments, $R^1$ may be pyridyl, optionally substituted with 1-3 $R^{1A}$.

In some embodiments, $R^2$ may be phenyl optionally substituted with 1-3 $R^{2A}$. In other embodiments, $R^2$ may be pyridyl optionally substituted with 1-3 $R^{2A}$. In yet other embodiments. $R^2$ may $C_{3-6}$ cycloalkyl optionally substituted with 1-2 $R^{2A}$. In some specific embodiments, $R^2$ may be cyclopropyl.

In some embodiments, G may be selected from the group consisting of:

phenyl, pyridine, imidazole, pyrrole, triazole, thiazole, furanyl, pyrazine, pyrimidine, indole, quinoline, isoquinoline, benzothiazole, benzimidazole, benzoxazole, and naphthyl, each of which is optionally substituted with 1-3 $R^G$. In some embodiments, G may be benzothiazole substituted 1-3 $R^G$.

In some embodiments provided herein, the compound may be a compound having the Formula (IIa):

(IIa)

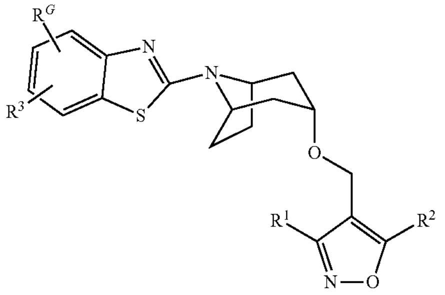

or a pharmaceutically acceptable salt thereof.

In some embodiments provided herein, the compound may be a compound having the Formula (IIaa):

(IIaa)

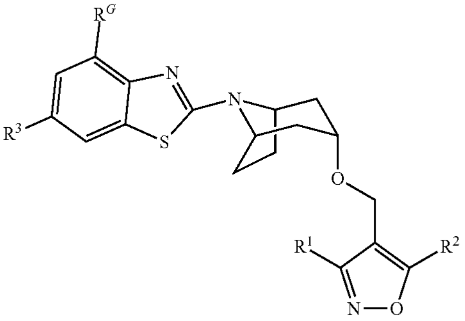

or a pharmaceutically acceptable salt thereof.

In some embodiments, $R^G$ may be halogen. In some specific embodiments, $R^G$ may be —F.

In some embodiments, $R^3$ may be —P(═O)(X)(Y). In some embodiments, X may be —$OR^4$ and $R^4$ may be hydrogen or $C_{1-6}$ alkyl. In some specific embodiments, $R^4$ may be —$CH_3$. In some embodiments, Y may be —$OR^4$ and $R^4$ may be hydrogen or $C_{1-6}$ alkyl. In some specific embodiments, $R^4$ may be —$CH_3$. In some embodiments, Y may be $C_{1-6}$ alkyl. In some embodiments, $R^3$ may be —P(═O)(X)(Y), wherein X may be $OR^4$ and Y may be $OR^4$. In some embodiments. $R^3$ may be —P(═O)(X)(Y), wherein X may be $OR^4$ and Y may be $C_{1-6}$ alkyl.

In some embodiments, $R^3$ may be -5-10 membered heteroaryl containing 1-2 heteroatoms selected from N, O and S optionally substituted with 1-2 $R^{3A}$ independently selected from halogen, —$OR^5$, $C_{1-6}$ alkyl, halo$C_{1-6}$ alkyl, $C_{1-6}$ alkoxy, halo$C_{1-6}$ alkoxy, or cyclopropyl. In some specific embodiments, $R^3$ is oxazolyl, optionally substituted with 1-2 $R^{3A}$ independently selected from the group consisting of halogen, —$OR^5$, $C_{1-6}$ alkyl, halo$C_{1-6}$ alkyl, $C_{1-6}$ alkoxy, halo$C_{1-6}$ alkoxy, or cyclopropyl.

In some embodiments, $R^3$ may be

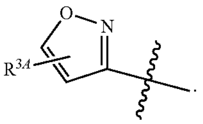

In other embodiments, $R^3$ may be

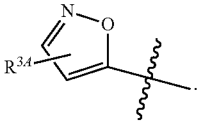

.

In some embodiments, $R^3$ may be

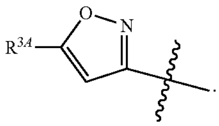

.

In other embodiments, $R^3$ may be

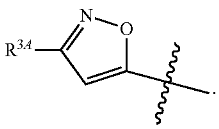

.

In some embodiments, $R^{3A}$ may be $C_{1-6}$ alkoxy. In other embodiments, $R^{3A}$ is hydroxy.

In some embodiments provided herein, the compound may be a compound selected from the group consisting of:

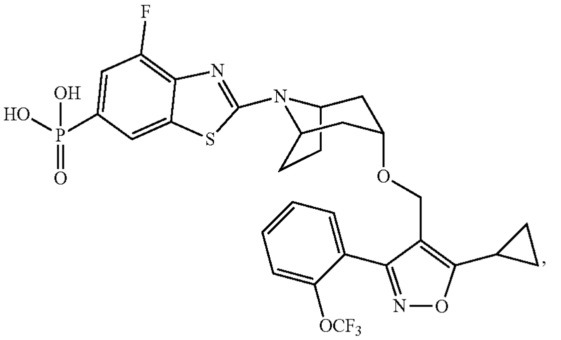

,

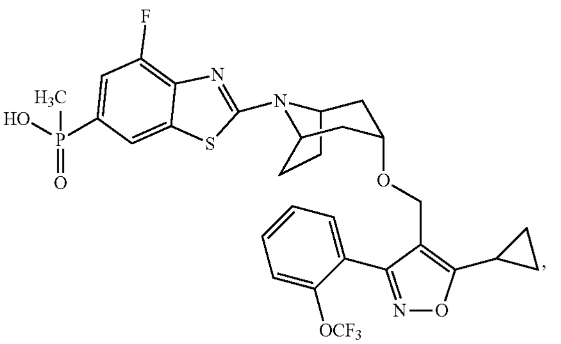

,

-continued

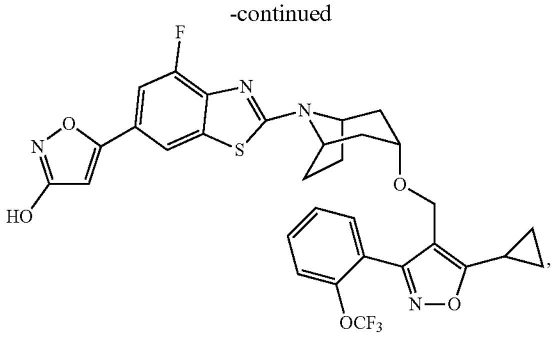

,

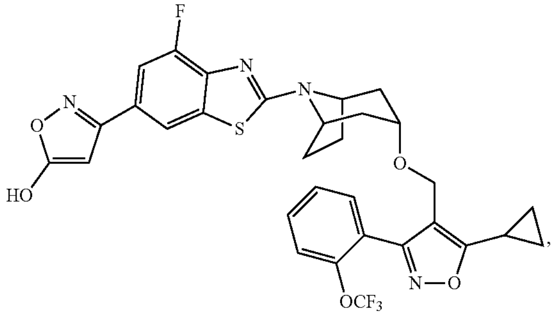

, and pharmaceutically acceptable salts thereof.

TR-β Agonist Compounds

In some embodiments, the TR-β agonist compounds for use as described herein include compounds according to Formula I:

(I)

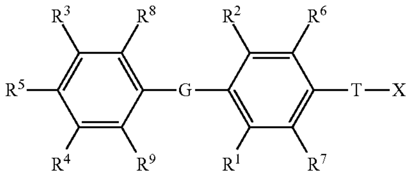

wherein:

G is selected from the group consisting of —O—, —S—, —S(═O)—, —S(═O)$_2$—, —Se—, —$CH_2$—, —$CF_2$—, —CHF—, —C(O)—, —CH(OH)—, —CH($C_1$-$C_4$ alkyl)-, —CH($C_1$-$C_4$ alkoxy)-, —C(═$CH_2$)—, —NH—, and —N($C_1$-$C_4$ alkyl)-;

T is selected from the group consisting of —$(CR^a{}_2)_k$—, —$CR^b$═$CR^b$—$(CR^a{}_2)_n$—, —$(CR^b{}_2)_n$—$CR^b$═$CR^b$—, —$(CR^a{}_2)$—$CR^b$═$CR^b$—$(CR^a{}_2)$—, —$O(CR^b{}_2)(CR^a{}_2)_n$—, —$S(CR^b{}_2)(CR^a{}_2)_n$—, $N(R^c)(CR^b{}_2)(CR^a{}_2)_n$—, $N(R^b)C(O)(CR^a{}_2)_n$, —$C(O)(CR^a{}_2)_m$—, —$(CR^a{}_2)_mC(O)$—, —$(CR^a{}_2)C(O)(CR^a{}_2)_n$, —$(CR^a{}_2)_nC(O)(CR^a{}_2)$—, and —$C(O)NH(CR^b{}_2)(CR^a{}_2)_p$—;

k is an integer from 1-4;

m is an integer from 0-3;

n is an integer from 0-2;

p is an integer from 0-1;

each $R^a$ is independently selected from the group consisting of hydrogen, optionally substituted —$C_1$-$C_4$ alkyl, halogen, —OH, optionally substituted —O—$C_1$-$C_4$ alkyl, —$OCF_3$, optionally substituted —S—$C_1$-$C_4$ alkyl, —$NR^bR^c$, optionally substituted —$C_2$-$C_4$ alkenyl, and optionally substituted —$C_2$-$C_4$ alkynyl; with the proviso that when one $R^a$ is attached to C through an O, S, or N atom, then the other $R^a$ attached to the same C is a hydrogen, or attached via a carbon atom;

each $R^b$ is independently selected from the group consisting of hydrogen and optionally substituted $-C_1$-$C_4$ alkyl;

each $R^c$ is independently selected from the group consisting of hydrogen and optionally substituted $-C_1$-$C_4$ alkyl, optionally substituted $-C(O)-C_1$-$C_4$ alkyl, and $-C(O)H$;

$R^1$, and $R^2$ are each independently selected from the group consisting of halogen, optionally substituted $-C_1$-$C_4$ alkyl, optionally substituted $-S-C_1$-$C_3$ alkyl, optionally substituted $-C_2$-$C_4$ alkenyl, optionally substituted $-C_2$-$C_4$ alkynyl, $-CF_3$, $-OCF_3$, optionally substituted-O$-C_1$-$C_3$ alkyl, and cyano;

$R^6$, $R^7$, $R^8$, and $R^9$ are each independently selected from the group consisting of are each independently selected from the group consisting of hydrogen, halogen, optionally substituted $-C$ $C_1$-$C_4$ alkyl, optionally substituted $-S-C_1$-$C_3$ alkyl, optionally substituted $-C_2$-$C_4$ alkenyl, optionally substituted $-C_2$-$C_4$ alkynyl, $-CF_3$, $-OCF_3$, optionally substituted-O$-C_1$-$C_3$ alkyl, and cyano; or $R^6$ and T are taken together along with the carbons they are attached to form a ring of 5 to 6 atoms including 0 to 2 heteroatoms independently selected from $-NR^i-$, $-O-$, and $-S-$, with the proviso that when there are 2 heteroatoms in the ring and both heteroatoms are different than nitrogen then both heteroatoms have to be separated by at least one carbon atom; and X is attached to this ring by a direct bond to a ring carbon, or by $-(CR^a{}_2)-$ or $-C(O)-$ bonded to a ring carbon or a ring nitrogen;

$R^i$ is selected from the group consisting of hydrogen, $-C(O)C_1$-$C_4$ alkyl, $-C_1$-$C_4$ alkyl, and $-C_1$-$C_4$-aryl;

$R^3$ and $R^4$ are independently selected from the group consisting of hydrogen, halogen, $-CF_3$, $-OCF_3$, cyano, optionally substituted $-C_1$-$C_{12}$ alkyl, optionally substituted $-C_2$-$C_{12}$ alkenyl, optionally substituted $-C_2$-$C_{12}$ alkynyl, $-SR^d$, $-S(=O)R^e$, $-S(=O)_2R^e$, $-S(=O)_2NR^fR^g$, $-C(O)OR^h$, $-C(O)R^e$, $-N(R^b)C(O)NR^fR^g$, $-N(R^b)S(=O)_2R^e$, $-N(R^b)S(=O)_2NR^fR^g$, and $-NR^fR^g$;

each $R^d$ is selected from the group consisting of optionally substituted $-C_1$-$C_{12}$ alkyl, optionally substituted $-C_2$-$C_{12}$ alkenyl, optionally substituted $-C_2$-$C_{12}$ alkynyl, optionally substituted $-(CR^b{}_2)_n$ aryl, optionally substituted $-(CR^b{}_2)_n$ cycloalkyl, optionally substituted $-(CR^b{}_2)_n$ heterocycloalkyl, and $-C(O)NR^fR^g$;

each $R^e$ is selected from the group consisting of optionally substituted $-C_1$-$C_{12}$ alkyl, optionally substituted $-C_2$-$C_{12}$ alkenyl, optionally substituted $-C_2$-$C_{12}$ alkynyl, optionally substituted $-(CR^a{}_2)_n$ aryl, optionally substituted $-(CR^a{}_2)_n$ cycloalkyl, and optionally substituted $-(CR^a{}_2)_n$ heterocycloalkyl;

$R^f$ and $R^g$ are each independently selected from the group consisting of hydrogen, optionally substituted $-C_1$-$C_{12}$ alkyl, optionally substituted $-C_2$-$C_{12}$ alkenyl, optionally substituted $-C_2$-$C_{12}$ alkynyl, optionally substituted $-(CR^b{}_2)_n$ aryl, optionally substituted $-(CR^b{}_2)_n$ cycloalkyl, and optionally substituted $-(CR^b{}_2)_n$ heterocycloalkyl, or $R^f$ and $R^g$ may together form an optionally substituted heterocyclic ring, which may contain a second heterogroup selected from the group consisting of O, $NR^C$, and S, wherein said optionally substituted heterocyclic ring may be substituted with 0-4 substituents selected from the group consisting of optionally substituted $-C_1$-$C_4$ alkyl, $-OR^b$, oxo, cyano, $-CF_3$, optionally substituted phenyl, and $-C(O)OR^h$;

each $R^h$ is selected from the group consisting of optionally substituted $-C_1$-$C_{12}$ alkyl, optionally substituted $-C_2$-$C_{12}$ alkenyl, optionally substituted $-C_2$-$C_{12}$ alkynyl, optionally substituted $-(CR^b{}_2)_n$ aryl, optionally substituted $-(CR^b{}_2)_n$ cycloalkyl, and optionally substituted $-(CR^b{}_2)_n$ heterocycloalkyl;

$R^5$ is selected from the group consisting of $-OH$, optionally substituted $-OC_1$-$C_6$ alkyl, $OC(O)R^e$, $-OC(O)OR^h$, $-F$, $-NHC(O)R^e$, $-NHS(=O)R^e$, $-NHS(=O)_2R^e$, $-NHC(=S)NH(R^h)$, and $-NHC(O)NH(R^h)$;

X is $P(O)YR^{11}Y'R^{11}$;

Y and Y' are each independently selected from the group consisting of $-O-$, and $-NR^v-$; when Y and Y' are $-O-$, $R^{11}$ attached to $-O-$ is independently selected from the group consisting of $-H$, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, $-C(R^z)_2OC(O)NR^z{}_2$, $-NR^z-C(O)-R^y$, $-C(R^z)_2-OC(O)R^y$, $-C(R^z)_2-O-C(O)OR^y$, $-C(R^z)_2OC(O)SR^y$, -alkyl-S$-C(O)R^y$, -alkyl-S$-$S-alkylhydroxy, and -alkyl-S$-$S$-$S-alkylhydroxy;

when Y and Y' are $-NR^v-$, then $R^{11}$ attached to $-NR^v-$ is independently selected from the group consisting of $-H$, $-[C(R^z)_2]_q-COOR^y$, $-C(R^x)_2COOR^Y$, $-[C(R^z)_2]_q-C(O)SR^y$, and -cycloalkylene-$COOR^y$;

when Y is $-O-$ and Y' is $NR^v$, then $R^{11}$ attached to $-O-$ is independently selected from the group consisting of $-H$, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, $-C(R^z)_2OC(O)NR^z{}_2$, $-NR^z-C(O)-R^y$, $-C(R^z)_2-OC(O)R^y$, $-C(R^z)_2-O-C(O)OR^y$, $-C(R^z)_2OC(O)SR^y$, -alkyl-S$-C(O)R^y$, -alkyl-S$-$S-alkylhydroxy, and -alkyl-S$-$S$-$S-alkylhydroxy; and $R^{11}$ attached to $-NR^v-$ is independently selected from the group consisting of H, $-[C(R^z)_2]_q-COOR^y$, $-C(R^x)_2COOR^y$, $-[C(R^z)_2]_q-C(O)SR^y$, and -cycloalkylene-$COOR^y$;

or when Y and Y' are independently selected from $-O-$ and $NR^v$, then together $R^{11}$ and $R^{11}$ are -alkyl-S$-$S-alkyl- to form a cyclic group, or together $R^{11}$ and $R^{11}$ are the group:

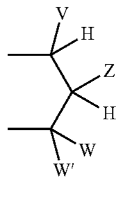

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus;

or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of $—CHR^zOH$, $—CHR^zOC(O)R^y$, $—CHR^zOC(S)R^y$, $—CHR^zOC(S)OR^y$, $—CHR^zOC(O)SR^y$, $—CHR^zOCO_2R^y$, $—OR^z$, $—SR^z$, $—CHR^zN_3$, $—CH_2$-aryl, —CH(aryl)OH, $—CH(CH{=}CR^z_2)OH$, $—CH(C{\equiv}CR^z)OH$, $—R^z$, $—NR^z_2$, $—OCOR^y$, $—OCO^2R^y$, $—SCOR^y$, $—SCO_2R^y$, $—NHCOR^z$, $—NHCO_2R^y$, $—CH_2NH$-aryl, $—(CH_2)_q—OR^z$, and $—(CH_2)_q—SR^z$;

q is an integer 2 or 3;

each $R^z$ is selected from the group consisting of $R^y$ and —H;

each $R^y$ is selected from the group consisting of alkyl, aryl, heterocycloalkyl, and aralkyl;

each $R^x$ is independently selected from the group consisting of —H, and alkyl, or together $R^x$ and $R^y$ form a cyclic alkyl group;

each $R^v$ is selected from the group consisting of —H, lower alkyl, acyloxyalkyl, alkoxycarbonyloxyalkyl, and lower acyl;

and pharmaceutically acceptable salts thereof.

In some embodiments, the compound of Formula I has the following provisos:

a) when G is —O—, T is $—CH_2—$, $R^1$ and $R^2$ are each bromo, $R^3$ is iso-propyl, $R^4$ is hydrogen, and $R^5$ is —OH, then X is not $P(O)(OH)_2$ or $P(O)(OCH_2CH_3)_2$;

b) V, Z, W, W' are not all —H; and c) when Z is $—R^z$, then at least one of V, W, and W' is not —H, alkyl, aralkyl, or heterocycloalkyl;

d) when G is —O—, T is $—(CH_2)_{1-4}—$, $R^1$ and $R^2$ are independently halogen, alkyl, and cycloalkyl, $R^3$ is alkyl, $R^4$ is hydrogen, and $R^5$ is —OH, then X is not $—P(O)(OH)_2$ or —P(O)(O-lower $alkyl)_2$; and e) when G is —O—, $R^5$ is $—NHC(O)R^e$, $—NHS(=O)_{1-2}R^e$, $—NHC(S)NH(R^b)$, or $—NHC(O)NH(R^h)$, T is $—(CH_2)^m—$, —CH=CH—, $—O(CH_2)_{1-2}—$, or $—NH(CH_2)_{1-2}—$, then X is not $—P(O)(OH)_2$ or $—P(O)(OH)NH_2$.

In some embodiments, the compound is selected from one or more of the following:

(Compound 1)

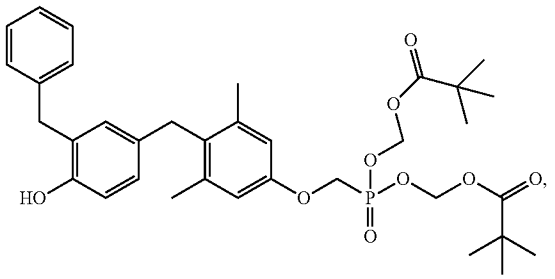

(Compound 2)

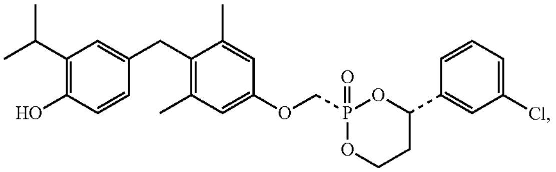

(Compound 3)

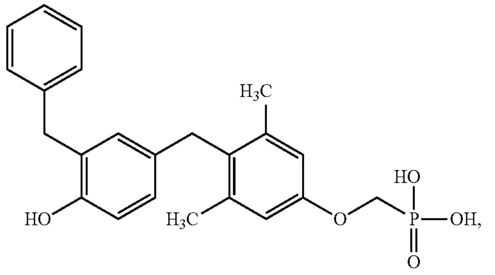

or (Compound 4)

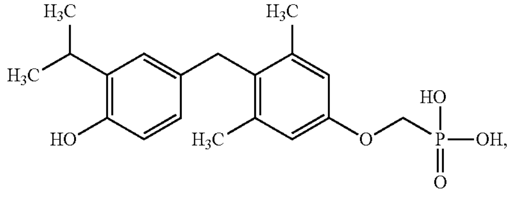

or pharmaceutically acceptable salts thereof.

In other embodiments, the compound is selected from:
| Structure | Compound Number |
|---|---|
| 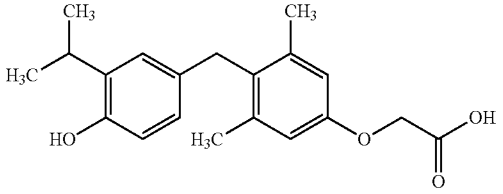 [SMILES: Cc1cc(OCC(=O)O)cc(C)c1Cc1ccc(O)c(C(C)C)c1] | 17 |
| 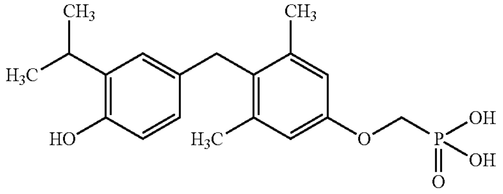 [SMILES: Cc1cc(OCP(=O)(O)O)cc(C)c1Cc1ccc(O)c(C(C)C)c1] | 7 |
| 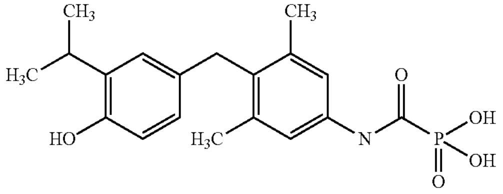 [SMILES: Cc1cc(NC(=O)P(=O)(O)O)cc(C)c1Cc1ccc(O)c(C(C)C)c1] | 1a |
| 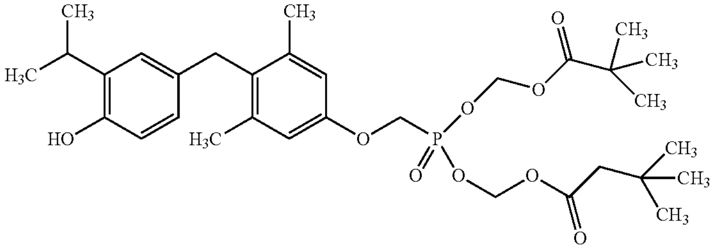 [SMILES: Cc1cc(OCP(=O)(OCOC(=O)CC(C)(C)C)OCOC(=O)C(C)(C)C)cc(C)c1Cc1ccc(O)c(C(C)C)c1] | 12-1 |
| 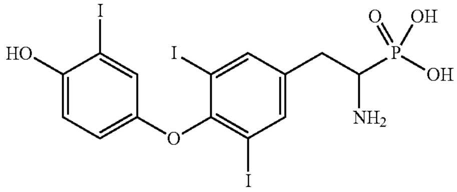 [SMILES: NC(Cc1cc(I)c(Oc2ccc(O)c(I)c2)c(I)c1)P(=O)(O)O] | 2a |
| 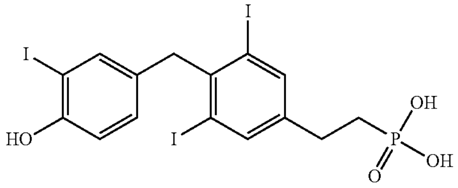 [SMILES: O=P(O)(O)CCc1cc(I)c(Cc2ccc(O)c(I)c2)c(I)c1] | 3a |
| 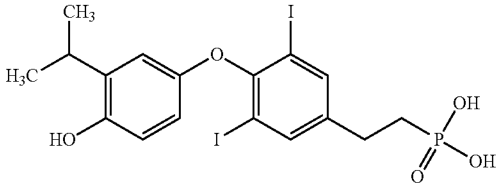 [SMILES: CC(C)c1cc(Oc2c(I)cc(CCP(=O)(O)O)cc2I)ccc1O] | 4a |

-continued
| Structure | Compound Number |
| --- | --- |
| 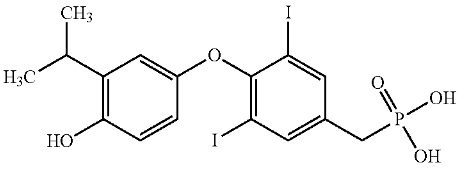 [SMILES: CC(C)c1cc(Oc2c(I)cc(CP(=O)(O)O)cc2I)ccc1O] | 5 |
| 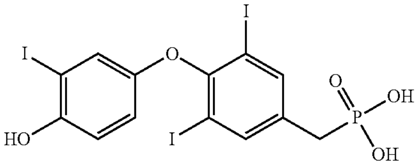 [SMILES: O=P(O)(O)Cc1cc(I)c(Oc2ccc(O)c(I)c2)c(I)c1] | 6 |
| 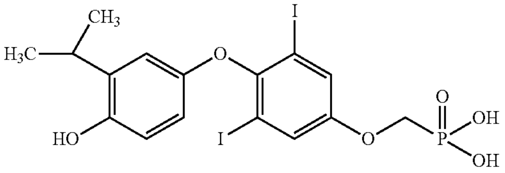 [SMILES: CC(C)c1cc(Oc2c(I)cc(OCP(=O)(O)O)cc2I)ccc1O] | 8 |
| 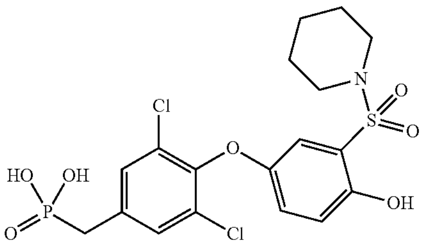 [SMILES: O=P(O)(O)Cc1cc(Cl)c(Oc2ccc(O)c(S(=O)(=O)N3CCCCC3)c2)c(Cl)c1] | 9 |
| 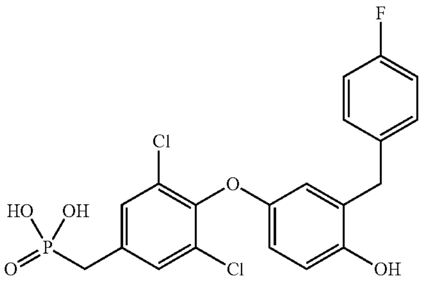 [SMILES: O=P(O)(O)Cc1cc(Cl)c(Oc2ccc(O)c(Cc3ccc(F)cc3)c2)c(Cl)c1] | 11 |
| 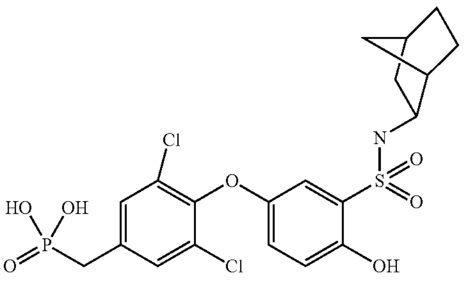 [SMILES: O=P(O)(O)Cc1cc(Cl)c(Oc2ccc(O)c(S(=O)(=O)NC3CC4CCC3C4)c2)c(Cl)c1] | 10 |

-continued
| Structure | Compound Number |
| --- | --- |
| 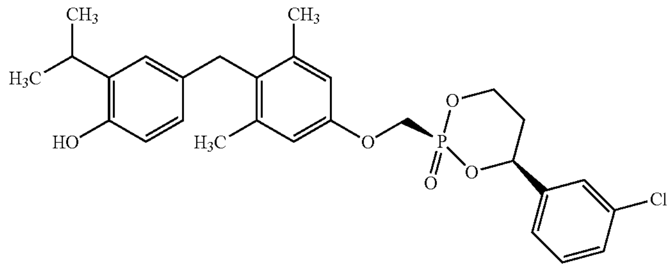 [SMILES: Cc1cc(OC[P@@]2(=O)OCC[C@@H](c3cccc(Cl)c3)O2)cc(C)c1Cc1ccc(O)c(C(C)C)c1] | cis-13-1 |
| 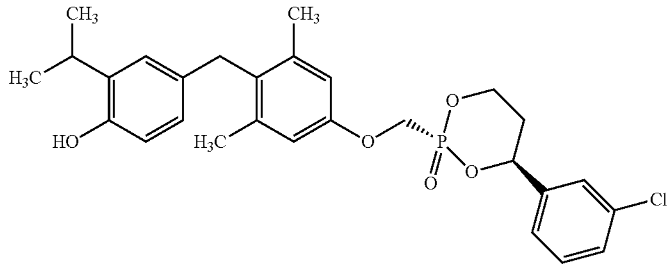 [SMILES: Cc1cc(OC[P@]2(=O)OCC[C@@H](c3cccc(Cl)c3)O2)cc(C)c1Cc1ccc(O)c(C(C)C)c1] | trans-13-1 |
| 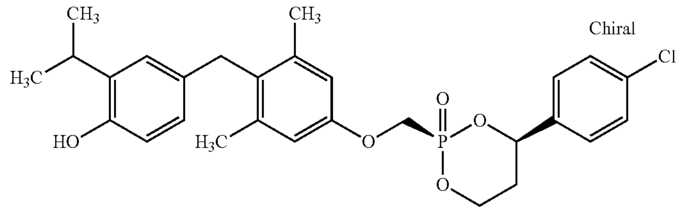 [SMILES: Cc1cc(OC[P@]2(=O)OCC[C@H](c3ccc(Cl)cc3)O2)cc(C)c1Cc1ccc(O)c(C(C)C)c1]  | cis-13-6 |
| 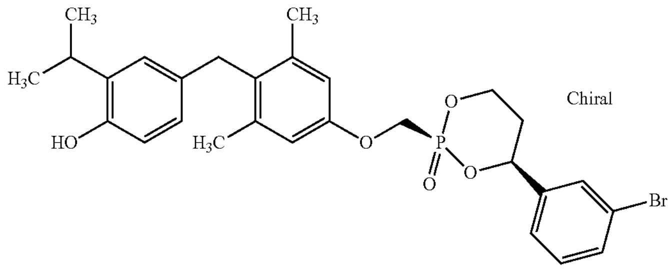 [SMILES: Cc1cc(OC[P@@]2(=O)OCC[C@@H](c3cccc(Br)c3)O2)cc(C)c1Cc1ccc(O)c(C(C)C)c1]  | cis-13-2 |
| 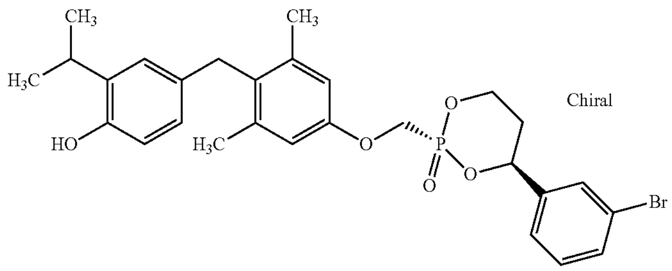 [SMILES: Cc1cc(OC[P@]2(=O)OCC[C@@H](c3cccc(Br)c3)O2)cc(C)c1Cc1ccc(O)c(C(C)C)c1]  | trans-13-2 |
| 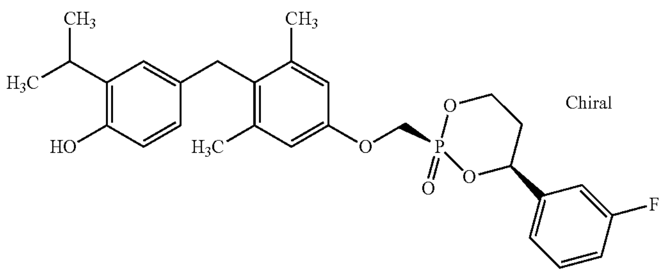 [SMILES: Cc1cc(OC[P@@]2(=O)OCC[C@@H](c3cccc(F)c3)O2)cc(C)c1Cc1ccc(O)c(C(C)C)c1]  | cis-13-3 |

-continued
| Structure | Compound Number |
|---|---|
| 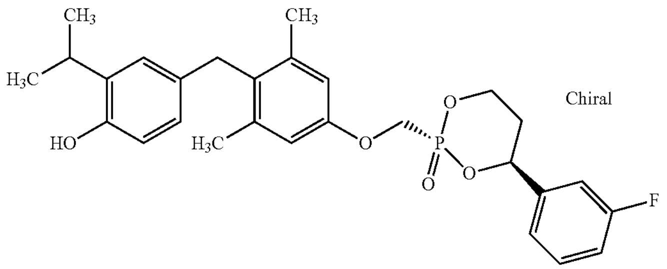 [SMILES: Cc1cc(OC[P@]2(=O)OCC[C@@H](c3cccc(F)c3)O2)cc(C)c1Cc1ccc(O)c(C(C)C)c1] | trans-13-3 |
| 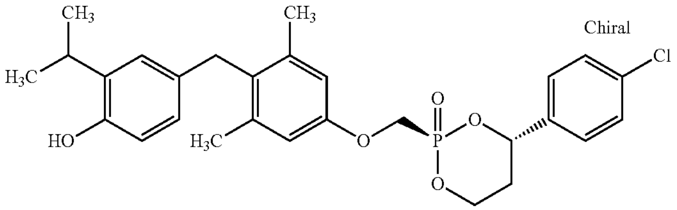 [SMILES: Cc1cc(OC[P@]2(=O)OCC[C@@H](c3ccc(Cl)cc3)O2)cc(C)c1Cc1ccc(O)c(C(C)C)c1] | trans-13-6 |
| 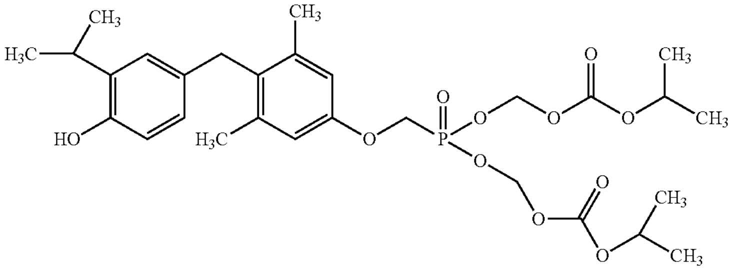 [SMILES: Cc1cc(OCP(=O)(OCOC(=O)OC(C)C)OCOC(=O)OC(C)C)cc(C)c1Cc1ccc(O)c(C(C)C)c1] | 12-3 |
| 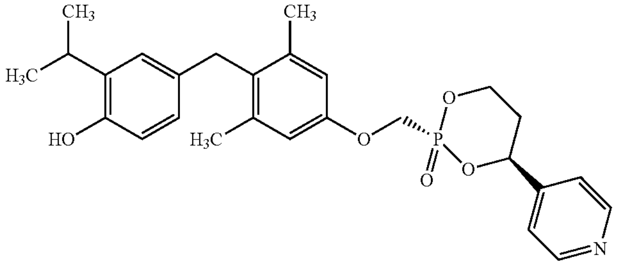 [SMILES: Cc1cc(OC[P@]2(=O)OCC[C@@H](c3ccncc3)O2)cc(C)c1Cc1ccc(O)c(C(C)C)c1] | trans-13-5 |
| 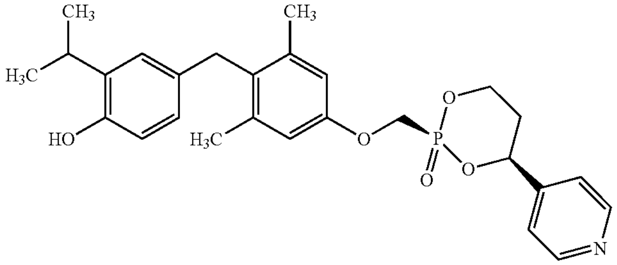 [SMILES: Cc1cc(OC[P@@]2(=O)OCC[C@@H](c3ccncc3)O2)cc(C)c1Cc1ccc(O)c(C(C)C)c1] | cis-13-5 |

-continued
| Structure | Compound Number |
|---|---|
| 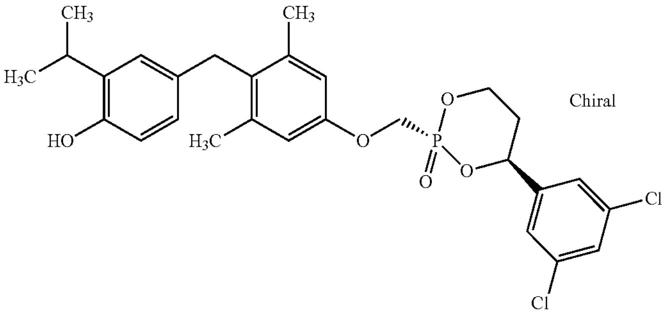 [SMILES: Cc1cc(OC[P@]2(=O)OCC[C@@H](c3cc(Cl)cc(Cl)c3)O2)cc(C)c1Cc1ccc(O)c(C(C)C)c1] | trans-13-7 |
| 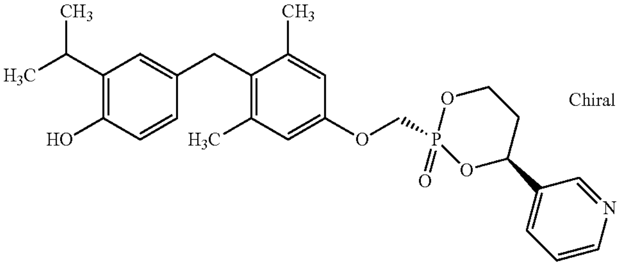 [SMILES: Cc1cc(OC[P@]2(=O)OCC[C@@H](c3cccnc3)O2)cc(C)c1Cc1ccc(O)c(C(C)C)c1] | trans-13-4 |
| 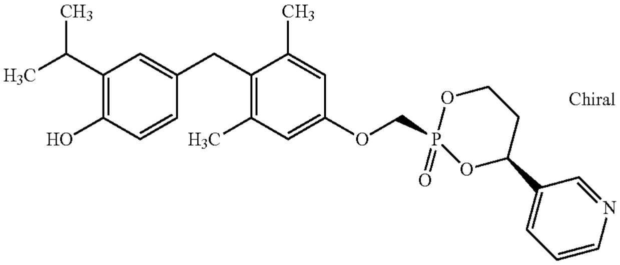 [SMILES: Cc1cc(OC[P@@]2(=O)OCC[C@@H](c3cccnc3)O2)cc(C)c1Cc1ccc(O)c(C(C)C)c1] | cis-13-4 |
| 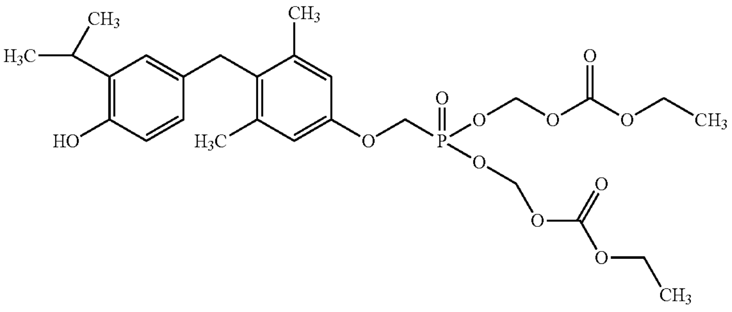 [SMILES: CCOC(=O)OCOP(=O)(COc1cc(C)c(Cc2ccc(O)c(C(C)C)c2)c(C)c1)OCOC(=O)OCC] | 12-2 |
| 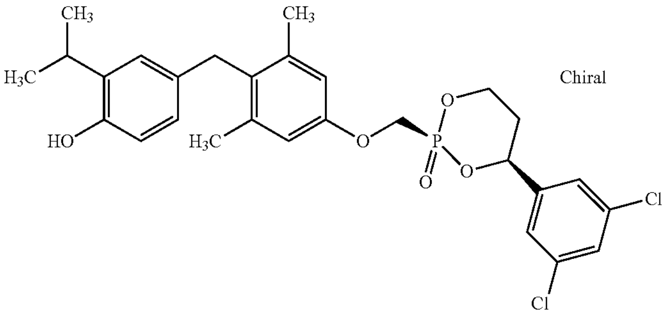 [SMILES: Cc1cc(OC[P@@]2(=O)OCC[C@@H](c3cc(Cl)cc(Cl)c3)O2)cc(C)c1Cc1ccc(O)c(C(C)C)c1] | cis-13-7 |

-continued
| Structure | Compound Number |
| --- | --- |
| 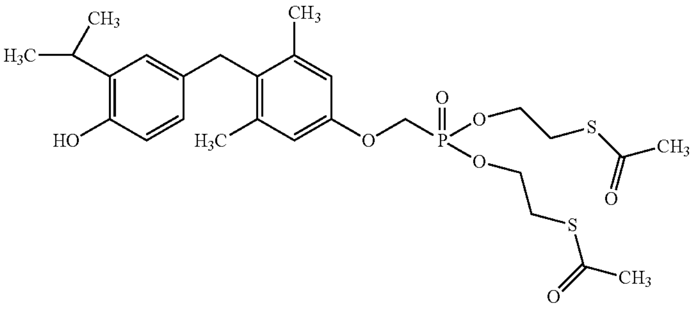 [SMILES: CC(=O)SCCOP(=O)(COc1cc(C)c(Cc2ccc(O)c(C(C)C)c2)c(C)c1)OCCSC(C)=O] | 14 |
| 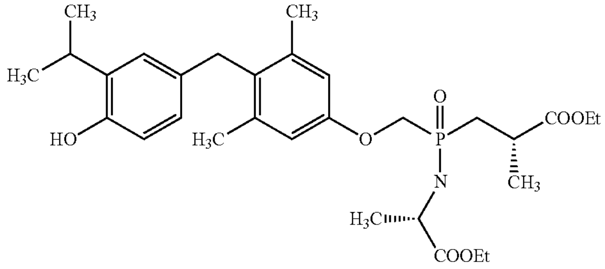 [SMILES: CCOC(=O)[C@H](C)CP(=O)(COc1cc(C)c(Cc2ccc(O)c(C(C)C)c2)c(C)c1)N[C@@H](C)C(=O)OCC] | 15-1 |
| 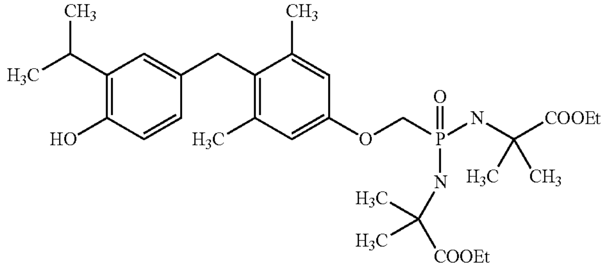 [SMILES: CCOC(=O)C(C)(C)NP(=O)(COc1cc(C)c(Cc2ccc(O)c(C(C)C)c2)c(C)c1)NC(C)(C)C(=O)OCC] | 15-2 |
| 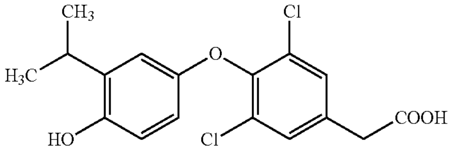 [SMILES: CC(C)c1cc(Oc2c(Cl)cc(CC(=O)O)cc2Cl)ccc1O] | 18 |
| 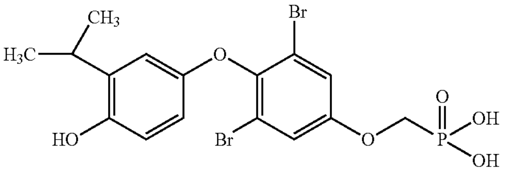 [SMILES: CC(C)c1cc(Oc2c(Br)cc(OCP(=O)(O)O)cc2Br)ccc1O] | 8-1 |
| 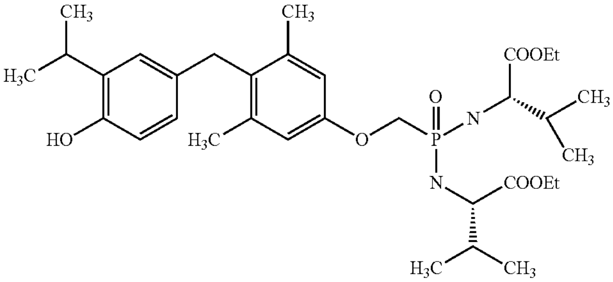 [SMILES: CCOC(=O)[C@@H](NP(=O)(COc1cc(C)c(Cc2ccc(O)c(C(C)C)c2)c(C)c1)N[C@H](C(=O)OCC)C(C)C)C(C)C] | 15-3 |

-continued
| Structure | Compound Number |
|---|---|
| 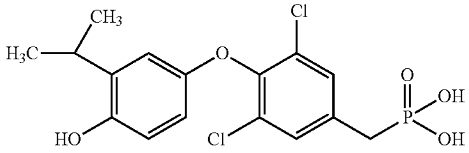 [SMILES: CC(C)c1cc(Oc2c(Cl)cc(CP(=O)(O)O)cc2Cl)ccc1O] | 19 |
| 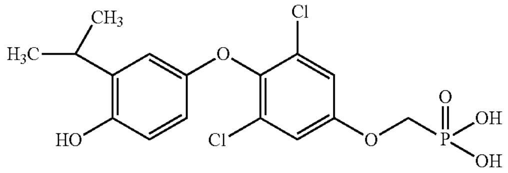 | 8-2 |
| 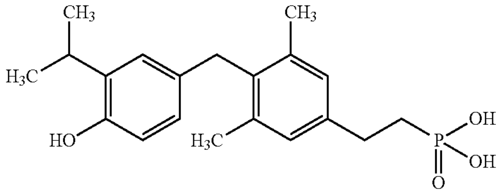 [SMILES: Cc1cc(CCP(=O)(O)O)cc(C)c1Cc1ccc(O)c(C(C)C)c1] | 24-1 |
| 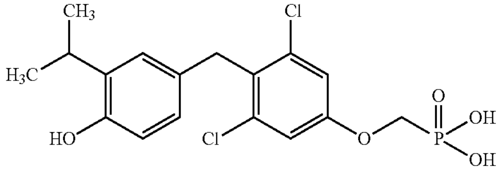 [SMILES: CC(C)c1cc(Cc2c(Cl)cc(OCP(=O)(O)O)cc2Cl)ccc1O] | 7-5 |
| 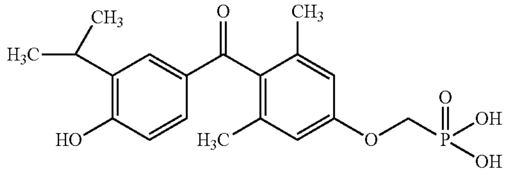 [SMILES: Cc1cc(OCP(=O)(O)O)cc(C)c1C(=O)c1ccc(O)c(C(C)C)c1] | 25 |
| 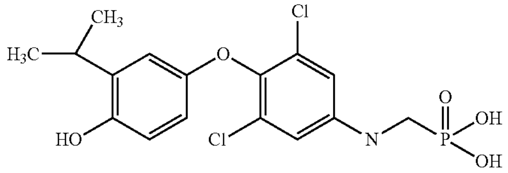 [SMILES: CC(C)c1cc(Oc2c(Cl)cc(NCP(=O)(O)O)cc2Cl)ccc1O] | 22 |
| 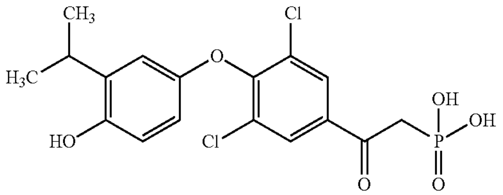 [SMILES: CC(C)c1cc(Oc2c(Cl)cc(C(=O)CP(=O)(O)O)cc2Cl)ccc1O] | 21 |
| 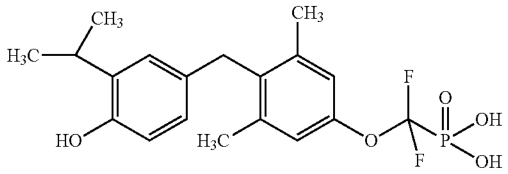 [SMILES: Cc1cc(OC(F)(F)P(=O)(O)O)cc(C)c1Cc1ccc(O)c(C(C)C)c1] | 7-6 |

-continued
| Structure | Compound Number |
|---|---|
| 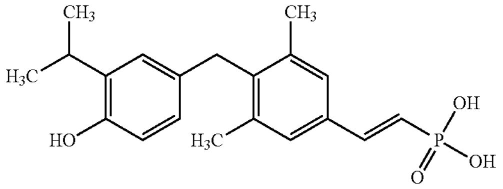 [SMILES: Cc1cc(/C=C/P(=O)(O)O)cc(C)c1Cc1ccc(O)c(C(C)C)c1] | 24-2 |
| 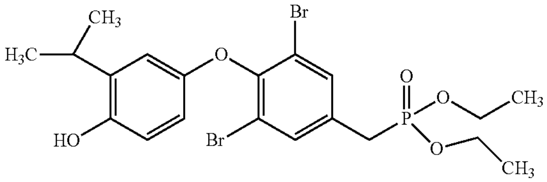 [SMILES: CCOP(=O)(Cc1cc(Br)c(Oc2ccc(O)c(C(C)C)c2)c(Br)c1)OCC] | 19-1 |
| 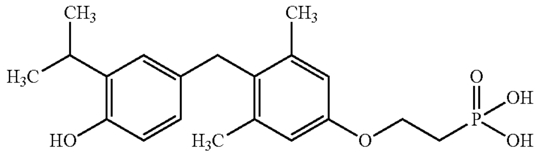 [SMILES: Cc1cc(OCCP(=O)(O)O)cc(C)c1Cc1ccc(O)c(C(C)C)c1] | 26 |
| 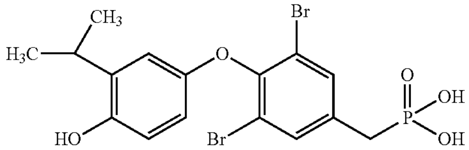 [SMILES: CC(C)c1cc(Oc2c(Br)cc(CP(=O)(O)O)cc2Br)ccc1O] | 19-2 |
| 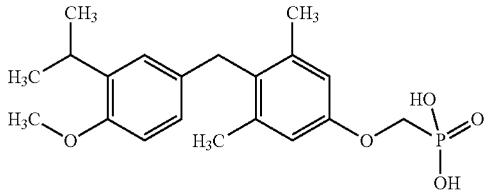 [SMILES: COc1ccc(Cc2c(C)cc(OCP(=O)(O)O)cc2C)cc1C(C)C] | 7-4 |
| 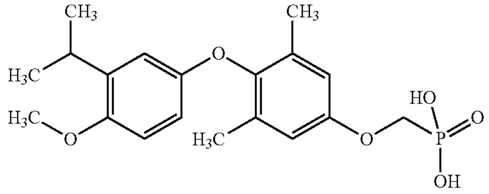 [SMILES: COc1ccc(Oc2c(C)cc(OCP(=O)(O)O)cc2C)cc1C(C)C] | 30 |
| 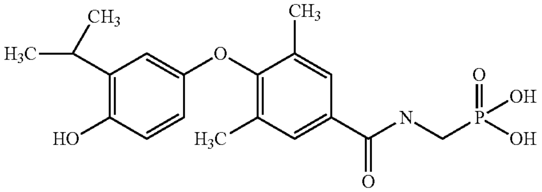 [SMILES: Cc1cc(C(=O)NCP(=O)(O)O)cc(C)c1Oc1ccc(O)c(C(C)C)c1] | 23 |
| 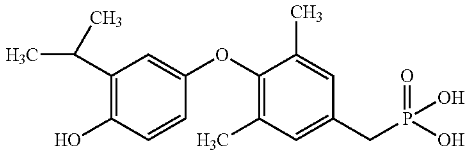 [SMILES: Cc1cc(CP(=O)(O)O)cc(C)c1Oc1ccc(O)c(C(C)C)c1] | 19-3 |

-continued
| Structure | Compound Number |
|---|---|
| 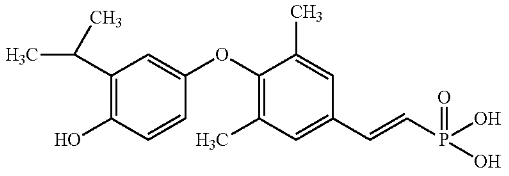 [SMILES: Cc1cc(/C=C/P(=O)(O)O)cc(C)c1Oc1ccc(O)c(C(C)C)c1] | 28 |
| 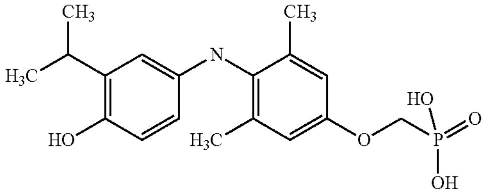 [SMILES: Cc1cc(OCP(=O)(O)O)cc(C)c1Nc1ccc(O)c(C(C)C)c1] | 20 |
| 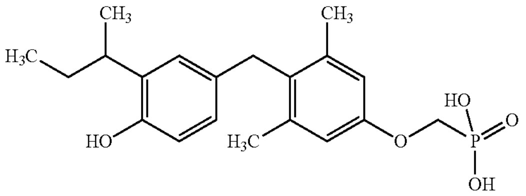 [SMILES: CCC(C)c1cc(Cc2c(C)cc(OCP(=O)(O)O)cc2C)ccc1O] | 7-3 |
| 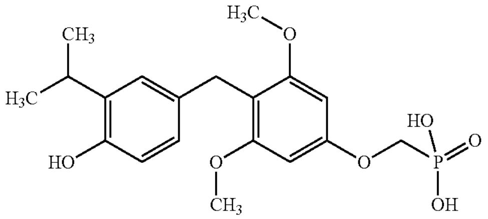 [SMILES: COc1cc(OCP(=O)(O)O)cc(OC)c1Cc1ccc(O)c(C(C)C)c1] | 7-2 |
| 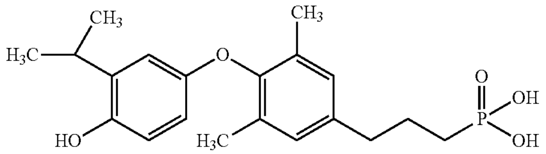 [SMILES: Cc1cc(CCCP(=O)(O)O)cc(C)c1Oc1ccc(O)c(C(C)C)c1] | 29 |
| 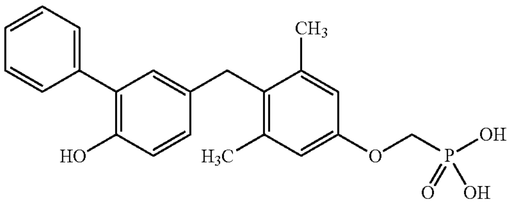 [SMILES: Cc1cc(OCP(=O)(O)O)cc(C)c1Cc1ccc(O)c(-c2ccccc2)c1] | 7-1 |
| 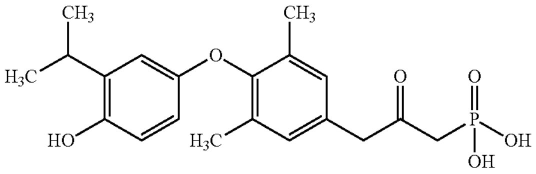 [SMILES: Cc1cc(CC(=O)CP(=O)(O)O)cc(C)c1Oc1ccc(O)c(C(C)C)c1] | 32 |
| 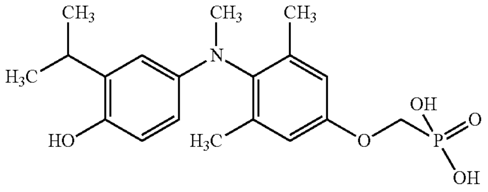 [SMILES: Cc1cc(OCP(=O)(O)O)cc(C)c1N(C)c1ccc(O)c(C(C)C)c1] | 20-1 |

-continued
| Structure | Compound Number |
|---|---|
| 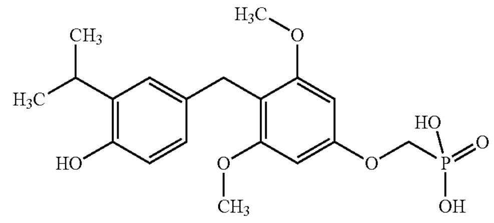 [SMILES: COc1cc(OCP(=O)(O)O)cc(OC)c1Cc1ccc(O)c(C(C)C)c1] | 24 |
| 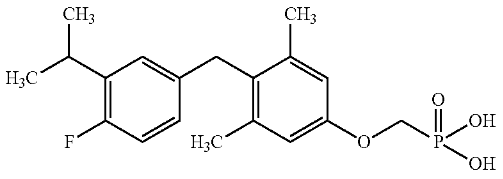 [SMILES: Cc1cc(OCP(=O)(O)O)cc(C)c1Cc1ccc(F)c(C(C)C)c1] | 27 |
| 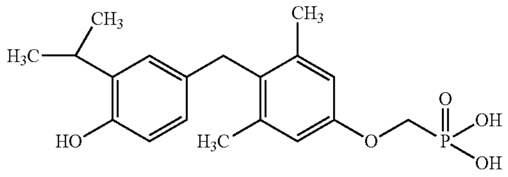 [SMILES: Cc1cc(OCP(=O)(O)O)cc(C)c1Cc1ccc(O)c(C(C)C)c1] | 31 |
| 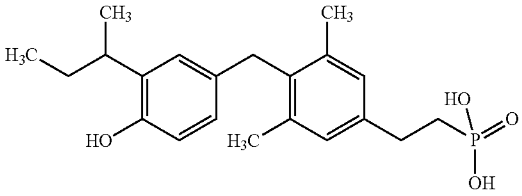 [SMILES: CCC(C)c1cc(Cc2c(C)cc(CCP(=O)(O)O)cc2C)ccc1O] | 24-3 |
| 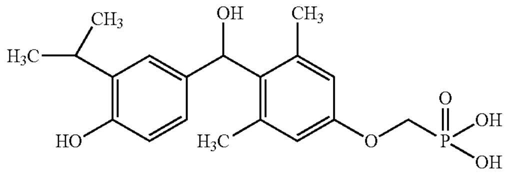 [SMILES: Cc1cc(OCP(=O)(O)O)cc(C)c1C(O)c1ccc(O)c(C(C)C)c1] | 33 |
| 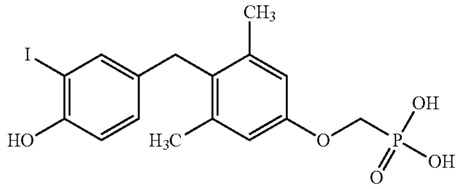 [SMILES: Cc1cc(OCP(=O)(O)O)cc(C)c1Cc1ccc(O)c(I)c1] | 34 |
| 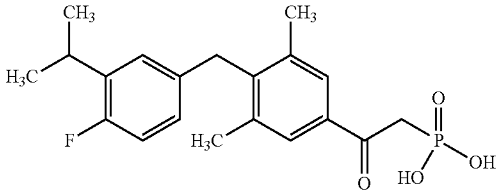 [SMILES: Cc1cc(C(=O)CP(=O)(O)O)cc(C)c1Cc1ccc(F)c(C(C)C)c1] | 41-2 |

-continued
| Structure | Compound Number |
|---|---|
| 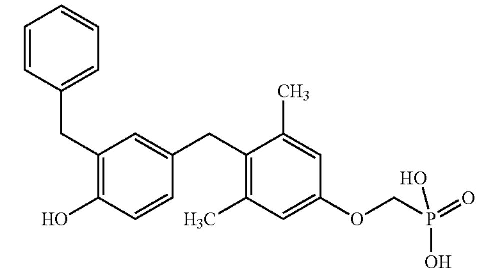 | 38 |
| 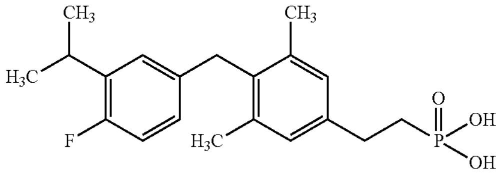 | 42-2 |
| 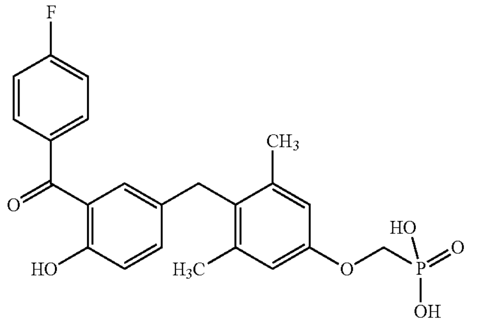 [SMILES: Cc1cc(OCP(=O)(O)O)cc(C)c1Cc1ccc(O)c(C(=O)c2ccc(F)cc2)c1] | 39 |
| 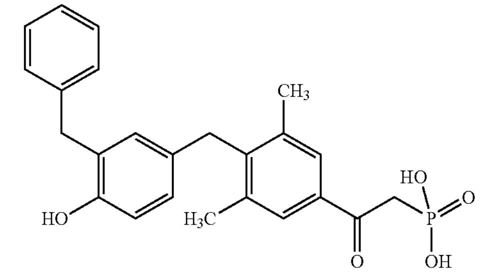 [SMILES: Cc1cc(C(=O)CP(=O)(O)O)cc(C)c1Cc1ccc(O)c(Cc2ccccc2)c1] | 41 |
| 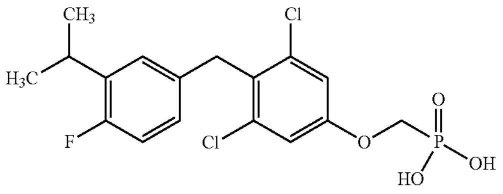 [SMILES: CC(C)c1cc(Cc2c(Cl)cc(OCP(=O)(O)O)cc2Cl)ccc1F] | 27-2 |
| 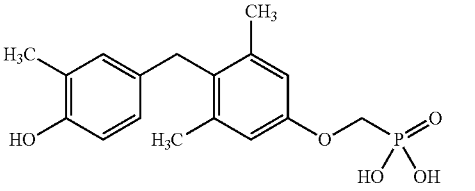 [SMILES: Cc1cc(Cc2c(C)cc(OCP(=O)(O)O)cc2C)ccc1O] | 7-7 |

-continued
| Structure | Compound Number |
|---|---|
| 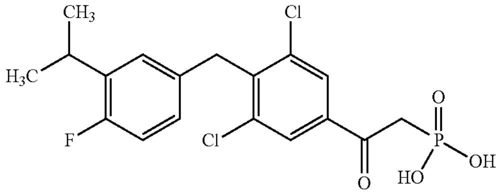 [SMILES: CC(C)c1cc(Cc2c(Cl)cc(C(=O)CP(=O)(O)O)cc2Cl)ccc1F] | 41-3 |
| 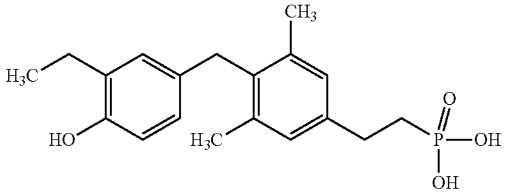 [SMILES: CCc1cc(Cc2c(C)cc(CCP(=O)(O)O)cc2C)ccc1O] | 24-4 |
| 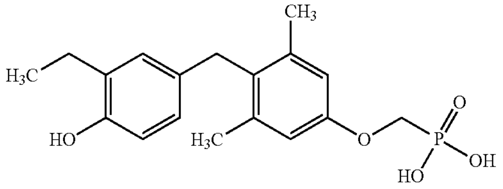 [SMILES: CCc1cc(Cc2c(C)cc(OCP(=O)(O)O)cc2C)ccc1O] | 7-8 |
| 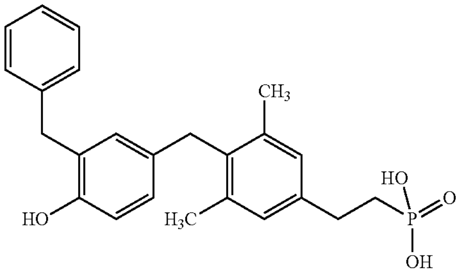 [SMILES: Cc1cc(CCP(=O)(O)O)cc(C)c1Cc1ccc(O)c(Cc2ccccc2)c1] | 42 |
| 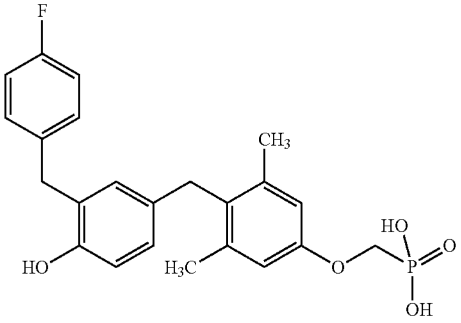 [SMILES: Cc1cc(OCP(=O)(O)O)cc(C)c1Cc1ccc(O)c(Cc2ccc(F)cc2)c1] | 40 |
| 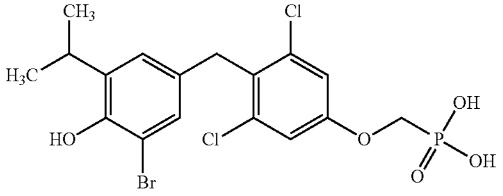 [SMILES: CC(C)c1cc(Cc2c(Cl)cc(OCP(=O)(O)O)cc2Cl)cc(Br)c1O] | 7-14 |

-continued
| Structure | Compound Number |
|---|---|
| 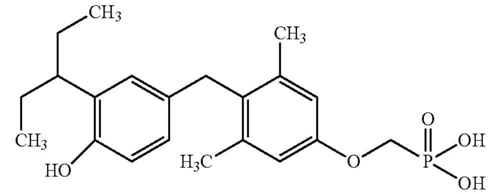 [SMILES: CCC(CC)c1cc(Cc2c(C)cc(OCP(=O)(O)O)cc2C)ccc1O] | 7-9 |
| 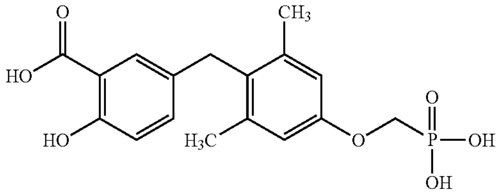 [SMILES: Cc1cc(OCP(=O)(O)O)cc(C)c1Cc1ccc(O)c(C(=O)O)c1] | 35 |
| 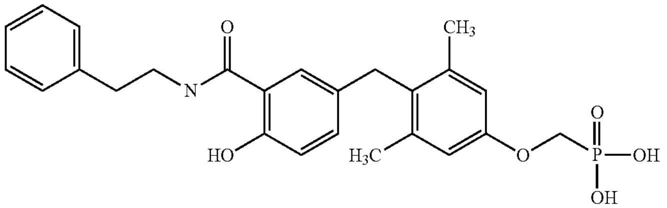 [SMILES: Cc1cc(OCP(=O)(O)O)cc(C)c1Cc1ccc(O)c(C(=O)NCCc2ccccc2)c1] | 37 |
| 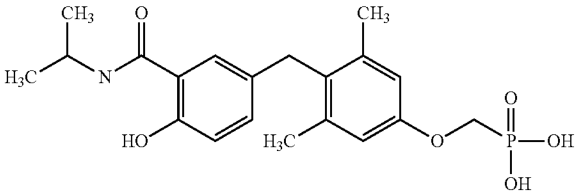 [SMILES: Cc1cc(OCP(=O)(O)O)cc(C)c1Cc1ccc(O)c(C(=O)NC(C)C)c1] | 36 |
| 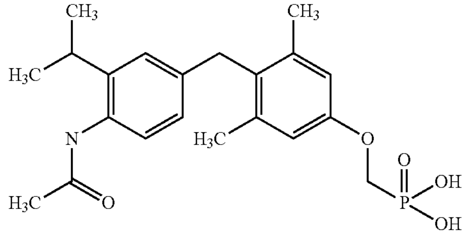 [SMILES: CC(=O)Nc1ccc(Cc2c(C)cc(OCP(=O)(O)O)cc2C)cc1C(C)C] | 7-12 |
| 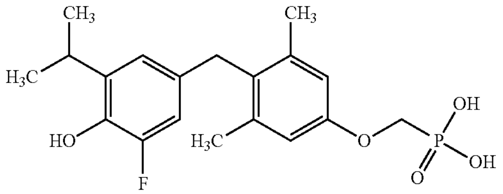 [SMILES: Cc1cc(OCP(=O)(O)O)cc(C)c1Cc1cc(F)c(O)c(C(C)C)c1] | 7-11 |
| 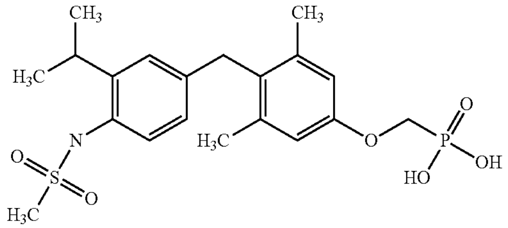 [SMILES: Cc1cc(OCP(=O)(O)O)cc(C)c1Cc1ccc(NS(C)(=O)=O)c(C(C)C)c1] | 7-13 |

-continued
| Structure | Compound Number |
|---|---|
| 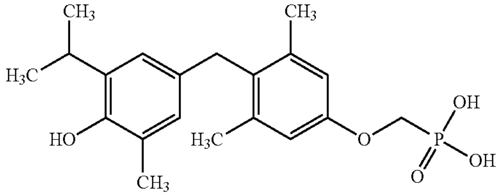 [SMILES: Cc1cc(Cc2c(C)cc(OCP(=O)(O)O)cc2C)cc(C(C)C)c1O] | 7-10 |
| 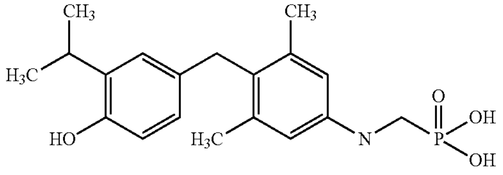 [SMILES: Cc1cc(NCP(=O)(O)O)cc(C)c1Cc1ccc(O)c(C(C)C)c1] | 47 |
| 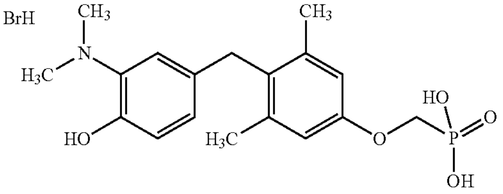 [SMILES: Br ; Cc1cc(OCP(=O)(O)O)cc(C)c1Cc1ccc(O)c(N(C)C)c1] | 49 |
| 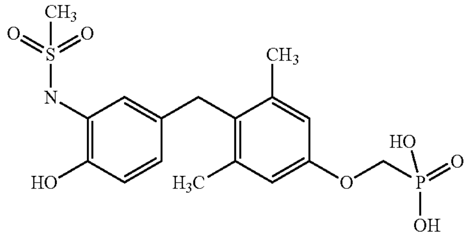 [SMILES: Cc1cc(OCP(=O)(O)O)cc(C)c1Cc1ccc(O)c(NS(C)(=O)=O)c1] | 51-1 |
| 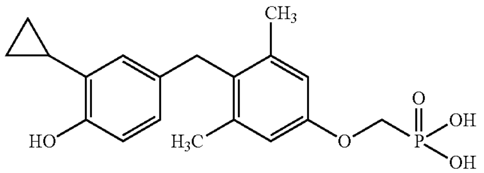 [SMILES: Cc1cc(OCP(=O)(O)O)cc(C)c1Cc1ccc(O)c(C2CC2)c1] | 48 |
| 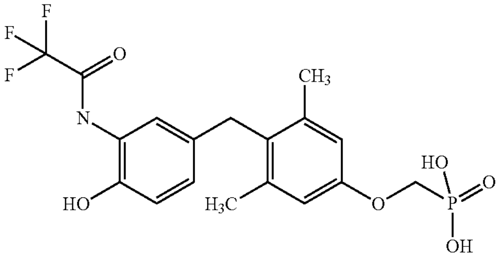 [SMILES: Cc1cc(OCP(=O)(O)O)cc(C)c1Cc1ccc(O)c(NC(=O)C(F)(F)F)c1] | 51-2 |
| 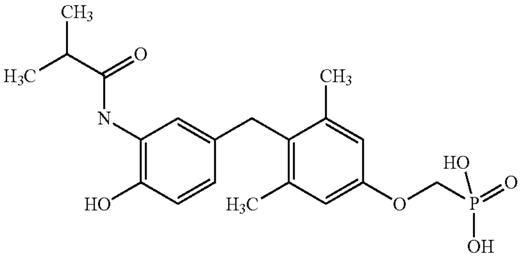 [SMILES: Cc1cc(OCP(=O)(O)O)cc(C)c1Cc1ccc(O)c(NC(=O)C(C)C)c1] | 51-3 |

-continued
| Structure | Compound Number |
|---|---|
| 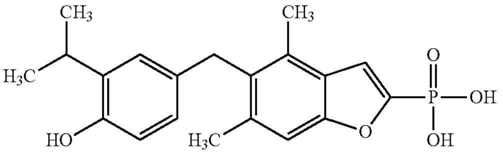 [SMILES: Cc1cc2oc(P(=O)(O)O)cc2c(C)c1Cc1ccc(O)c(C(C)C)c1] | 45 |
| 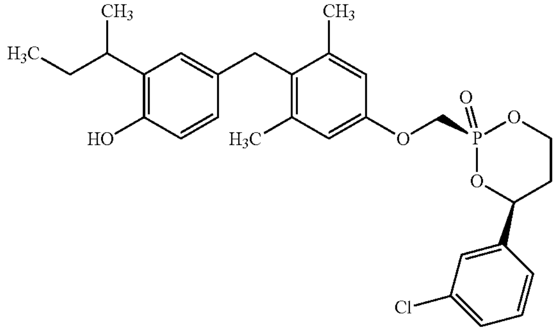 [SMILES: CCC(C)c1cc(Cc2c(C)cc(OC[P@@]3(=O)OCC[C@@H](c4cccc(Cl)c4)O3)cc2C)ccc1O] | 13-8 |
| 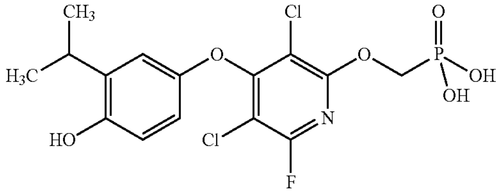 [SMILES: CC(C)c1cc(Oc2c(Cl)c(F)nc(OCP(=O)(O)O)c2Cl)ccc1O] | 57 |
| 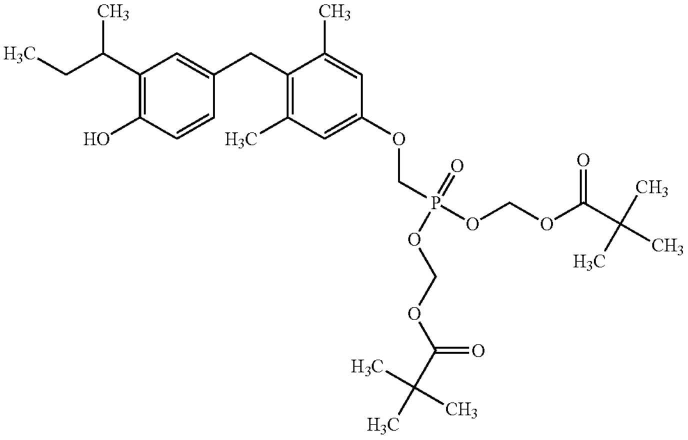 [SMILES: CCC(C)c1cc(Cc2c(C)cc(OCP(=O)(OCOC(=O)C(C)(C)C)OCOC(=O)C(C)(C)C)cc2C)ccc1O] | 12-4 |
| 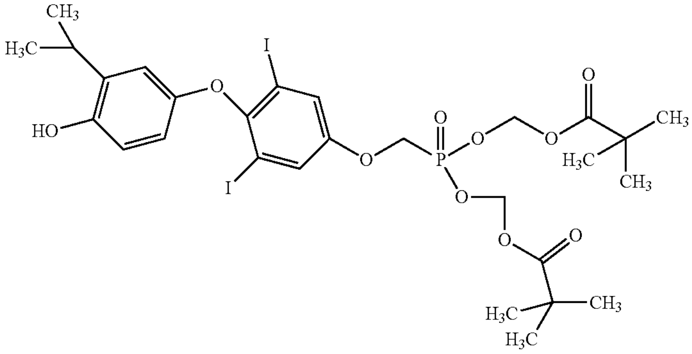 [SMILES: CC(C)c1cc(Oc2c(I)cc(OCP(=O)(OCOC(=O)C(C)(C)C)OCOC(=O)C(C)(C)C)cc2I)ccc1O] | 12-7 |

-continued
| Structure | Compound Number |
|---|---|
| 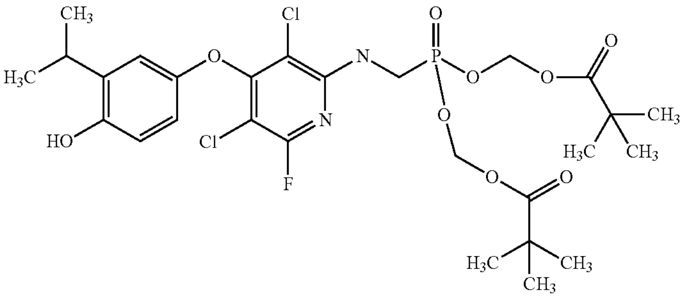 [SMILES: CC(C)c1cc(Oc2c(Cl)c(F)nc(NCP(=O)(OCOC(=O)C(C)(C)C)OCOC(=O)C(C)(C)C)c2Cl)ccc1O] | 12-9 |
| 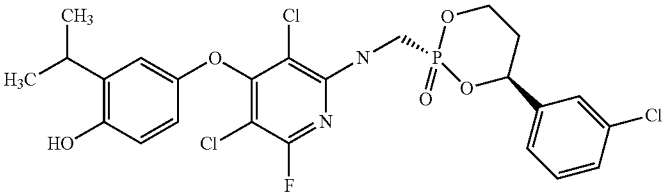 [SMILES: CC(C)c1cc(Oc2c(Cl)c(F)nc(NC[P@]3(=O)OCC[C@@H](c4cccc(Cl)c4)O3)c2Cl)ccc1O] | 13-12-trans |
| 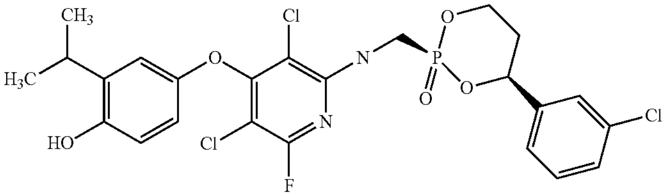 [SMILES: CC(C)c1cc(Oc2c(Cl)c(F)nc(NC[P@@]3(=O)OCC[C@@H](c4cccc(Cl)c4)O3)c2Cl)ccc1O] | 13-12-cis |
| 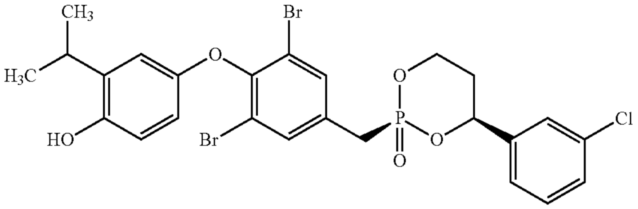 [SMILES: CC(C)c1cc(Oc2c(Br)cc(C[P@@]3(=O)OCC[C@@H](c4cccc(Cl)c4)O3)cc2Br)ccc1O] | 13-9 |
| 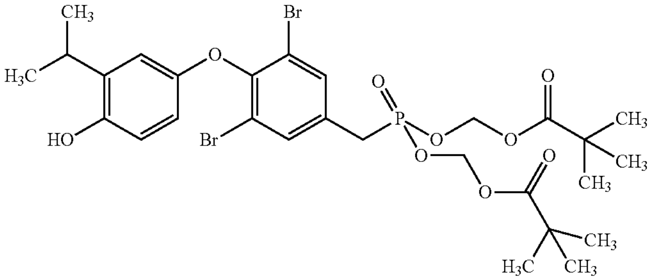 [SMILES: CC(C)c1cc(Oc2c(Br)cc(CP(=O)(OCOC(=O)C(C)(C)C)OCOC(=O)C(C)(C)C)cc2Br)ccc1O] | 12-5 |
| 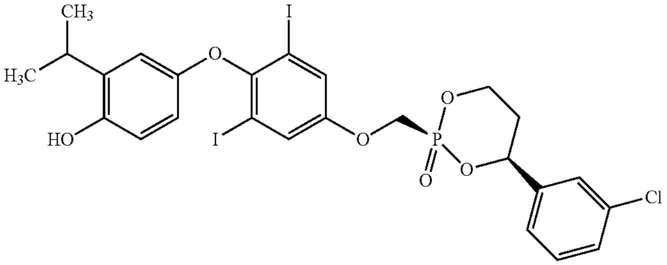 [SMILES: CC(C)c1cc(Oc2c(I)cc(OC[P@@]3(=O)OCC[C@@H](c4cccc(Cl)c4)O3)cc2I)ccc1O] | 13-10 |

-continued
| Structure | Compound Number |
|---|---|
| 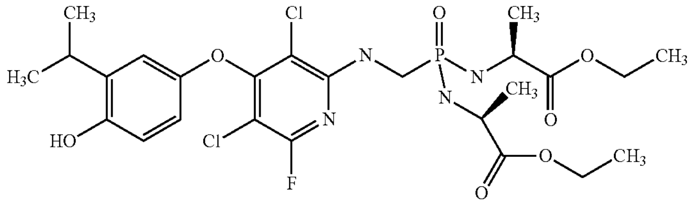 [SMILES: CCOC(=O)[C@H](C)NP(=O)(CNc1nc(F)c(Cl)c(Oc2ccc(O)c(C(C)C)c2)c1Cl)N[C@@H](C)C(=O)OCC] | 15-6 |
| 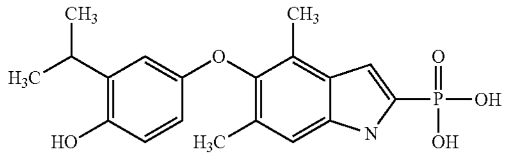 [SMILES: Cc1cc2[nH]c(P(=O)(O)O)cc2c(C)c1Oc1ccc(O)c(C(C)C)c1] | 66 |
| 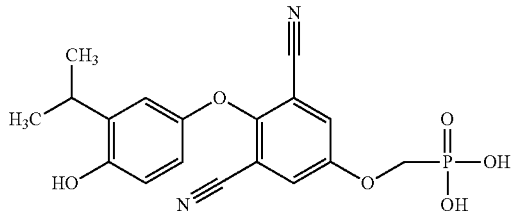 [SMILES: CC(C)c1cc(Oc2c(C#N)cc(OCP(=O)(O)O)cc2C#N)ccc1O] | 56 |
| 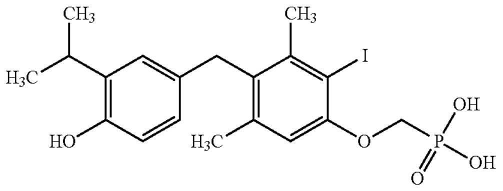 [SMILES: Cc1cc(OCP(=O)(O)O)c(I)c(C)c1Cc1ccc(O)c(C(C)C)c1] | 46 |
| 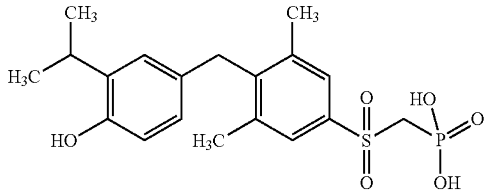 [SMILES: Cc1cc(S(=O)(=O)CP(=O)(O)O)cc(C)c1Cc1ccc(O)c(C(C)C)c1] | 52 |
| 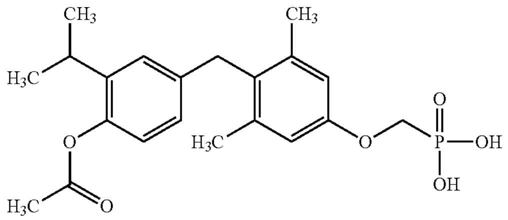 [SMILES: CC(=O)Oc1ccc(Cc2c(C)cc(OCP(=O)(O)O)cc2C)cc1C(C)C] | 58 |
| 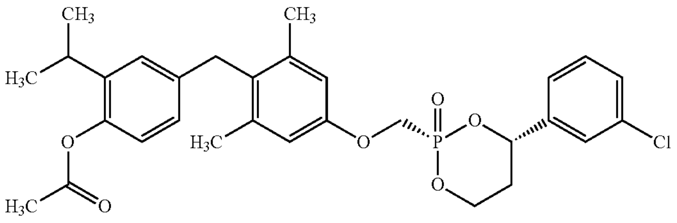 [SMILES: CC(=O)Oc1ccc(Cc2c(C)cc(OC[P@@]3(=O)OCC[C@@H](c4cccc(Cl)c4)O3)cc2C)cc1C(C)C] | 59 |

-continued
| Structure | Compound Number |
|---|---|
| 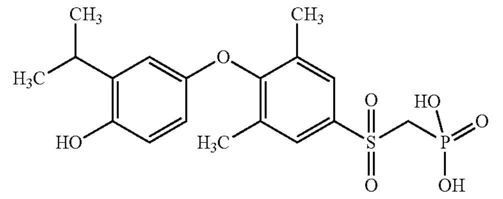 | 53 |
| 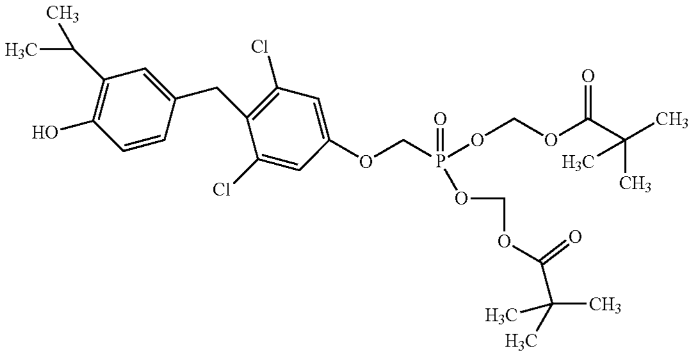 [SMILES: CC(C)c1cc(Cc2c(Cl)cc(OCP(=O)(OCOC(=O)C(C)(C)C)OCOC(=O)C(C)(C)C)cc2Cl)ccc1O] | 12-8 |
| 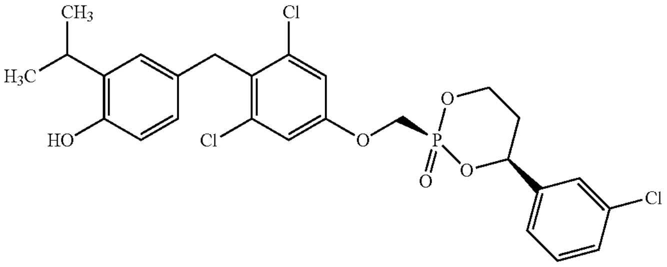 | 13-11 |
| 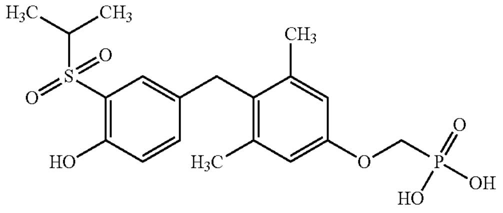 [SMILES: Cc1cc(OCP(=O)(O)O)cc(C)c1Cc1ccc(O)c(S(=O)(=O)C(C)C)c1] | 44 |
| 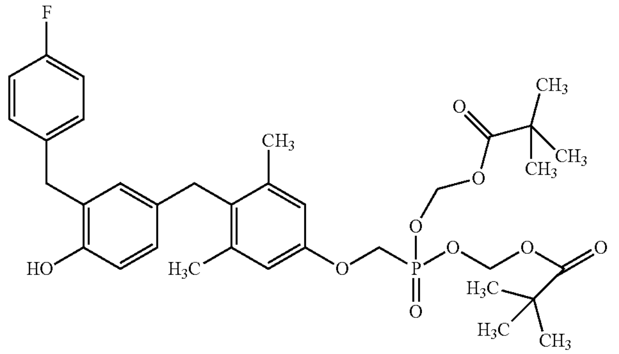 [SMILES: Cc1cc(OCP(=O)(OCOC(=O)C(C)(C)C)OCOC(=O)C(C)(C)C)cc(C)c1Cc1ccc(O)c(Cc2ccc(F)cc2)c1] | 12-6 |

-continued
| Structure | Compound Number |
|---|---|
| 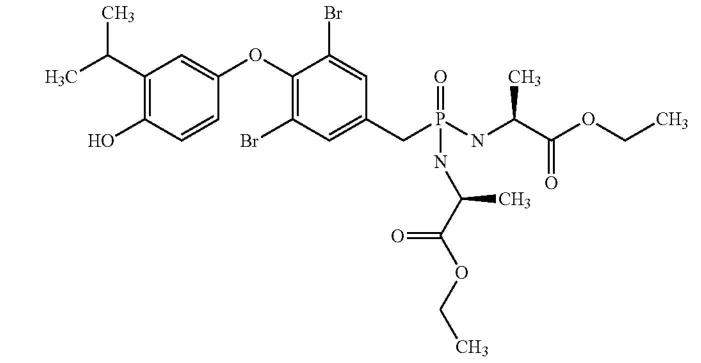 [SMILES: CCOC(=O)[C@H](C)NP(=O)(Cc1cc(Br)c(Oc2ccc(O)c(C(C)C)c2)c(Br)c1)N[C@@H](C)C(=O)OCC] | 15-5 |
| 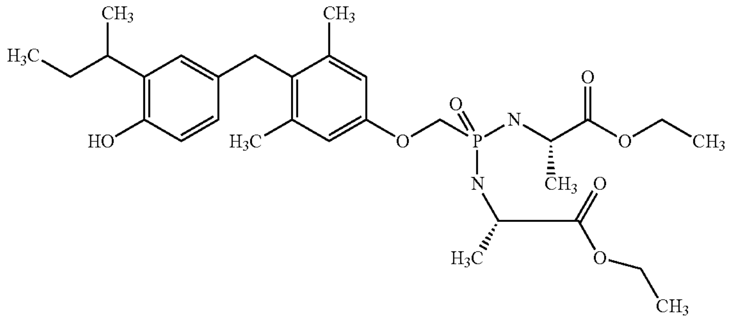 [SMILES: CCOC(=O)[C@H](C)NP(=O)(COc1cc(C)c(Cc2ccc(O)c(C(C)CC)c2)c(C)c1)N[C@@H](C)C(=O)OCC] | 15-4 |
| 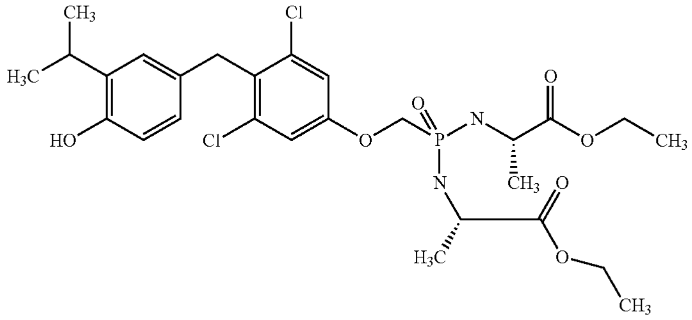 | 15-7 |
| 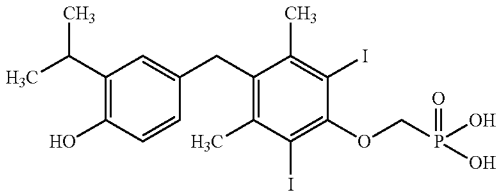 [SMILES: Cc1c(I)c(OCP(=O)(O)O)c(I)c(C)c1Cc1ccc(O)c(C(C)C)c1] | 65-1 |
| 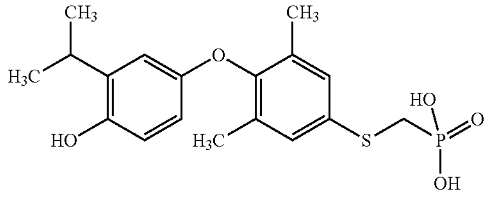 [SMILES: Cc1cc(SCP(=O)(O)O)cc(C)c1Oc1ccc(O)c(C(C)C)c1] | 54 |

-continued
| Structure | Compound Number |
|---|---|
| 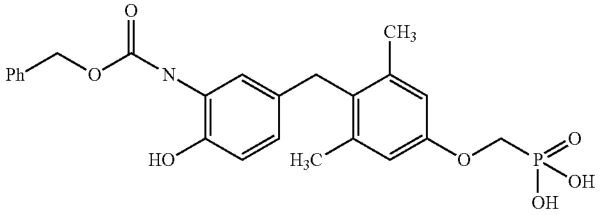 [SMILES: Cc1cc(OCP(=O)(O)O)cc(C)c1Cc1ccc(O)c(NC(=O)OCc2ccccc2)c1] | 50 |
| 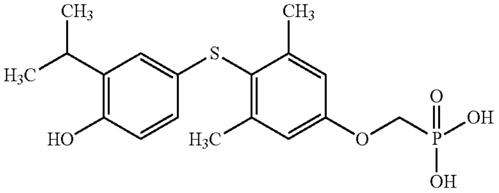 [SMILES: Cc1cc(OCP(=O)(O)O)cc(C)c1Sc1ccc(O)c(C(C)C)c1] | 43 |
| 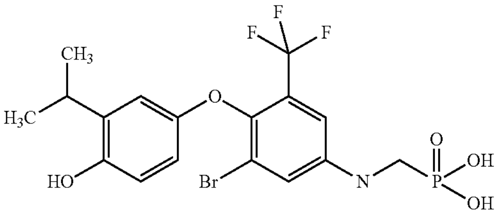 [SMILES: CC(C)c1cc(Oc2c(Br)cc(NCP(=O)(O)O)cc2C(F)(F)F)ccc1O] | 63 |
| 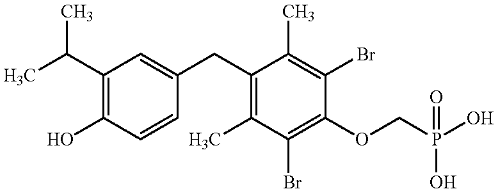 [SMILES: Cc1c(Br)c(OCP(=O)(O)O)c(Br)c(C)c1Cc1ccc(O)c(C(C)C)c1] | 65-2 |
| 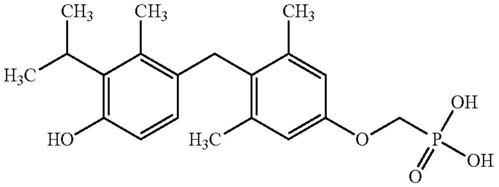 [SMILES: Cc1cc(OCP(=O)(O)O)cc(C)c1Cc1ccc(O)c(C(C)C)c1C] | 7-16 |
| 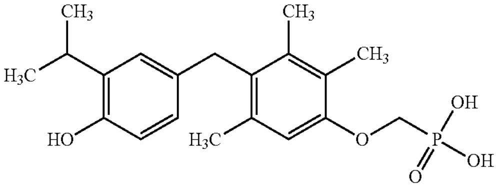 [SMILES: Cc1cc(OCP(=O)(O)O)c(C)c(C)c1Cc1ccc(O)c(C(C)C)c1] | 61 |

-continued
| Structure | Compound Number |
|---|---|
| 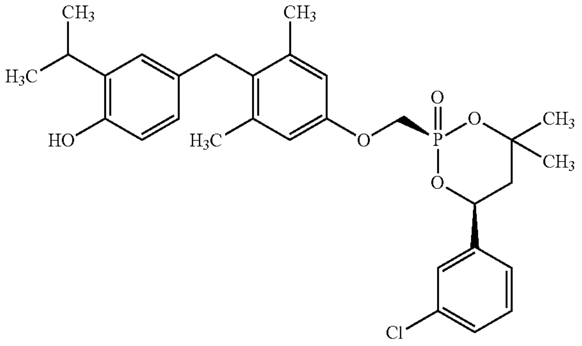 [SMILES: Cc1cc(OC[P@]2(=O)O[C@H](c3cccc(Cl)c3)CC(C)(C)O2)cc(C)c1Cc1ccc(O)c(C(C)C)c1] | 13-13-cis |
| 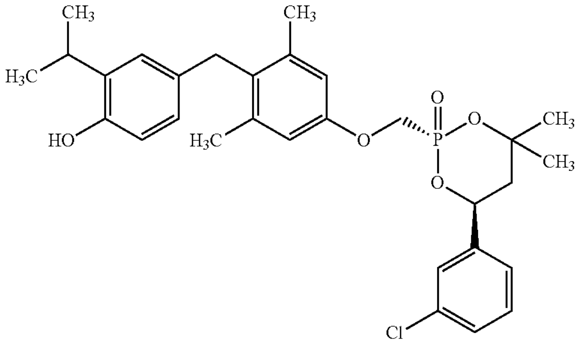 [SMILES: Cc1cc(OC[P@@]2(=O)O[C@H](c3cccc(Cl)c3)CC(C)(C)O2)cc(C)c1Cc1ccc(O)c(C(C)C)c1] | 13-13-trans |
| 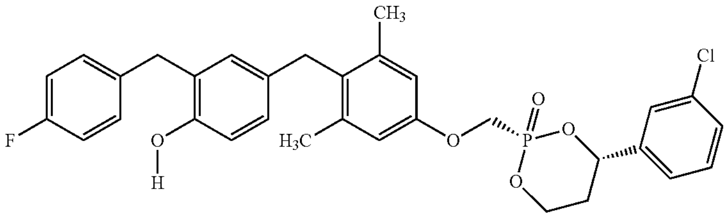 [SMILES: Cc1cc(OC[P@@]2(=O)OCC[C@@H](c3cccc(Cl)c3)O2)cc(C)c1Cc1ccc(O)c(Cc2ccc(F)cc2)c1] | 13-14-cis |
| 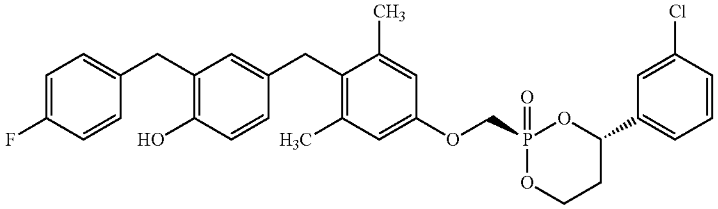 [SMILES: Cc1cc(OC[P@]2(=O)OCC[C@@H](c3cccc(Cl)c3)O2)cc(C)c1Cc1ccc(O)c(Cc2ccc(F)cc2)c1] | 13-14-trans |
| 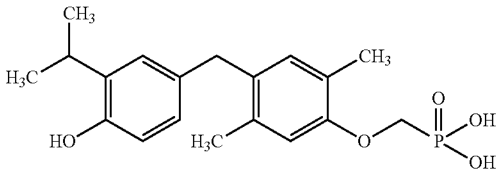 [SMILES: Cc1cc(OCP(=O)(O)O)c(C)cc1Cc1ccc(O)c(C(C)C)c1] | 7-17 |

-continued

| Structure | Compound Number |
|---|---|
| 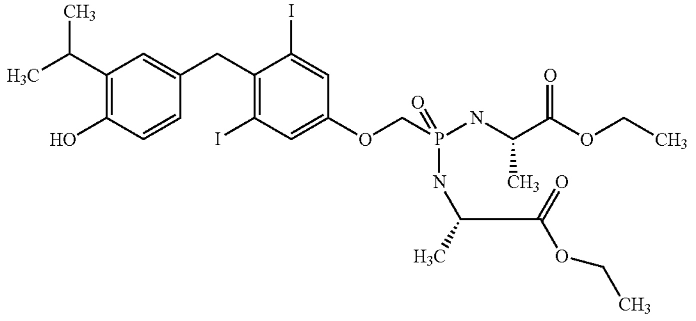 [SMILES: CCOC(=O)[C@H](C)NP(=O)(COc1cc(I)c(Cc2ccc(O)c(C(C)C)c2)c(I)c1)N[C@@H](C)C(=O)OCC] | 15-8 |
| 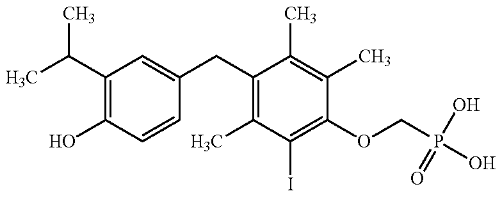 [SMILES: Cc1c(C)c(OCP(=O)(O)O)c(I)c(C)c1Cc1ccc(O)c(C(C)C)c1] | 62 |
| 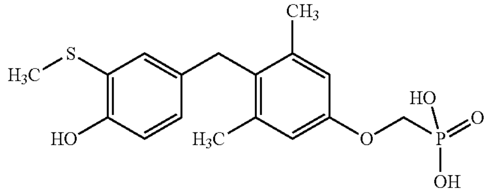 [SMILES: CSc1cc(Cc2c(C)cc(OCP(=O)(O)O)cc2C)ccc1O] | 55 |
| 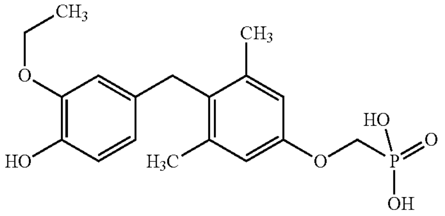 [SMILES: CCOc1cc(Cc2c(C)cc(OCP(=O)(O)O)cc2C)ccc1O] | 7-15 |

or pharmaceutically acceptable salts thereof.

The compounds described above may be prepared according to known methods, including those described in U.S. Pat. No. 7,829,552, which is incorporated herein by reference in its entirety. Additional thyroid receptor agonists are described in U.S. Pat. No. 7,514,419; U.S. Application Publication No. 2009/002895; U.S. Application Publication No. 2010/0081634; U.S. Application Publication No. 2012/0046364; and PCT Application Publication No. WO 2011/038207, all of which are incorporated herein by reference in their entirety.

In some embodiments, the TR-β agonist is a compound having the structure of Formula (A)

(A)

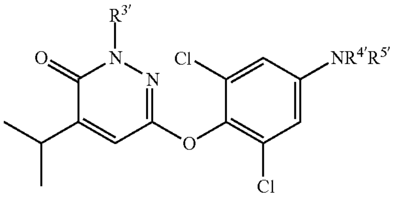

wherein $R^{3'}$ is H or $CH_2R^{a'}$, in which $R^{a'}$ is hydroxyl, O-linked amino acid, —$OP(O)(OH)_2$ or $OC(O)R^{b'}$, $R^{b'}$ being lower alkyl, alkoxy, alkyl acid, cycloalkyl, aryl, heteroaryl, or —$(CH_2)_{n'}$-heteroaryl and n' being 0 or 1;

$R^{4'}$ is H, and $R^{5'}$ is $CH_2COOH$, $C(O)CO_2H$, or an ester or amide thereof, or $R^{4'}$ and $R^{5'}$ together are —N═C($R^{c'}$)—C—(O)—NH—C(O)—; in which $R^{c'}$ is H or cyano;

or pharmaceutically acceptable salts thereof.

In some embodiments, the TR-β agonist is selected from the group consisting of:

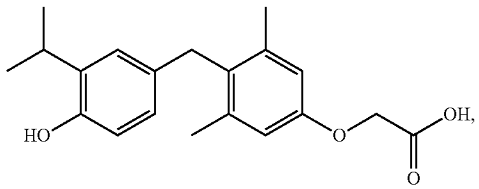

-continued
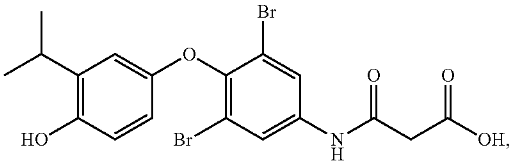
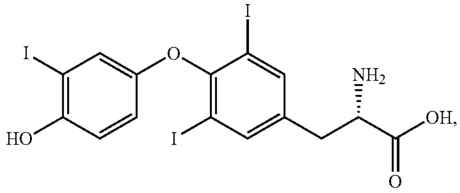
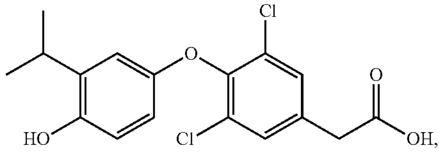
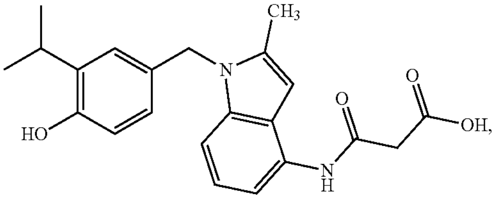
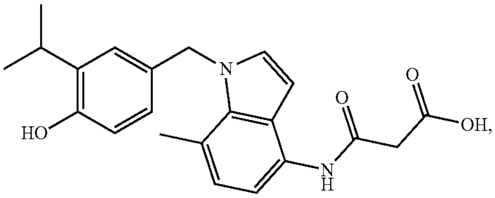
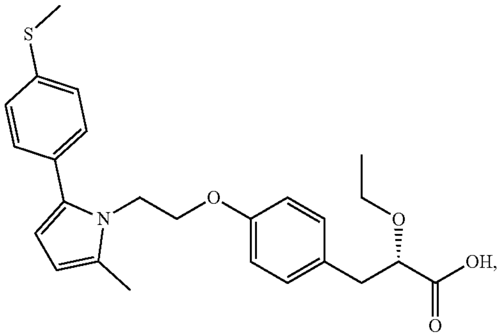
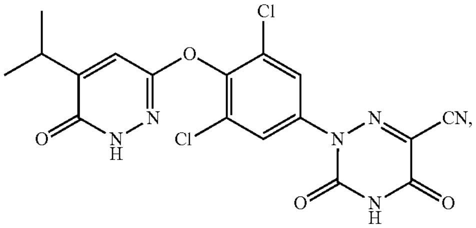
and pharmaceutically acceptable salts thereof.
In some embodiments, the TR-β agonist is a compound selected from the group consisting of
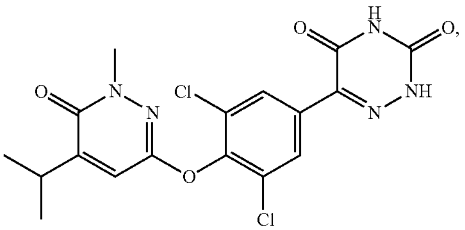
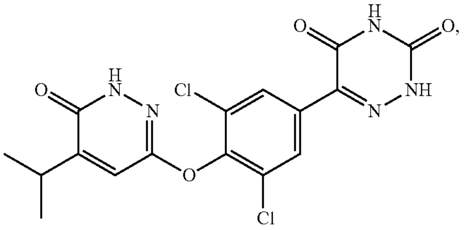
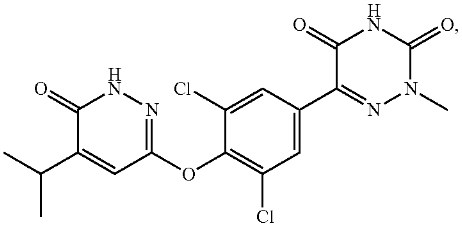
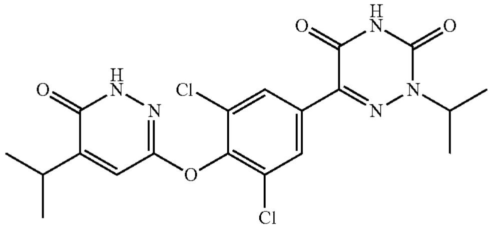
,
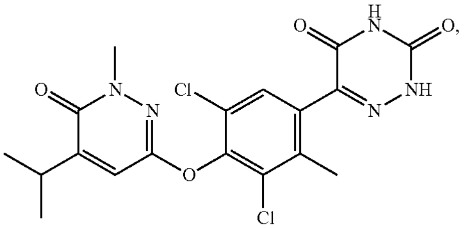
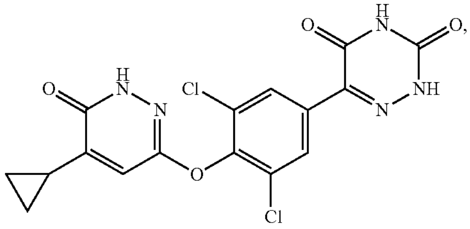
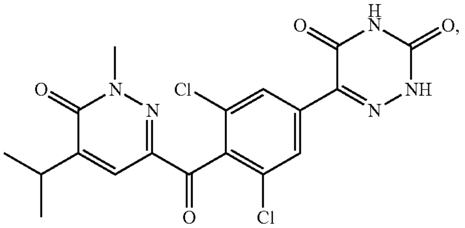

-continued
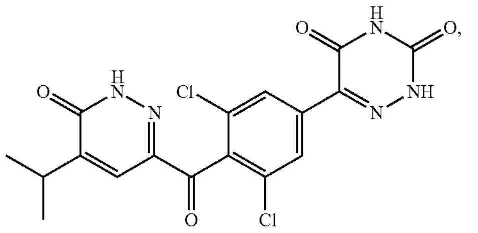
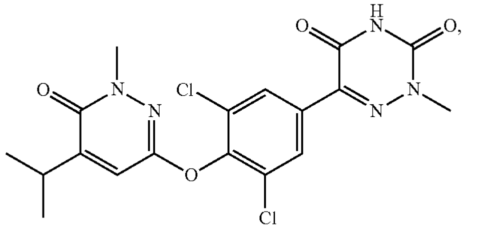
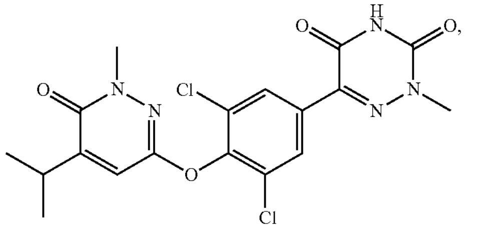
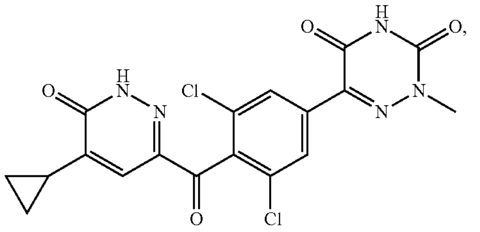
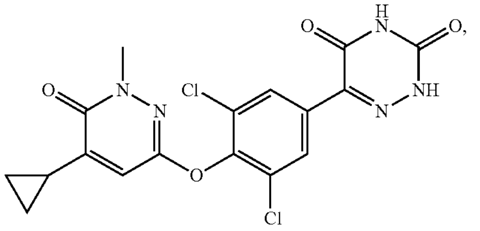
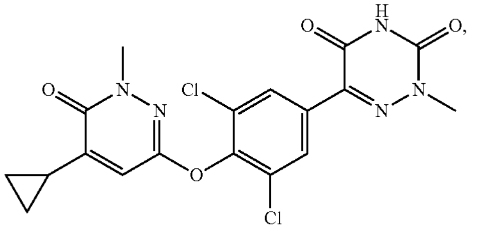
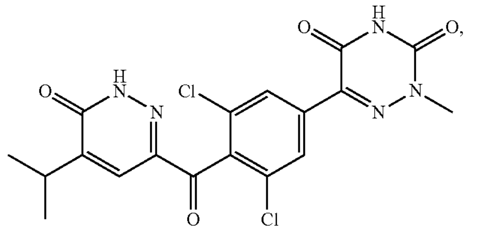
-continued
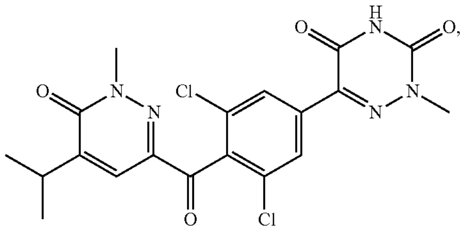
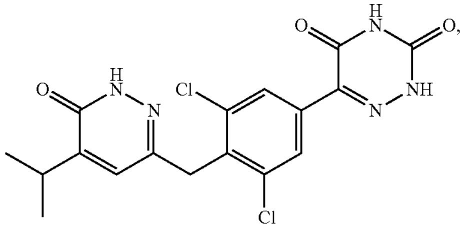
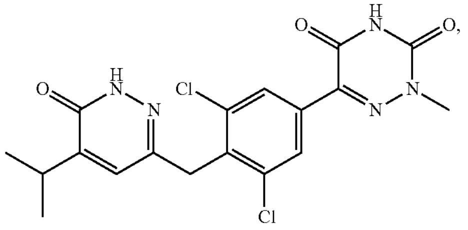
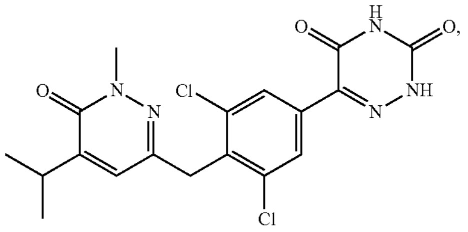
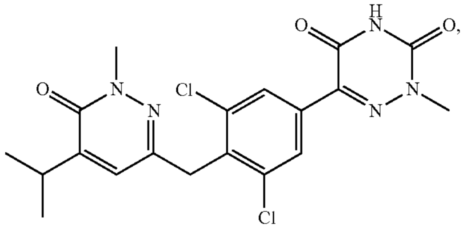
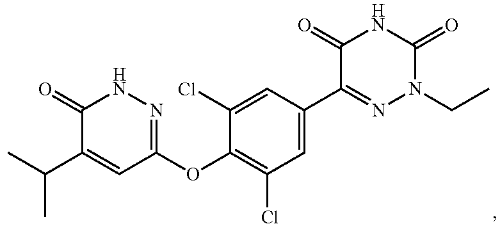
,
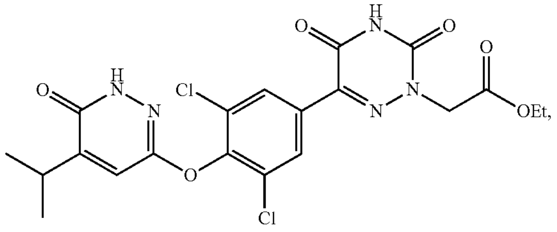

-continued
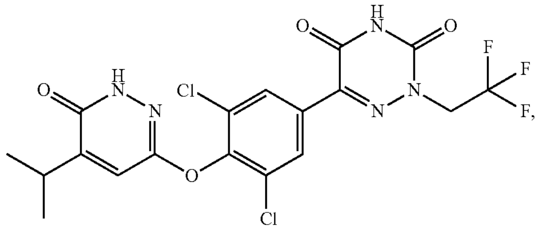
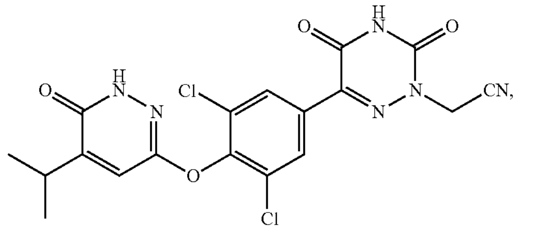
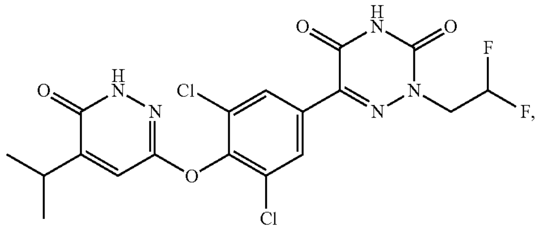
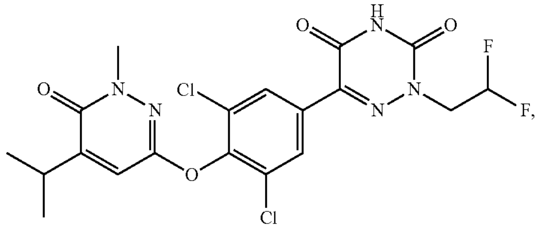
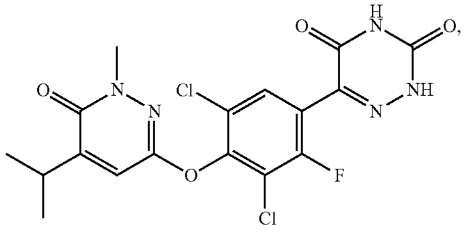
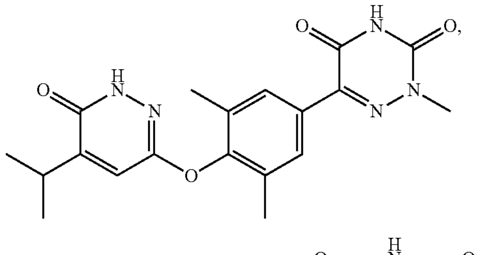
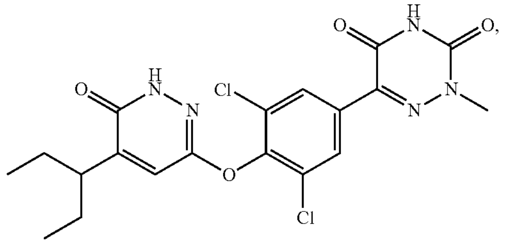
-continued
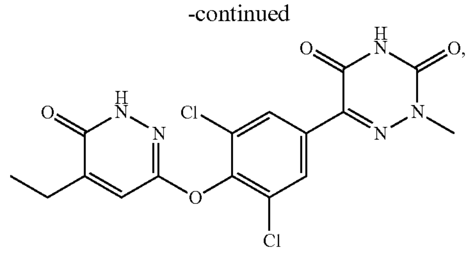
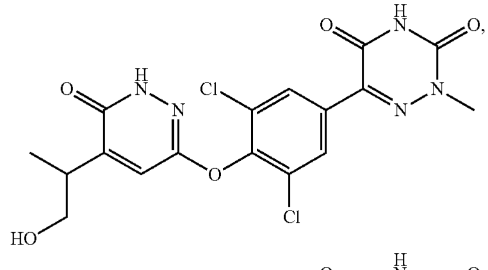
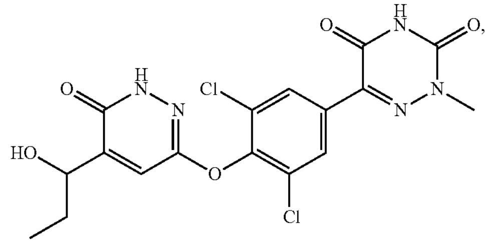
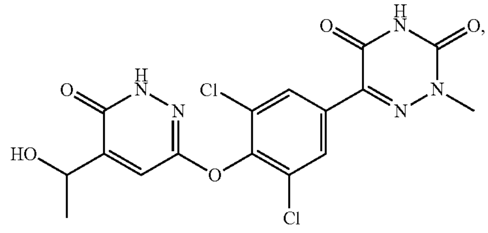
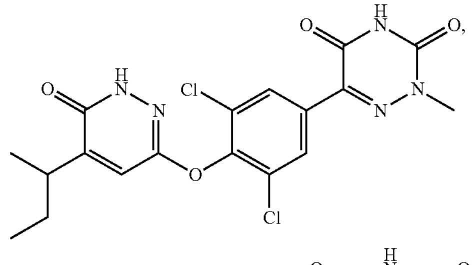
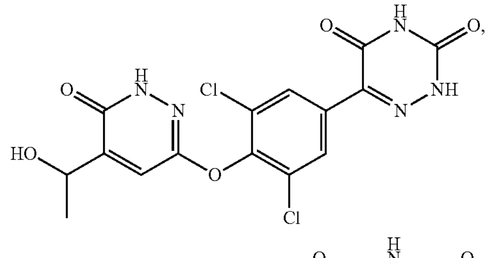
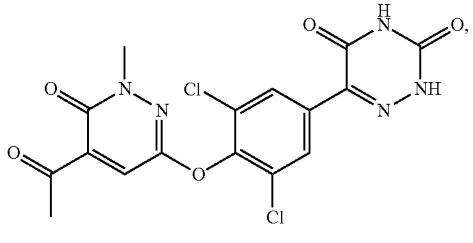 [SMILES: CC(=O)c1cc(Oc2c(Cl)cc(-c3n[nH]c(=O)[nH]c3=O)cc2Cl)nn(C)c1=O]
and pharmaceutically acceptable salts and stereoisomers thereof.

In some embodiments, the TR-β agonist is a compound selected from the group consisting of
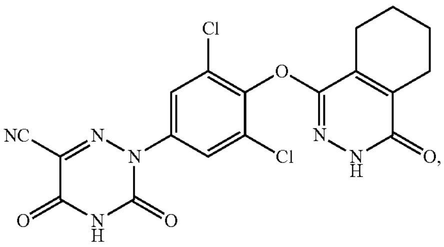
,
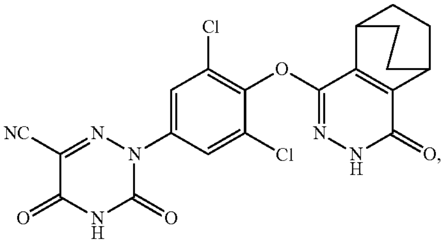
,
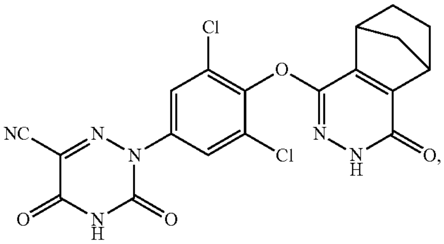
,
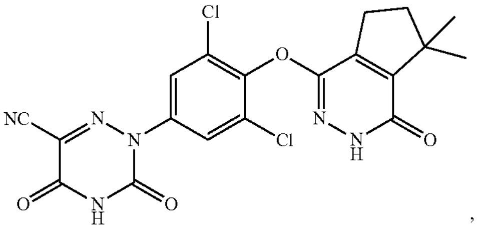
,
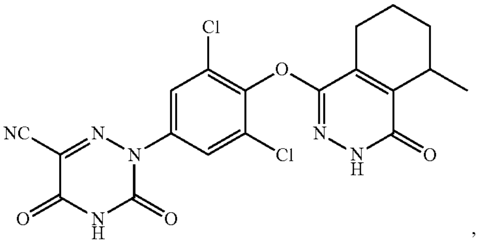
,
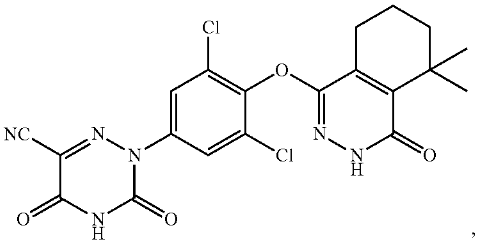
,
-continued
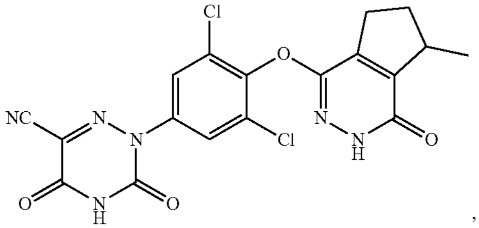
,
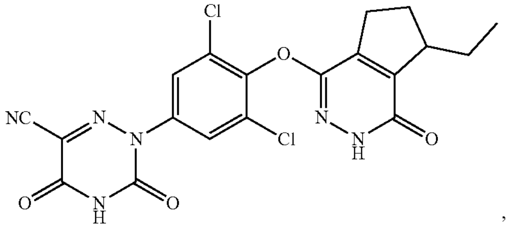
,
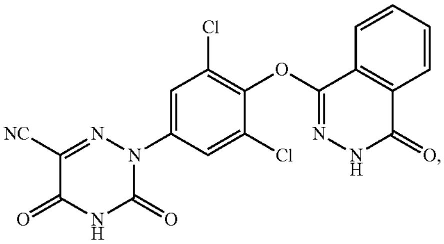
,
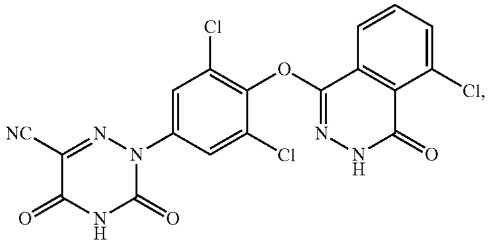
,
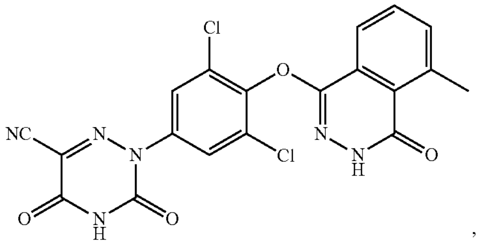
,
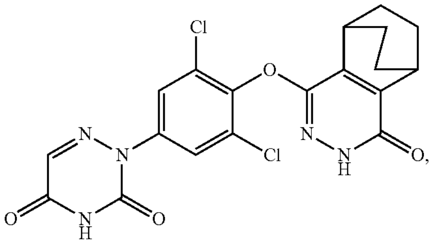
,
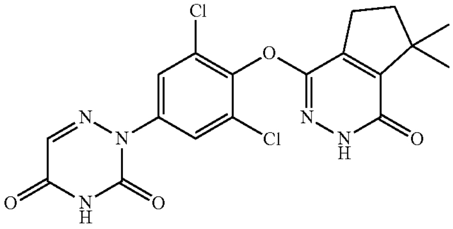
, -continued
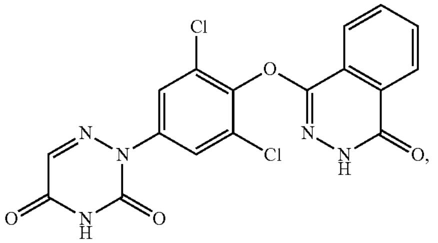
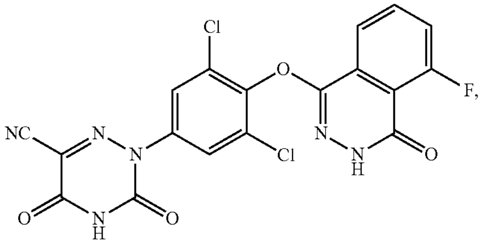
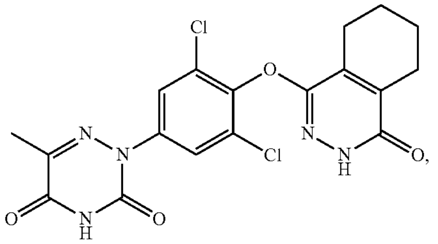
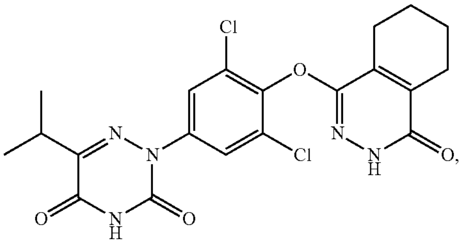
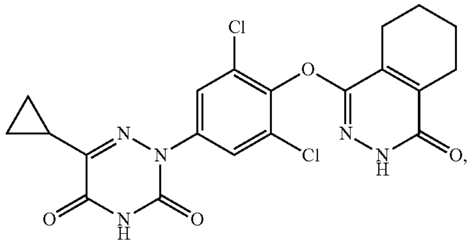
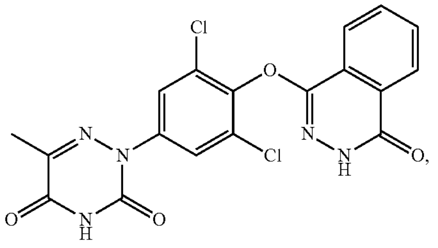
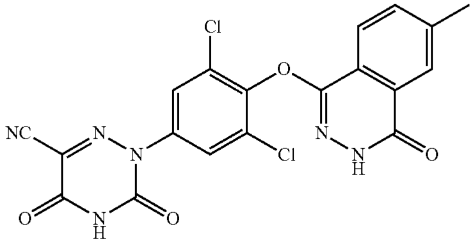
,
-continued
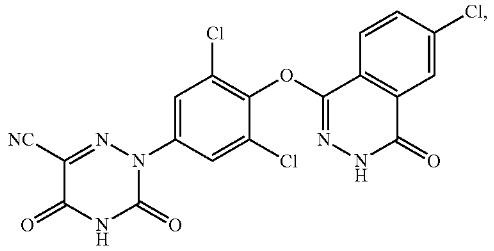 [SMILES: N#Cc1nn(-c2cc(Cl)c(Oc3n[nH]c(=O)c4cc(Cl)ccc34)c(Cl)c2)c(=O)[nH]c1=O]
and pharmaceutically acceptable salts and stereoisomers thereof.
In some embodiments, the TR-β agonist is a compound selected from the group consisting of
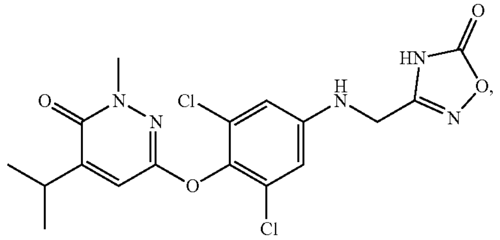
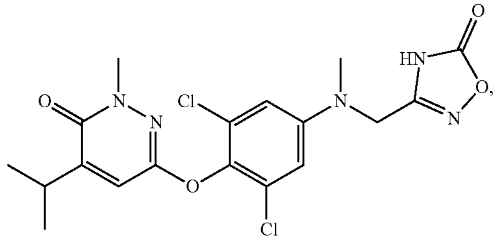
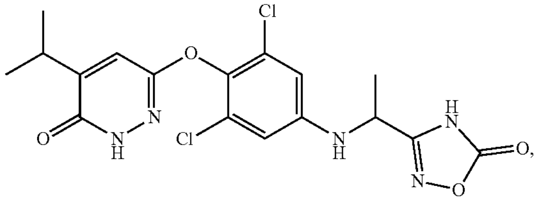
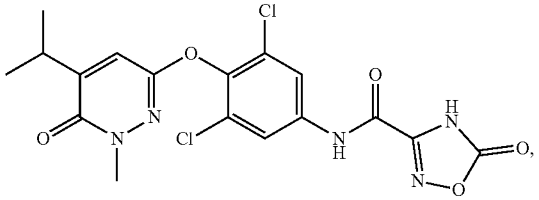
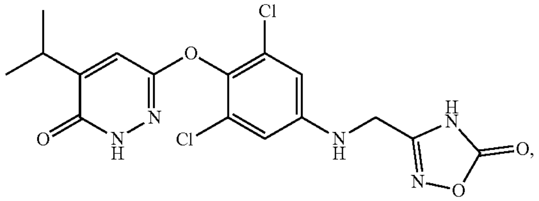
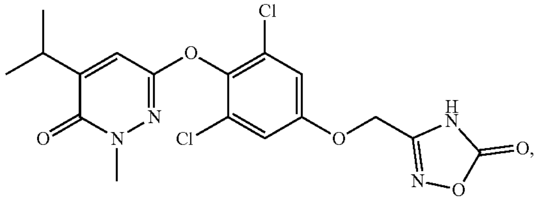

-continued
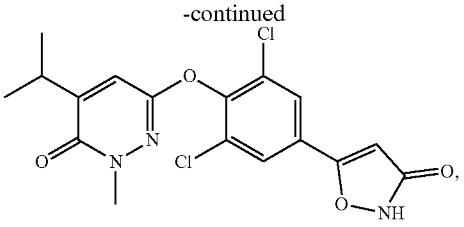
,
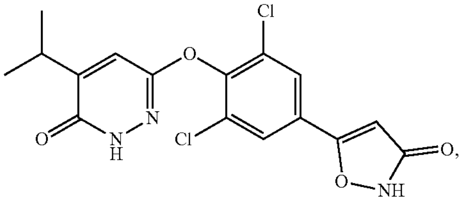
,
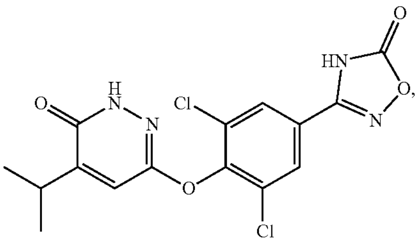
,
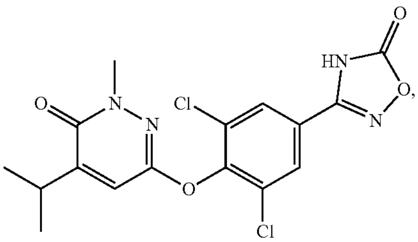
,
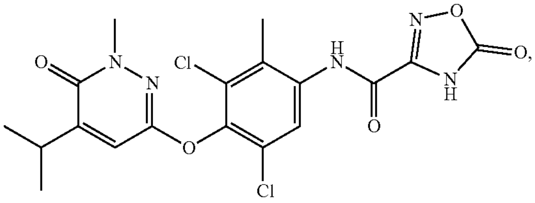
,
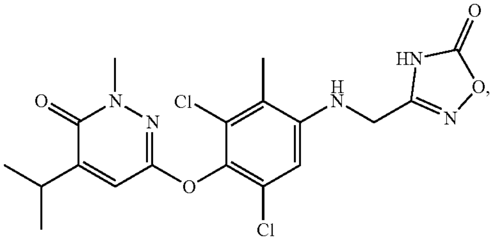
,
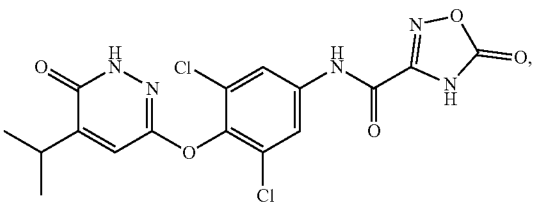
,
-continued
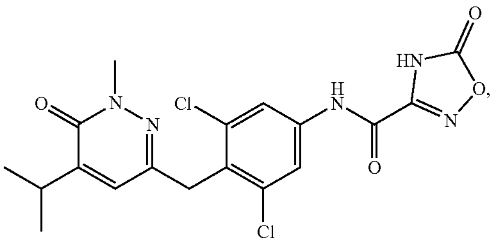
,
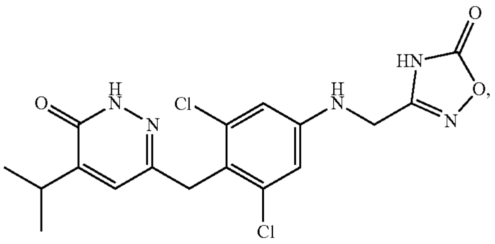
,
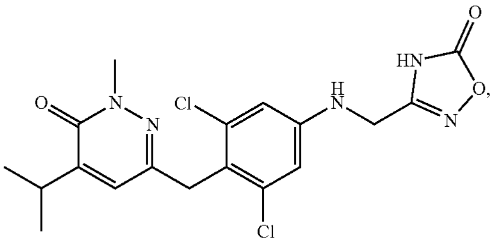
,
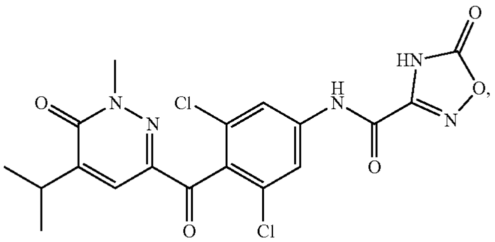
,
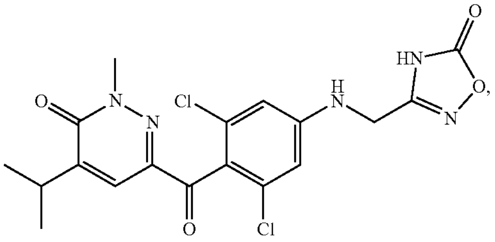
,
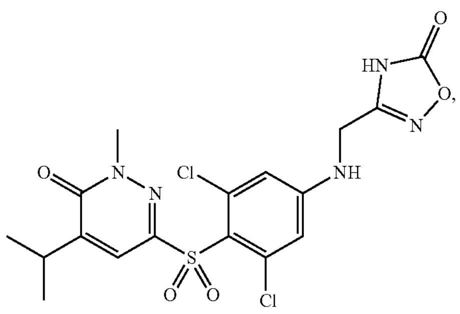
, -continued
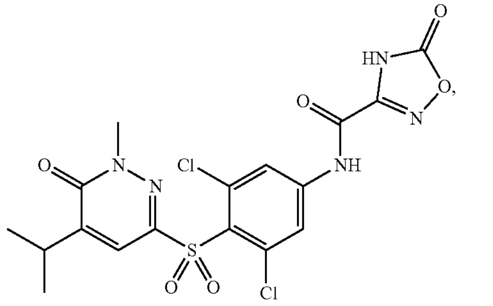
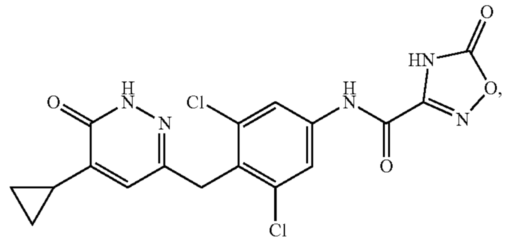
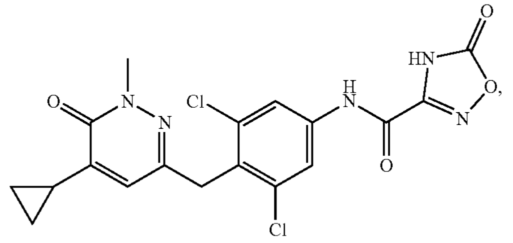
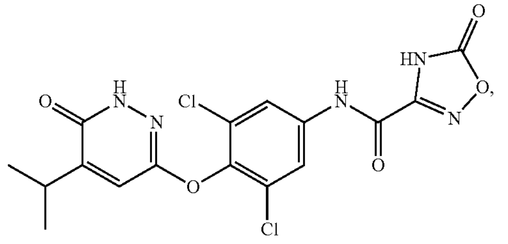
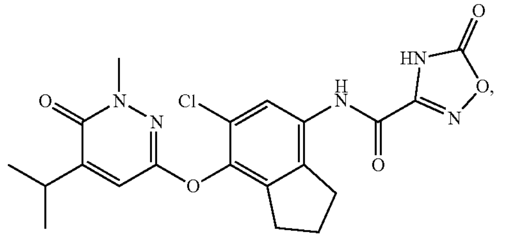
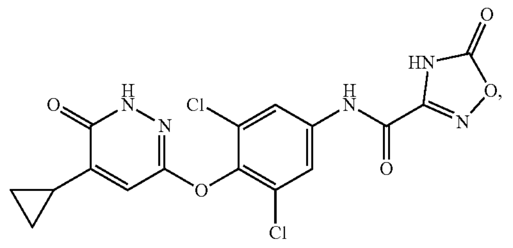
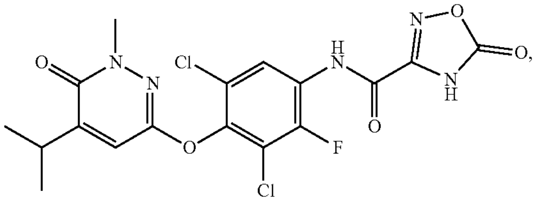
-continued
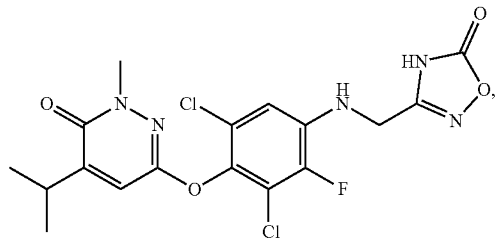
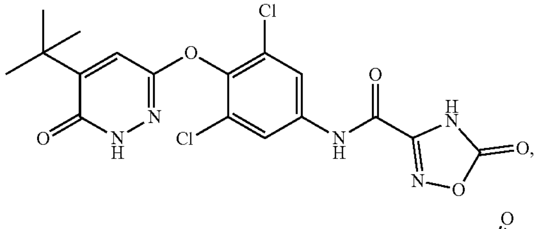
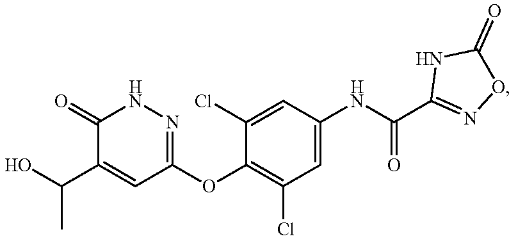
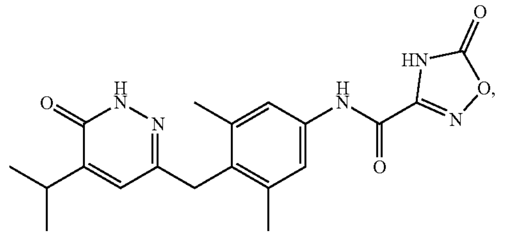
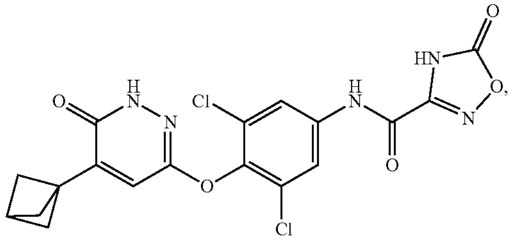
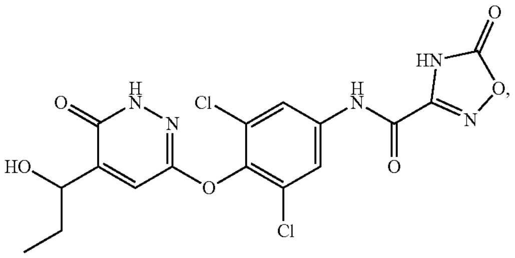
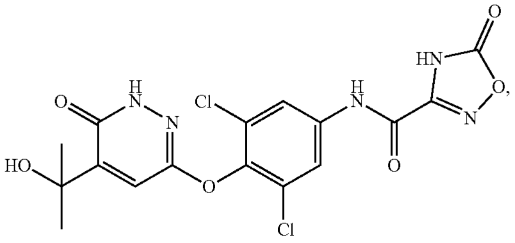

-continued
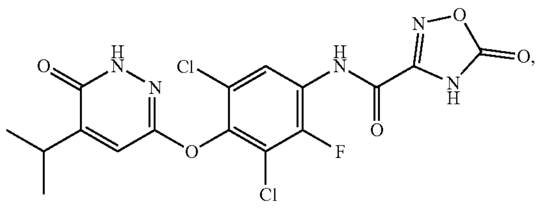
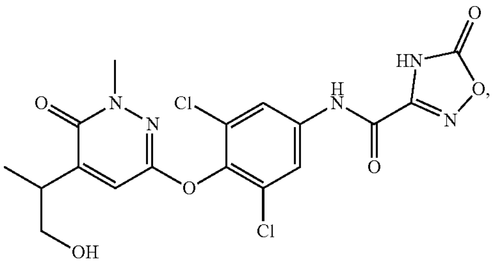
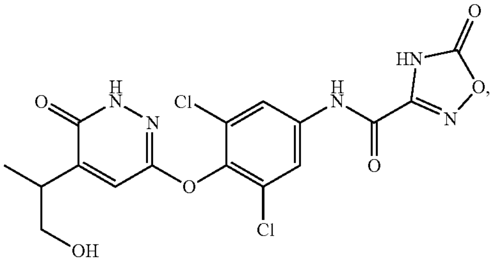
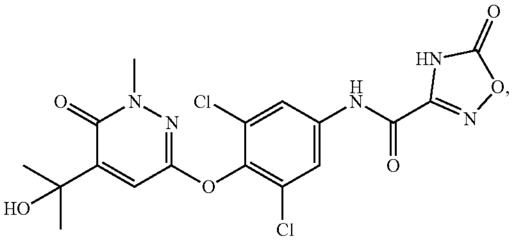
and pharmaceutically acceptable salts and stereoisomers thereof.
In some embodiments, the TR-β agonist is a compound selected from the group consisting of
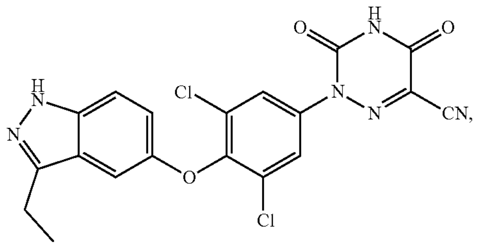
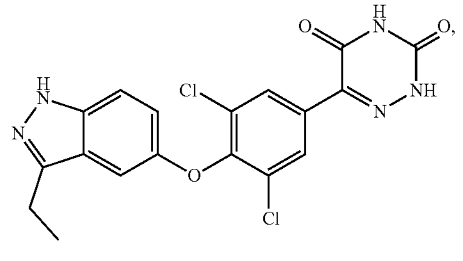
-continued
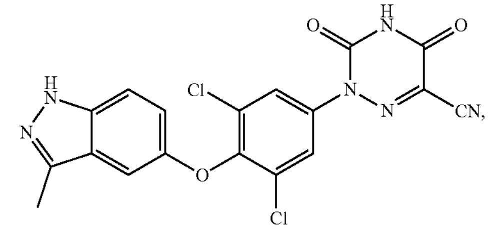
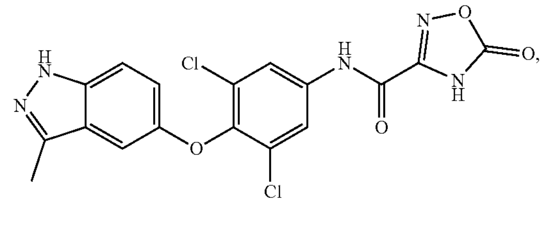
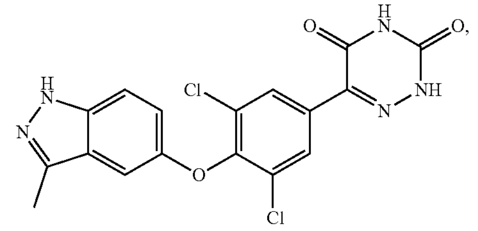
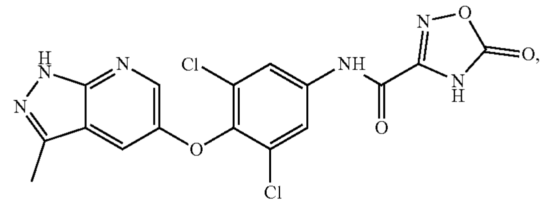
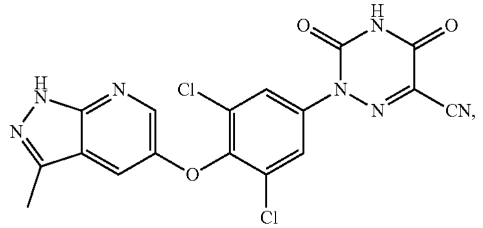
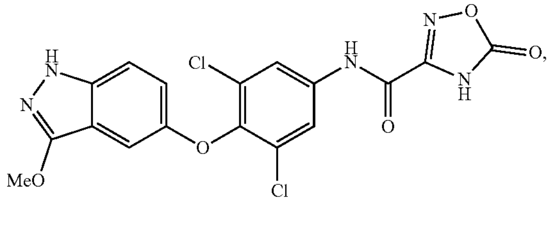
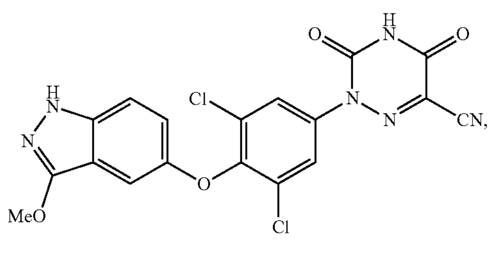

-continued
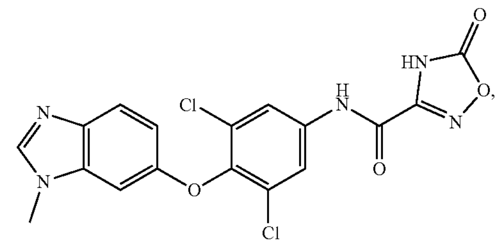
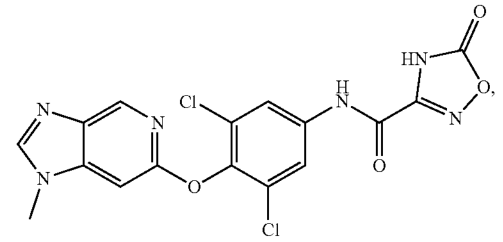
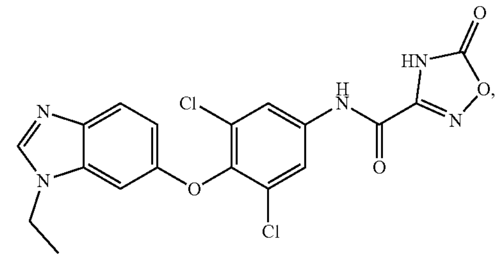
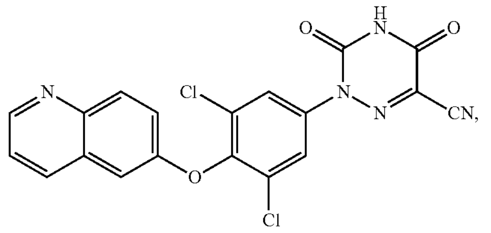
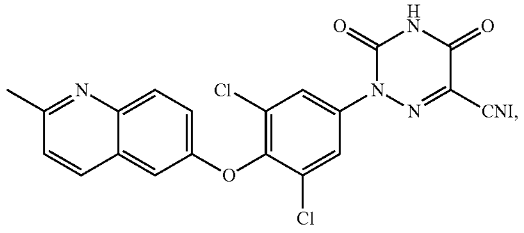
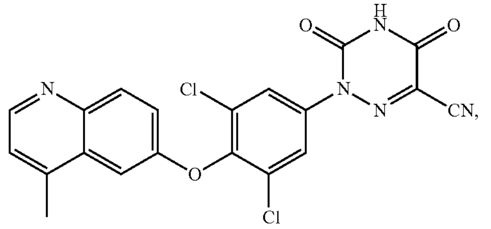
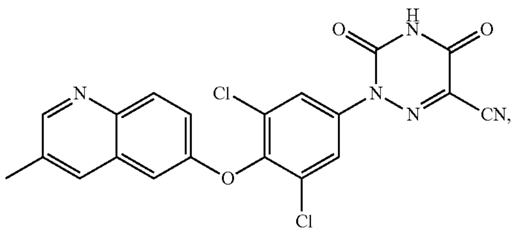
-continued
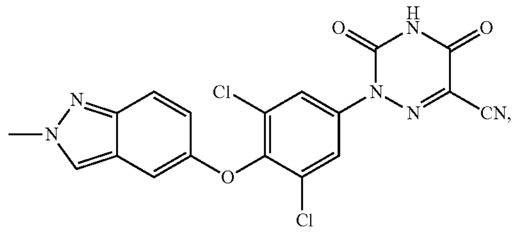
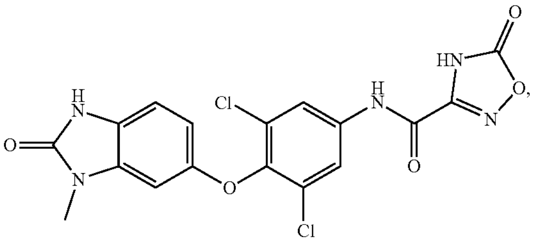
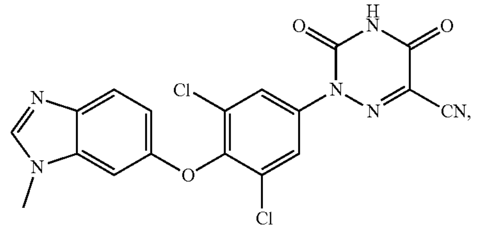
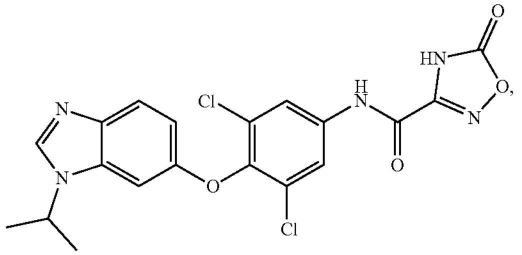
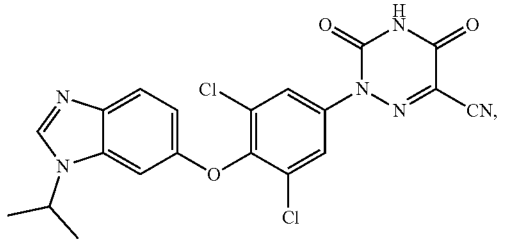
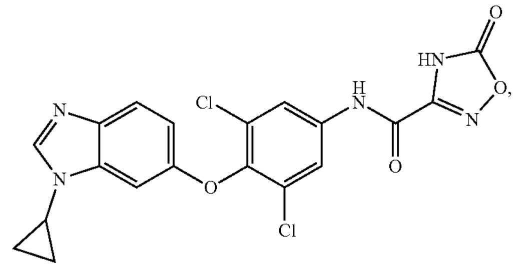
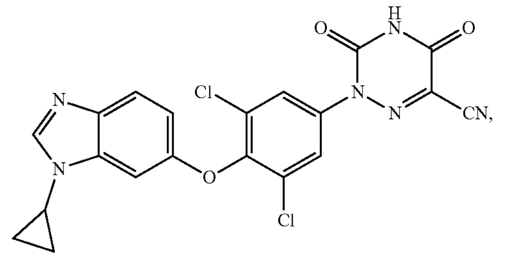

-continued
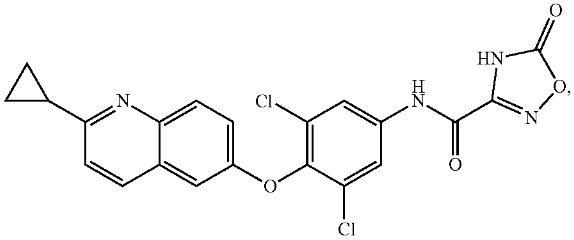
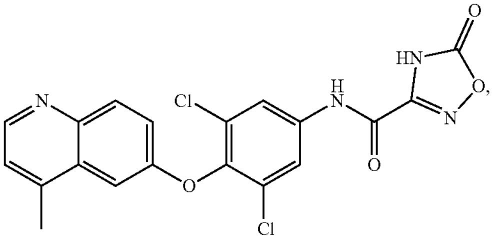
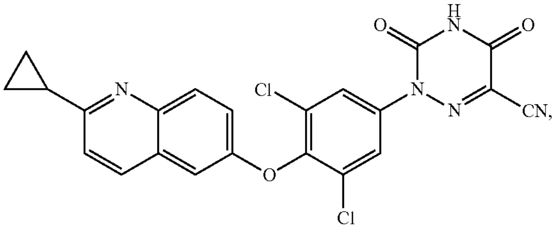
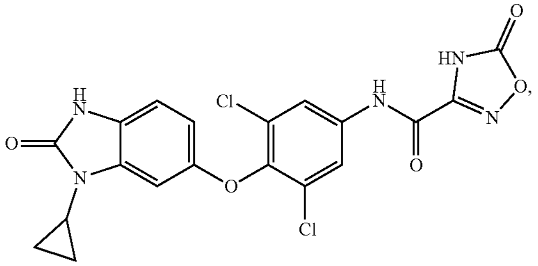
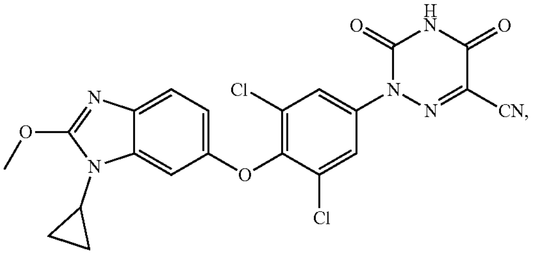
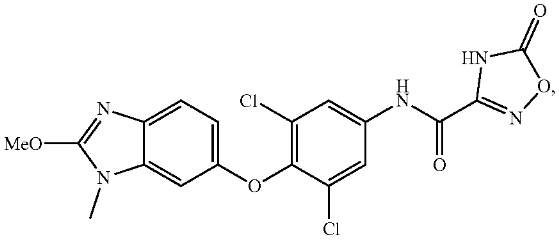
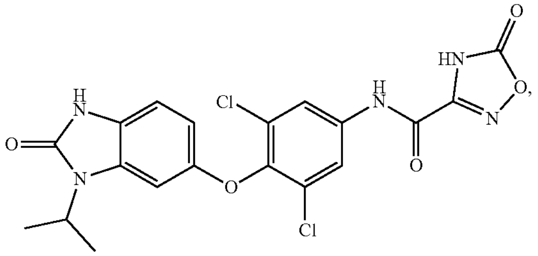
-continued
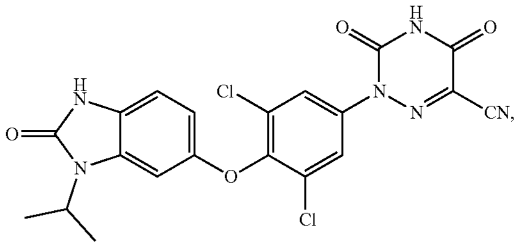
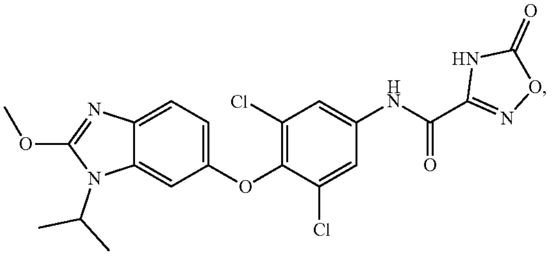
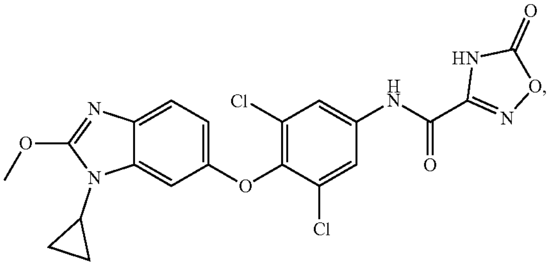
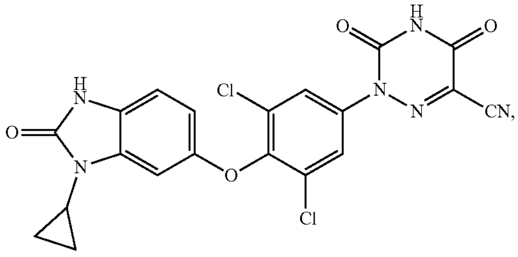
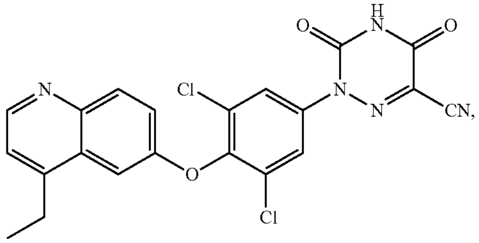
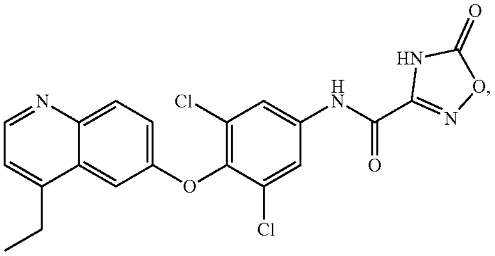

-continued
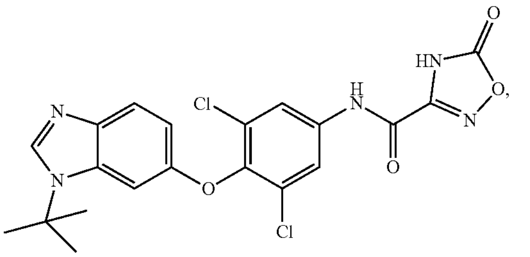
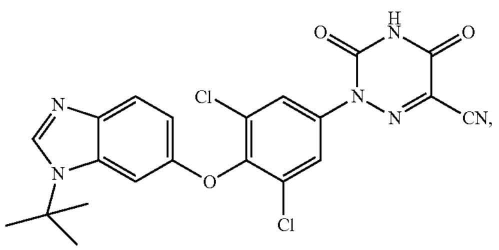
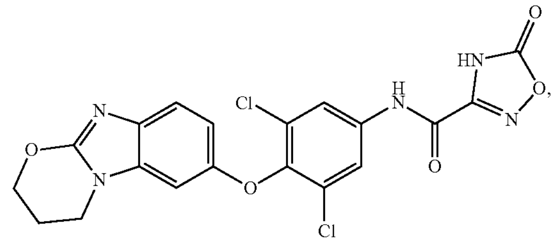
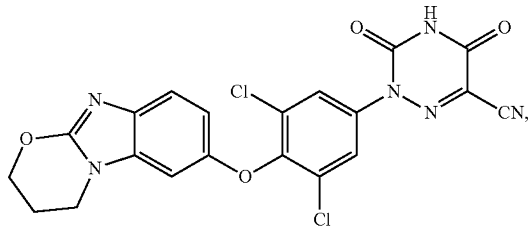
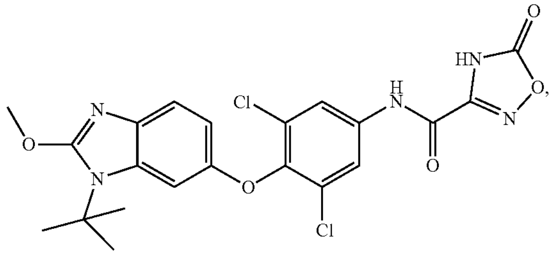
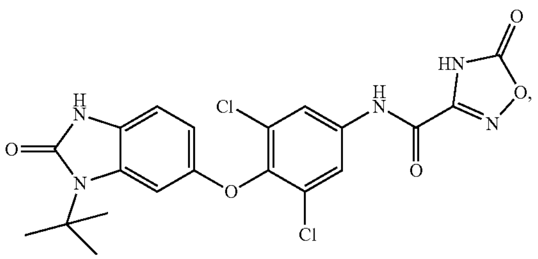
-continued
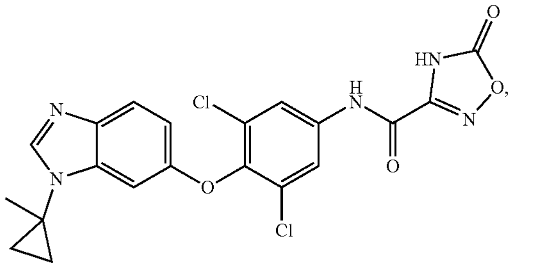
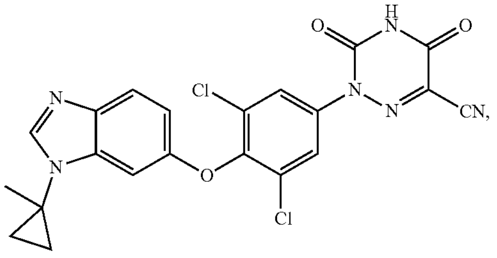
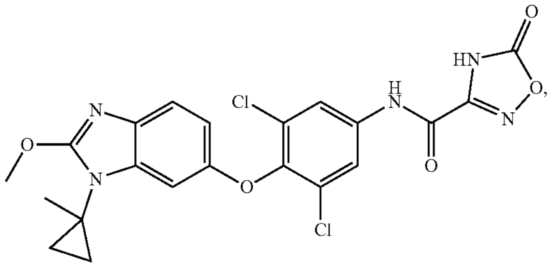
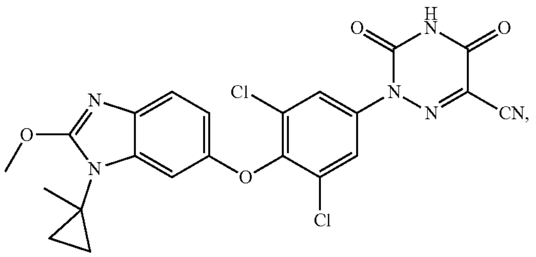
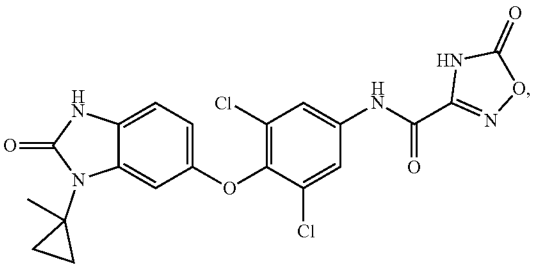
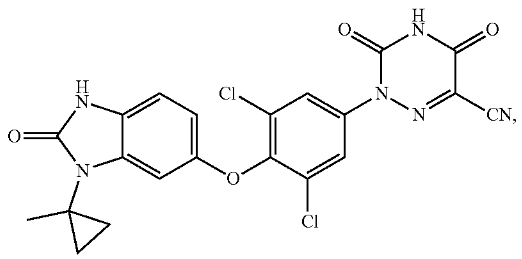

-continued
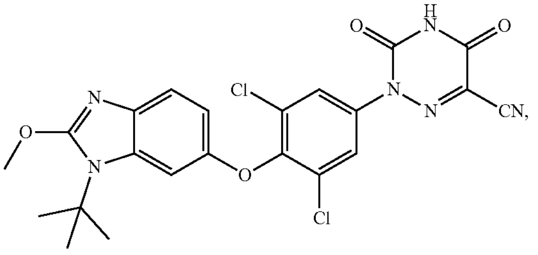
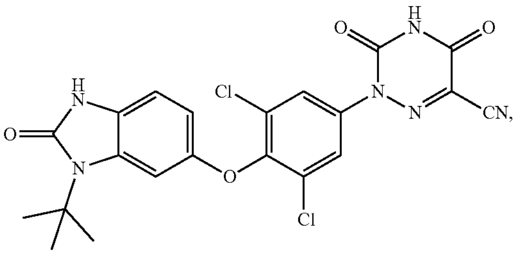
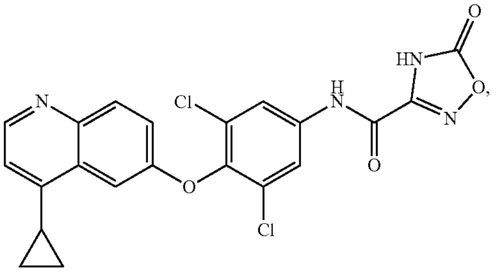
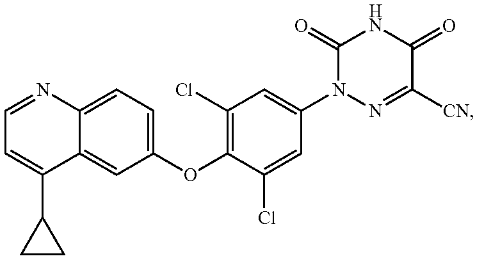
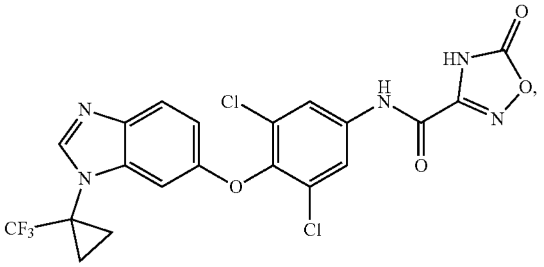
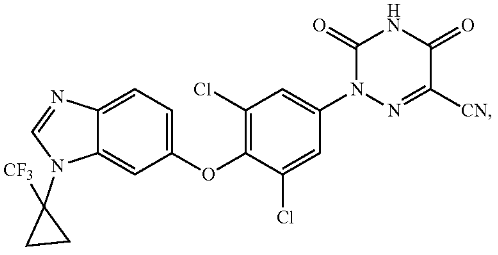
-continued
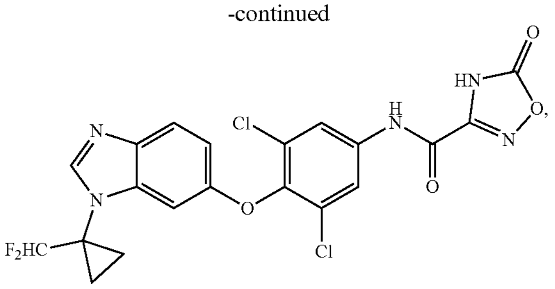
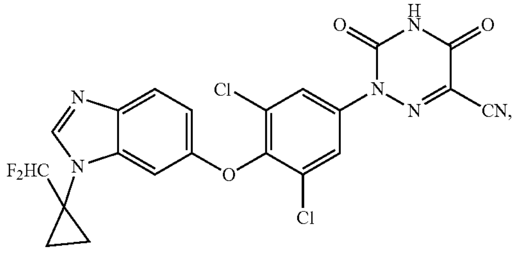
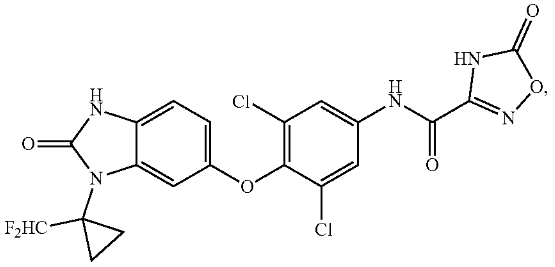
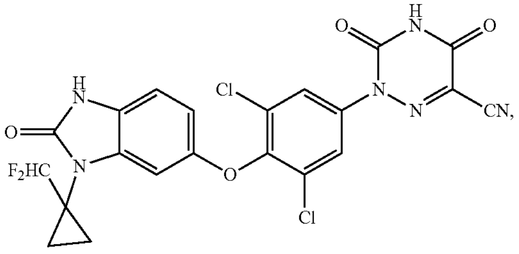
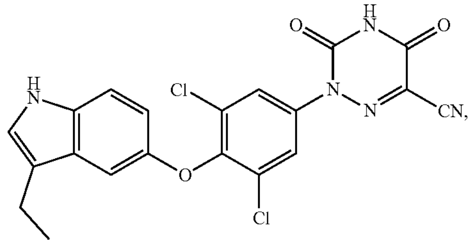
and pharmaceutically acceptable salts and stereoisomers thereof.
In some embodiments, the TR-β agonist is a compound selected from the group consisting of
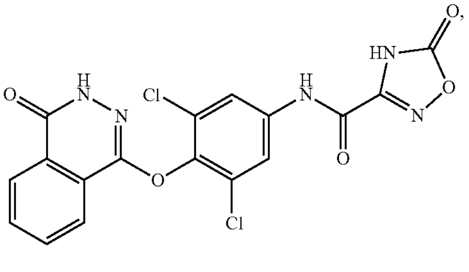

-continued
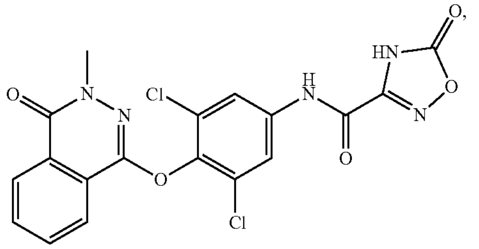
and pharmaceutically acceptable salts and stereoisomers thereof.
In some embodiments, the TR-β agonist is a compound selected from the group consisting of
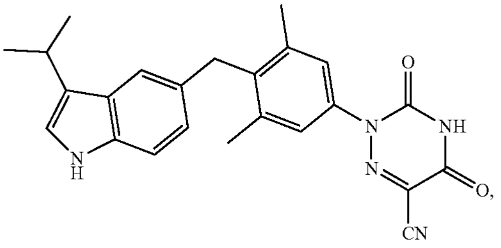
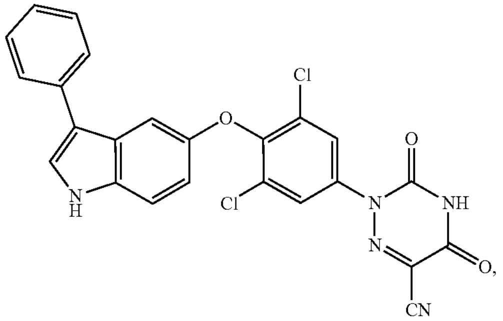
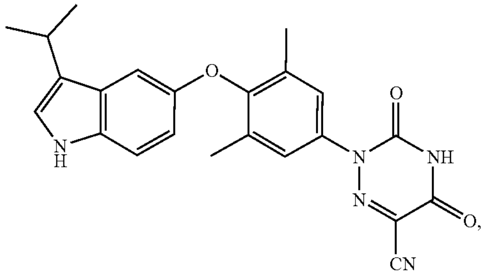
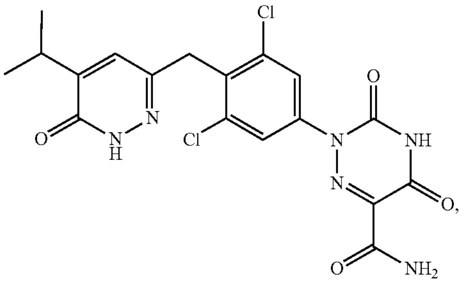
-continued
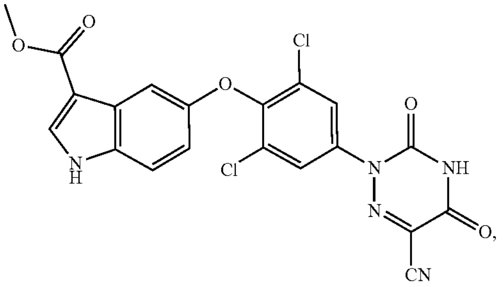
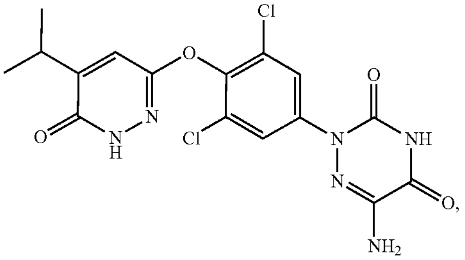
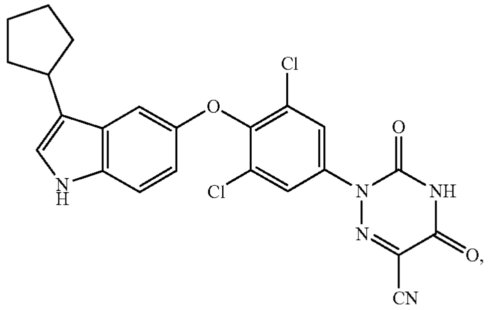
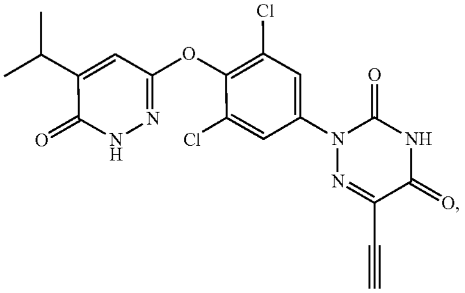
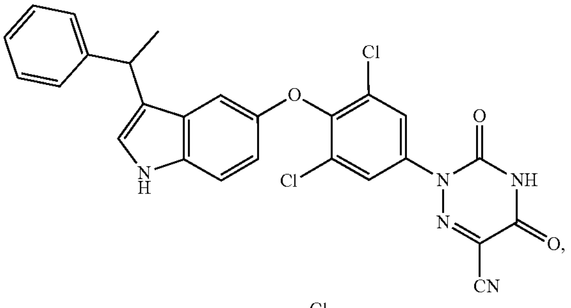
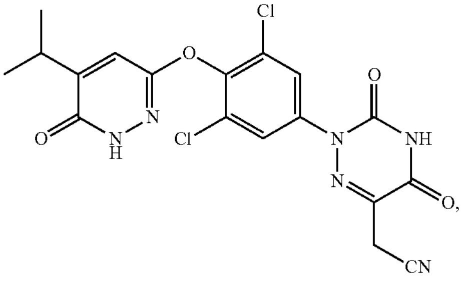

-continued
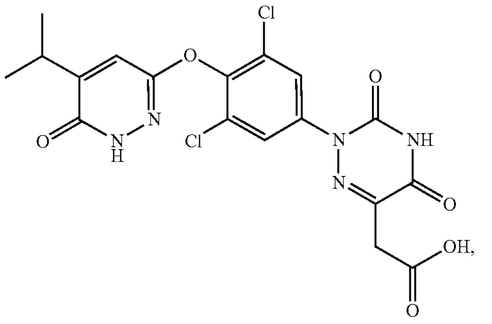
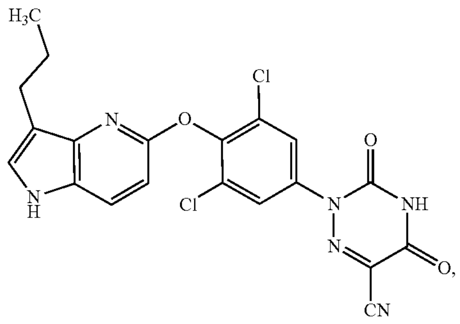
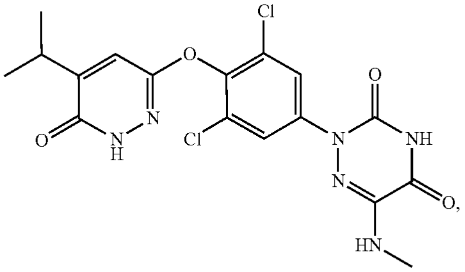
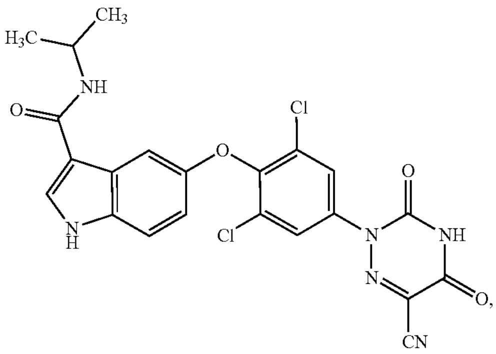
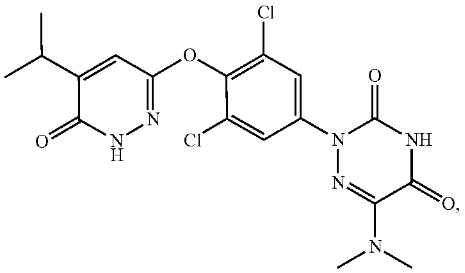
-continued
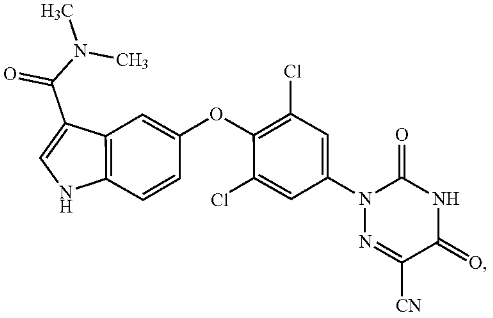
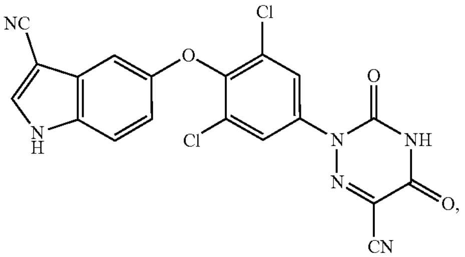
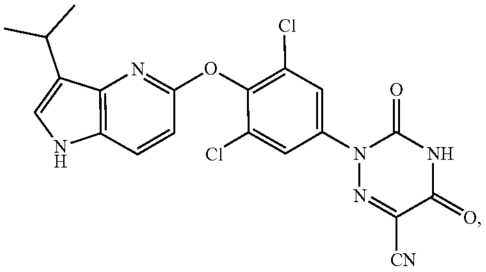
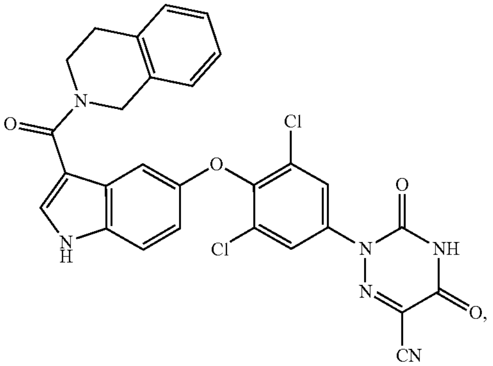
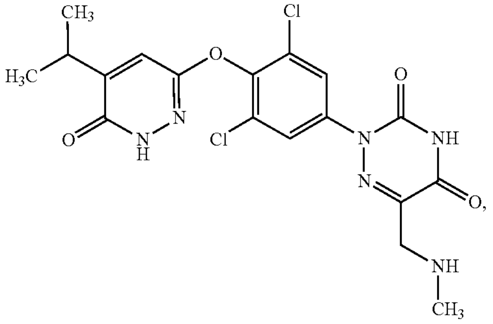

-continued
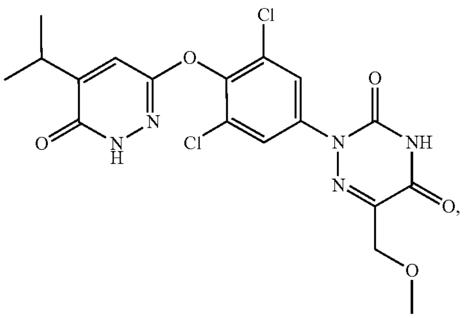,
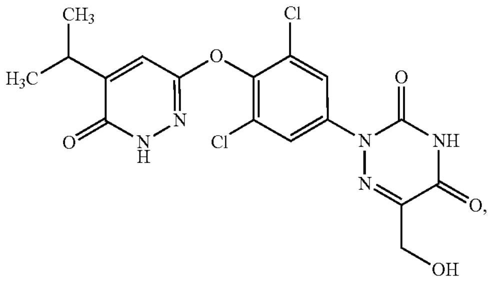,
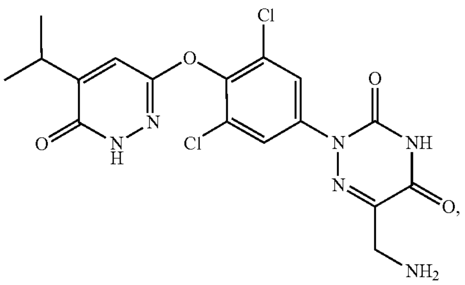,
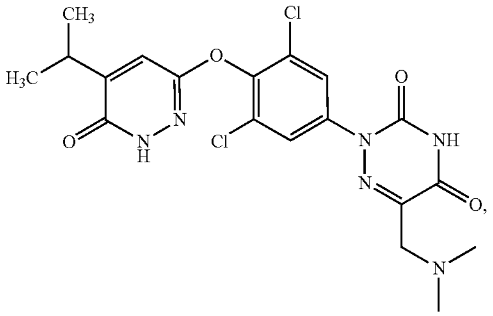,
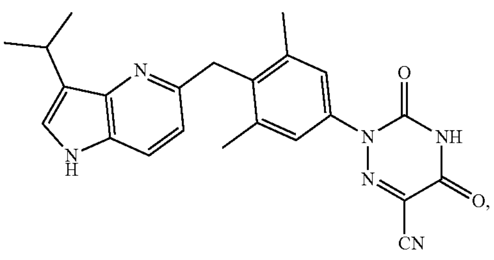,
-continued
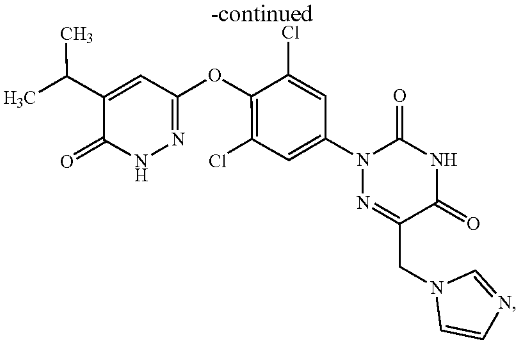,
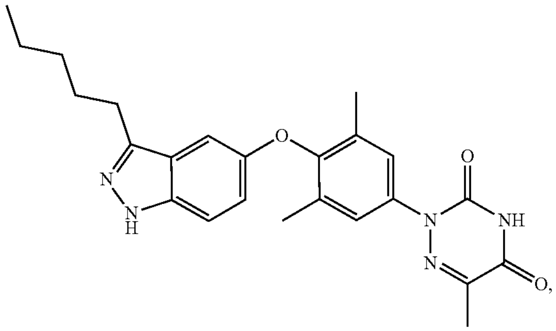,
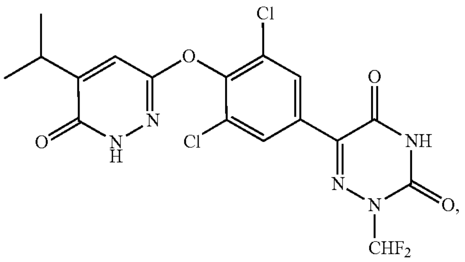,
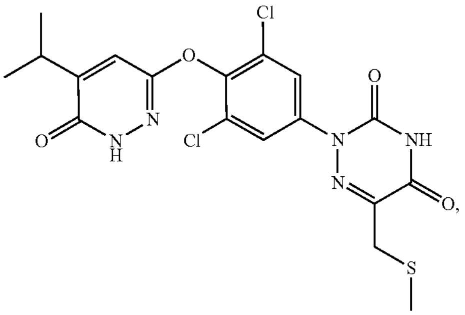,
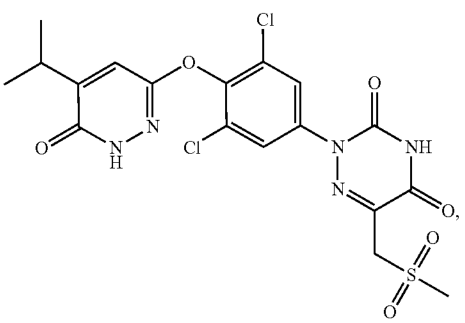, -continued
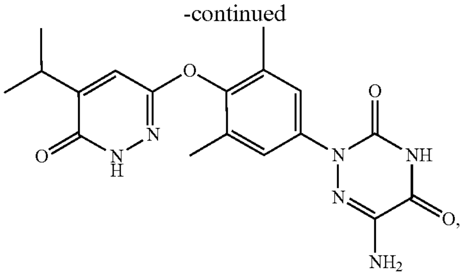
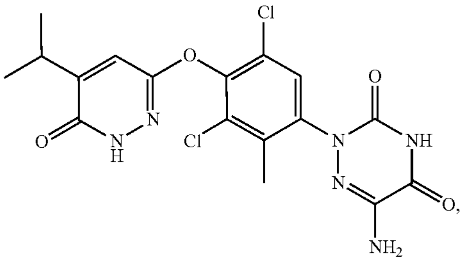
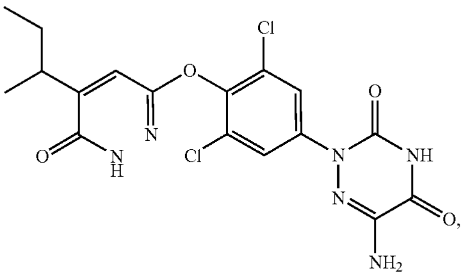
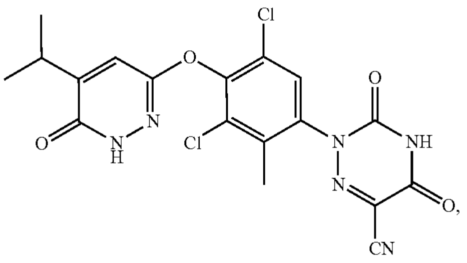
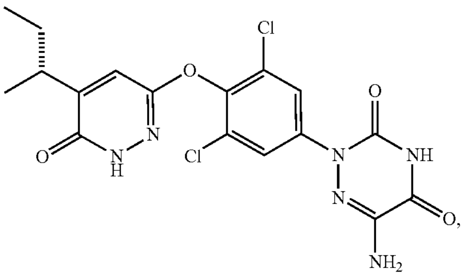
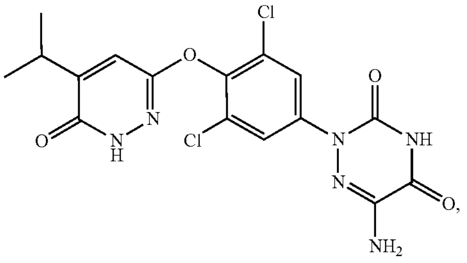
-continued
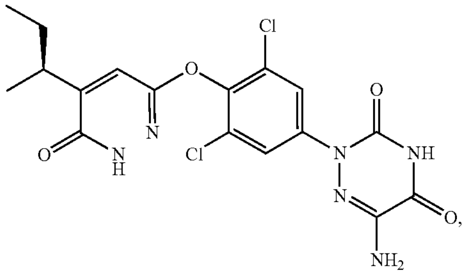
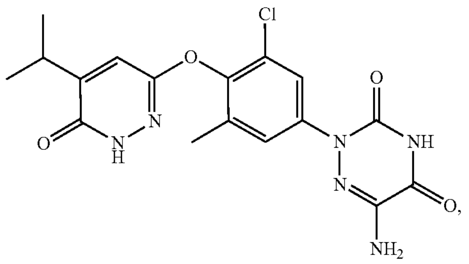
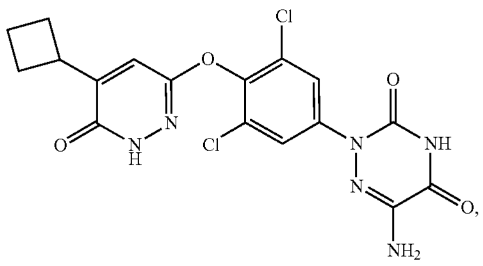
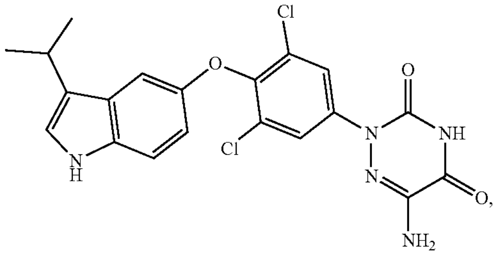
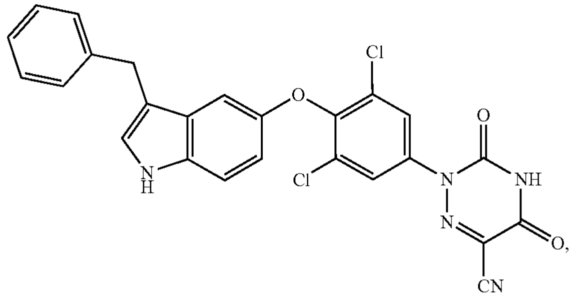
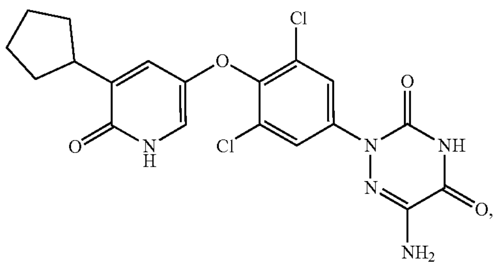

-continued
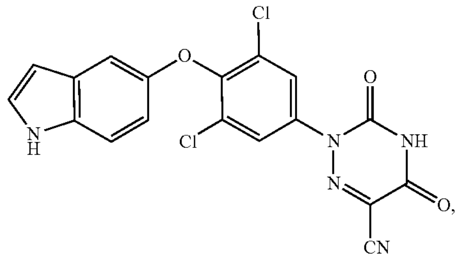
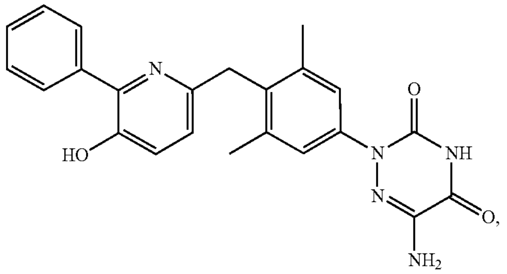
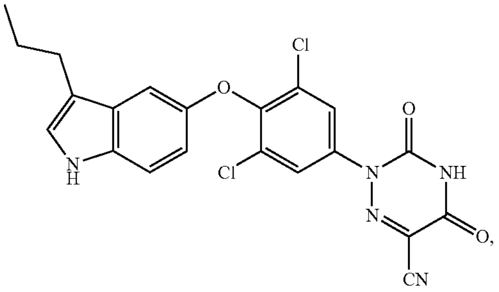
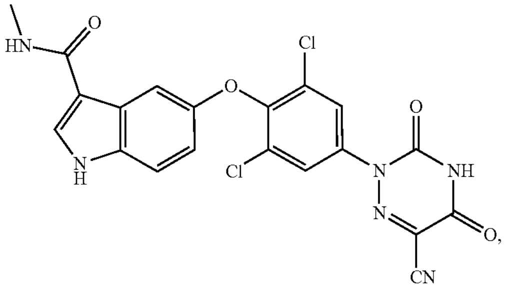
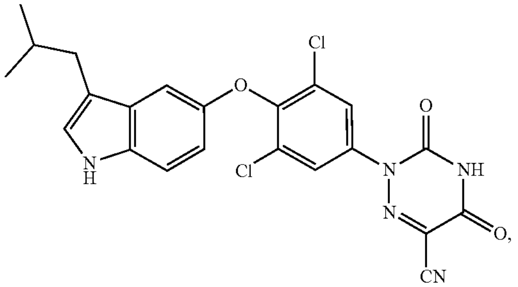
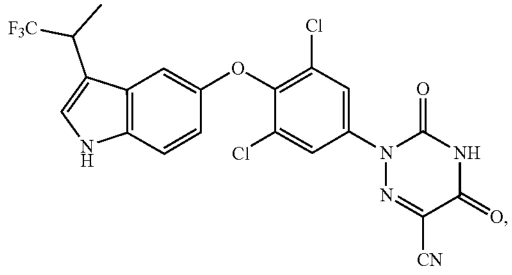
-continued
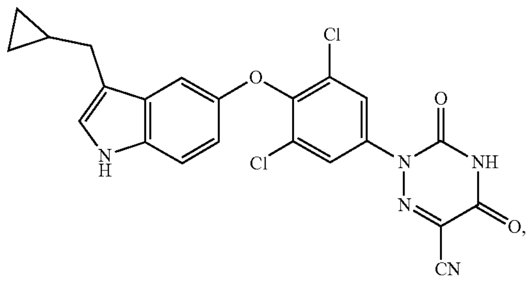
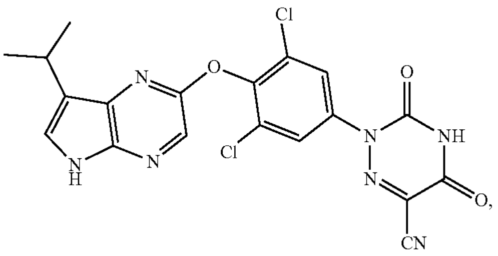
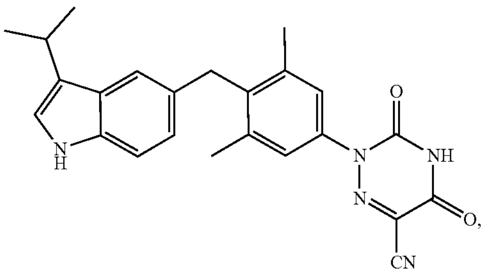
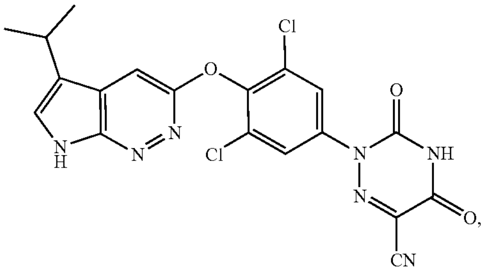
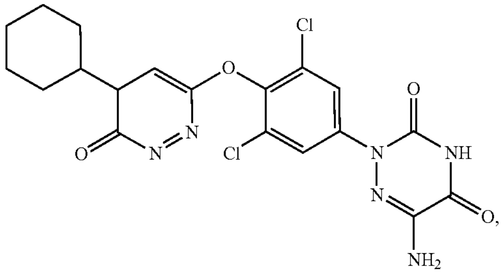
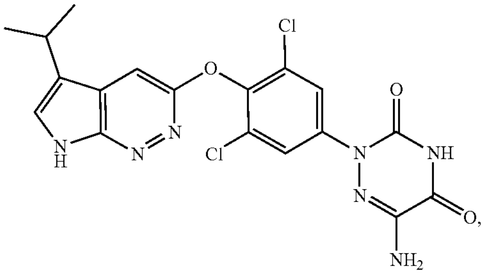

-continued
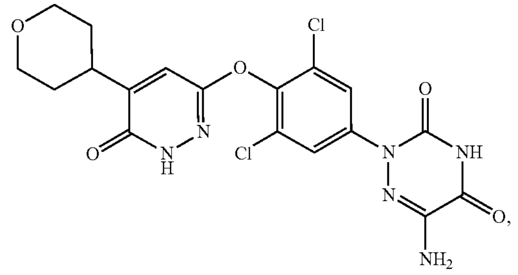
,
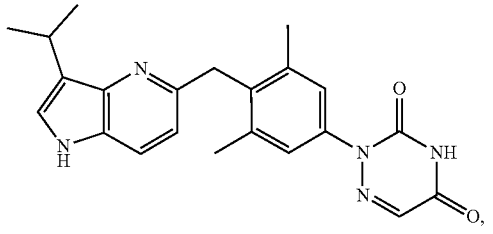
,
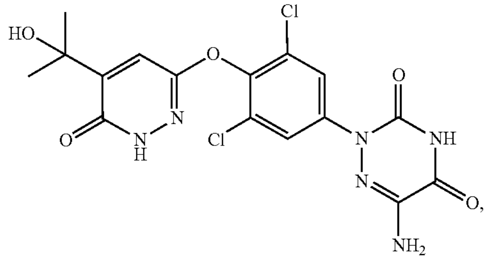
,
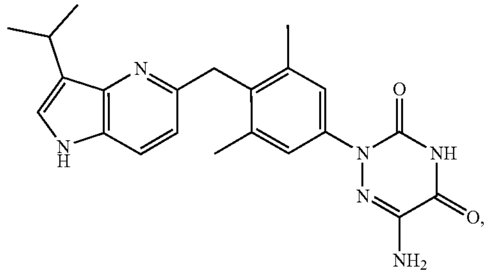
,
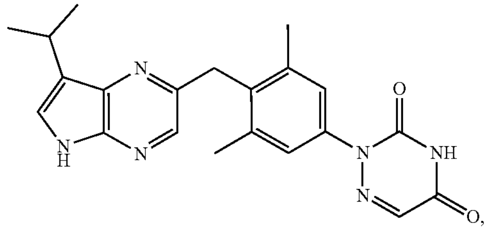
,
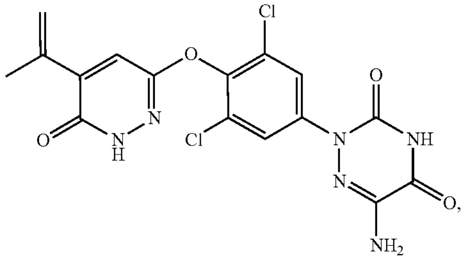
,
-continued
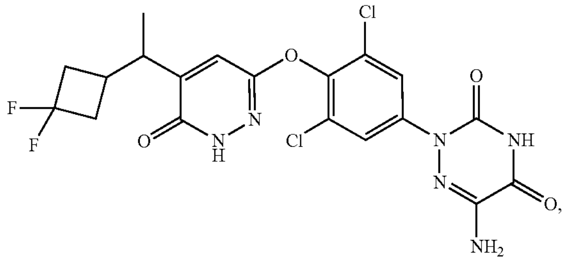
,
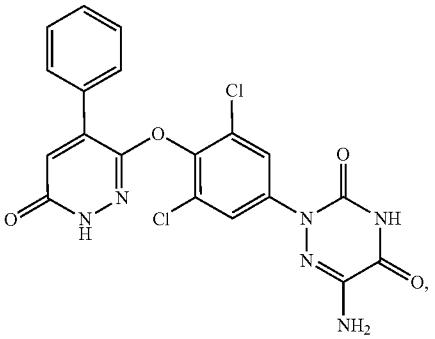
,
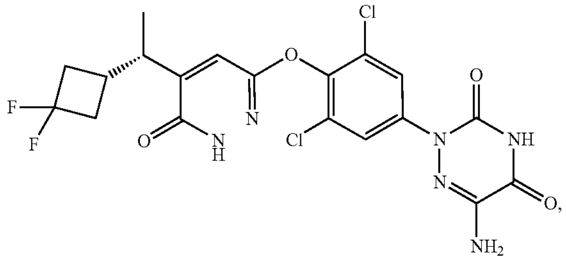
,
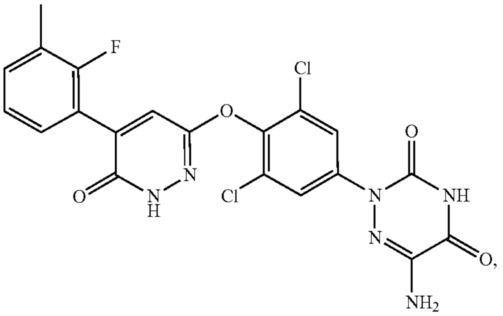
,
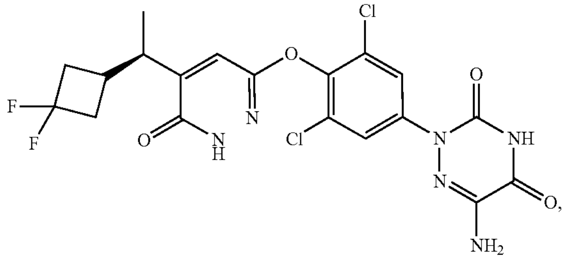
, -continued
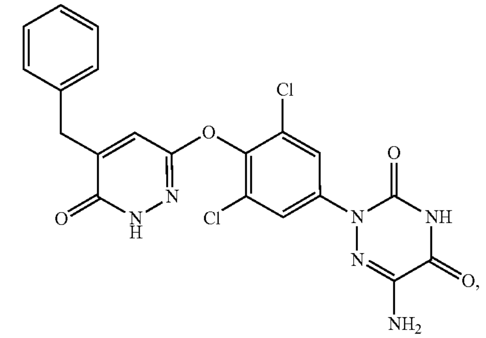
,
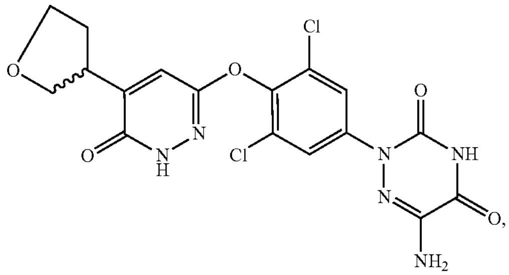
,
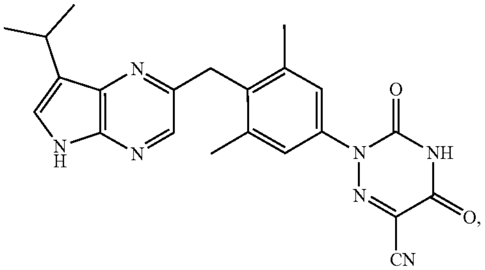
,
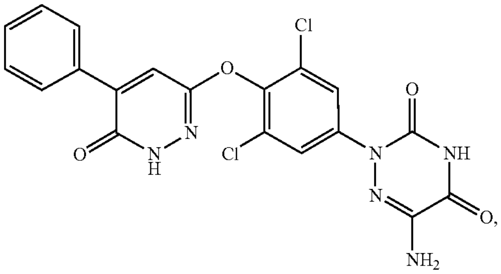
,
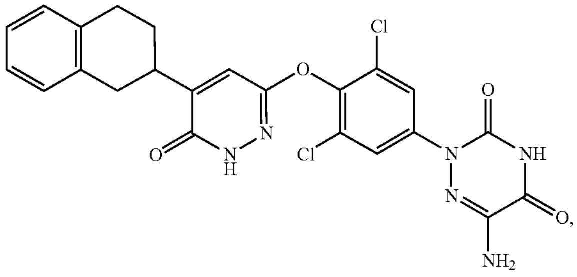
,
-continued
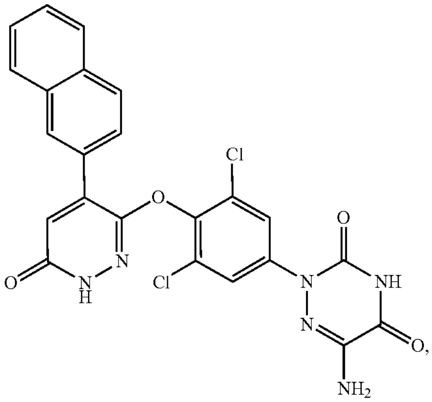
,
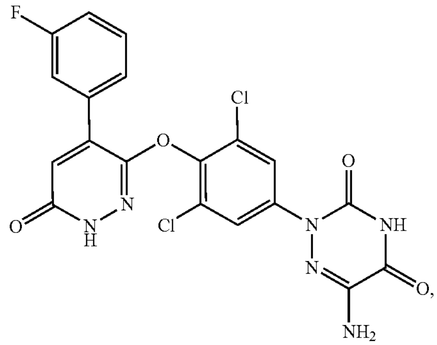
,
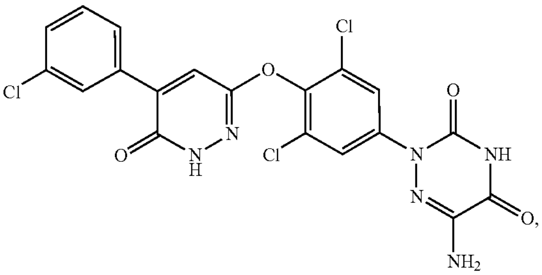
,
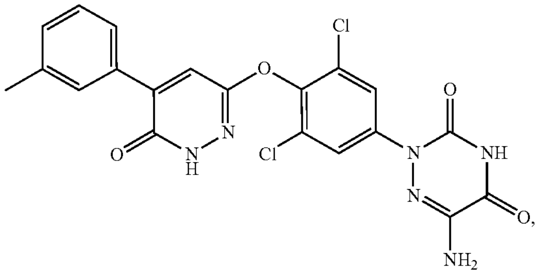
,
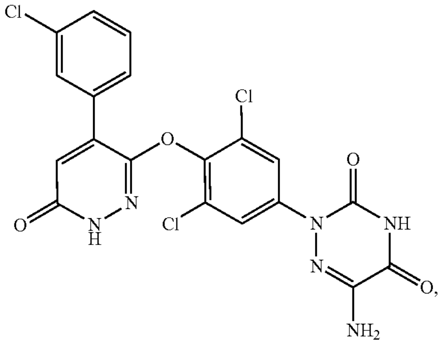
, -continued
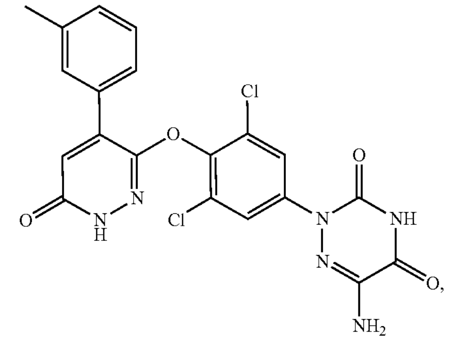
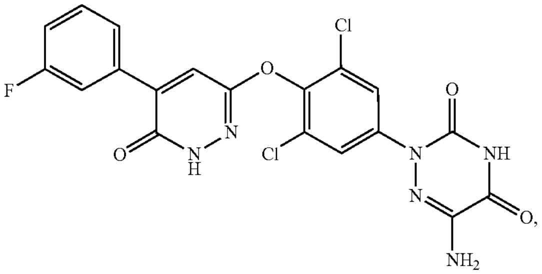
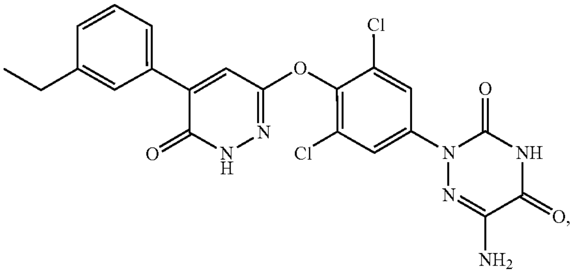
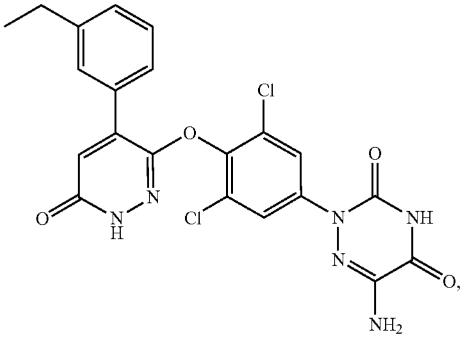
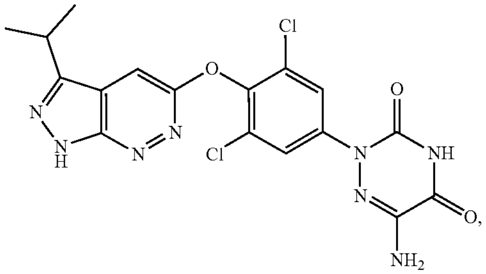
-continued
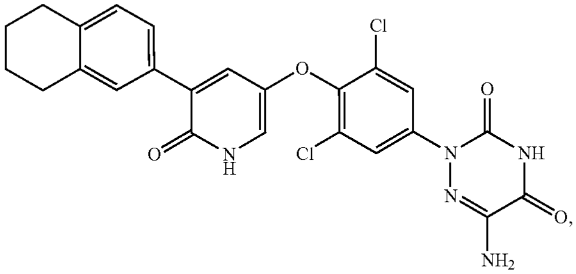
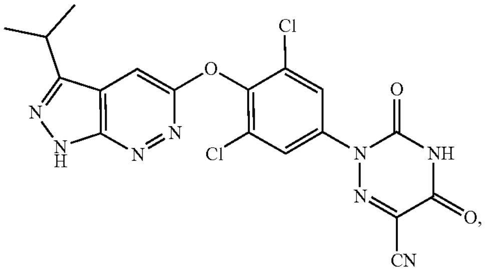
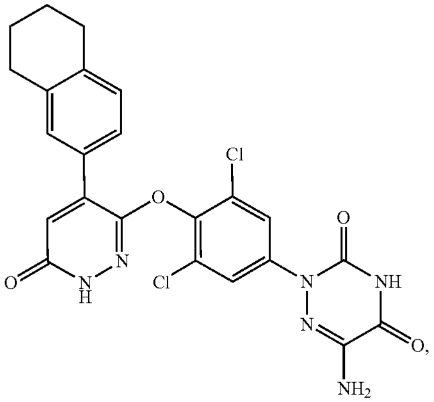
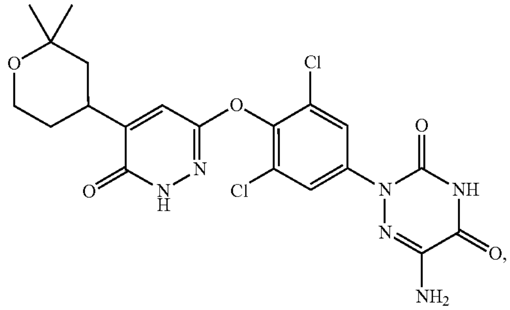
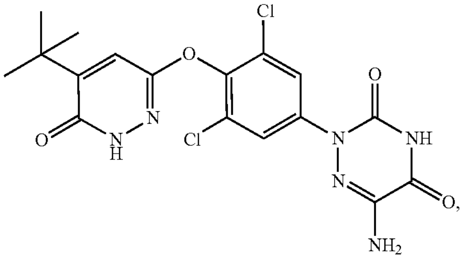

-continued
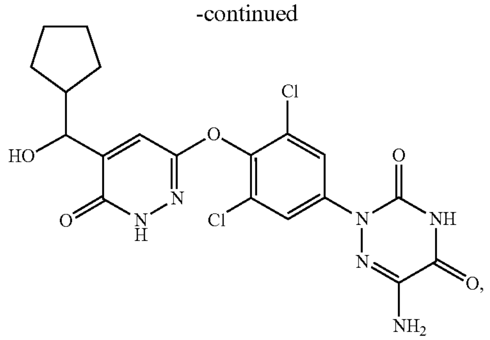
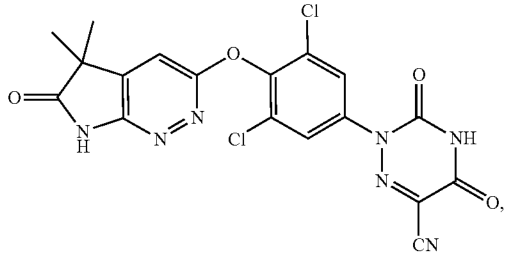
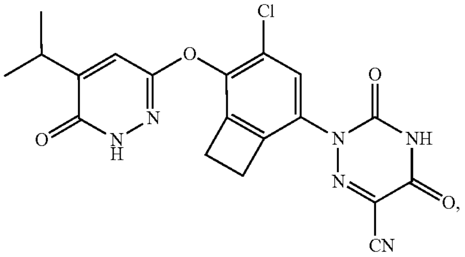
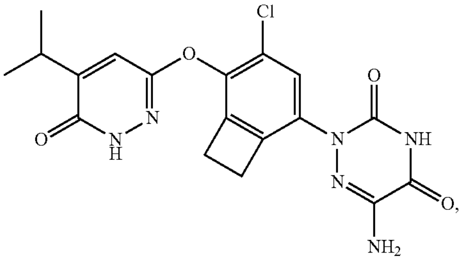
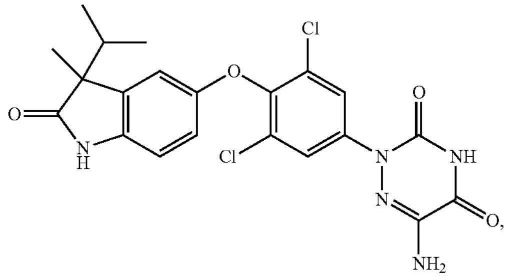
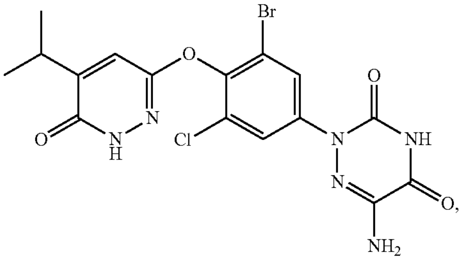
-continued
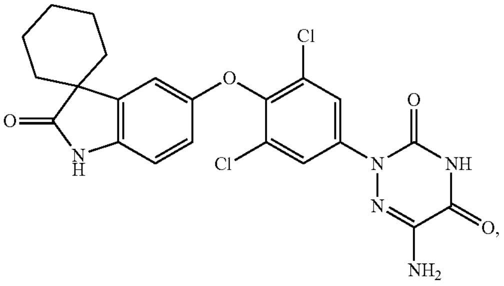
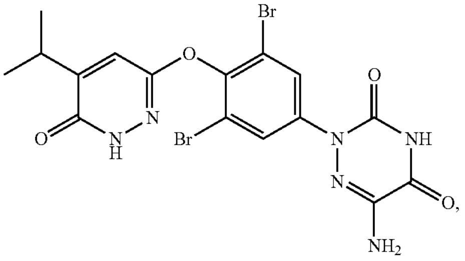
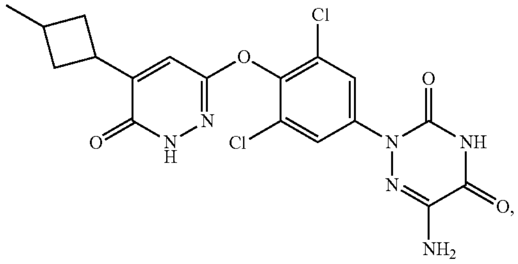
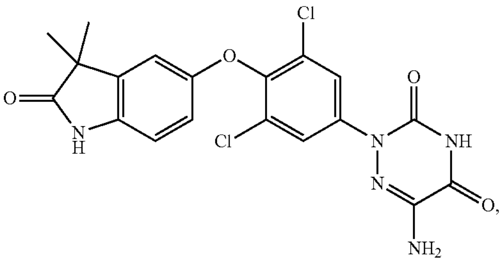
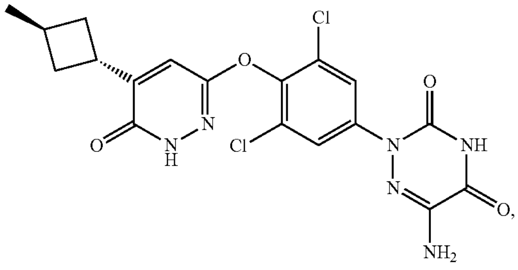
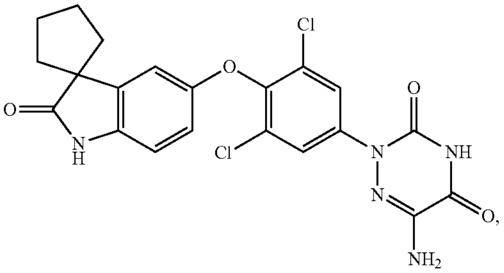

-continued
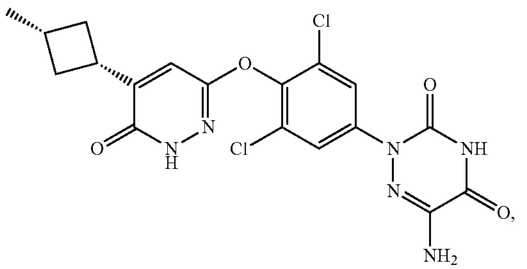
,
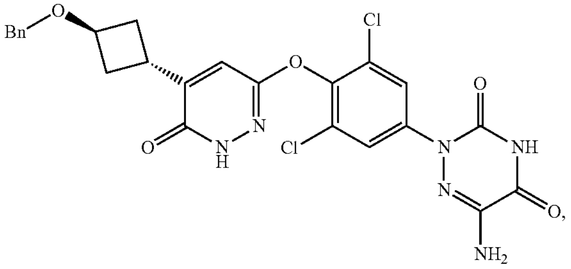
,
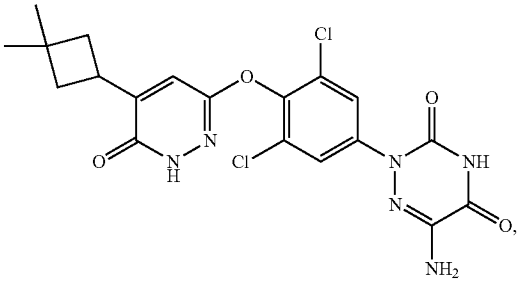
,
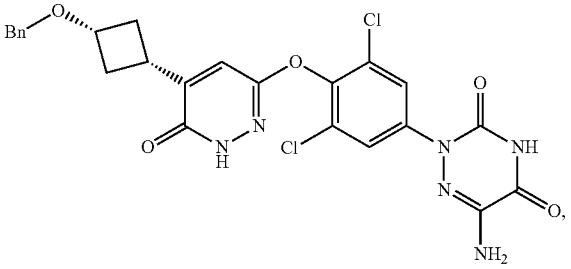
,
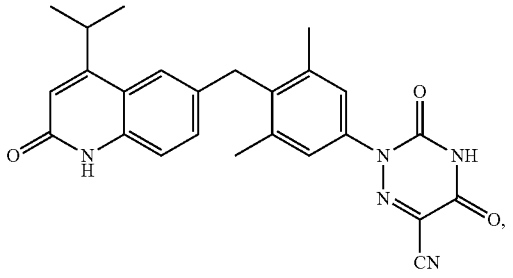
,
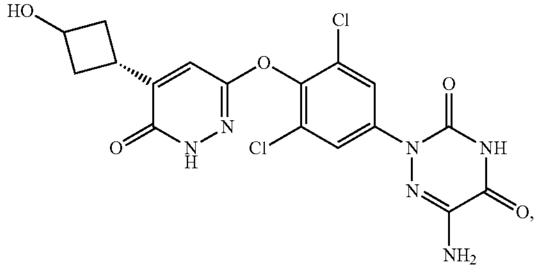
,
-continued
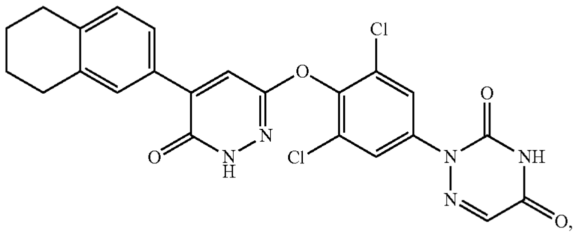
,
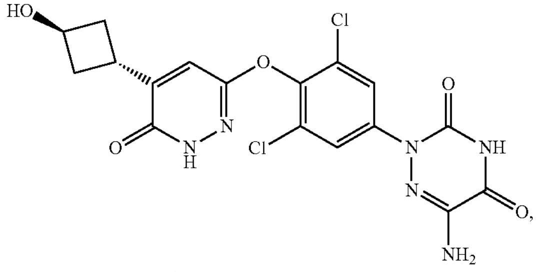
,
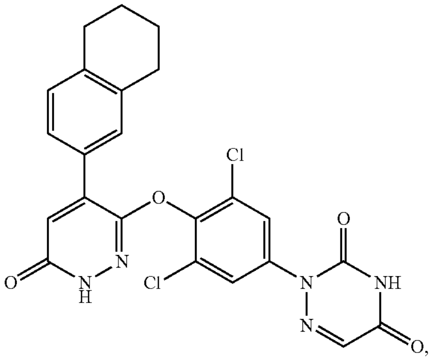
,
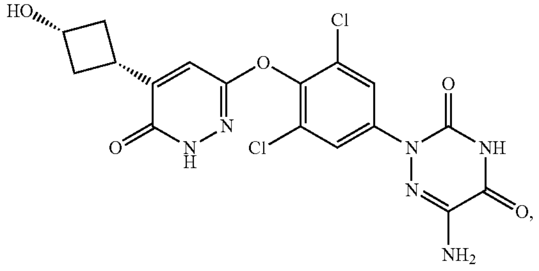
,
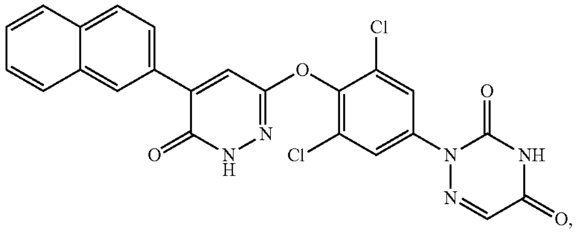
,
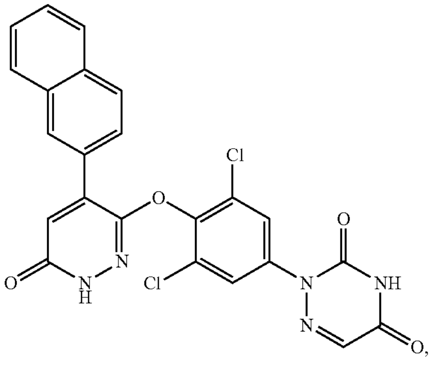
, -continued
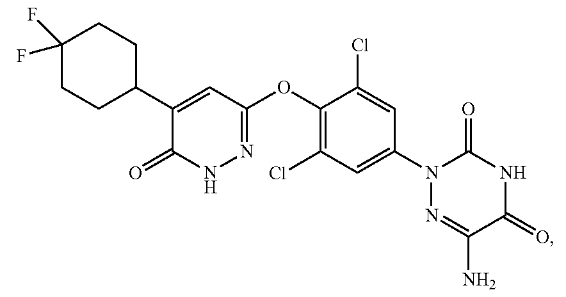
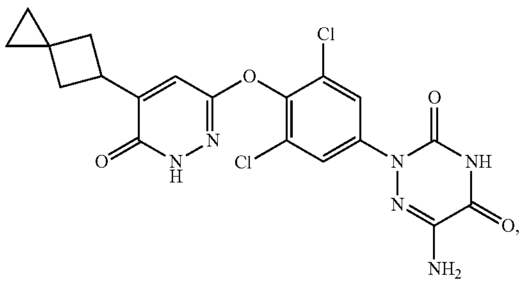
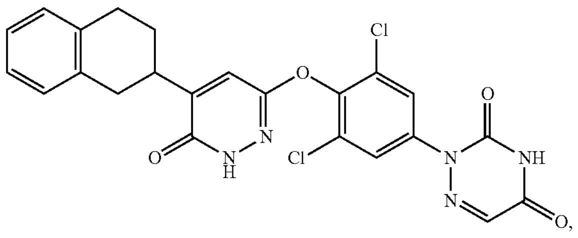
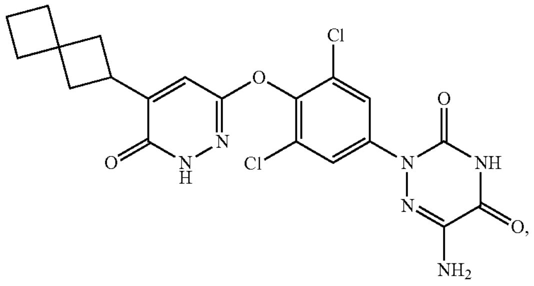
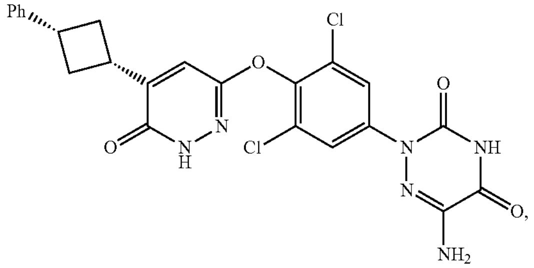
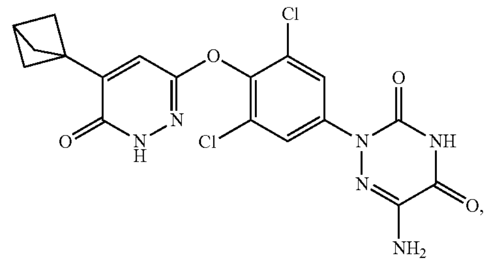
-continued
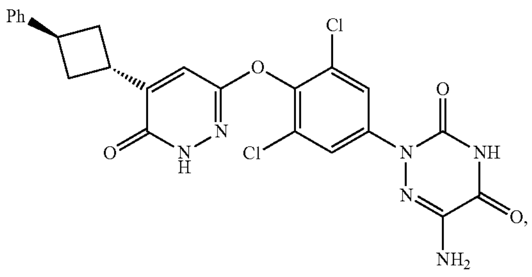
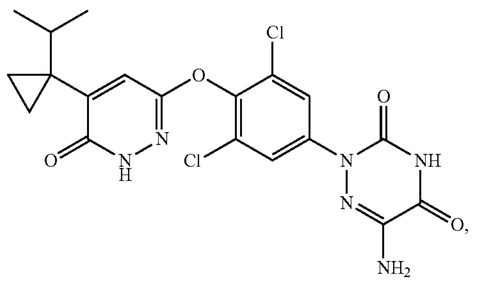
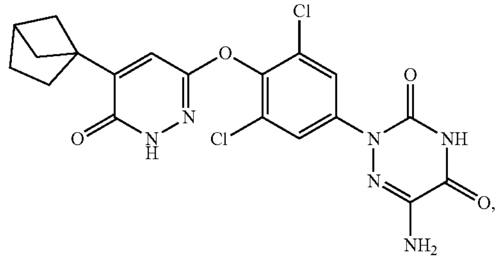
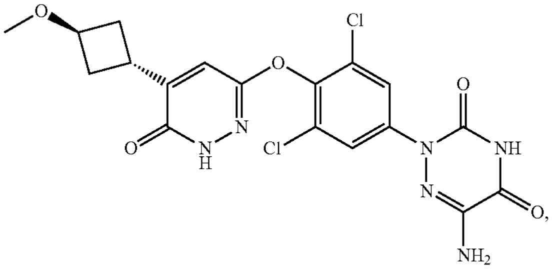
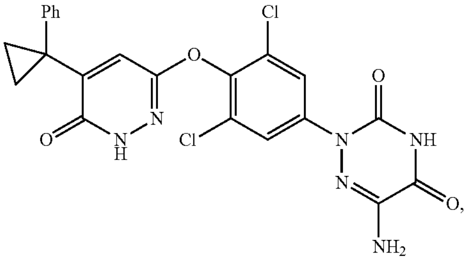
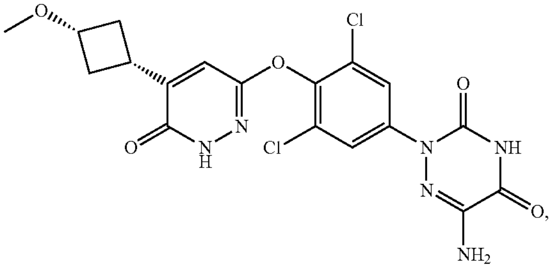

-continued
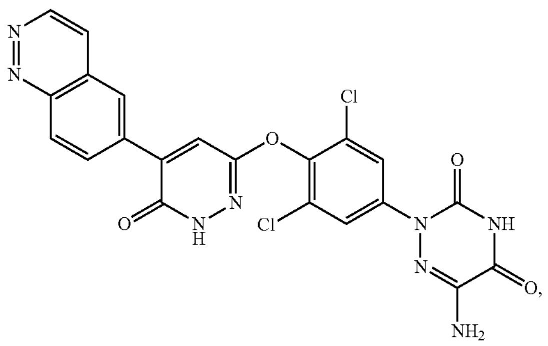
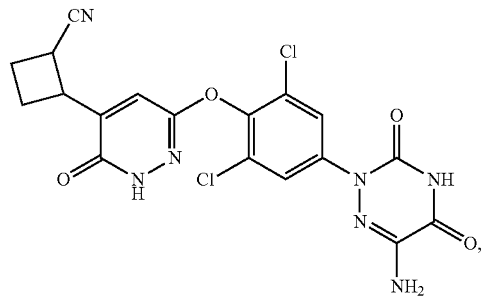
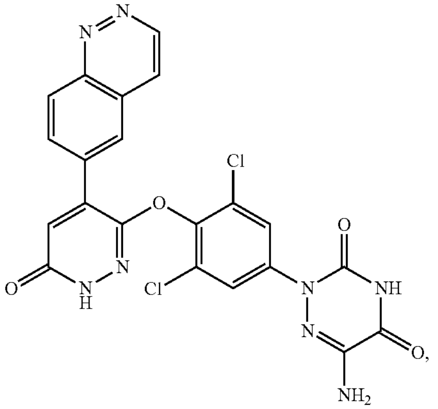
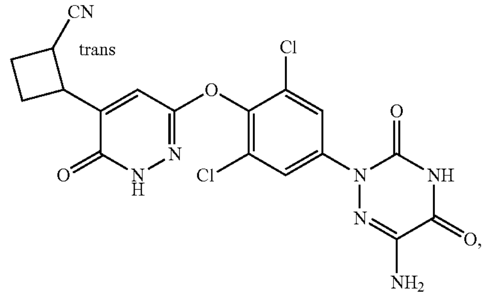
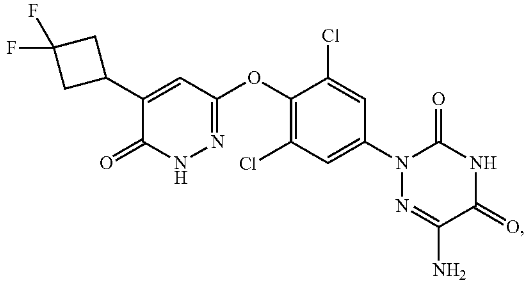
-continued
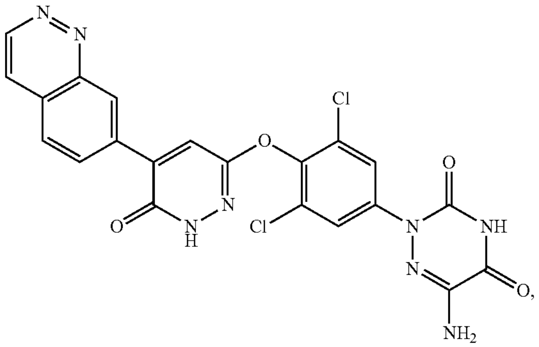
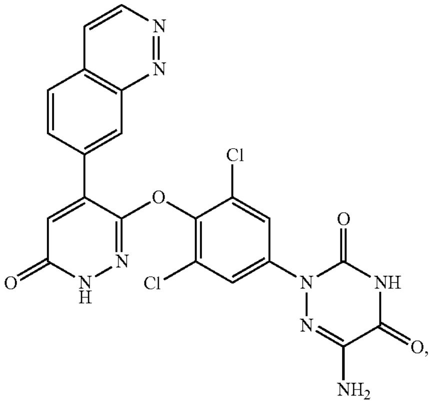
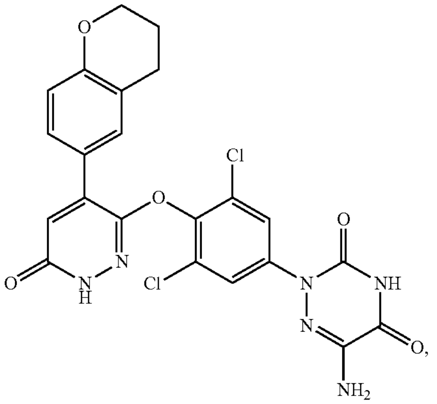
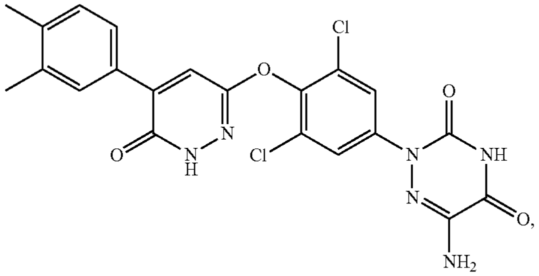
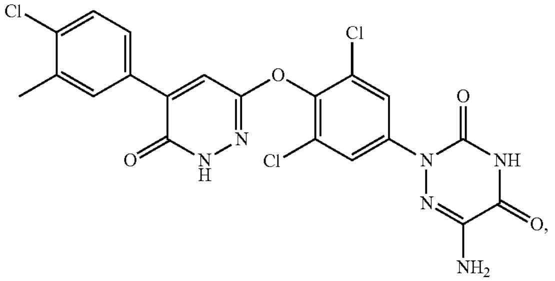

-continued
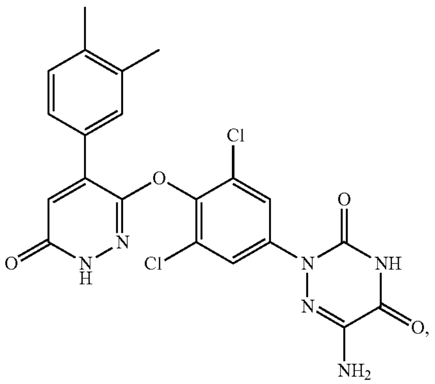,
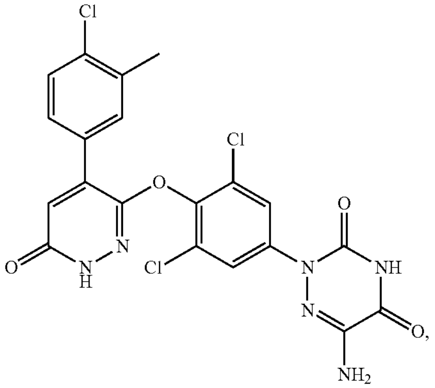,
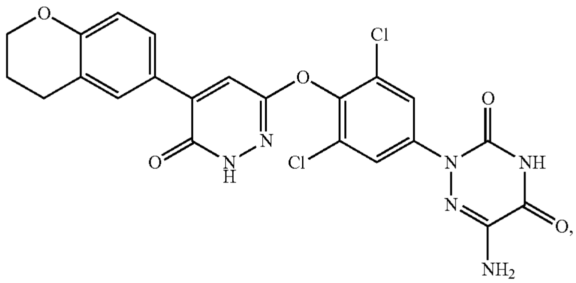,
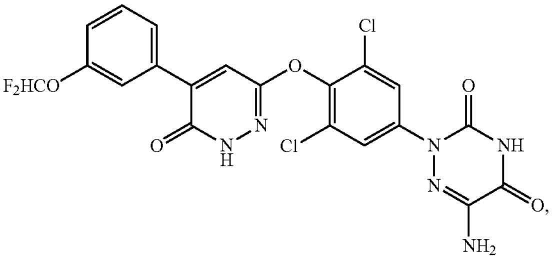,
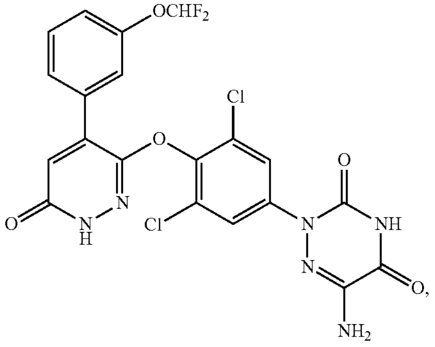,
-continued
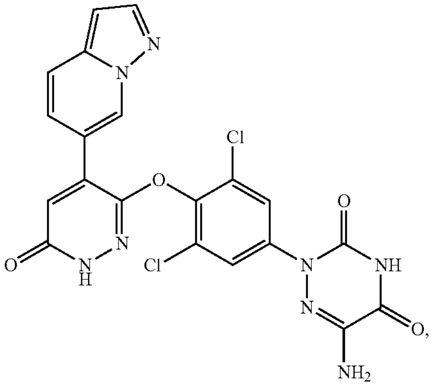,
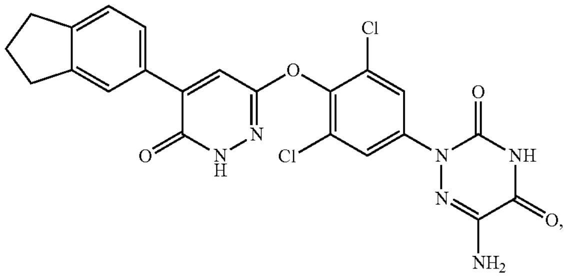,
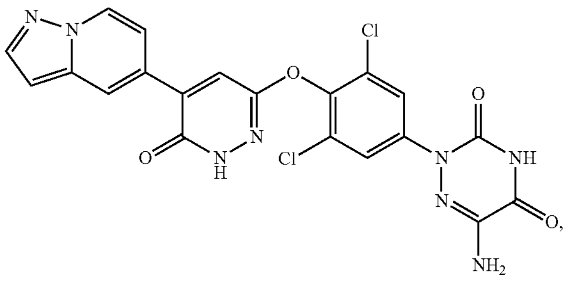,
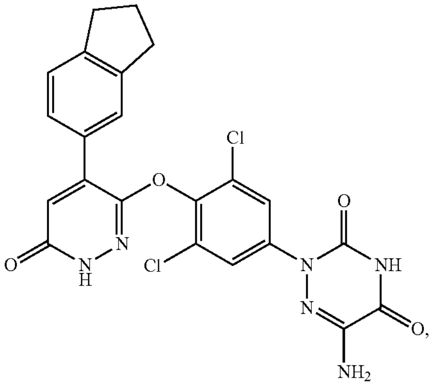,
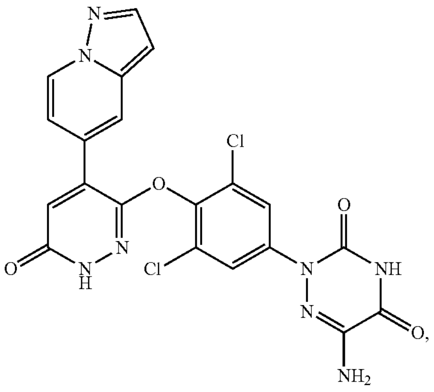, -continued
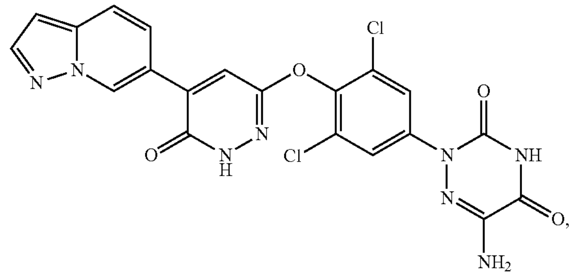
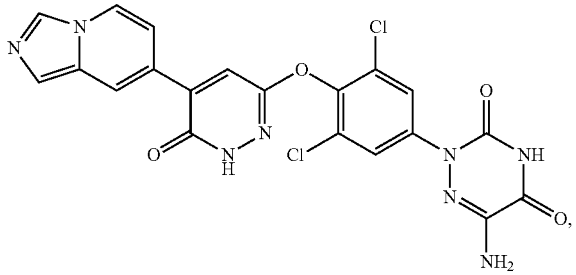
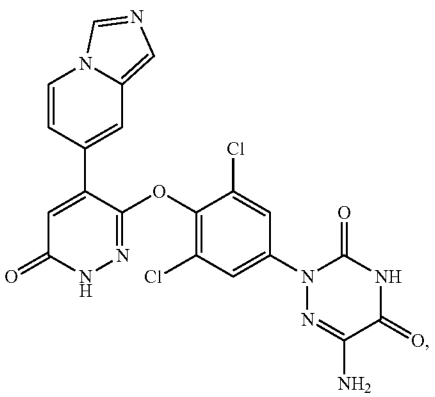
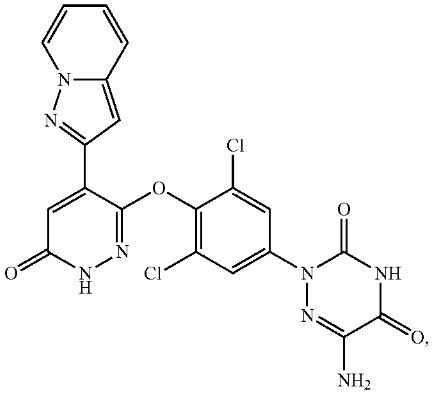
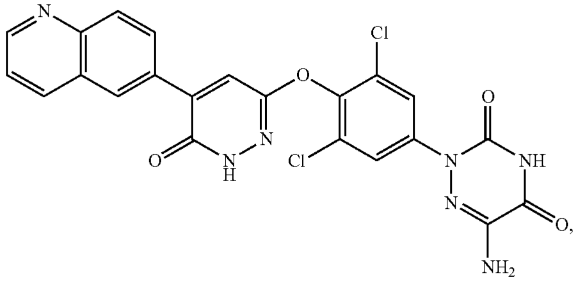
-continued
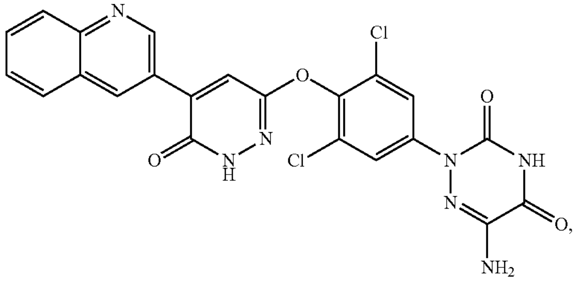
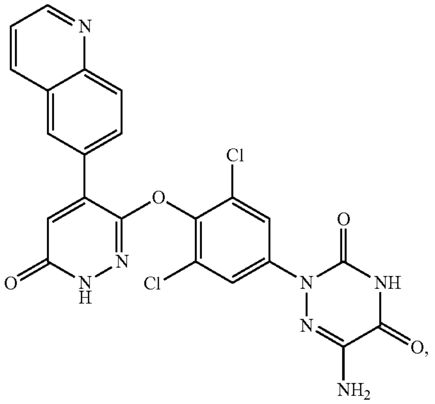
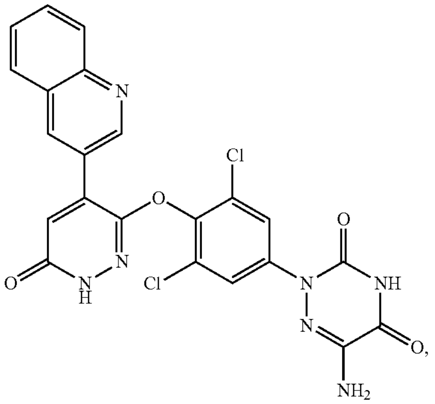
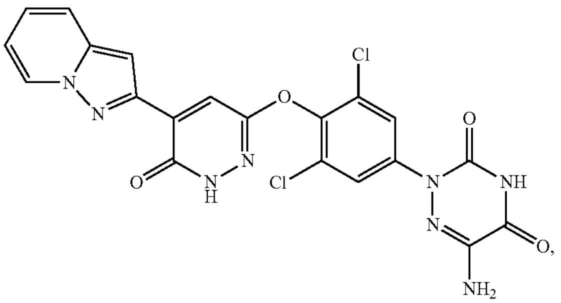

-continued
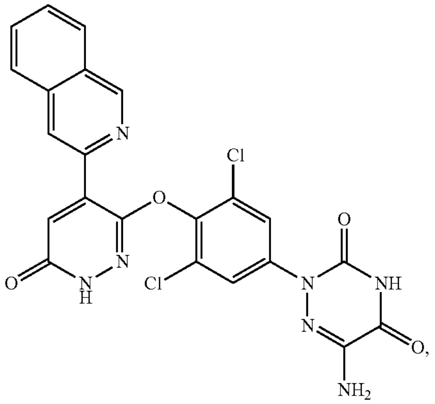
,
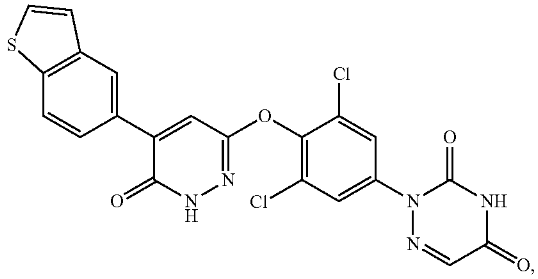
,
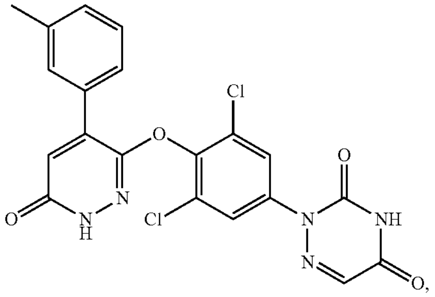
,
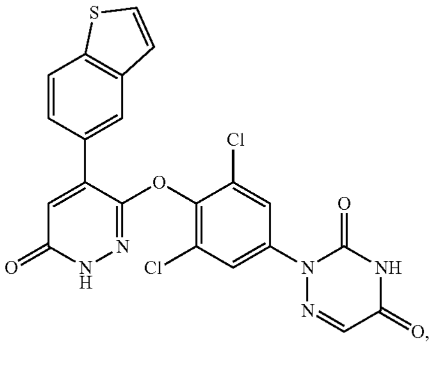
,
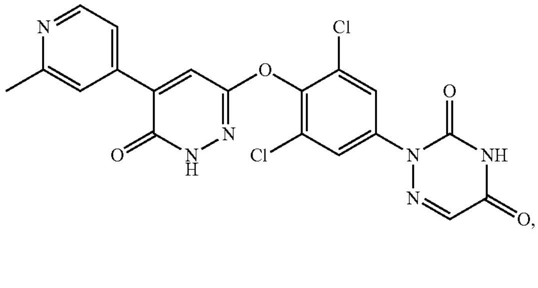
,
-continued
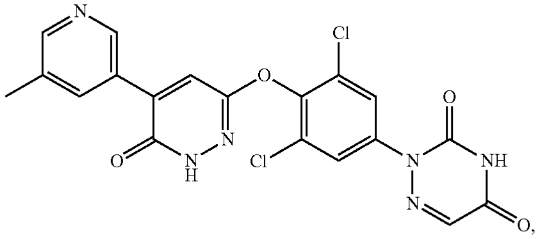
,
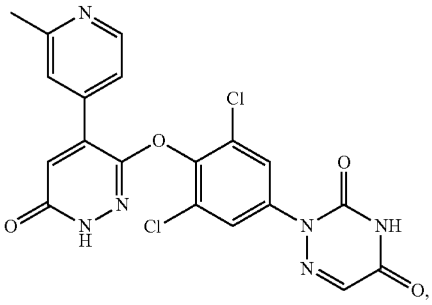
,
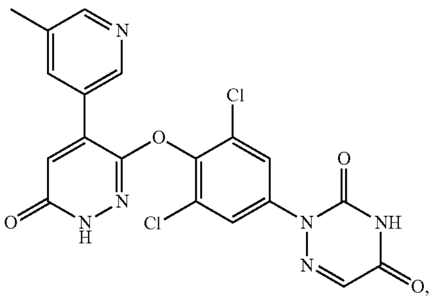
,
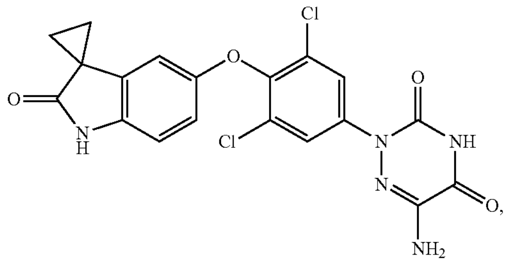
,
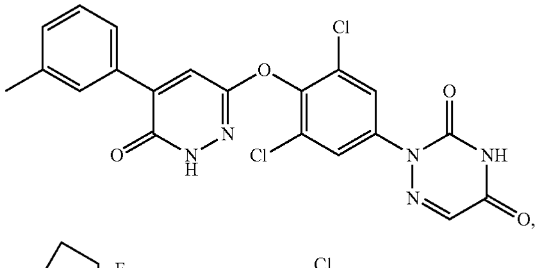
,
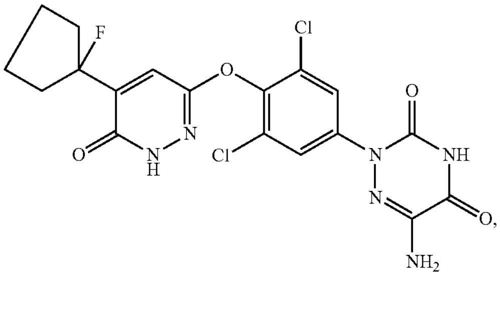
, -continued
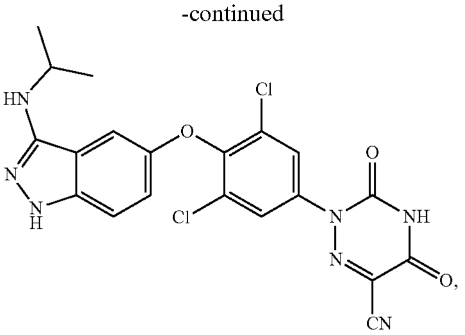
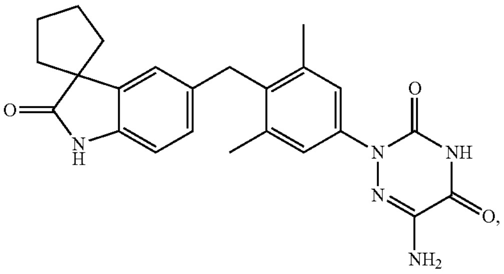
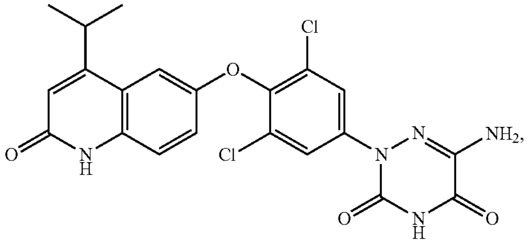
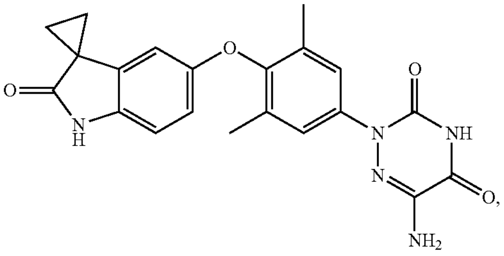
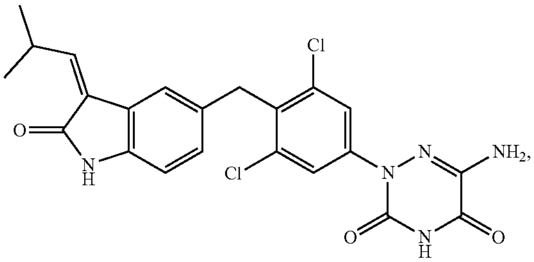
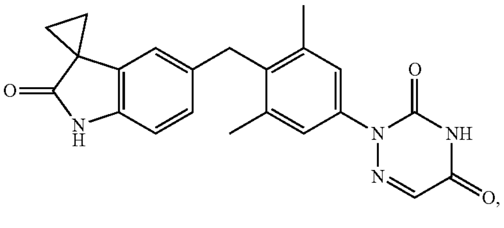
-continued
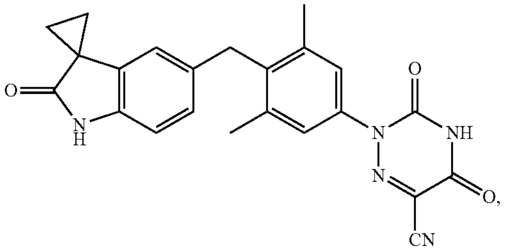
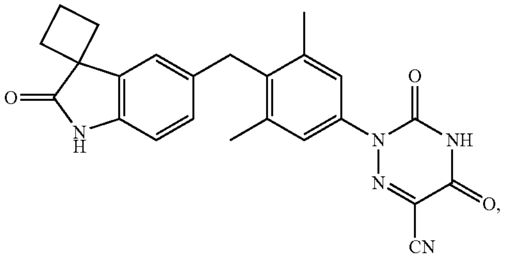
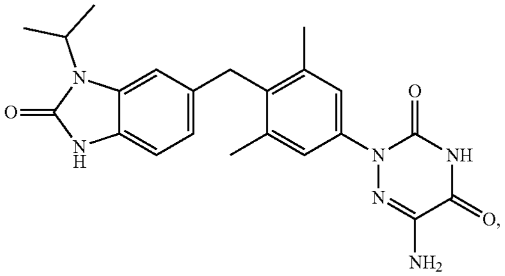
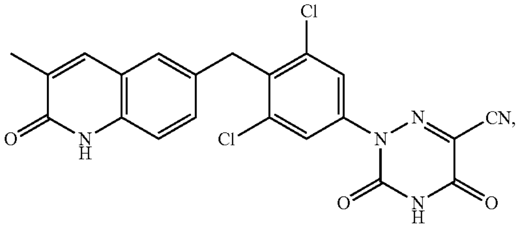
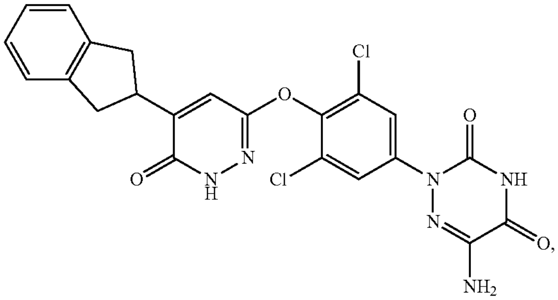
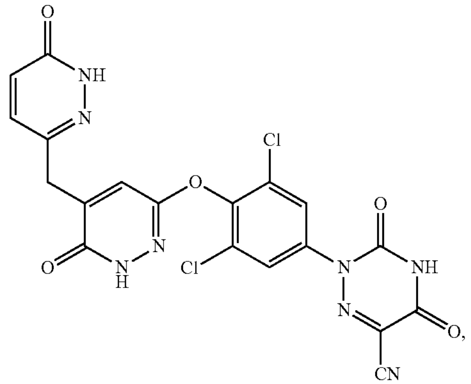

-continued
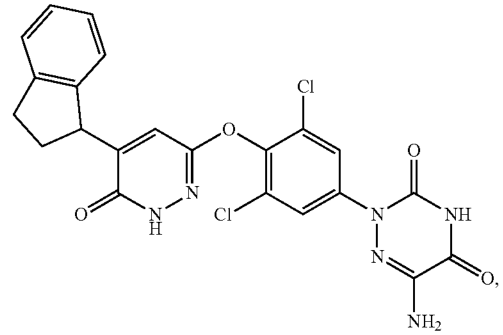
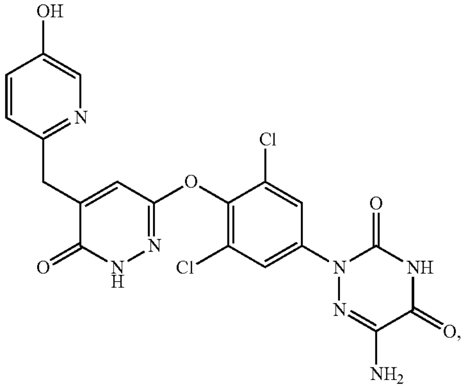
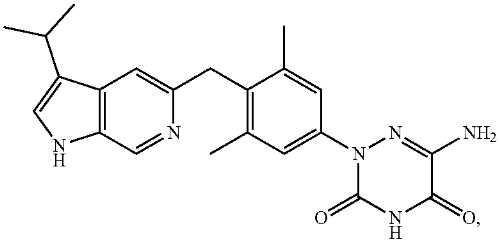
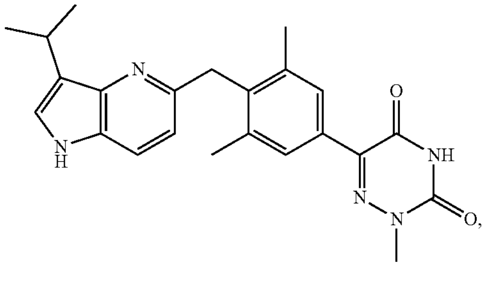
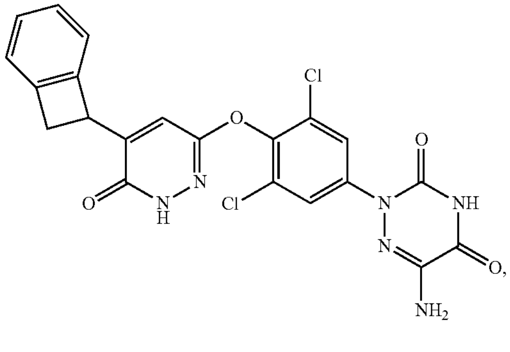
-continued
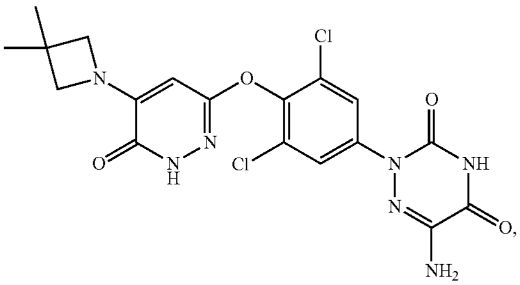
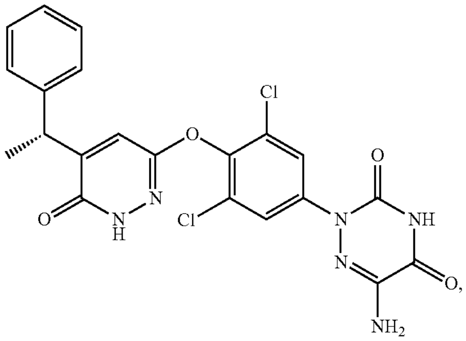
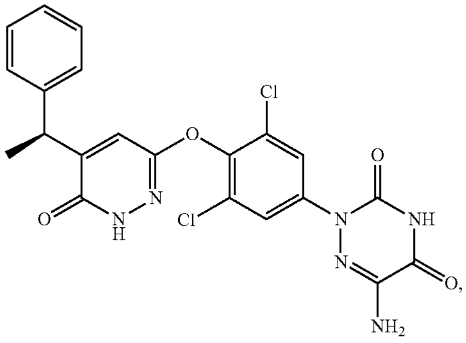
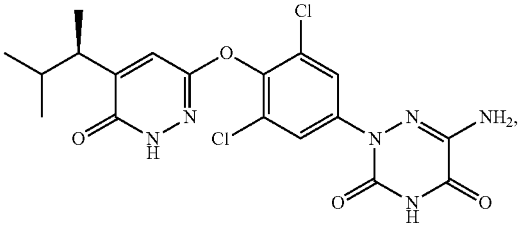
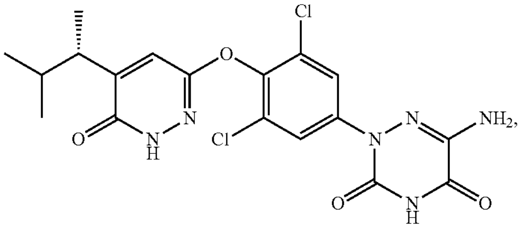

-continued

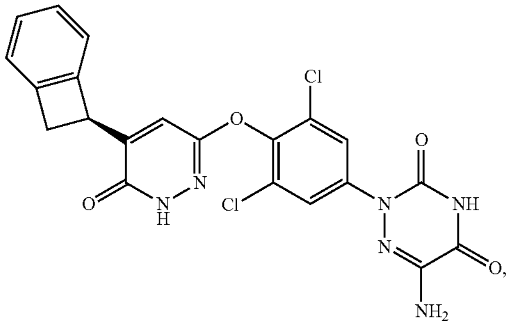

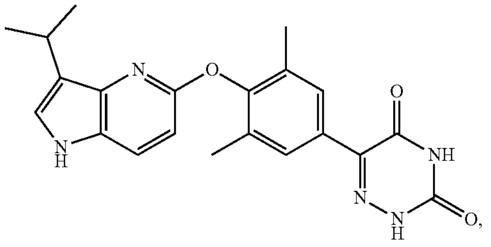

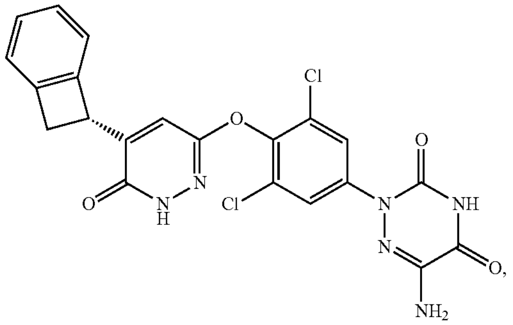

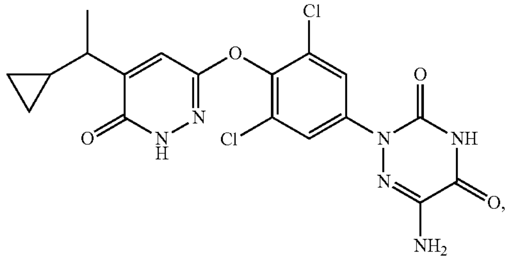

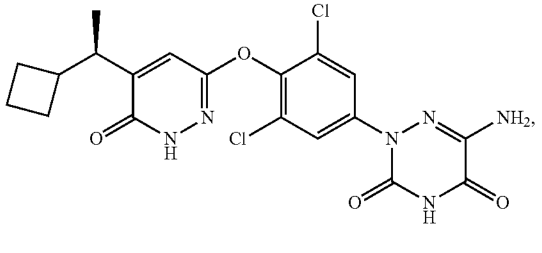

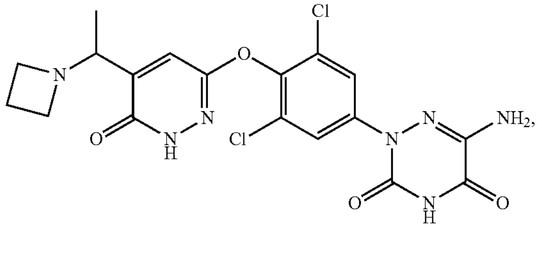

-continued

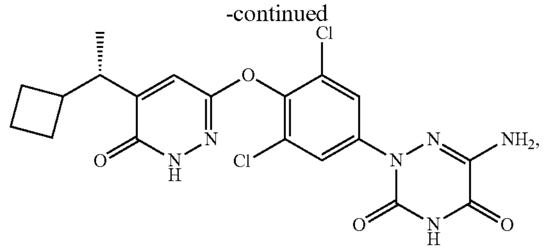

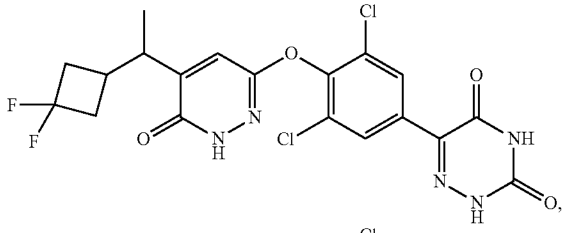

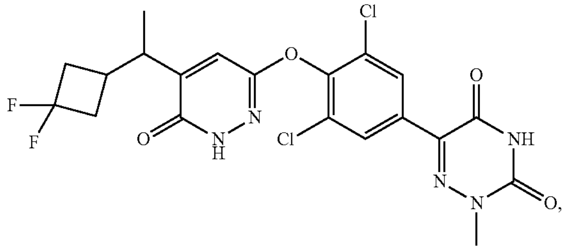

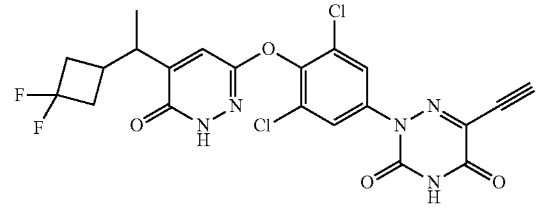

and pharmaceutically acceptable salts and stereoisomers thereof.

In some embodiments, the TR-β agonist may be a compound described in U.S. Patent Publication No. 2020/0115362. In some embodiments, the TR-β agonist may be a compound described in U.S. Patent Publication No. 2020/0399249. In some embodiments, the TR-β agonist may be a compound described in U.S. Pat. No. 10,800,767. In some embodiments, the TR-β agonist may be a compound described in International Patent Publication No. WO 2021/041237. In some embodiments, the TR-β agonist may be a compound described in International Patent Publication No. WO 2021/050945. In some embodiments, the TR-β agonist may be a compound described in U.S. Patent Publication No. 2020/0354345. Each of the aforementioned references is hereby incorporated in its entirety.

In some embodiments, the TR-β agonist may be TERN-501. In other embodiments, the TR-β agonist may be ASC41. In yet other embodiments, the TR-β agonist may be ASC41-A. In still yet other embodiments, the TR-β agonist may be ALG-055009.

Pharmaceutical Compositions

The compounds as described herein can be formulated into pharmaceutical compositions for use in treatment of the conditions described herein. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of one or more compounds described herein, or pharmaceutically acceptable salts thereof; and (b) a pharmaceutically acceptable carrier, diluent, excipient or combination thereof.

In some embodiments, a formulation comprising the compounds provided herein may be administered in combination with one or more second pharmaceutical agents or a pharmaceutical composition comprising one or more second pharmaceutical agents.

The term "pharmaceutically acceptable carrier" or "pharmaceutically acceptable excipient" includes any and all solvents, diluents, emulsifiers, binders, buffers, dispersion media, coatings, antibacterial and antifungal agents, isotonic and absorption delaying agents and the like, or any other such compound as is known by those of skill in the art to be useful in preparing pharmaceutical formulations. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, NJ. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is determined by the way the compound is to be administered.

The compositions described herein are preferably provided in unit dosage form. As used herein, a "unit dosage form" is a composition containing an amount of a compound that is suitable for administration to a subject, in a single dose, according to good medical practice. The preparation of a single or unit dosage form however, does not imply that the dosage form is administered once per day or once per course of therapy. A unit dosage form may comprise a single daily dose or a fractional sub-dose wherein several unit dosage forms are to be administered over the course of a day in order to complete a daily dose. According to the present disclosure, a unit dosage form may be given more or less often that once daily, and may be administered more than once during a course of therapy. Such dosage forms may be administered in any manner consistent with their formulation, including orally, parenterally, and may be administered as an infusion over a period of time (e.g., from about 30 minutes to about 2-6 hours). While single administrations are specifically contemplated, the compositions administered according to the methods described herein may also be administered as a continuous infusion or via an implantable infusion pump.

The methods as described herein may utilize any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropes, surface-active agents, and encapsulating substances. Optional pharmaceutically-active materials may be included, which do not substantially interfere with the activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid, microcrystalline cellulose, carboxymethyl cellulose, and talc. Tablets may also comprise solubilizers or emulsifiers, such as poloxamers, cremophor/Kolliphor®/Lutrol®, methylcellulose, hydroxypropylmethylcellulose, or others as are known in the art. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which can be readily made by a person skilled in the art.

Peroral (PO) compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, including for transdermal administration, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, PDA J Pharm Sci and Tech 1998, 52 238-311 and Nema et al., Excipients and Their Role in Approved Injectable Products: Current Usage and Future Directions, PDA J. Pharm. Sci. Tech. 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual unit dose of the compounds described herein depends on the specific compound, and on the condition to be treated. In some embodiments, the dose may be from about 0.01 mg/kg to about 120 mg/kg or more of body weight, from about 0.05 mg/kg or less to about 70 mg/kg, from about 0.1 mg/kg to about 50 mg/kg of body weight, from about 1.0 mg/kg to about 10 mg/kg of body weight, from about 5.0 mg/kg to about 10 mg/kg of body weight, or from about 10.0 mg/kg to about 20.0 mg/kg of body weight. In some embodiments, the dose may be less than 100 mg/kg, 90 mg/kg, 80 mg/kg, 70 mg/kg, 60 mg/kg, 50 mg/kg, 40 mg/kg, 30 mg/kg, 25 mg/kg, 20 mg/kg, 10 mg/kg, 7.5 mg/kg, 6 mg/kg, 5 mg/kg, 4 mg/kg, 3 mg/kg, 2.5 mg/kg, 1 mg/kg, 0.5 mg/kg, 0.1 mg/kg, 0.05 mg/kg or 0.005 mg/kg of body weight. In some embodiments, the actual unit dose is 0.05, 0.07, 0.1, 0.3, 1.0, 3.0, 5.0, 10.0 or 25.0 mg/kg of body weight. Thus, for administration to a 70 kg person, the dosage range would be from about 0.1 mg to 70 mg, from about 1 mg to about 50 mg, from about 0.5 mg to about 10 mg, from about 1 mg to about 10 mg, from about 2.5 mg to about 30 mg, from about 35 mg or less to about 700 mg or more, from about 7 mg to about 600 mg, from about 10 mg to about 500 mg, or from about 20 mg to about 300 mg, or from about 200 mg to about 2000 mg. In some embodiments, the actual unit dose is 0.1 mg. In some embodiments, the actual unit dose is 0.5 mg. In some embodiments, the actual unit dose is 1 mg. In some embodiments, the actual unit dose is 1.5 mg. In some embodiments, the actual unit dose is 2 mg. In some embodiments, the actual unit dose is 2.5 mg. In some embodiments, the actual unit dose is 3 mg. In some embodiments, the actual unit dose is 3.5 mg. In some embodiments, the actual unit dose is 4 mg. In some embodiments, the actual unit dose is 4.5 mg. In some embodiments, the actual unit dose is 5 mg. In some embodiments the actual unit dose is 10 mg. In some embodiments, the actual unit dose is 25 mg. In some embodiments, the actual unit dose is 250 mg or less. In some embodiments, the actual unit dose is 100 mg or less. In some embodiments, the actual unit dose is 70 mg or less.

In some embodiments, the compound of Formula (II) is administered at a dose in the range of about 1-50 mg/$m^2$ of the body surface area. In some embodiments, the compound of Formula (II) is administered at a dose in the range of about 1-2, 1-3, 1-4, 1-5, 1-6, 1-7, 1-8, 1-9, 1-10, 1-11, 1-12, 1-13, 1-13.75, 1-14, 1-15, 1-16, 1-17, 1-18, 1-19, 1-20, 1-22.5, 1-25, 1-27.5, 1-30, 1.5-2, 1.5-3, 1.5-4, 1.5-5, 1.5-6, 1.5-7, 1.5-8, 1.5-9, 1.5-10, 1.5-11, 1.5-12, 1.5-13, 1.5-13.75, 1.5-14, 1.5-15, 1.5-16, 1.5-17, 1.5-18, 1.5-19, 1.5-20, 1.5-22.5, 1.5-25, 1.5-27.5, 1.5-30, 2.5-2, 2.5-3, 2.5-4, 2.5-5, 2.5-6, 2.5-7, 2.5-8, 2.5-9, 2.5-10, 2.5-11, 2.5-12, 2.5-13, 2.5-13.75, 2.5-14, 2.5-15, 2.5-16, 2.5-17, 2.5-18, 2.5-19, 2.5-20, 2.5-22.5, 2.5-25, 2.5-27.5, 2.5-30, 2.5-7.5, 3-4, 3-5, 3-6, 3-7, 3-8, 3-9, 3-10, 3-11, 3-12, 3-13, 3-13.75, 3-14, 3-15, 3-16, 3-17, 3-18, 3-19, 3-20, 3-22.5, 3-25, 3-27.5, 3-30, 3.5-6.5, 3.5-13.75, 3.5-15, 2.5-17.5, 4-5, 4-6, 4-7, 4-8, 4-9, 4-10, 4-11, 4-12, 4-13, 4-13.75, 4-14, 4-15, 4-16, 4-17, 4-18, 4-19, 4-20, 4-22.5, 4-25, 4-27.5, 4-30, 5-6, 5-7, 5-8, 5-9, 5-10, 5-11, 5-12, 5-13, 5-13.75, 5-14, 5-15, 5-16, 5-17, 5-18, 5-19, 5-20, 5-22.5, 5-25, 5-27.5, 5-30, 6-7, 6-8, 6-9, 6-10, 6-11, 6-12, 6-13, 6-13.75, 6-14, 6-15, 6-16, 6-17, 6-18, 6-19, 6-20, 6-22.5, 6-25, 6-27.5, 6-30, 7-8, 7-9, 7-10, 7-11, 7-12, 7-13, 7-13.75, 7-14, 7-15, 7-16, 7-17, 7-18, 7-19, 7-20, 7-22.5, 7-25, 7-27.5, 7-30, 7.5-12.5, 7.5-13.5, 7.5-15, 8-9, 8-10, 8-11, 8-12, 8-13, 8-13.75, 8-14, 8-15, 8-16, 8-17, 8-18, 8-19, 8-20, 8-22.5, 8-25, 8-27.5, 8-30, 9-10, 9-11, 9-12, 9-13, 9-13.75, 9-14, 9-15, 9-16, 9-17, 9-18, 9-19, 9-20, 9-22.5, 9-25, 9-27.5, 9-30, 10-11, 10-12, 10-13, 10-13.75, 10-14, 10-15, 10-16, 10-17, 10-18, 10-19, 10-20, 10-22.5, 10-25, 10-27.5, 10-30, 11.5-15.5, 12.5-14.5, 7.5-22.5, 8.5-32.5, 9.5-15.5, 15.5-24.5, 5-35, 17.5-22.5, 22.5-32.5, 25-35, 25.5-24.5, 27.5-32.5, 2-20, 2.5-22.5, or 9.5-21.5 mg/$m^2$, of the body surface area. In some embodiments, compound of Formula (II) is administered at a dose of about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/$m^2$ of the body surface area. In some embodiments, compound of Formula (II) is administered at a dose less than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/$m^2$ of the body surface area. In some embodiments, the compound of Formula (II) is administered at a dose greater than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50 mg/$m^2$ of the body surface area.

In some embodiments, the compound of Formula (II) dose is about 0.1 mg-100 mg, 0.1 mg-50 mg, 0.1 mg-20 mg, 0.1 mg-10 mg, 0.5 mg-100 mg, 0.5 mg-50 mg, 0.5 mg-20 mg, 0.5 mg-10 mg, 1 mg-100 mg, 1 mg-50 mg, 1 mg-20 mg, 1 mg-10 mg, 2.5 mg-50 mg, 2.5 mg-20 mg, 2.5 mg-10 mg, or about 2.5 mg-5 mg. In some embodiments, the compound of Formula (II) dose is about 5 mg-300 mg, 5 mg-200 mg, 7.5 mg-200 mg, 10 mg-100 mg, 15 mg-100 mg, 20 mg-100 mg, 30 mg-100 mg, 40 mg-100 mg, 10 mg-80 mg, 15 mg-80 mg, 20 mg-80 mg, 30 mg-80 mg, 40 mg-80 mg, 10 mg-60 mg, 15 mg-60 mg, 20 mg-60 mg, 30 mg-60 mg, or about 40 mg-60 mg. In some embodiments, the amount of a compound of Formula (II) administered is about 20 mg-60 mg, 27 mg-60 mg, 20 mg-45 mg, or 27 mg-45 mg. In some embodiments, the amount of compound of Formula (II) administered is about 5 mg-7.5 mg, 5 mg-9 mg, 5 mg-10 mg, 5 mg-12 mg, 5 mg-14 mg, 5 mg-15 mg, 5 mg-16 mg, 5 mg-18 mg, 5 mg-20 mg, 5 mg-22 mg, 5 mg-24 mg, 5 mg-26 mg, 5 mg-28 mg, 5 mg-30 mg, 5 mg-32 mg, 5 mg-34 mg, 5 mg-36 mg, 5 mg-38 mg, 5 mg-40 mg, 5 mg-42 mg, 5 mg-44 mg, 5 mg-46 mg, 5 mg-48 mg, 5 mg-50 mg, 5 mg-52 mg, 5 mg-54 mg, 5 mg-56 mg, 5 mg-58 mg, 5 mg-60 mg, 7 mg-7.7 mg, 7 mg-9 mg, 7 mg-10 mg, 7 mg-12 mg, 7 mg-14 mg, 7 mg-15 mg, 7 mg-16 mg, 7 mg-18 mg, 7 mg-20 mg, 7 mg-22 mg, 7 mg-24 mg, 7 mg-26 mg, 7 mg-28 mg, 7 mg-30 mg, 7 mg-32 mg, 7 mg-34 mg, 7 mg-36 mg, 7 mg-38 mg, 7 mg-40 mg, 7 mg-42 mg, 7 mg-44 mg, 7 mg-46 mg, 7 mg-48 mg, 7 mg-50 mg, 7 mg-52 mg, 7 mg-54 mg, 7 mg-56 mg, 7 mg-58 mg, 7 mg-60 mg, 9 mg-10 mg, 9 mg-12 mg, 9 mg-14 mg, 9 mg-15 mg, 9 mg-16 mg, 9 mg-18 mg, 9 mg-20 mg, 9 mg-22 mg, 9 mg-24 mg, 9 mg-26 mg, 9 mg-28 mg, 9 mg-30 mg, 9 mg-32 mg, 9 mg-34 mg, 9 mg-36 mg, 9 mg-38 mg, 9 mg-40 mg, 9 mg-42 mg, 9 mg-44 mg, 9 mg-46 mg, 9 mg-48 mg, 9 mg-50 mg, 9 mg-52 mg, 9 mg-54 mg, 9 mg-56 mg, 9 mg-58 mg, 9 mg-60 mg, 10 mg-12 mg, 10 mg-14 mg, 10 mg-15 mg, 10 mg-16 mg, 10 mg-18 mg, 10 mg-20 mg, 10 mg-22 mg, 10 mg-24 mg, 10 mg-26 mg, 10 mg-28 mg, 10 mg-30 mg, 10 mg-32 mg, 10 mg-34 mg, 10 mg-36 mg, 10 mg-38 mg, 10 mg-40 mg, 10 mg-42 mg, 10 mg-44 mg, 10 mg-46 mg, 10 mg-48 mg, 10 mg-50 mg, 10 mg-52 mg, 10 mg-54 mg, 10 mg-56 mg, 10 mg-58 mg, 10 mg-60 mg, 12 mg-14 mg, 12 mg-15 mg, 12 mg-16 mg, 12 mg-18 mg, 12 mg-20 mg, 12 mg-22 mg, 12 mg-24 mg, 12 mg-26 mg, 12 mg-28 mg, 12 mg-30 mg, 12 mg-32 mg, 12 mg-34 mg, 12 mg-36 mg, 12 mg-38 mg, 12 mg-40 mg, 12 mg-42 mg, 12 mg-44 mg, 12 mg-46 mg, 12 mg-48 mg, 12 mg-50 mg, 12 mg-52 mg, 12 mg-54 mg, 12 mg-56 mg, 12 mg-58 mg, 12 mg-60 mg, 15 mg-16 mg, 15 mg-18 mg, 15 mg-20 mg, 15 mg-22 mg, 15 mg-24 mg, 15 mg-26 mg, 15 mg-28 mg, 15 mg-30 mg, 15 mg-32 mg, 15 mg-34 mg, 15 mg-36 mg, 15 mg-38 mg, 15 mg-40 mg, 15 mg-42 mg, 15 mg-44 mg, 15 mg-46 mg, 15 mg-48 mg, 15 mg-50 mg, 15 mg-52 mg, 15 mg-54 mg, 15 mg-56 mg, 15 mg-58 mg, 15 mg-60 mg, 17 mg-18 mg, 17 mg-20 mg, 17 mg-22 mg, 17 mg-24 mg, 17 mg-26 mg, 17 mg-28 mg, 17 mg-30 mg, 17 mg-32 mg, 17 mg-34 mg, 17 mg-36 mg, 17 mg-38 mg, 17 mg-40 mg, 17 mg-42 mg, 17 mg-44 mg, 17 mg-46 mg, 17 mg-48 mg, 17 mg-50 mg, 17 mg-52 mg, 17 mg-54 mg, 17 mg-56 mg, 17 mg-58 mg, 17 mg-60 mg, 20 mg-22 mg, 20 mg-24 mg, 20 mg-26 mg, 20 mg-28 mg, 20 mg-30 mg, 20 mg-32 mg, 20 mg-34 mg, 20 mg-36 mg, 20 mg-38 mg, 20 mg-40 mg, 20 mg-42 mg, 20 mg-44 mg, 20 mg-46 mg, 20 mg-48 mg, 20 mg-50 mg, 20 mg-52 mg, 20 mg-54 mg, 20 mg-56 mg, 20 mg-58 mg, 20 mg-60 mg, 22 mg-24 mg, 22 mg-26 mg, 22 mg-28 mg, 22 mg-30 mg, 22 mg-32 mg, 22 mg-34 mg, 22 mg-36 mg, 22 mg-38 mg, 22 mg-40 mg, 22 mg-42 mg, 22 mg-44 mg, 22 mg-46 mg, 22 mg-48 mg, 22 mg-50 mg, 22 mg-52 mg, 22 mg-54 mg, 22 mg-56 mg, 22 mg-58 mg, 22 mg-60 mg, 25 mg-26 mg, 25 mg-28 mg, 25 mg-30 mg, 25 mg-32 mg, 25 mg-34 mg, 25 mg-36 mg, 25 mg-38 mg, 25 mg-40 mg, 25 mg-42 mg, 25 mg-44 mg, 25 mg-46 mg, 25 mg-48 mg, 25 mg-50 mg, 25 mg-52 mg, 25 mg-54 mg, 25 mg-56 mg, 25 mg-58 mg, 25 mg-60 mg, 27 mg-28 mg, 27 mg-30 mg, 27 mg-32 mg, 27 mg-34 mg, 27 mg-36 mg, 27 mg-38 mg, 27 mg-40 mg, 27 mg-42 mg, 27 mg-44 mg, 27 mg-46 mg, 27 mg-48 mg, 27 mg-50 mg, 27 mg-52 mg, 27 mg-54 mg, 27 mg-56 mg, 27 mg-58 mg, 27 mg-60 mg, 30 mg-32 mg, 30 mg-34 mg, 30 mg-36 mg, 30 mg-38 mg, 30 mg-40 mg, 30 mg-42 mg, 30 mg-44 mg, 30 mg-46 mg, 30 mg-48 mg, 30 mg-50 mg, 30 mg-52 mg, 30 mg-54 mg, 30 mg-56 mg, 30 mg-58 mg, 30 mg-60 mg, 33 mg-34 mg, 33 mg-36 mg, 33 mg-38 mg, 33 mg-40 mg, 33 mg-42 mg, 33 mg-44 mg, 33 mg-46 mg, 33 mg-48 mg, 33 mg-50 mg, 33 mg-52 mg, 33 mg-54 mg, 33 mg-56 mg, 33 mg-58 mg, 33 mg-60 mg, 36 mg-38 mg, 36 mg-40 mg, 36 mg-42 mg, 36 mg-44 mg, 36 mg-46 mg, 36 mg-48 mg, 36 mg-50 mg, 36 mg-52 mg, 36 mg-54 mg, 36 mg-56 mg, 36 mg-58 mg, 36 mg-60 mg, 40 mg-42 mg, 40 mg-44 mg, 40 mg-46 mg, 40 mg-48 mg, 40 mg-50 mg, 40 mg-52 mg, 40 mg-54 mg, 40 mg-56 mg, 40 mg-58 mg, 40 mg-60 mg, 43 mg-46 mg, 43 mg-48 mg, 43 mg-50 mg, 43 mg-52 mg, 43 mg-54 mg, 43 mg-56 mg, 43 mg-58 mg, 42 mg-60 mg, 45 mg-48 mg, 45 mg-50 mg, 45 mg-52 mg, 45 mg-54 mg, 45 mg-56 mg, 45 mg-58 mg, 45 mg-60 mg, 48 mg-50 mg, 48 mg-52 mg, 48 mg-54 mg, 48 mg-56 mg, 48 mg-58 mg, 48 mg-60 mg, 50 mg-52 mg, 50 mg-54 mg, 50 mg-56 mg, 50 mg-58 mg, 50 mg-60 mg, 52 mg-54 mg, 52 mg-56 mg, 52 mg-58 mg, or 52 mg-60 mg. In some embodiments, the compound of Formula (II) dose is greater than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, the compound of Formula (II) dose is about less than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, the compound of Formula (II) dose is about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, about 200 mg, about 225 mg, about 250 mg, about 275 mg, or about 300 mg.

The compounds of Formula (II) described herein may also be incorporated into formulations for delivery outside the systemic circulation. Such formulations may include enteric-coated capsules, tablets, soft-gels, spray dried powders, polymer matrices, hydrogels, enteric-coated solids, crystalline solids, amorphous solids, glassy solids, coated micronized particles, liquids, nebulized liquids, aerosols, or microcapsules.

The actual unit dose of the TR-β agonist compounds described herein and/or depends on the specific compound, and on the condition to be treated. In some embodiments, the dose may be from about 0.01 mg/kg to about 120 mg/kg or more of body weight, from about 0.05 mg/kg or less to about 70 mg/kg, from about 0.1 mg/kg to about 50 mg/kg of body weight, from about 1.0 mg/kg to about 10 mg/kg of body weight, from about 5.0 mg/kg to about 10 mg/kg of body weight, or from about 10.0 mg/kg to about 20.0 mg/kg of body weight. In some embodiments, the dose may be less than 100 mg/kg, 90 mg/kg, 80 mg/kg, 70 mg/kg, 60 mg/kg, 50 mg/kg, 40 mg/kg, 30 mg/kg, 25 mg/kg, 20 mg/kg, 10 mg/kg, 7.5 mg/kg, 6 mg/kg, 5 mg/kg, 4 mg/kg, 3 mg/kg, 2.5 mg/kg, 1 mg/kg, 0.5 mg/kg, 0.1 mg/kg, 0.05 mg/kg or 0.005 mg/kg of body weight. In some embodiments, the actual unit dose is 0.05, 0.07, 0.1, 0.3, 1.0, 3.0, 5.0, 10.0 or 25.0 mg/kg of body weight. Thus, for administration to a 70 kg person, the dosage range would be from about 0.1 mg to 70 mg, from about 1 mg to about 50 mg, from about 0.5 mg to about 10 mg, from about 1 mg to about 10 mg, from about 2.5 mg to about 30 mg, from about 35 mg or less to about 700 mg or more, from about 7 mg to about 600 mg, from about 10 mg to about 500 mg, or from about 20 mg to about 300 mg, or from about 200 mg to about 2000 mg. In some embodiments, the actual unit dose is 0.1 mg. In some embodiments, the actual unit dose is 0.5 mg. In some embodiments, the actual unit dose is 1 mg. In some embodiments, the actual unit dose is 1.5 mg. In some embodiments, the actual unit dose is 2 mg. In some embodiments, the actual unit dose is 2.5 mg. In some embodiments, the actual unit dose is 3 mg. In some embodiments, the actual unit dose is 3.5 mg. In some embodiments, the actual unit dose is 4 mg. In some embodiments, the actual unit dose is 4.5 mg. In some embodiments, the actual unit dose is 5 mg. In some embodiments the actual unit dose is 10 mg. In some embodiments, the actual unit dose is 25 mg. In some embodiments, the actual unit dose is 250 mg or less. In some embodiments, the actual unit dose is 100 mg or less. In some embodiments, the actual unit dose is 70 mg or less.

In some embodiments, the TR-β agonist compound is administered at a dose in the range of about 1-50 $mg/m^2$ of the body surface area. In some embodiments, the TR-β agonist compound is administered at a dose in the range of about 1-2, 1-3, 1-4, 1-5, 1-6, 1-7, 1-8, 1-9, 1-10, 1-11, 1-12, 1-13, 1-13.75, 1-14, 1-15, 1-16, 1-17, 1-18, 1-19, 1-20, 1-22.5, 1-25, 1-27.5, 1-30, 1.5-2, 1.5-3, 1.5-4, 1.5-5, 1.5-6, 1.5-7, 1.5-8, 1.5-9, 1.5-10, 1.5-11, 1.5-12, 1.5-13, 1.5-13.75, 1.5-14, 1.5-15, 1.5-16, 1.5-17, 1.5-18, 1.5-19, 1.5-20, 1.5-22.5, 1.5-25, 1.5-27.5, 1.5-30, 2.5-2, 2.5-3, 2.5-4, 2.5-5, 2.5-6, 2.5-7, 2.5-8, 2.5-9, 2.5-10, 2.5-11, 2.5-12, 2.5-13, 2.5-13.75, 2.5-14, 2.5-15, 2.5-16, 2.5-17, 2.5-18, 2.5-19, 2.5-20, 2.5-22.5, 2.5-25, 2.5-27.5, 2.5-30, 2.5-7.5, 3-4, 3-5, 3-6, 3-7, 3-8, 3-9, 3-10, 3-11, 3-12, 3-13, 3-13.75, 3-14, 3-15, 3-16, 3-17, 3-18, 3-19, 3-20, 3-22.5, 3-25, 3-27.5, 3-30, 3.5-6.5, 3.5-13.75, 3.5-15, 2.5-17.5, 4-5, 4-6, 4-7, 4-8, 4-9, 4-10, 4-11, 4-12, 4-13, 4-13.75, 4-14, 4-15, 4-16, 4-17, 4-18, 4-19, 4-20, 4-22.5, 4-25, 4-27.5, 4-30, 5-6, 5-7, 5-8, 5-9, 5-10, 5-11, 5-12, 5-13, 5-13.75, 5-14, 5-15, 5-16, 5-17, 5-18, 5-19, 5-20, 5-22.5, 5-25, 5-27.5, 5-30, 6-7, 6-8, 6-9, 6-10, 6-11, 6-12, 6-13, 6-13.75, 6-14, 6-15, 6-16, 6-17, 6-18, 6-19, 6-20, 6-22.5, 6-25, 6-27.5, 6-30, 7-8, 7-9, 7-10, 7-11, 7-12, 7-13, 7-13.75, 7-14, 7-15, 7-16, 7-17, 7-18, 7-19, 7-20, 7-22.5, 7-25, 7-27.5, 7-30, 7.5-12.5, 7.5-13.5, 7.5-15, 8-9, 8-10, 8-11, 8-12, 8-13, 8-13.75, 8-14, 8-15, 8-16, 8-17, 8-18, 8-19, 8-20, 8-22.5, 8-25, 8-27.5, 8-30, 9-10, 9-11, 9-12, 9-13, 9-13.75, 9-14, 9-15, 9-16, 9-17, 9-18, 9-19, 9-20, 9-22.5, 9-25, 9-27.5, 9-30, 10-11, 10-12, 10-13, 10-13.75, 10-14, 10-15, 10-16, 10-17, 10-18, 10-19, 10-20, 10-22.5, 10-25, 10-27.5, 10-30, 11.5-15.5, 12.5-14.5, 7.5-22.5, 8.5-32.5, 9.5-15.5, 15.5-24.5, 5-35, 17.5-22.5, 22.5-32.5, 25-35, 25.5-24.5, 27.5-32.5, 2-20, 2.5-22.5, or 9.5-21.5 mg/m$^2$, of the body surface area. In some embodiments, the TR-β agonist compound is administered at a dose of about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, the TR-β agonist compound is administered at a dose less than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, the TR-β agonist compound is administered at a dose greater than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50 mg/m$^2$ of the body surface area.

In some embodiments, the TR-β agonist compound dose is about 0.1 mg-100 mg, 0.1 mg-50 mg, 0.1 mg-20 mg, 0.1 mg-10 mg, 0.5 mg-100 mg, 0.5 mg-50 mg, 0.5 mg-20 mg, 0.5 mg-10 mg, 1 mg-100 mg, 1 mg-50 mg, 1 mg-20 mg, 1 mg-10 mg, 2.5 mg-50 mg, 2.5 mg-20 mg, 2.5 mg-10 mg, or about 2.5 mg-5 mg. In some embodiments, the TR-β agonist compound dose is about 5 mg-300 mg, 5 mg-200 mg, 7.5 mg-200 mg, 10 mg-100 mg, 15 mg-100 mg, 20 mg-100 mg, 30 mg-100 mg, 40 mg-100 mg, 10 mg-80 mg, 15 mg-80 mg, 20 mg-80 mg, 30 mg-80 mg, 40 mg-80 mg, 10 mg-60 mg, 15 mg-60 mg, 20 mg-60 mg, 30 mg-60 mg, or about 40 mg-60 mg. In some embodiments, the TR-β agonist compound administered is about 20 mg-60 mg, 27 mg-60 mg, 20 mg-45 mg, or 27 mg-45 mg. In some embodiments, the TR-β agonist compound administered is about 5 mg-7.5 mg, 5 mg-9 mg, 5 mg-10 mg, 5 mg-12 mg, 5 mg-14 mg, 5 mg-15 mg, 5 mg-16 mg, 5 mg-18 mg, 5 mg-20 mg, 5 mg-22 mg, 5 mg-24 mg, 5 mg-26 mg, 5 mg-28 mg, 5 mg-30 mg, 5 mg-32 mg, 5 mg-34 mg, 5 mg-36 mg, 5 mg-38 mg, 5 mg-40 mg, 5 mg-42 mg, 5 mg-44 mg, 5 mg-46 mg, 5 mg-48 mg, 5 mg-50 mg, 5 mg-52 mg, 5 mg-54 mg, 5 mg-56 mg, 5 mg-58 mg, 5 mg-60 mg, 7 mg-7.7 mg, 7 mg-9 mg, 7 mg-10 mg, 7 mg-12 mg, 7 mg-14 mg, 7 mg-15 mg, 7 mg-16 mg, 7 mg-18 mg, 7 mg-20 mg, 7 mg-22 mg, 7 mg-24 mg, 7 mg-26 mg, 7 mg-28 mg, 7 mg-30 mg, 7 mg-32 mg, 7 mg-34 mg, 7 mg-36 mg, 7 mg-38 mg, 7 mg-40 mg, 7 mg-42 mg, 7 mg-44 mg, 7 mg-46 mg, 7 mg-48 mg, 7 mg-50 mg, 7 mg-52 mg, 7 mg-54 mg, 7 mg-56 mg, 7 mg-58 mg, 7 mg-60 mg, 9 mg-10 mg, 9 mg-12 mg, 9 mg-14 mg, 9 mg-15 mg, 9 mg-16 mg, 9 mg-18 mg, 9 mg-20 mg, 9 mg-22 mg, 9 mg-24 mg, 9 mg-26 mg, 9 mg-28 mg, 9 mg-30 mg, 9 mg-32 mg, 9 mg-34 mg, 9 mg-36 mg, 9 mg-38 mg, 9 mg-40 mg, 9 mg-42 mg, 9 mg-44 mg, 9 mg-46 mg, 9 mg-48 mg, 9 mg-50 mg, 9 mg-52 mg, 9 mg-54 mg, 9 mg-56 mg, 9 mg-58 mg, 9 mg-60 mg, 10 mg-12 mg, 10 mg-14 mg, 10 mg-15 mg, 10 mg-16 mg, 10 mg-18 mg, 10 mg-20 mg, 10 mg-22 mg, 10 mg-24 mg, 10 mg-26 mg, 10 mg-28 mg, 10 mg-30 mg, 10 mg-32 mg, 10 mg-34 mg, 10 mg-36 mg, 10 mg-38 mg, 10 mg-40 mg, 10 mg-42 mg, 10 mg-44 mg, 10 mg-46 mg, 10 mg-48 mg, 10 mg-50 mg, 10 mg-52 mg, 10 mg-54 mg, 10 mg-56 mg, 10 mg-58 mg, 10 mg-60 mg, 12 mg-14 mg, 12 mg-15 mg, 12 mg-16 mg, 12 mg-18 mg, 12 mg-20 mg, 12 mg-22 mg, 12 mg-24 mg, 12 mg-26 mg, 12 mg-28 mg, 12 mg-30 mg, 12 mg-32 mg, 12 mg-34 mg, 12 mg-36 mg, 12 mg-38 mg, 12 mg-40 mg, 12 mg-42 mg, 12 mg-44 mg, 12 mg-46 mg, 12 mg-48 mg, 12 mg-50 mg, 12 mg-52 mg, 12 mg-54 mg, 12 mg-56 mg, 12 mg-58 mg, 12 mg-60 mg, 15 mg-16 mg, 15 mg-18 mg, 15 mg-20 mg, 15 mg-22 mg, 15 mg-24 mg, 15 mg-26 mg, 15 mg-28 mg, 15 mg-30 mg, 15 mg-32 mg, 15 mg-34 mg, 15 mg-36 mg, 15 mg-38 mg, 15 mg-40 mg, 15 mg-42 mg, 15 mg-44 mg, 15 mg-46 mg, 15 mg-48 mg, 15 mg-50 mg, 15 mg-52 mg, 15 mg-54 mg, 15 mg-56 mg, 15 mg-58 mg, 15 mg-60 mg, 17 mg-18 mg, 17 mg-20 mg, 17 mg-22 mg, 17 mg-24 mg, 17 mg-26 mg, 17 mg-28 mg, 17 mg-30 mg, 17 mg-32 mg, 17 mg-34 mg, 17 mg-36 mg, 17 mg-38 mg, 17 mg-40 mg, 17 mg-42 mg, 17 mg-44 mg, 17 mg-46 mg, 17 mg-48 mg, 17 mg-50 mg, 17 mg-52 mg, 17 mg-54 mg, 17 mg-56 mg, 17 mg-58 mg, 17 mg-60 mg, 20 mg-22 mg, 20 mg-24 mg, 20 mg-26 mg, 20 mg-28 mg, 20 mg-30 mg, 20 mg-32 mg, 20 mg-34 mg, 20 mg-36 mg, 20 mg-38 mg, 20 mg-40 mg, 20 mg-42 mg, 20 mg-44 mg, 20 mg-46 mg, 20 mg-48 mg, 20 mg-50 mg, 20 mg-52 mg, 20 mg-54 mg, 20 mg-56 mg, 20 mg-58 mg, 20 mg-60 mg, 22 mg-24 mg, 22 mg-26 mg, 22 mg-28 mg, 22 mg-30 mg, 22 mg-32 mg, 22 mg-34 mg, 22 mg-36 mg, 22 mg-38 mg, 22 mg-40 mg, 22 mg-42 mg, 22 mg-44 mg, 22 mg-46 mg, 22 mg-48 mg, 22 mg-50 mg, 22 mg-52 mg, 22 mg-54 mg, 22 mg-56 mg, 22 mg-58 mg, 22 mg-60 mg, 25 mg-26 mg, 25 mg-28 mg, 25 mg-30 mg, 25 mg-32 mg, 25 mg-34 mg, 25 mg-36 mg, 25 mg-38 mg, 25 mg-40 mg, 25 mg-42 mg, 25 mg-44 mg, 25 mg-46 mg, 25 mg-48 mg, 25 mg-50 mg, 25 mg-52 mg, 25 mg-54 mg, 25 mg-56 mg, 25 mg-58 mg, 25 mg-60 mg, 27 mg-28 mg, 27 mg-30 mg, 27 mg-32 mg, 27 mg-34 mg, 27 mg-36 mg, 27 mg-38 mg, 27 mg-40 mg, 27 mg-42 mg, 27 mg-44 mg, 27 mg-46 mg, 27 mg-48 mg, 27 mg-50 mg, 27 mg-52 mg, 27 mg-54 mg, 27 mg-56 mg, 27 mg-58 mg, 27 mg-60 mg, 30 mg-32 mg, 30 mg-34 mg, 30 mg-36 mg, 30 mg-38 mg, 30 mg-40 mg, 30 mg-42 mg, 30 mg-44 mg, 30 mg-46 mg, 30 mg-48 mg, 30 mg-50 mg, 30 mg-52 mg, 30 mg-54 mg, 30 mg-56 mg, 30 mg-58 mg, 30 mg-60 mg, 33 mg-34 mg, 33 mg-36 mg, 33 mg-38 mg, 33 mg-40 mg, 33 mg-42 mg, 33 mg-44 mg, 33 mg-46 mg, 33 mg-48 mg, 33 mg-50 mg, 33 mg-52 mg, 33 mg-54 mg, 33 mg-56 mg, 33 mg-58 mg, 33 mg-60 mg, 36 mg-38 mg, 36 mg-40 mg, 36 mg-42 mg, 36 mg-44 mg, 36 mg-46 mg, 36 mg-48 mg, 36 mg-50 mg, 36 mg-52 mg, 36 mg-54 mg, 36 mg-56 mg, 36 mg-58 mg, 36 mg-60 mg, 40 mg-42 mg, 40 mg-44 mg, 40 mg-46 mg, 40 mg-48 mg, 40 mg-50 mg, 40 mg-52 mg, 40 mg-54 mg, 40 mg-56 mg, 40 mg-58 mg, 40 mg-60 mg, 43 mg-46 mg, 43 mg-48 mg, 43 mg-50 mg, 43 mg-52 mg, 43 mg-54 mg, 43 mg-56 mg, 43 mg-58 mg, 42 mg-60 mg, 45 mg-48 mg, 45 mg-50 mg, 45 mg-52 mg, 45 mg-54 mg, 45 mg-56 mg, 45 mg-58 mg, 45 mg-60 mg, 48 mg-50 mg, 48 mg-52 mg, 48 mg-54 mg, 48 mg-56 mg, 48 mg-58 mg, 48 mg-60 mg, 50 mg-52 mg, 50 mg-54 mg, 50 mg-56 mg, 50 mg-58 mg, 50 mg-60 mg, 52 mg-54 mg, 52 mg-56 mg, 52 mg-58 mg, or 52 mg-60 mg. In some embodiments, the TR-β agonist compound dose is greater than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, the TR-β agonist compound dose is about less than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, TR-β agonist compound dose is about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, about 200 mg, about 225 mg, about 250 mg, about 275 mg, or about 300 mg.

In some embodiments, a TR-β agonist compound described herein is administered in combination with a compound of Formula (II) described herein. In some embodiments, the mass ratio of TR-β agonist compound to the compound of Formula (II) is from about 10:1 to about 1:10. In some embodiments, the mass ratio of TR-β agonist compound to the compound of Formula (II) is from about 7:1 to about 1:7. In some embodiments, the mass ratio of TR-β agonist compound to the compound of Formula (II) is from about 5:1 to about 1:5. In some embodiments, the mass ratio of TR-β agonist compound to the compound of Formula (II) is from about 3:1 to about 1:3. In some embodiments, the mass ratio of TR-β agonist compound to the compound of Formula (II) is from about 2:1 to about 1:2. In some embodiments, the mass ratio of TR-β agonist compound to the compound of Formula (II) is from about 10:1 to about 1:1, from about 7:1 to about 1:1, from about 5:1 to about 1:1, from about 3:1 to about 1:1, or from about 2:1 to about 1:1. In some embodiments, the mass ratio of TR-β agonist compound to the compound of Formula (IT) is from about 1:1 to about 1:2, from about 1:1 to about 1:3, from about 1:1 to about 1:5, from about 1:1 to about 1:7, or from about 1:1 to about 1:10. In some embodiments, the mass ratio of TR-β agonist compound to the compound of Formula (II) is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10, or any range between two of these values.

In some embodiments, the TR-β agonist compound is Compound 2 and the compound of Formula (II) is:

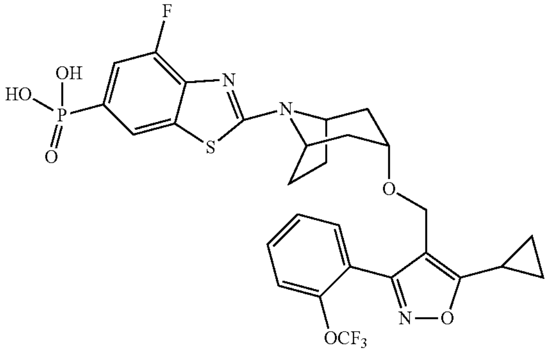

,

-continued

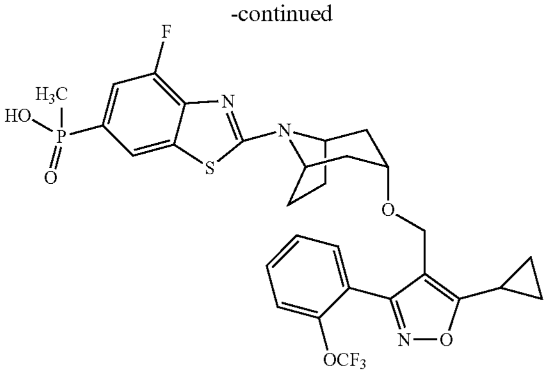

,

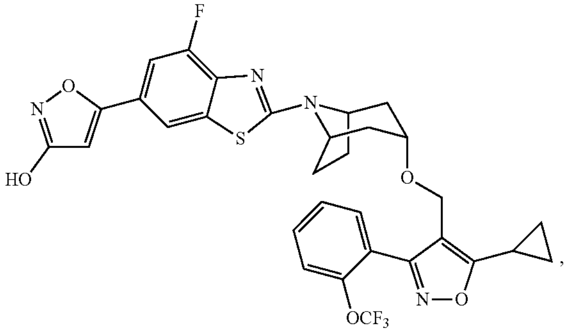

,

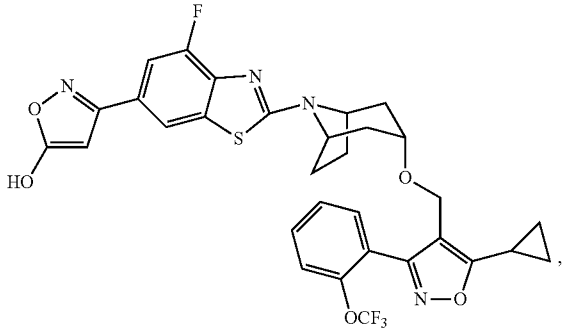

, or a pharmaceutically acceptable salt thereof.

The compounds described herein may also be incorporated into formulations for delivery outside the systemic circulation. Such formulations may include enteric-coated capsules, tablets, soft-gels, spray dried powders, polymer matrices, hydrogels, enteric-coated solids, crystalline solids, amorphous solids, glassy solids, coated micronized particles, liquids, nebulized liquids, aerosols, or microcapsules.

Methods of Administration

The compounds and compositions described above may be administered through any suitable route of administration, for example, by injection, such as subcutaneously, intramuscularly, intraperitoneally, intravenously, or intraarterially; topically, such as by cream, lotion, or patch; orally, such as by a pill, dissolved liquid, oral suspension, buccal film, or mouthrinse; nasally, such as by a nasal aerosol, powder, or spray; or ocularly, such as by an eye drop). In some embodiments, the composition may be administered one, twice, three times, our four times per day. In other embodiments, the composition may be administered once, twice, or three times per week. In other embodiments, the composition is administered every other day, every three days, or every four days. In other embodiments, the composition every other week, every three weeks, or every four weeks. In other embodiments, the composition is administered once per month or twice per month.

In some embodiments, an initial loading dose is administered which is higher than subsequent doses (maintenance doses). The dosage form or mode of administration of a maintenance dose may be different from that used for the loading dose. In any of the embodiments disclosed herein, a maintenance dose may comprise administration of the unit dosage form on any dosing schedule contemplated herein, including but not limited to, monthly or multiple times per month, biweekly or multiple times each two weeks, weekly or multiple times per week, daily or multiple times per day. It is contemplated within the present disclosure that dosing holidays may be incorporated into the dosing period of the maintenance dose. Such dosing holidays may occur immediately after the administration of the loading dose or at any time during the period of administration of the maintenance dose. In some embodiments, the loading dose is 300 mg or less; 250 mg or less, 200 mg or less, 150 mg or less, or 100 mg or less. In some embodiments, the maintenance dose is 300 mg or less; 200 mg or less, 100 mg or less, 50 mg or less, 25 mg or less, 10 mg or less, 5 mg or less, or 1 mg or less.

In some embodiments, the compounds of Formula (II) presented herein may be administered simultaneously with one or more additional pharmaceutical agents. When administered simultaneously, the compound of Formula (II) and the additional pharmaceutical agent may be in the same pharmaceutical composition or in separate pharmaceutical compositions. In other embodiments, the compounds of the present disclosure may be administered sequentially with one or more additional pharmaceutical agents. In some embodiments, the additional pharmaceutical agent may be a TR-β agonist compound.

In some embodiments, the compounds of Formula (II) provided herein may be administered prior to administration of the additional pharmaceutical agent. In some embodiments, the compounds of Formula (II) provided herein may be administered about 15 minutes, about 30 minutes, about 45 minutes, about 1 hour, about 2 hours, about 3 hours, about 4 hours, about 6 hours, about 8 hours, about 12 hours, or about 24 hours prior to administration of the additional pharmaceutical agent. In some embodiments, the compounds of Formula (II) provided herein may be administered after administration of the additional pharmaceutical agent. In some embodiments, the compounds of Formula (II) provided herein may be administered about 15 minutes, about 30 minutes, about 45 minutes, about 1 hour, about 2 hours, about 3 hours, about 4 hours, about 6 hours, about 8 hours, about 12 hours, or about 24 hours after administration of the additional pharmaceutical agent.

Methods of Treatment

Some embodiments according to the methods and compositions of the present disclosure relate to a method for preventing, treating, or ameliorating one or more fatty liver diseases in a subject comprising administering an effective amount of a compound of Formula (I) described herein to a subject in need thereof. In some embodiments, the fatty liver disease may be steatosis. In other embodiments, the fatty liver disease may be non-alcoholic fatty liver disease. In some embodiments, the fatty liver disease may be non-alcoholic steatohepatitis (NASH). In some embodiments, the subject may have two or more of the aforementioned fatty liver diseases.

Some embodiments according to the methods and compositions of the present disclosure relate to a method of preventing, treating, or ameliorating one or more diseases or disorders in a subject, comprising administering an effective amount of a compound of Formula (IT) described herein. In some embodiments, the compound of Formula (II) may be administered in combination with a TR-β agonist compound described herein. In some embodiments, the disease or disorder may be liver fibrosis, renal fibrosis, biliary fibrosis, pancreatic fibrosis, nonalcoholic steatohepatitis, non-alcoholic fatty liver disease, chronic kidney disease, diabetic kidney disease, primary sclerosing cholangitis, primary biliary cirrhosis, or idiopathic fibrosis. In some embodiments, the disease or disorder may nonalcoholic steatohepatitis, non-alcoholic fatty liver disease, chronic kidney disease, diabetic kidney disease, primary sclerosing cholangitis, or primary biliary cirrhosis.

Some embodiments according to the methods and compositions of the present disclosure relate to a method for the reduction or prevention of the deposition of extracellular matrix proteins, comprising administering an effective amount of a compound of Formula (II) described herein to a subject in need thereof. In some embodiments, the compound of Formula (II) may be administered in combination with a TR-β agonist compound described herein. In some embodiments, said deposition of extracellular matrix proteins may comprise abnormal or excessive deposition of said proteins. In some embodiments, said extracellular matrix proteins may comprise one or more of collagen, keratin, elastin, or fibrin. In some embodiments, said extracellular matrix proteins may comprise collagen. In some embodiments, said extracellular matrix proteins may comprise Type I collagen. In some embodiments, said extracellular matrix proteins may comprise Collagen Type Ia. In some embodiments, said extracellular matrix proteins may comprise Type III collagen. Some embodiments according to the compositions and methods of the present disclosure relate to a method for the treatment of a fibrosis or its symptoms or sequelae, comprising administering an effective amount of a compound described herein to a subject in need thereof.

In some embodiments, the compounds and compositions comprising a compound of Formula (II) described herein can be used to treat a variety of conditions arising from fibrosis or inflammation, and specifically including those associated with abnormal collagen deposition. In some embodiments, the compounds and compositions comprising the compound of Formula (II) may be used in combination with a TR-pi agonist compound described herein. Example conditions include glycogen storage disease type III (GSD III), glycogen storage disease type VI (GSD VT), glycogen storage disease type IX (GSD IX), non-alcoholic steatohepatitis (NASH), cirrhosis, hepatitis, scleroderma, alcoholic fatty liver disease, atherosclerosis, asthma, cardiac fibrosis, organ transplant fibrosis, muscle fibrosis, pancreatic fibrosis, bone-marrow fibrosis, liver fibrosis, cirrhosis of liver and gallbladder, fibrosis of the spleen, pulmonary fibrosis, idiopathic pulmonary fibrosis, diffuse parenchymal lung disease, idiopathic interstitial fibrosis, diffuse interstitial fibrosis, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis, or symptoms or sequelae thereof, or other diseases or conditions resulting in the excessive deposition of extracellular matrix components, such as collagen.

In some embodiments the methods of the present disclosure comprise methods for the treatment, amelioration, or prevention of a fibrotic condition. In some embodiments, said fibrotic condition may be secondary to another condition. In some embodiments, said fibrotic condition or primary condition may further comprise chronic inflammation of an organ, tissue, spatial region, or fluid-connected area of the body of a subject. In some embodiments, said inflammation may comprise activation of one or more TGF-beta dependent signaling pathways. In some embodiments, said TGF-β dependent signaling pathways may comprise one or more elements responsive to T3 or T4. In some embodiments, said fibrotic condition may comprise abnormal or excessive deposition of one or more of collagen, keratin, or elastin. In some embodiments, said fibrotic condition may comprise abnormal or excessive deposition of collagen. In some embodiments, said fibrotic condition may comprise abnormal or excessive deposition of Type I collagen. In some embodiments, said fibrotic condition may comprise abnormal or excessive deposition of Collagen Type Ia. In some embodiments, said fibrotic condition may comprise abnormal or excessive deposition of Type III collagen. In some embodiments said fibrotic condition may comprise one or more of glycogen storage disease type III (GSD III), glycogen storage disease type VI (GSD VI), glycogen storage disease type IX (GSD IX), non-alcoholic steatohepatitis (NASH), cirrhosis, hepatitis, scleroderma, alcoholic fatty liver disease, atherosclerosis, asthma, cardiac fibrosis, organ transplant fibrosis, muscle fibrosis, pancreatic fibrosis, bone-marrow fibrosis, liver fibrosis, cirrhosis of liver and gallbladder, fibrosis of the spleen, scleroderma, pulmonary fibrosis, idiopathic pulmonary fibrosis, diffuse parenchymal lung disease, idiopathic interstitial fibrosis, diffuse interstitial fibrosis, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis. In some embodiments, said fibrotic condition may comprise one or more of GSD III, GSD IX, Non Alcoholic Steatohepatitis, cirrhosis of the liver and/or pancreas, scleroderma, idiopathic pulmonary fibrosis, psoriasis, alcoholic fatty liver disease, Dupuytren's disease, and/or any combination thereof.

According to the methods and compositions of the present disclosure, thyroid receptor agonists such as those disclosed herein, and especially including Compounds 1-4, may be administered in combination with one or more compounds of Formula (I) described herein to a subject for the treatment, amelioration, prevention, or cure of a fibrotic condition, or a condition for which fibrosis is a symptom or sequela. According to the methods and composition as disclosed herein, said fibrotic condition or condition having fibrosis as a sequela may further comprise chronic inflammation. According to the methods and compositions as disclosed herein, said fibrotic condition or condition having fibrosis as a sequela may further comprise activation of one or more TGF-β dependent signaling pathways. According to the methods and compositions as disclosed herein, said fibrotic condition or condition having fibrosis as a sequela may further comprise activation and/or repression of one or more Thyroid Receptor Beta (TRβ) dependent signaling pathways. According to the methods and compositions as disclosed herein, said fibrotic condition or condition having fibrosis as a sequela may further comprise the involvement of signaling pathways responsive to triiodothyronine (T3), thyroxine (T4), any combination thereof, or mimetics thereof. According to the methods and compositions as disclosed herein, said fibrotic condition or condition having fibrosis as a sequela may further comprise the involvement of receptors responsive to T3, T4, any combination thereof, or mimetics thereof. In some embodiments according to the methods and compositions disclosed herein, said fibrotic condition or condition having fibrosis as a sequela may comprise the involvement of TRβ. In some embodiments according to the methods and compositions disclosed herein, said fibrotic condition or condition having fibrosis as a sequela may comprise one or more conditions which are prevented, ameliorated, or cured by the administration of one or more agonists of TRβ. In some embodiments according to the methods and compositions disclosed herein, said fibrotic condition or condition having fibrosis as a sequela may comprise one or more conditions which are prevented, ameliorated, or cured by the administration of one or more of Compounds 1-4 in combination with one or more compounds of Formula (II) described herein. In some embodiments, said one or more agonists of TRβ, or said one or more of Compounds 1-4, and said one or more compounds of Formula (II), may be co-administered with one or more excipients. In some embodiments, said one or more agonists of TRβ, or said one or more of Compounds 1-4, and said one or more compounds of Formula (I), may be administered prior to, during, or after a surgical intervention, phototherapy, or ultrasound therapy.

In some embodiments, the compositions and methods described herein provide compositions and methods for the treatment, amelioration, prevention or cure of collagen deposition. In some embodiments, said collagen deposition comprises and abnormal or excessive deposition of collagen. In some embodiments, said collagen deposition may comprise abnormal or excessive deposition of Type I collagen. In some embodiments, said collagen deposition may comprise abnormal or excessive deposition of Collagen Type Ia. In some embodiments, said collagen deposition may comprise abnormal or excessive deposition of Type III collagen. According to the methods and compositions as disclosed herein, said collagen deposition may further comprise the involvement of receptors responsive to T3, T4, any combination thereof, or mimetics thereof. In some embodiments according to the methods and compositions disclosed herein, said collagen deposition may comprise the involvement of TRβ. In some embodiments according to the methods and compositions disclosed herein, said collagen deposition may be prevented, ameliorated, or cured by the administration of one or more agonists of TRβ. In some embodiments according to the methods and compositions disclosed herein, said collagen deposition may be prevented, ameliorated, or cured by the administration of one or more of Compounds 1-4 in combination with one or more compounds of Formula (II). In some embodiments, said one or more agonists of TRO, or said one or more of Compounds 1-4, and one or more compounds of Formula (II), may be co-administered with one or more excipients. In some embodiments, said one or more agonists of TRβ, or said one or more of Compounds 1-4 and one or more compounds of Formula (II), may be administered prior to, during, or after a surgical intervention, phototherapy, or ultrasound therapy. In some embodiments, the second pharmaceutical agent is a compound of Formula (II), or a pharmaceutically acceptable salt thereof In some embodiments, administration of compounds 1-4, of compound 2, or of any of the compounds or compositions as disclosed herein in combination with one or more compounds of Formula (II) described herein results in a reduction in the expression of the Cola1, Col3a1, αSMA, and/or Galectin1 genes or any combination or product thereof in the subject to which said combination is administered. In some embodiments, administration of compounds 1-4, of compound 2, or of any of the compounds or compositions as disclosed herein in combination with one or more compounds of Formula (II) results in a reduction in the degree of fibrosis observable by histology, histochemistry, immunohistochemistry, or the like, and/or reduction s in the amount, accumulation, or distribution of type 1 collagen and/or hydroxyproline or any combination thereof in the subject to which said combination is administered. In some embodiments, administration of compounds 1-4, of compound 2, or of any of the compounds or compositions in combination with one or compounds of Formula (II) as disclosed herein results in a reduction in total serum lipids, total serum cholesterol, total serum triglycerides, total liver lipids, total liver cholesterol, total liver triglycerides, or any combination thereof.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

General Procedures

It will be apparent to the skilled artisan that methods for preparing precursors and functionality related to the compounds claimed herein are generally described in the literature. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like. All the intermediate compounds of the present invention were used without further purification unless otherwise specified.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

The following abbreviations have the indicated meanings:

DCM=dichloromethane
DIEA=N,N-Diisopropylethylamine
DIPEA=N,N-Diisopropylethylamine
DMF=N,N-dimethylformamide
DMP=Dess Martin Periodinane
DNs=dinitrosulfonyl
dppf=1,1'-Bis (diphenylphosphino)ferrocene
ESBL=extended-spectrum β-lactamase
EtOAc=ethyl acetate
FCC=Flash Column Chromatography
MeCN=acetonitrile
NCS=N-chlorosuccinimide
N-BOC=N-tert-butyloxycarbonyl
NMR=nuclear magnetic resonance
PE=Petroleum Ether
Prep=preparatory
Sat.=saturated aqueous TBDMSCl=tert-butyldimethylsilyl chloride
TBS=tert-butyldimethylsilyl
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Example 1: Synthesis of (2-((1R,5S)-3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazol-6-yl)phosphonic acid (II-1)

Synthesis of Tropane Core 2-(Trifluoromethoxy)benzaldehyde was condensed with hydroxylamine hydrochloride in the presence of sodium hydroxide in ethanol to give the corresponding oxime. Oxidation of the oxime with N-chlorosuccinimide (NCS) gave a chloroxime, which was then immediately reacted with methyl 3-cyclopropyl-3-oxopropanoate and potassium carbonate to form an isoxazole product. Reduction of the methyl ester with lithium aluminum hydride in THE afforded the corresponding alcohol. The alcohol was then converted to the bromide with carbontetrabromide and triphenylphosphine. The bromide alkylated the hydroxy group of the endo isomer of N-BOC desmethyltropine with KOtBu, THF, and 18-crown-6 ether. Removal of the N-BOC group with trifluoroacetic acid (TFA) gave the N—H tropane core (Scheme 1).

Scheme 1

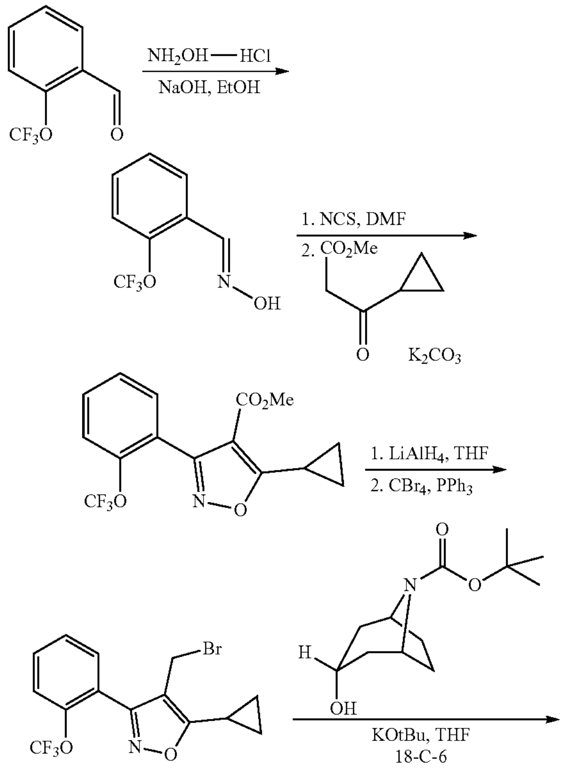

-continued

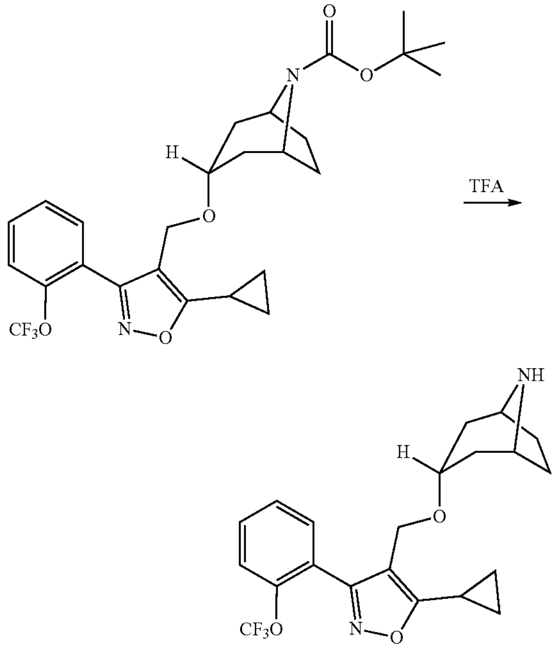

tropane core

Synthesis of
2-amino-4-fluoro-6-bromobenzothiazole

4-Bromo-2-fluoroaniline reacts with bromine and potassium thiocyanate in acetic acid to form 2-amino-4-fluoro-6-bromobenzothiazole.

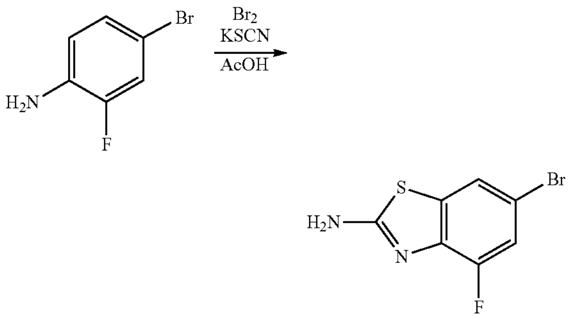

Synthesis of Compound II-1

2-Amino-4-fluoro-6-bromobenzothiazole was coupled with diethyl phosphite in the presence of Pd(dppf)$Cl_2$ and triethylamine in 1,4-dioxane to give the corresponding diethyl phosphonate ester. Diazotization and bromination of the thiazole ring with t-butyl nitrite and $CuBr_2$ in acetonitrile converted the amino group to a bromide. The thiazole ring underwent nucleophilic aromatic substitution at the 2-position through reaction with the N—H tropane core with cesium carbonate in dimethylacetamide to afford the diethyl phosphonate ester of Compound II-1. Cleavage of the ethyl groups with TMS-Br gave Compound II-1 as a phosphonic acid (Scheme 2).

Scheme 2

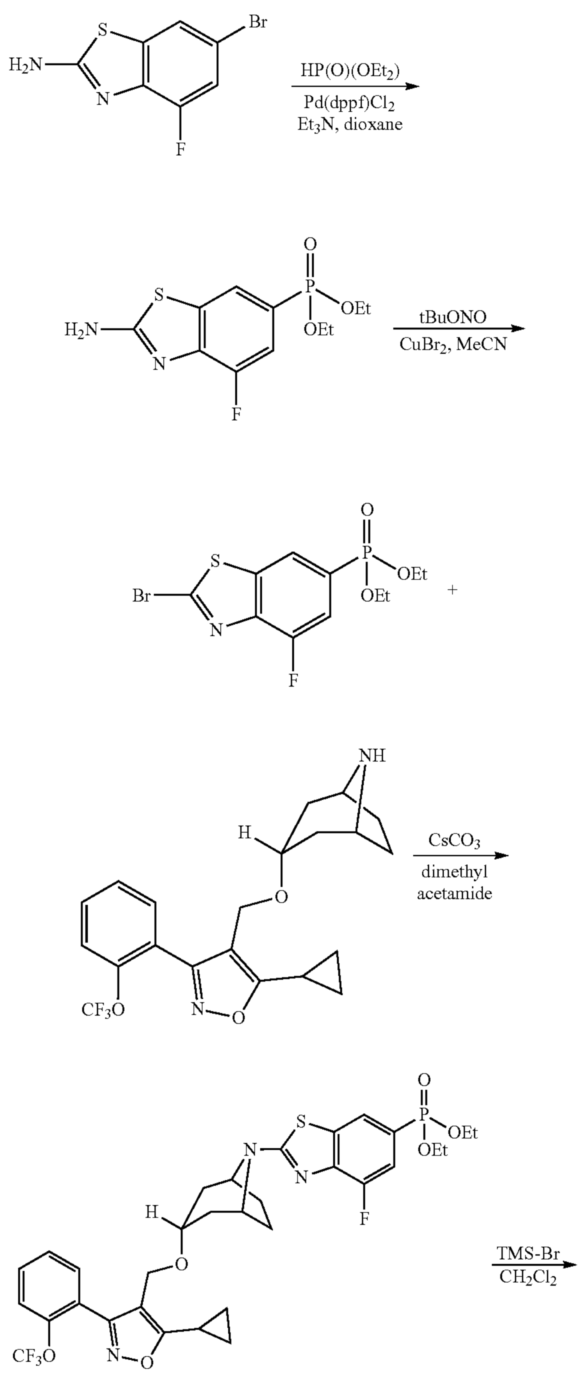

-continued

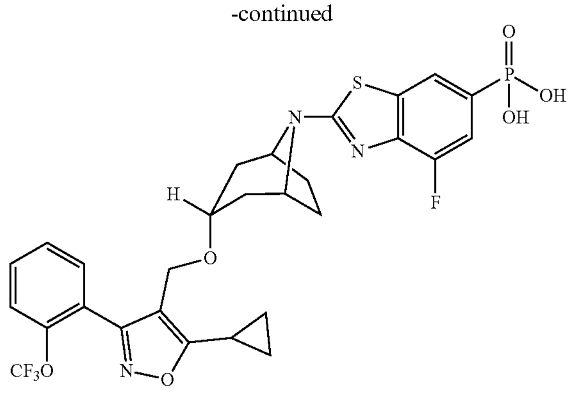

II-1

Example 2: Synthesis of (2-((1R,5S)-3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazol-6-yl(methyl)phosphinic acid (II-2)

The tropane core and 2-amino-4-fluoro-6-bromobenzothiazole were prepared as discussed above in Example 1. 2-Amino-4-fluoro-6-bromobenzothiazole was coupled with diethyl methylphosphonite in the presence of Pd(dppf)$Cl_2$ and triethylamine in DMF to give the corresponding ethyl P-methyl phosphinate ester. Diazotization and bromination of the thiazole ring with t-butyl nitrite and $CuBr_2$ in acetonitrile converted the amino group to a bromide. The thiazole ring underwent nucleophilic aromatic substitution at the 2-position through reaction with the N—H tropane core with cesium carbonate in DMF to afford the ethyl phosphinate ester of Compound II-2. Cleavage of the ethyl group with TMS-Br gave Compound II-2 as a methylphosphinic acid.

Example 3: Synthesis of 5-(2-((1R,5S)-3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazol-6-yl)isoxazol-3-ol (II-3)

Synthesis of Ethyl Beta-Ketoester Precursor

Methyl 4-amino-3-fluorobenzoate reacted with potassium thiocyanate and bromine in acetic acid to afford 2-amino-6-carbomethoxy-4-fluorobenzothiazole. Diazotization and bromination of the thiazole ring with t-butyl nitrite and $CuBr_2$ in acetonitrile converted the amino group to a bromide. Nucleophilic aromatic substitution at the 2-position of the thiazole with the N—H tropane core with cesium carbonate in DMF gave the completed scaffold. Hydrolysis of the methyl ester with KOH in THF and methanol generated a carboxylic acid which was then reacted with carbonyl diimidazole (CDT) followed by ethyl potassium malonate, $MgCl_2$, and triethyl amine to form an ethyl beta-ketoester as the common precursor of Compound II-3 and Compound II-4 (Scheme 3).

Scheme 3

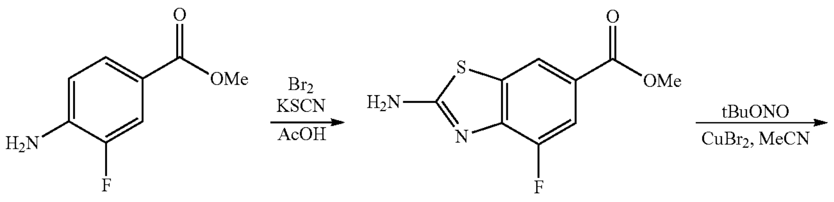

-continued
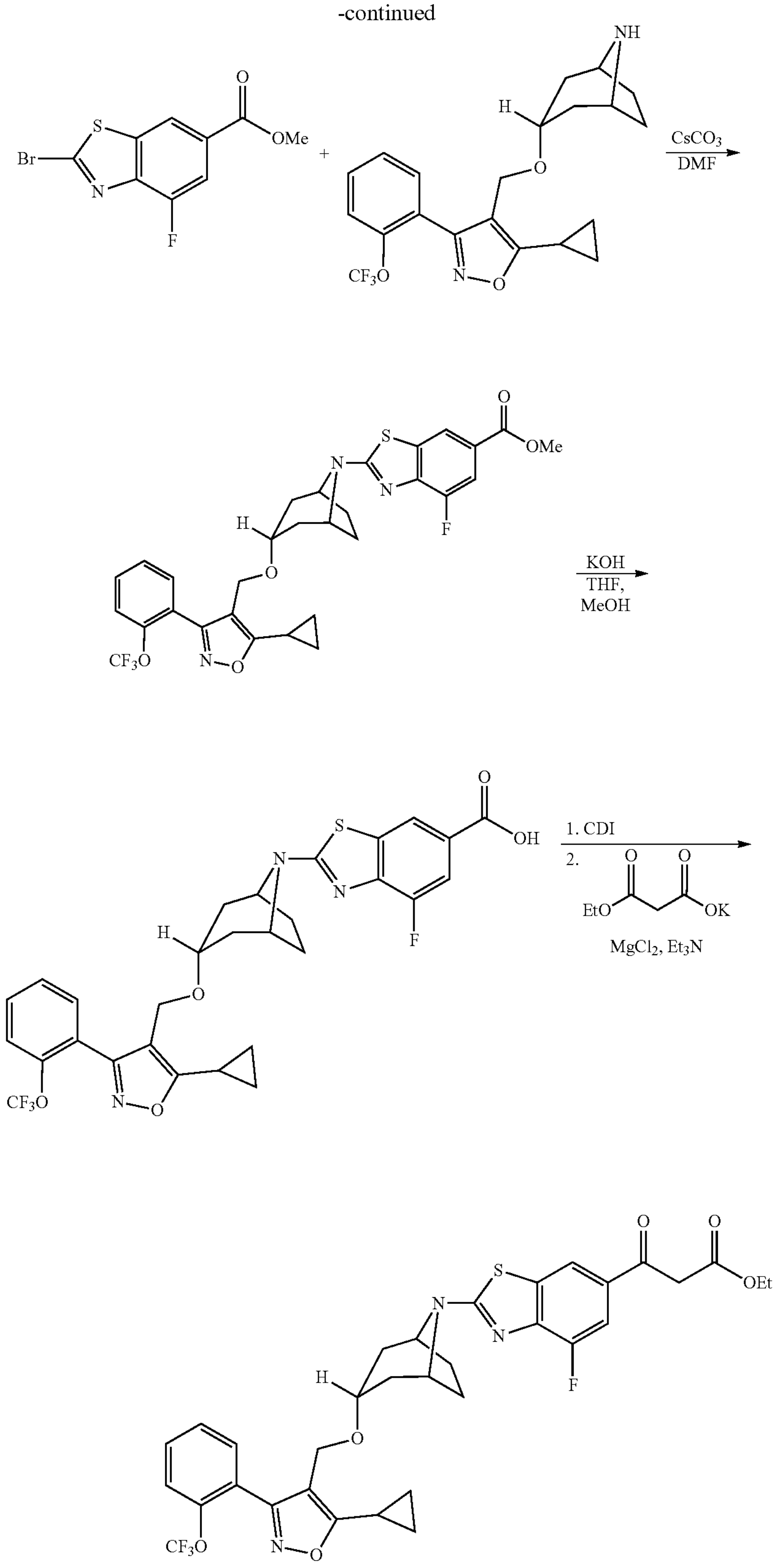
The beta-ketoester precursor reacted with a mixture of triphenylphosphine oxide and trifluoroacetic anhydride in the presence of triethylamine to generate a propynoate ester. The alkyne ester condenses with hydroxylamine hydrochloride in KOH and methanol to form the 5-aryl-3-hydroxy-isoxazole structure of Compound II-3 (Scheme 4).

Scheme 4

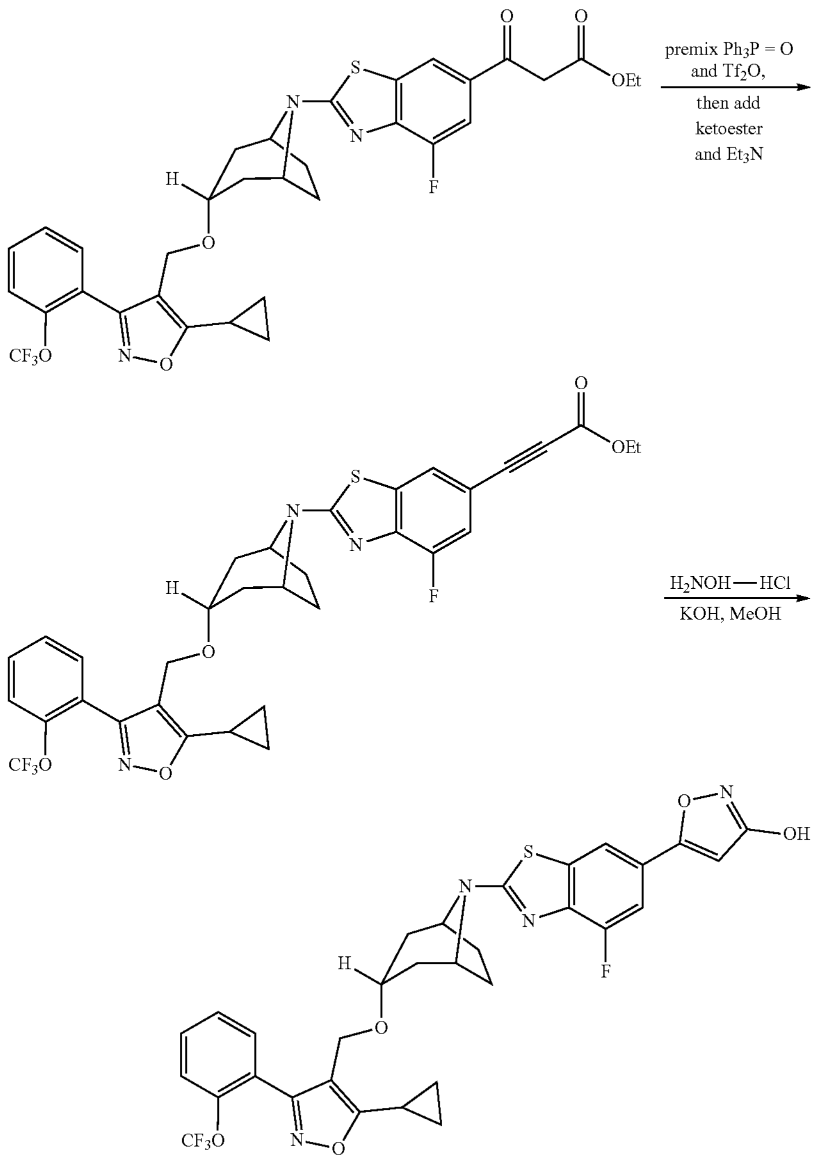

II-3

Example 4: Synthesis of 3-(2-((1R,5S)-3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazol-6-yl)isoxazol-5-ol (II-4)

The ethyl beta-ketoester was prepared according to the methods provided in Example 3. The beta-ketoester precursor was then condensed with hydroxylamine hydrochloride in the presence of ethanol to give the 3-aryl-5-hydroxyisoxazole structure of Compound II-14.

Example 5: In Vitro FXR Binding Activity

A stably transfected, clonally derived Chinese Hamster Ovary (CHO) cell-line which features novel in vivo applications of Enzyme Fragment Complementation (EFC) technology in which the β-galactosidase (β-gal) enzyme has been split into two inactive fragments, based on PathHunter technology, was utilized to evaluate engagement of the FXR receptor. Cells were seeded in cell plating reagent in a total volume of 20 μL into 384-well microplates and incubated at 37° C., 5% $CO_2$ humidified incubator for 24 or 48 hours prior to testing. FXR agonists were dissolved in DMSO (dimethyl sulfoxide). Ligands were subsequently diluted in the cell plating reagent to make up desired concentration stock solution. Ten-point dose curve serial dilutions were prepared in cell plating reagent. 5 μL of 5× sample was added to cells and incubated at 37° C. or room temperature for 3-16 hours. Final assay vehicle concentration was 1%. Chemiluminescent signals were generated through addition of 12.5 μL or 15 μL of detection reagent cocktail (500% v/v), followed by incubation at room temperature for 1 hour. Microplates were read for signal generation using a PerkinElmer Envision instrument to detect chemiluminescence.

The percentage activity was calculated using the following formula: % Activity=100%×(mean RLU of test sample−mean RLU of vehicle control)/(mean MAX control ligand−mean RLU of vehicle control). Binding and response results for Compounds II-1 to II-4 are shown below.

| Compound | $EC_{50}$ (μM) | Max Response (%) |
|---|---|---|
| II-1 | 2.86 | 52 |
| II-2 | 3.08 | 90 |
| II-3 | 0.0246 | 151 |
| II-4 | 0.0811 | 159 |

Example 6: Biological Effects of Compounds in Mice

NASH was induced in mice by feeding mice a Gubra amylin NASH (GAN) diet as described in Boland et al. *World J Gastroenterol.* 2019, 25(33): 4904-4920. One week prior to administration of a first dose of compounds, the mice were weighed and randomized, and their food intake was measured. Mice were randomly assigned to dosing groups, with 12 mice per group. Assigned dosages were: Compound II-1 (10 mg/kg); Compound II-2 (10 mg/kg) One group was mock treated with vehicle only as a control. Dosage of Compound II-1 and Compound II-2 were titrated over 3 days, with a dosage of 3 mg/kg administered on days 0, 1 and 2. Dosage of tropifexor was titrated over 2 days, with a dosage of 0.1 mg/kg administered on days 0 and 1. Absolute and relative body weight of the mice were recorded daily.

Fed blood glucose and fed plasma levels of alanine transaminase (ALT) aspartate transaminase (AST), triglycerides (TG), and total cholesterol (TC) were measured at days 7, 14, 21.

After 8 weeks, animals were sacrificed. Plasma enzymes (P-ALT (alanine aminotransferase) and P-AST (aspartate aminotransferase)), total plasma triglycerides, and total plasma cholesterol were measured, and terminal necropsy of each liver was carried out, determining relative liver weight as a percentage of body weight, assaying total liver biochemistry including total liver triglycerides, plasma insulin and total liver cholesterol, as well as histological evaluation of total liver hydroxyproline, and steatosis. Tissue samples were preserved for characterization using RNAseq.

Figure 2:
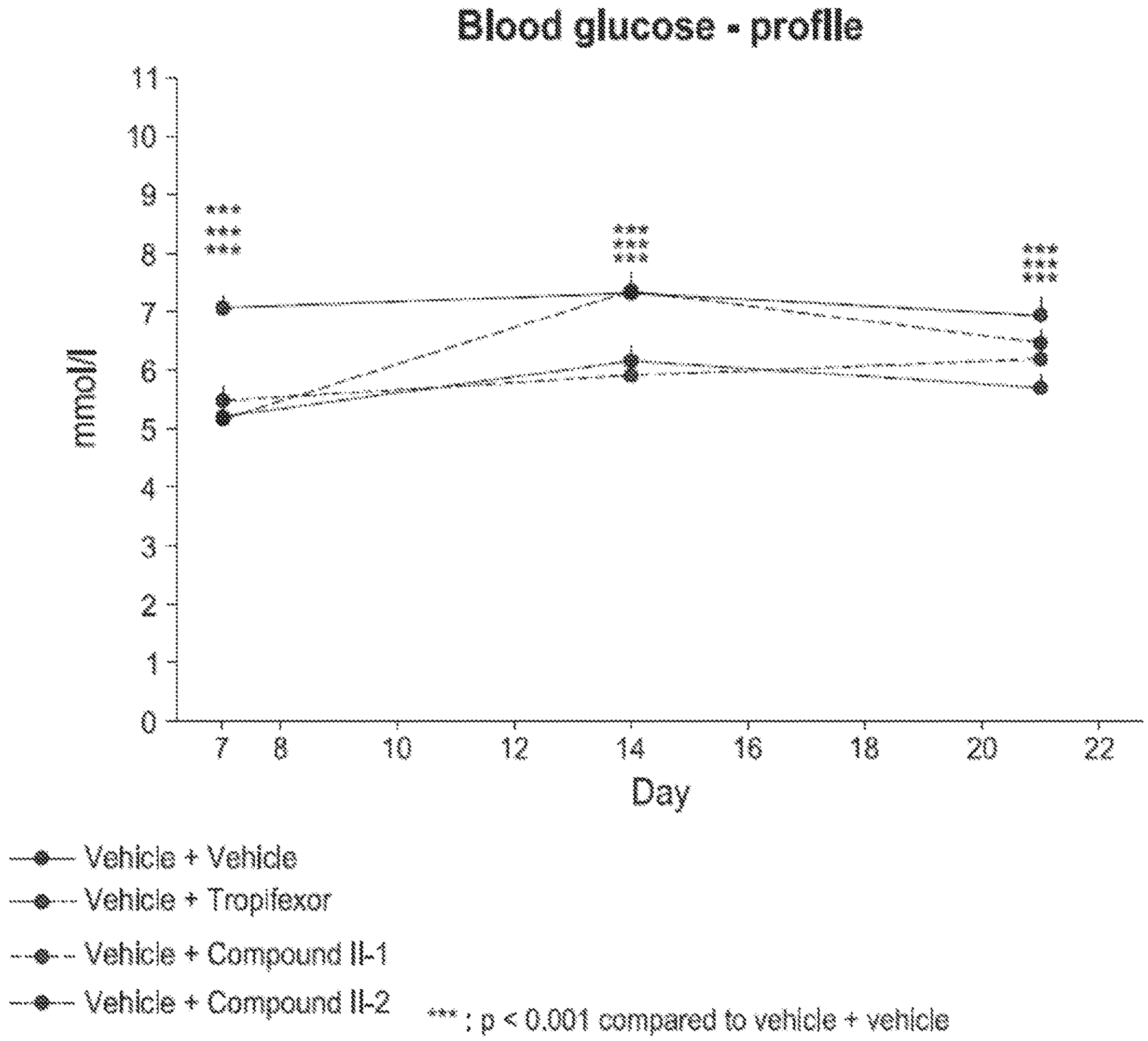
FIG. 2 shows the blood glucose levels of diet-induced NASH mice upon administration of vehicle, tropifexor, Compound II-1, or Compound II-2 for the duration of the 21-day study measured at day 7, day 14, and day 21 of the study.

Relative body weight of the mice on study day 21 is shown in FIG. 1. The data shows that that administration of either Compound II-1 or Compound II-2 resulted in a lower relative terminal body weight as compared to administration of vehicle alone. Administration of Compound II-1 or Compound II-2 resulted in a lower blood glucose level as compared to as compared to administration of vehicle alone (FIG. 2).

Figure 3:
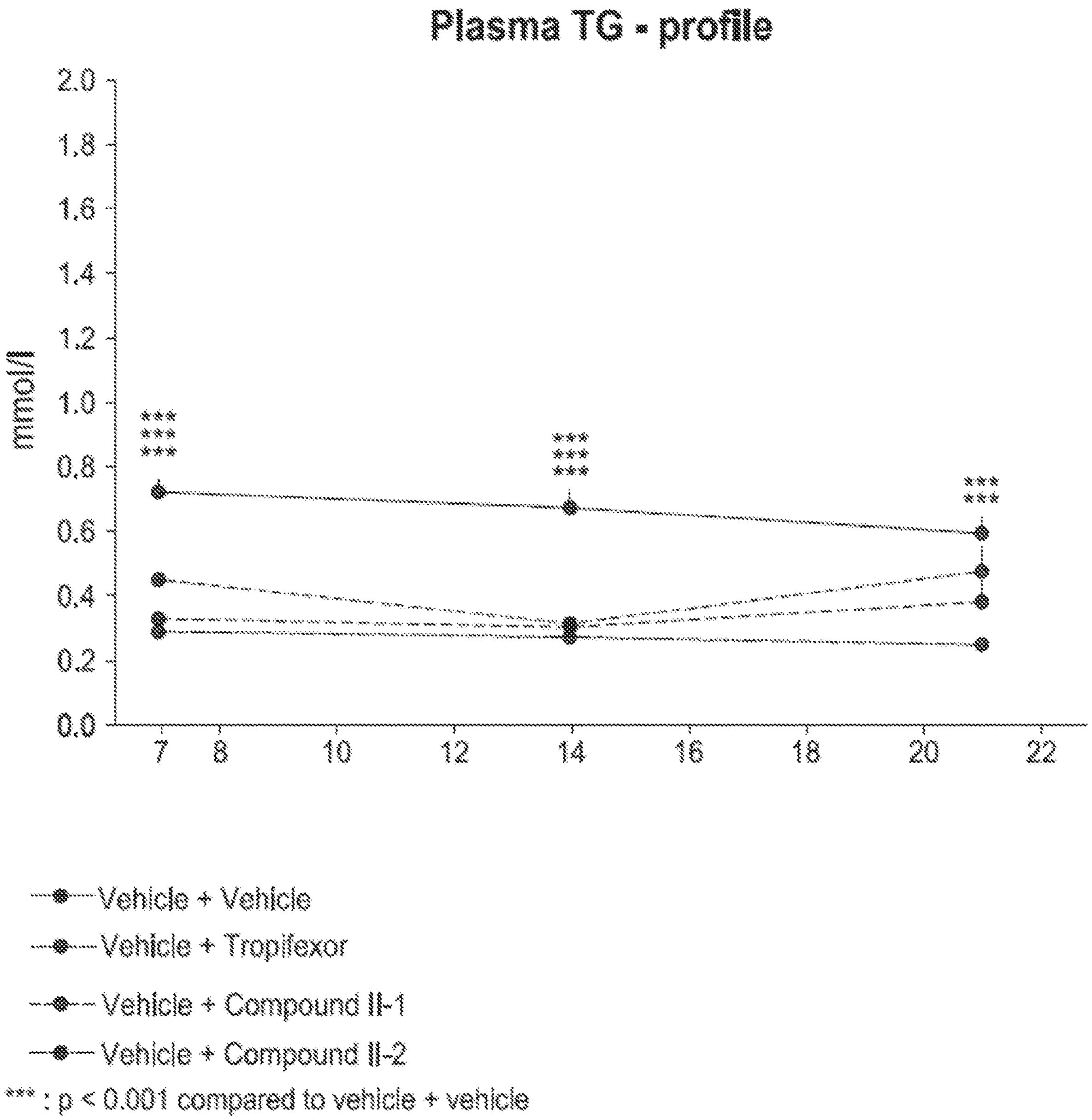
FIG. 3 shows the plasma triglyceride (TG) levels of diet-induced NASH mice upon administration of vehicle, tropifexor, Compound II-1, or Compound II-2 for the duration of the 21-day study measured at day 7, day 14, and day 21 of the study.
Figure 4:
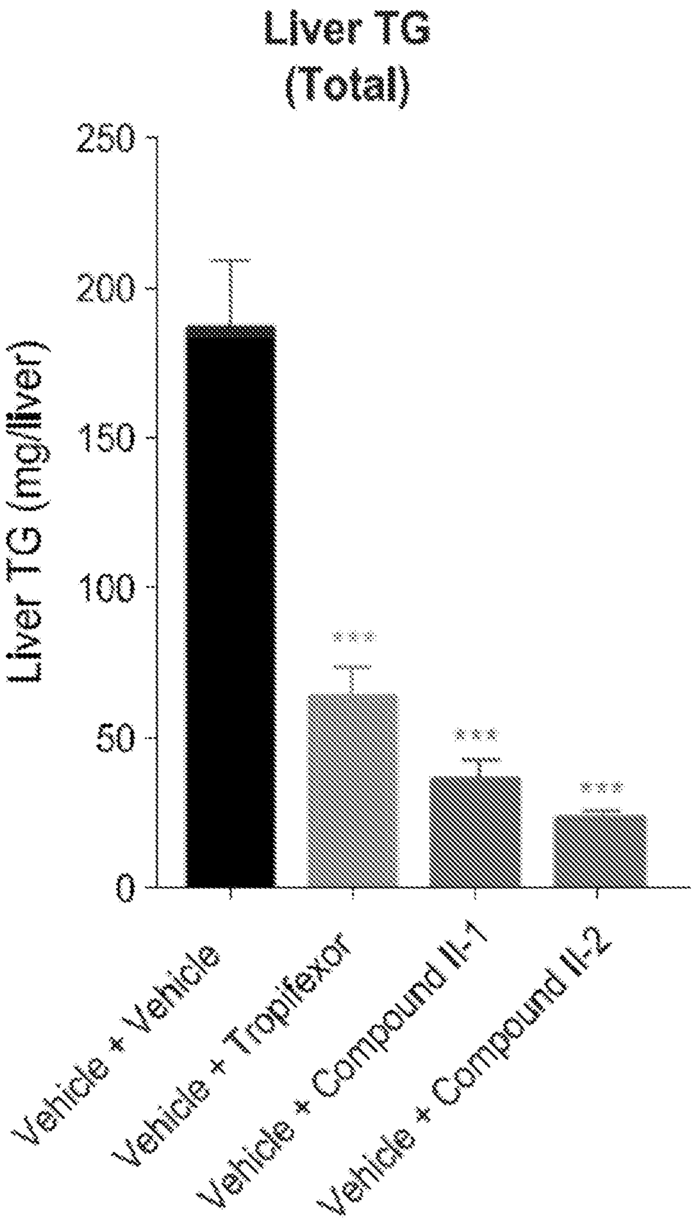
FIG. 4 shows the liver TG levels of diet-induced NASH mice upon administration of vehicle, tropifexor, Compound II-1, or Compound II-2 at study termination.

Plasma triglyceride (TG) levels were also significantly reduced as early as seven days after administration of Compound II-1 or Compound II-2 as compared to administration of vehicle only (FIG. 3). Total liver triglycerides were similarly decreased over the course of the study (FIG. 4). Additionally, Compound II-2 demonstrated greater efficacy in lowering plasma TG levels than the FXR agonist tropifexor ($p<0.05$), while both Compound II-1 ($p<0.05$) and Compound II-2 ($p<0.01$) demonstrated greater efficacy in lowering liver TG levels than the FXR agonist tropifexor.

Example 7: Biological Effects of Compounds in Mice

NASH was induced in mice by feeding mice a Gubra amylin NASH (GAN) diet as described in Boland et al. *World J Gastroenterol.* 2019, 25(33): 4904-4920. One week prior to administration of a first dose of compounds, the mice were weighed and randomized, and their food intake was measured. Mice were randomly assigned to dosing groups, with 12 mice per group. Assigned dosages included the following; Compound 2 (10 mg/kg); tropifexor (0.3 mg/kg); Compound 2 (10 mg/kg)+tropifexor (0.3 mg/kg); Compound II-1 (10 mg/kg); Compound 2 (10 mg/kg)+Compound II-1 (30 mg/kg); Compound II-2 (10 mg/kg); and Compound 2 (10 mg/kg)+Compound II-2 (30 mg/kg). One group was mock treated with vehicle only as a control. Dosage of Compound II-1 and Compound II-2 were titrated over 6 days, with a dosage of 3 mg/kg administered on days 0, 1 and 2 and a dosage of 10 mg/kg administered on days 3, 4, and 5. Absolute and relative body weight of the mice were recorded daily.

Fed blood glucose and fed plasma levels of alanine transaminase (ALT) aspartate transaminase (AST), triglycerides (TG), and total cholesterol (TC) were measured at days 7, 14, 21.

After 3 weeks, animals were sacrificed. Plasma enzymes (P-ALT (alanine aminotransferase) and P-AST (aspartate aminotransferase)), total plasma triglycerides, and total plasma cholesterol were measured, and terminal necropsy of each liver was carried out, determining relative liver weight as a percentage of body weight, assaying total liver biochemistry including total liver triglycerides, plasma insulin and total liver cholesterol, as well as histological evaluation of total liver hydroxyproline, and steatosis. Tissue samples were preserved for characterization using RNAseq.

Figure 5:
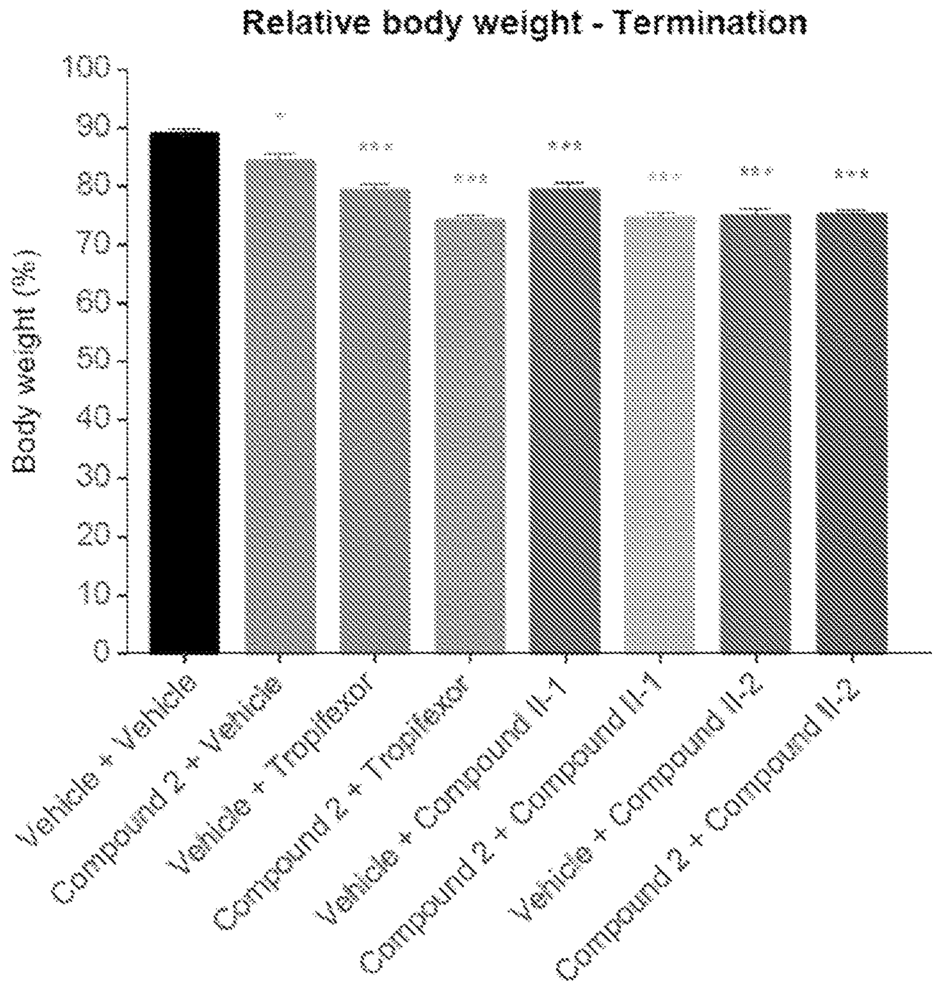
FIG. 5 shows the relative body weight of diet-induced NASH mice upon administration of vehicle, Compound 2, tropifexor, Compound II-1, Compound II-2, Compound 2+tropifexor, Compound 2+Compound II-1, or Compound 2+Compound II-2 for the duration of the 21-day study.
Figure 6:
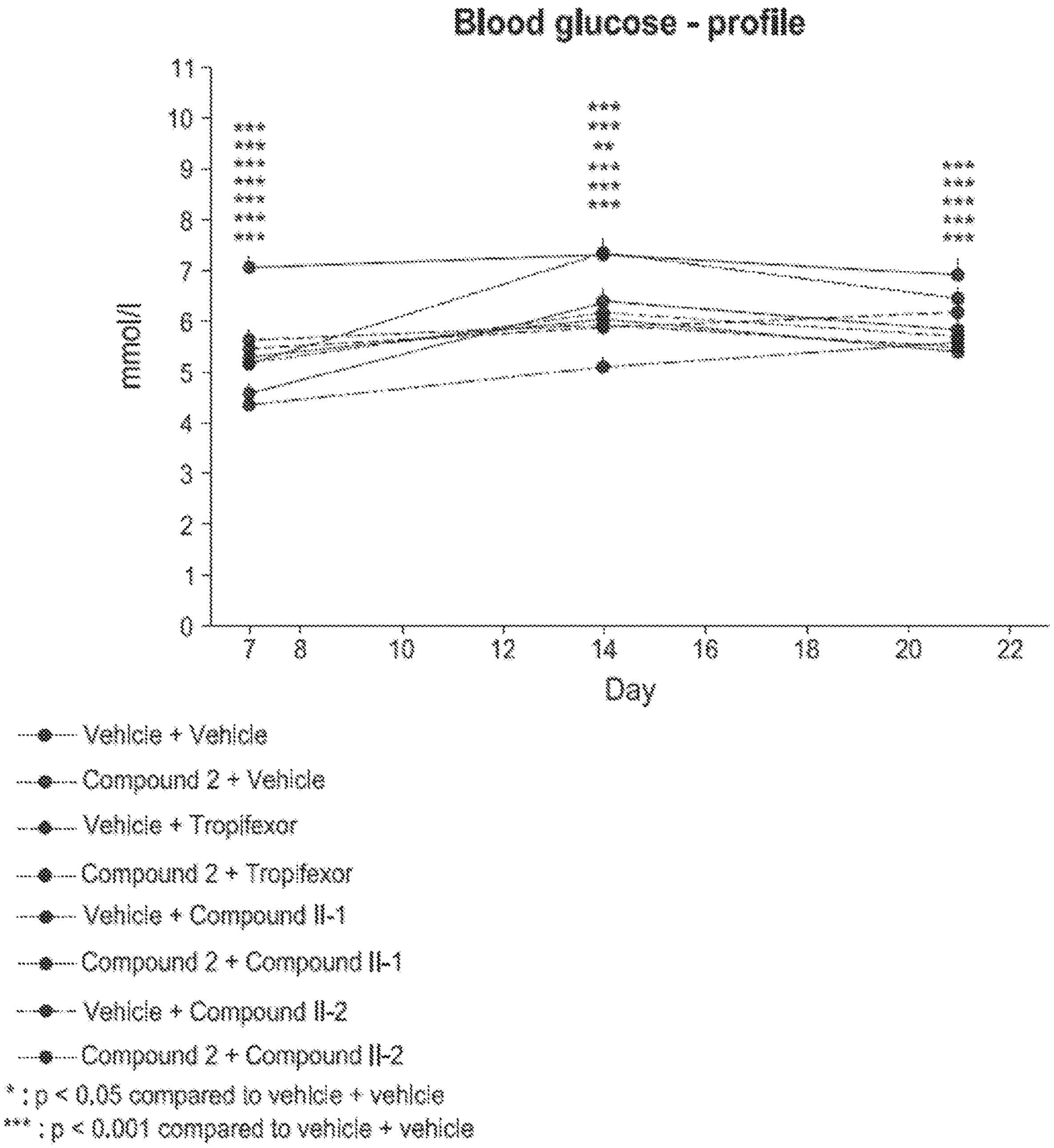
FIG. 6 shows the blood glucose levels of diet-induced NASH mice upon administration of vehicle, Compound 2, tropifexor, Compound II-1, Compound II-2, Compound 2+tropifexor, Compound 2+Compound II-1, or Compound 2+Compound II-2 for the duration of the 21-day study measured at day 7, day 14, and day 21 of the study.

Relative body weight of the mice on study day 21 is shown in FIG. 5. The data shows that administration of any of Compound 2, Compound II-1, or Compound II-2 resulted in a lower relative terminal body weight as compared to administration of vehicle alone. Administration of any of Compound 2, Compound II-1, or Compound II-2 resulted in a lower blood glucose level as compared to as compared to administration of vehicle alone (FIG. 6).

Figure 7:
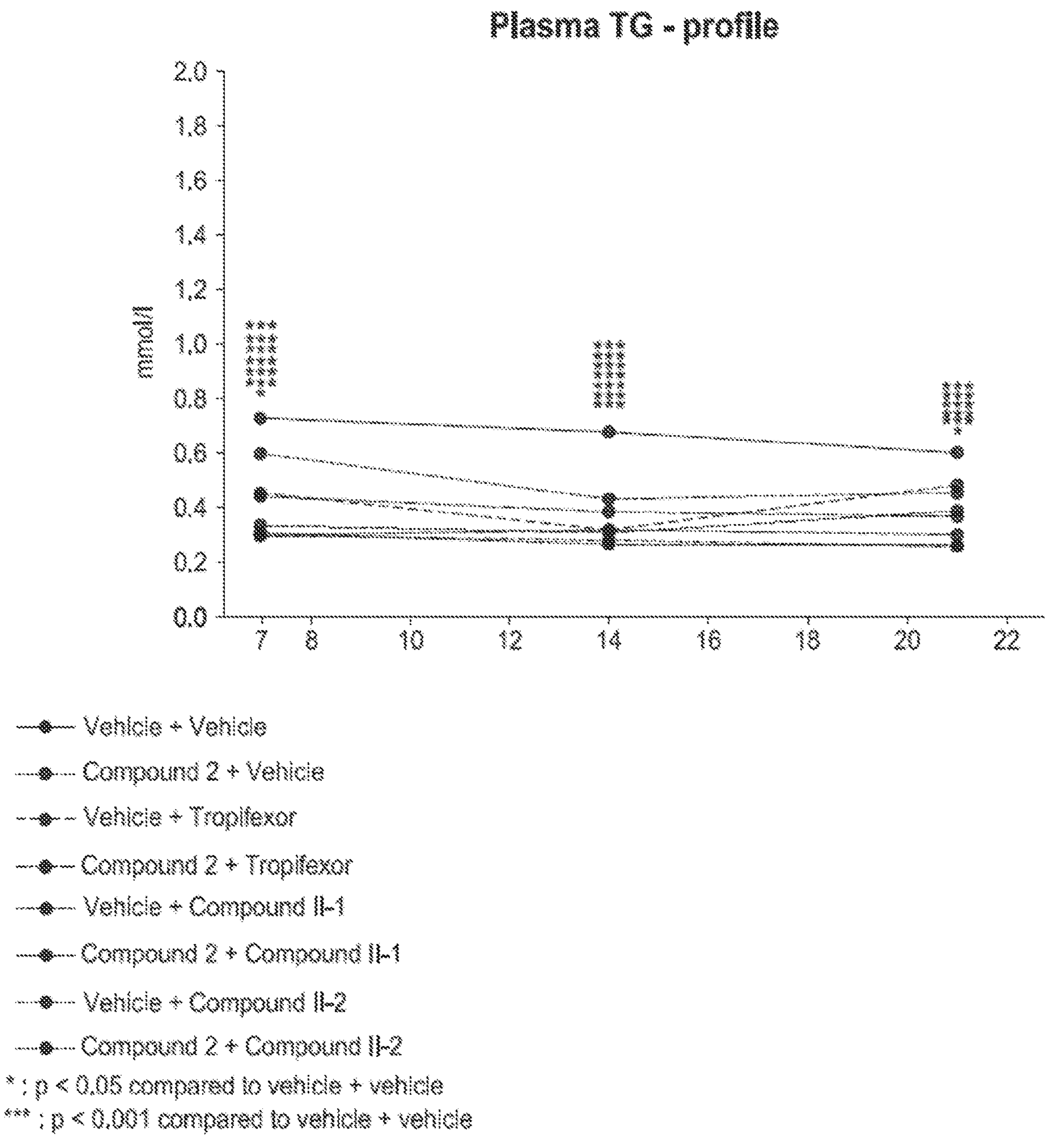
FIG. 7 shows the plasma triglyceride (TG) levels of diet-induced NASH mice upon administration of vehicle, Compound 2, tropifexor, Compound II-1, Compound II-2, Compound 2+tropifexor, Compound 2+Compound II-1, or Compound 2+Compound II-2 for the duration of the 21-day study measured at day 7, day 14, and day 21 of the study.
Figure 8:
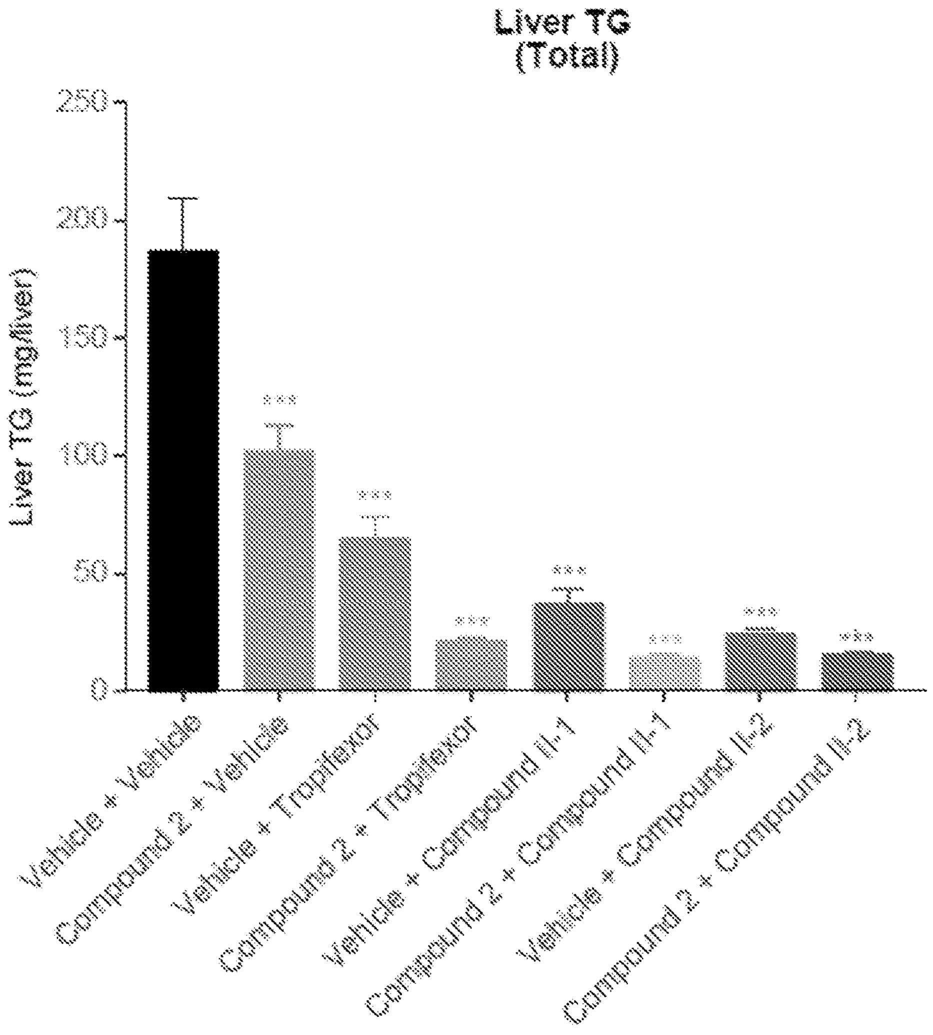
FIG. 8 shows the liver TG levels of diet-induced NASH mice upon administration of vehicle, Compound 2, tropifexor, Compound II-1, Compound II-2, Compound 2+tropifexor, Compound 2+Compound II-1, or Compound 2+Compound II-2 at study termination.

Plasma triglyceride (TG) levels were also significantly reduced as early as seven days after administration of any of Compound 2, Compound II-1, Compound II-2, Compound 2+Compound II-1, or Compound 2+Compound II-2 (FIG. 7). Importantly, the combination of Compound 2+Compound II-1 ($p<0.05$) and the combination of Compound 2+Compound II-2 ($p<0.001$) showed an improvement in plasma TG levels compared to the combination of Compound 2+tropifexor. Administration of any of Compound 2, Compound II-1, Compound II-2, Compound 2+Compound II-1, or Compound 2+Compound II-2 resulted in lowered liver TG levels at the termination of the study (FIG. 8). Moreover, the combination of Compound 2+Compound II-1 was more effective in reducing liver TG compared to either Compound 2 alone ($p<0.00001$) or Compound II-1 alone ($p<0.01$), while the combination of Compound 2+Compound II-2 was more effective in reducing liver TG compared to either Compound 2 alone ($p<0.00001$) or Compound II-2 alone ($p<0.01$).

Figure 9:
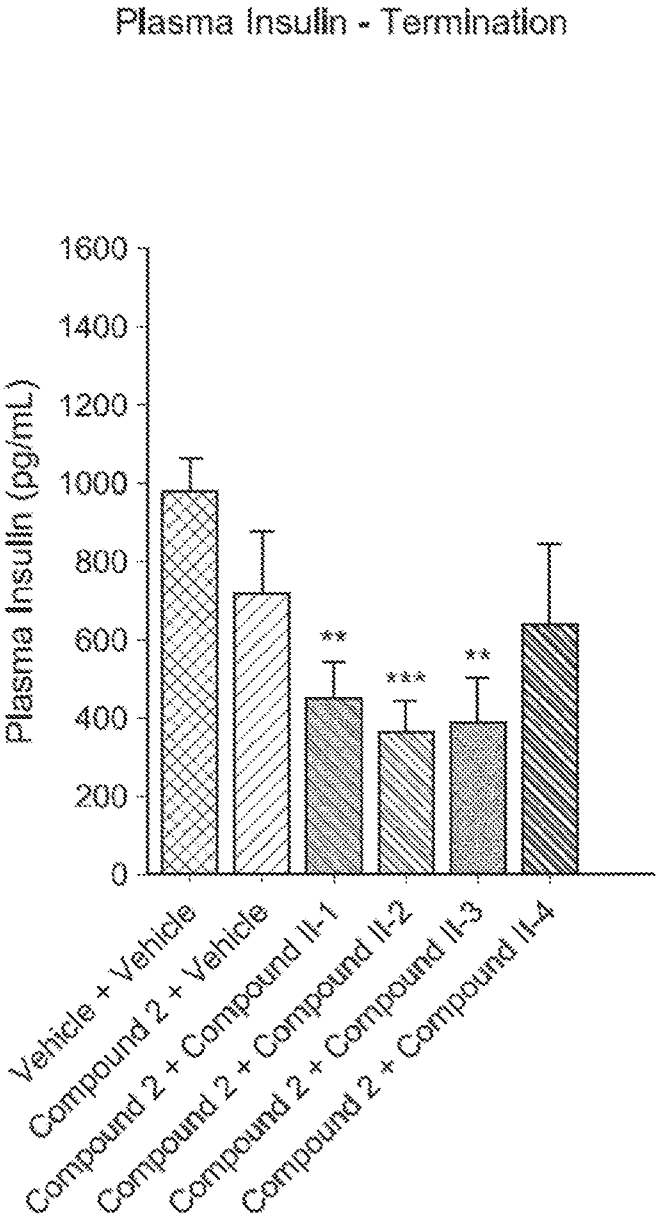
FIG. 9 shows the plasma insulin levels of diet-induced NASH mice upon administration of vehicle, Compound 2, and the combinations of Compound 2 with each of Compound II-1, II-2, II-3, and II-4 for the duration of the 21-day study.

Total plasma insulin levels of the mice on study day 21 is shown in FIG. 9. The data shows that administration Compounds 11-1, 11-2, 11-3, and II-4 resulted in a lower insulin levels compared to administration of vehicle alone and compared to administration of Compound 2, with a statistically significant reduction of plasma insulin level observed for Compounds II-1, II-2, and II-3 as comparted to vehicle.

Figure 10:
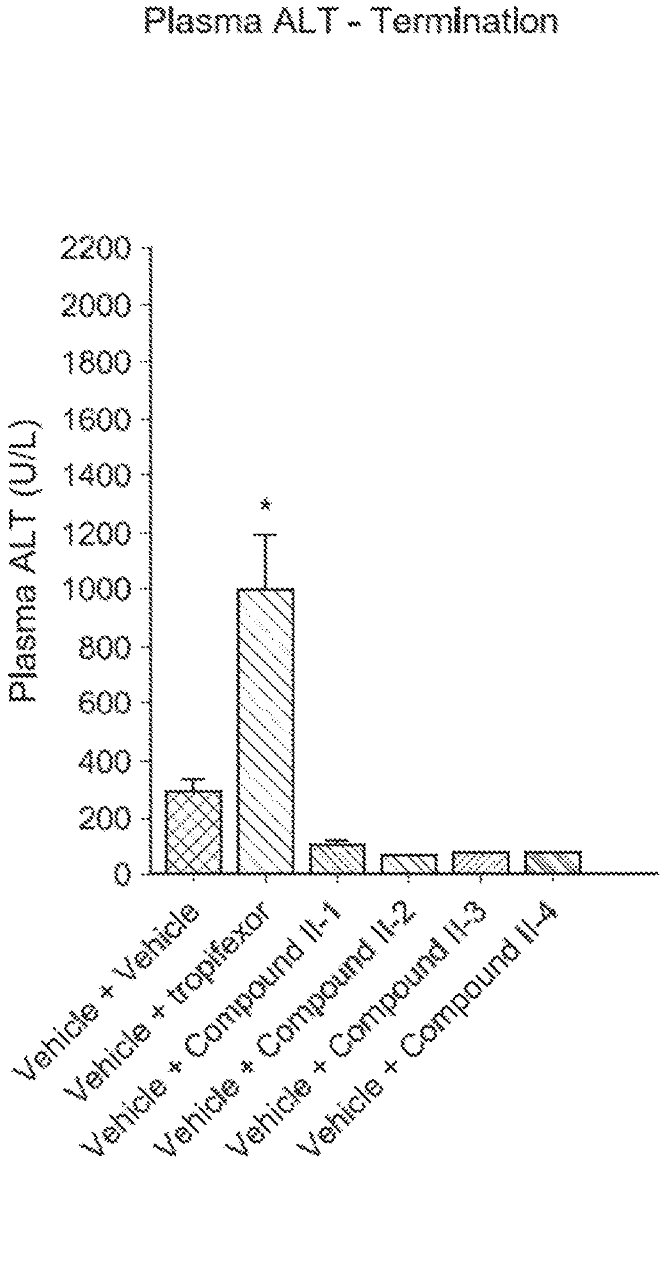
FIG. 10 shows the plasma alanine transaminase (ALT) levels of diet-induced NASH mice upon administration of vehicle, tropifexor, and each of Compound II-1, II-2, II-3, and II-4 for the duration of the 21-day study.

Total plasma ALT levels of the mice on study day 21 is shown in FIG. 10. The data shows that administration of Compounds II-1, II-2, II-3, and 1-4 resulted in a lower plasma ALT level compared to administration of vehicle alone, and also resulted in lower plasma ALT levels comparted to administration of tropifexor.

Figure 11:
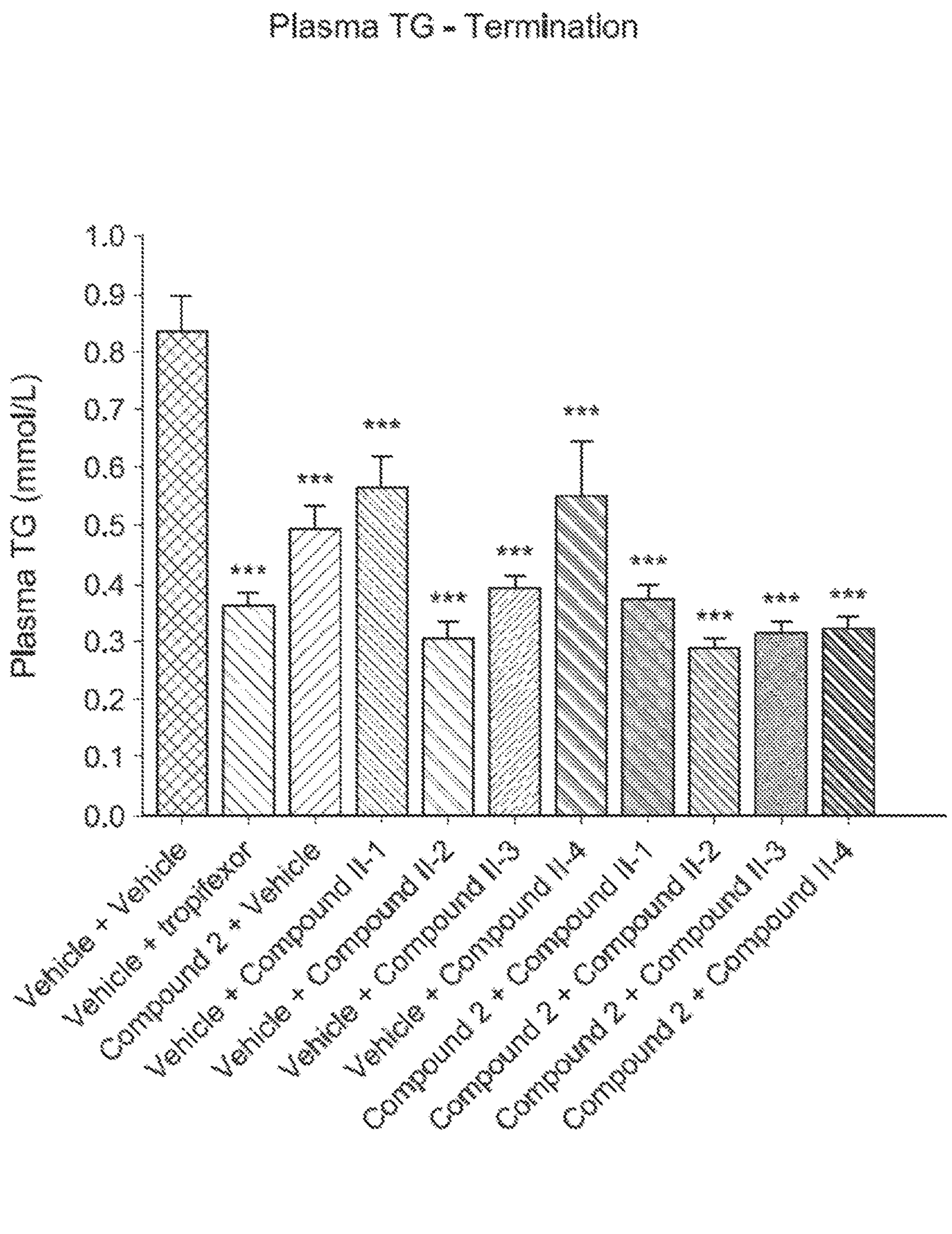
FIG. 11 shows the plasma triglyceride (TG) levels of diet-induced NASH mice upon administration of vehicle, Compound 2, tropifexor, each of Compound II-1, II-2, II-3, and II-4, and the combinations of Compound 2 with each of Compound II-1, II-2, II-3, and II-4 for the duration of the 21-day study measured at the conclusion of the study (day 21).
Figure 12:
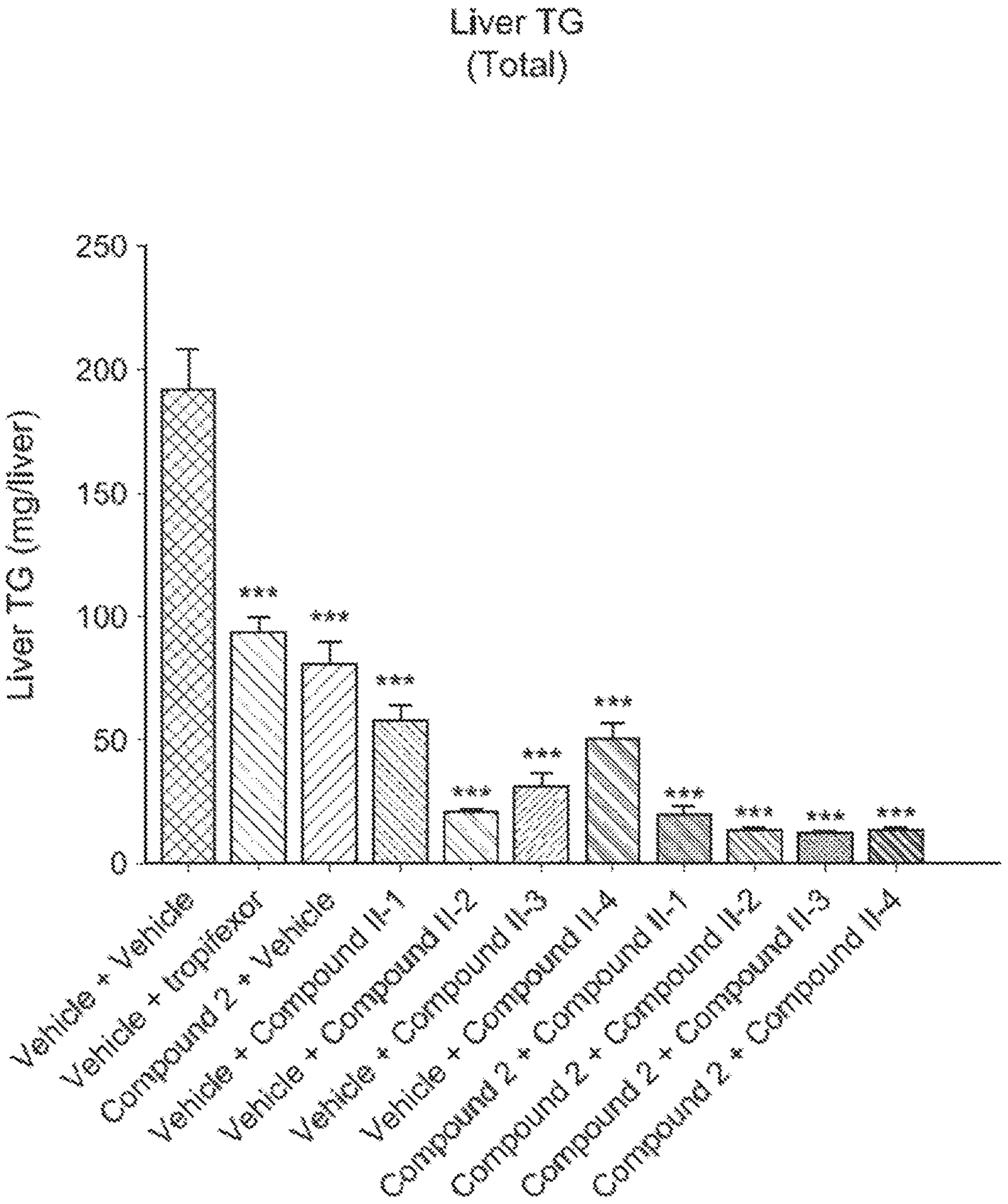
FIG. 12 shows the liver triglyceride (TG) levels of diet-induced NASH mice upon administration of vehicle, Compound 2, tropifexor, each of Compound II-1, II-2, II-3, and II-4, and the combinations of Compound 2 with each of Compound II-1, II-2, II-3, and II-4 for the duration of the 21-day study measured at the conclusion of the study (day 21).

Plasma triglyceride (TG) levels and liver TG levels of the mice upon termination of the study at day 21 for administration of vehicle, Compound 2, tropifexor, each of Compound II-1, II-2, 11-3, and II-4, and the combinations of Compound 2 with each of Compound II-1, II-2, II-3, and II-4 are shown in FIGS. 11 and 12, respectively. Each of Compound II-1, II-2, II-3, and II-4 as well as the combination of Compound 2 and each of Compound II-1, II-2, II-3, and II-4 showed a significant reduction of plasma TG levels as compared to vehicle. Each of Compound II-1, II-2, 11-3, and 1-4 and of the combination Compound 2 and each of Compound II-1, II-2, II-3, and II-4 reduced total liver triglycerides than tropifexor, With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A compound of Formula (II):

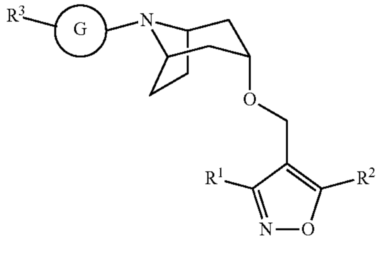

(II)

or a pharmaceutically acceptable salt thereof; wherein $R^1$ is selected from the group consisting of: $C_{6-10}$ aryl, 5-10 membered heteroaryl, $C_{3-10}$ cycloalkyl, or 5-10 membered heterocyclyl, each of which is optionally substituted with 1-3 $R^{1A}$;

$R^2$ is halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, or 5-10 membered heterocyclyl each of which is optionally substituted with 1-3 $R^{2A}$;

G is selected from the group consisting of: $C_{6-10}$ aryl, 5-10 membered heteroaryl, $C_{3-10}$ cycloalkyl, or 5-10 membered heterocyclyl, each of which is optionally substituted with 1-3 $R^G$;

$R^3$ is —P(=O)(X)(Y) or 5-10 membered heteroaryl containing 1-2 heteroatoms selected from N, O and S optionally substituted with 1-2 $R^{3A}$ independently selected from halogen, —$OR^5$, $C_{1-6}$ alkyl, halo$C_{1-6}$ alkyl, halo$C_{1-6}$ alkoxy, or $C_{3-10}$ cycloalkyl;

each $R^{1A}$ is independently selected from the group consisting of halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, and 5-10 membered heterocyclyl;

each $R^{2A}$ is independently selected from the group consisting of halogen, $C_{1-6}$ alkyl, halo$C_{1-6}$ alkyl, $C_{1-6}$ alkoxy, halo$C_{1-6}$ alkoxy, $C_{6-10}$ aryl, 5-10 membered heteroaryl, $C_{3-10}$ cycloalkyl, and 5-10 membered heterocyclyl;

each $R^G$ is independently selected from the group consisting of halogen, $C_{1-6}$ alkyl, halo$C_{1-6}$ alkyl, $C_{1-6}$ alkoxy, and halo$C_{1-6}$ alkoxy;

X and Y are each independently —$OR^4$, $NR^5R^6$, $C_{1-6}$ alkyl, or halo$C_{1-6}$ alkyl;

each $R^4$ is independently hydrogen, $C_{1-6}$ alkyl, or halo$C_{1-6}$ alkyl;

each $R^5$ is independently hydrogen or $C_{1-6}$ alkyl; and each $R^6$ is independently hydrogen or $C_{1-6}$ alkyl.

2. The compound of claim 1, wherein $R^1$ is (trifluoromethoxy)phenyl.

3. The compound of claim 1, wherein $R^2$ is cyclopropyl.

4. The compound of claim 1, wherein G is selected from the group consisting of: phenyl, pyridine, imidazole, pyrrole, triazole, thiazole, furanyl, pyrazine, pyrimidine, indole, quinoline, isoquinoline, benzothiazole, benzimidazole, benzoxazole, and naphthyl, each of which is optionally substituted with 1-3 $R^G$.

5. The compound of claim 1, having the Formula (IIaa):

(IIaa)

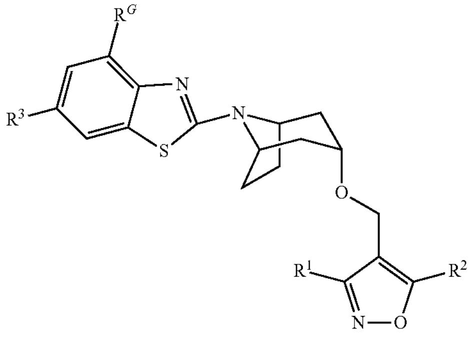

or a pharmaceutically acceptable salt thereof.

6. The compound of claim 1, wherein $R^G$ is halogen.

7. The compound of claim 1, wherein $R^3$ is —P(=O)(X)(Y).

8. The compound of claim 7, wherein X is —$OR^4$.

9. The compound of claim 8, wherein $R^4$ is hydrogen or $C_{1-6}$ alkyl.

10. The compound of claim 7, wherein Y is —$OR^4$.

11. The compound of claim 10, wherein $R^4$ is hydrogen or $C_{1-6}$ alkyl.

12. The compound of claim 7, wherein Y is $C_{1-6}$ alkyl.

13. The compound of claim 1, wherein $R^3$ is

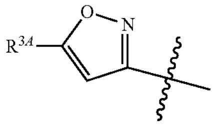

or

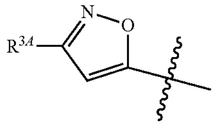

.

14. The compound of claim 13, wherein $R^{1A}$ is $C_{1-6}$ alkoxy or hydroxy.

15. The compound of claim 1 selected from the group consisting of:

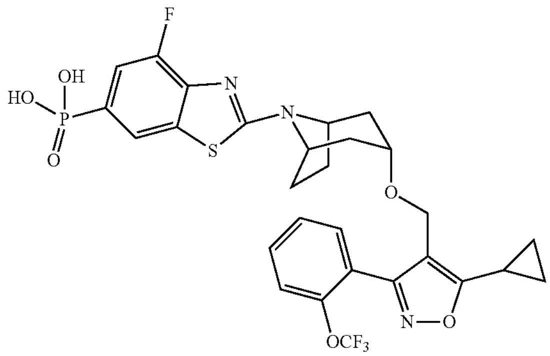

,

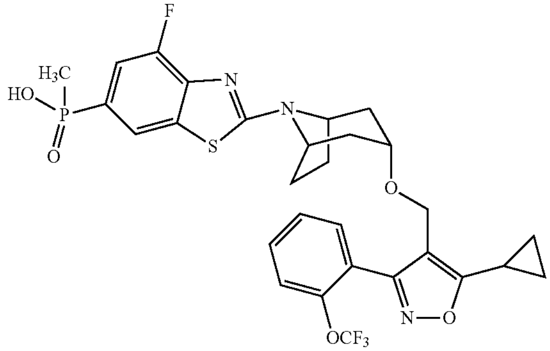

,

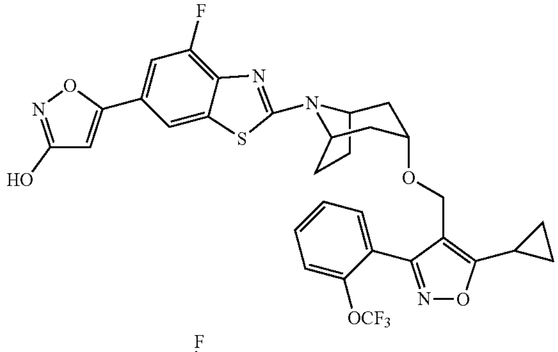

,

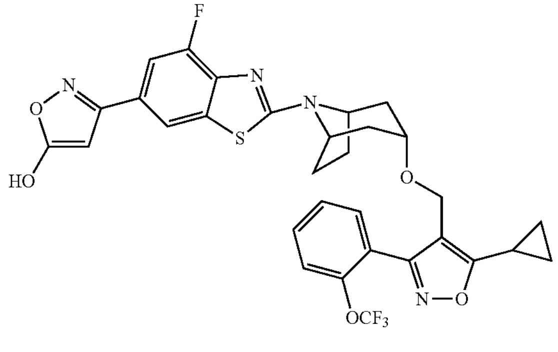

, and pharmaceutically acceptable salts thereof.

16. A method of preventing, treating, or ameliorating one or more fatty liver diseases in a subject, comprising administering a compound of claim 1, or a pharmaceutically acceptable salt thereof, to a subject in need thereof.

17. A method of preventing, treating, or ameliorating one or disease or disorders in a subject, comprising administering a compound of claim 1, or a pharmaceutically acceptable salt thereof, to a subject in need thereof, wherein said disease or disorder is liver fibrosis, renal fibrosis, biliary fibrosis, pancreatic fibrosis, nonalcoholic steatohepatitis, non-alcoholic fatty liver disease, chronic kidney disease, diabetic kidney disease, primary sclerosing cholangitis, primary biliary cirrhosis, or idiopathic fibrosis.

18. The method of claim 17, further comprising administering to the subject at least one TR-β agonist or a pharmaceutically acceptable salt thereof, in combination with the compound of claim 1, or the pharmaceutically acceptable salt thereof.

19. The method of claim 18, wherein the TR-β agonist is a compound of Formula (I):

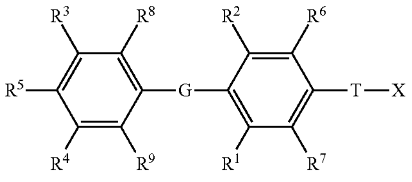

(I)

or a pharmaceutically acceptable salt thereof, wherein:

G is selected from the group consisting of —O—, —S—, —S(═O)—, —S(═O)$_2$—, —Se—, —CH$_2$—, —CF$_2$—, —CHF—, —C(O)—, —CH(OH)—, —CH(C$_1$-C$_4$ alkyl)-, —CH(C$_1$-C$_4$ alkoxy)-, —C(═CH$_2$)—, —NH—, and —N(C$_1$-C$_4$ alkyl)-;

T is selected from the group consisting of —$(CR^a_2)_k$—, —$CR^b$═$CR^b$—$(CR^a_2)_n$—, —$(CR^a_2)_n$—$CR^b$═$CR^b$—, —$(CR^a_2)$—$CR^b$═$CR^b$—$(CR^a_2)$—, —O$(CR^b_2)(CR^a_2)_n$—, —S$(CR^b_2)(CR^a_2)_n$—, N$(R^c)(CR^b_2)(CR^a_2)_n$—, N$(R^b)$C(O)$(CR^a_2)_n$, —C(O)$(CR^a_2)_n$—, —$(CR^a_2)_m$C(O)—, —$(CR^a_2)$C(O)$(CR^a_2)_n$, —$(CR^a_2)_n$C(O)$(CR^a_2)$—, and —C(O)NH$(CR^b_2)(CR^a_2)_p$—;

k is an integer from 1-4;

m is an integer from 0-3;

n is an integer from 0-2;

p is an integer from 0-1;

each $R^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one $R^a$ is attached to C through an O, S, or N atom, then the other $R^a$ attached to the same C is a hydrogen, or attached via a carbon atom;

each $R^b$ is independently selected from the group consisting of hydrogen and optionally substituted —C$_1$-C$_4$ alkyl;

each $R^c$ is independently selected from the group consisting of hydrogen and optionally substituted —C$_1$-C$_4$ alkyl, optionally substituted —C(O)—C$_1$-C$_4$ alkyl, and —C(O)H;

$R^1$, and $R^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted —O—C$_1$-C$_3$ alkyl, and cyano;

$R^6$, $R^7$, $R^8$, and $R^9$ are each independently selected from the group consisting of are each independently selected from the group consisting of hydrogen, halogen, optionally substituted —C C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano; or $R^6$ and T are taken together along with the carbons they are attached to form a ring of 5 to 6 atoms including 0 to 2 heteroatoms independently selected from —NR$^i$—, —O—, and —S—, with the proviso that when there are 2 heteroatoms in the ring and both heteroatoms are different than nitrogen then both heteroatoms have to be separated by at least one carbon atom;

and X is attached to this ring by a direct bond to a ring carbon, or by —$(CR^a_2)$— or —C(O)— bonded to a ring carbon or a ring nitrogen;

$R^i$ is selected from the group consisting of hydrogen, —C(O)C$_1$-C$_4$ alkyl, —C$_1$-C$_4$ alkyl, and —C$_1$-C$_4$-aryl;

$R^3$ and $R^4$ are independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, —SR$^d$, —S(═O)R$^e$, —S(═O)$_2$R$^e$, —S(═O)$_2$NR$^f$R$^g$, —C(O)OR$^h$, —C(O)R$^e$, —N(R$^b$)C(O)NR$^f$R$^g$, —N(R$^e$)S(═O)$_2$R$^e$, —N(R$^e$)S(═O)$_2$NR$^f$R$^g$, and —NR$^f$R$^g$;

each $R^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —$(CR^b_2)_n$ aryl, optionally substituted —$(CR^b_2)_n$ cycloalkyl, optionally substituted —$(CR^a_2)_n$ heterocycloalkyl, and —C(O)NR$^f$R$^g$;

each $R^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —$(CR^a_2)_n$ aryl, optionally substituted —$(CR^a_2)_n$ cycloalkyl, and optionally substituted —$(CR^a_2)_n$ heterocycloalkyl;

$R^f$ and $R^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —$(CR^b_2)_n$ aryl, optionally substituted —$(CR^b_2)_n$ cycloalkyl, and optionally substituted —$(CR^b_2)_n$ heterocycloalkyl, or $R^f$ and $R^g$ may together form an optionally substituted heterocyclic ring, which may contain a second heterogroup selected from the group consisting of O, NR$^C$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

each $R^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —$(CR^b_2)_n$ aryl, optionally substituted —$(CR^b_2)_n$ cycloalkyl, and optionally substituted —$(CR^b_2)_n$ heterocycloalkyl;

$R^5$ is selected from the group consisting of —OH, optionally substituted —OC$_1$-C$_6$ alkyl, OC(O)R$^e$, —OC(O)

$OR^h$, —F, —NHC(O)$R^e$, —NHS(═O)$R^e$, —NHS(═O)$_2R^e$, —NHC(═S)NH($R^h$), and —NHC(O)NH($R^h$);

X is P(O)Y$R^{11}$Y'$R^{11}$;

Y and Y' are each independently selected from the group consisting of —O—, and —$NR^v$—; when Y and Y' are —O—, $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)N$R^z_2$, —N$R^z$—C(O)—$R^y$, —C($R^z$)$_2$—OC(O)$R^y$, —C($R^z$)—(O)O$R^y$, —C($R^z$)OC(O)S$R^y$, -alkyl-S—C(O)$R^y$, -alkyl-S—S-alkylhydroxy, and -alkyl-S—S—S-alkylhydroxy;

when Y and Y' are —$NR^v$—, then $R^{11}$ attached to —$NR^v$— is independently selected from the group consisting of —H, —[C($R^z$)$_2$]$_q$—COO$R^y$, —C($R^x$)$_2$COO$R^Y$, —[C($R^z$)$_2$]$_q$—C(O)S$R^y$, and -cycloalkylene-COO$R^y$;

when Y is —O— and Y' is $NR^v$, then $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)N$R^z_2$, —N$R^z$—C(O)—$R^y$, —C($R^z$)$_2$—OC(O)$R^y$, —C($R^z$)$_2$—O—(O)O$R^y$, —C($R^z$)$_2$OC(O)S$R^y$, -alkyl-S—C(O)$R^y$, -alkyl-S—S-alkylhydroxy, and -alkyl-S—S—S-alkylhydroxy; and $R^{11}$ attached to —$NR^v$— is independently selected from the group consisting of H, —[C($R^z$)$_2$]$_q$—COO$R^y$, —C($R^x$)$_2$COO$R^y$, —[C($R^z$)$_2$]$_q$—C(O)S$R^y$, and -cycloalkylene-COO$R^y$;

or when Y and Y' are independently selected from —O— and $NR^v$, then together $R^{11}$ and $R^{11}$ are -alkyl-S—S-alkyl- to form a cyclic group, or together $R^{11}$ and $R^{11}$ are the group:

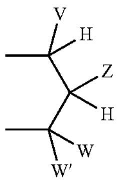

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus;

or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —CH$R^z$OH, —CH$R^z$OC(O)$R^y$, —CH$R^z$OC(S)$R^y$, —CH$R^z$OC(S)O$R^y$, —CH$R^z$OC(O)S$R^y$, —CH$R^z$OCO$_2R^y$, —O$R^z$, —S$R^z$, —CH$R^z$N$_3$, —CH$_2$-aryl, —CH(aryl)OH, —CH(CH═C$R^z_2$)OH, —CH(C≡C$R^z$)OH, —$R^z$, —$N^z_2$, —OCO$R^y$, —OCO$_2R^y$, —SCO$R^y$, —SCO$_2R^y$, —NHCO$R^z$, —NHCO$_2R^y$, —CH$_2$NH-aryl, —(CH$_2$)$_q$—O$R^z$, and —(CH$_2$)$_q$—S$R^z$;

q is an integer 2 or 3;

each $R^z$ is selected from the group consisting of $R^y$ and —H;

each $R^y$ is selected from the group consisting of alkyl, aryl, heterocycloalkyl, and aralkyl;

each $R^x$ is independently selected from the group consisting of —H, and alkyl, or together $R^x$ and $R^x$ form a cyclic alkyl group; and each $R^1$ is selected from the group consisting of —H, lower alkyl, acyloxyalkyl, alkoxycarbonyloxyalkyl, and lower acyl.

20. The method of claim 18, wherein the TR-β agonist is a compound having the structure of Formula (A):

(A)

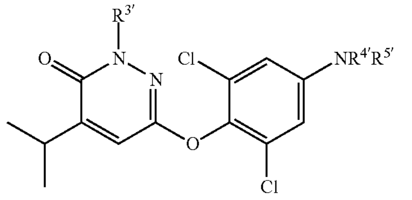

wherein $R^{3'}$ is H or CH$_2R^{a'}$, in which $R^{a'}$ is hydroxyl, O-linked amino acid, —OP(O)(OH)$_2$ or OC(O)$R^{b'}$, $R^{b'}$ being lower alkyl, alkoxy, alkyl acid, cycloalkyl, aryl, heteroaryl, or —(CH$_2$)$_{n'}$-heteroaryl and n' being 0 or 1;

$R^{4'}$ is H, and $R^{5'}$ is CH$_2$COOH, C(O)CO$_2$H, or an ester or amide thereof, or $R^{4'}$ and $R^{5'}$ together are —N═C($R^{c'}$)—C—(O)—NH—C(O)—; in which $R^{c'}$ is H or cyano;

or pharmaceutically acceptable salts thereof.

* * * * *